(12) United States Patent
Clark

(10) Patent No.: US 10,287,311 B2
(45) Date of Patent: *May 14, 2019

(54) MODIFIED FLUORINATED NUCLEOSIDE ANALOGUES

(75) Inventor: Jeremy Clark, Snellville, GA (US)

(73) Assignee: GILEAD PHARMASSET LLC, Foster City, CA (US)

( * ) Notice: Subject to any disclaimer, the term of this patent is extended or adjusted under 35 U.S.C. 154(b) by 1798 days.

This patent is subject to a terminal disclaimer.

(21) Appl. No.: 11/854,218

(22) Filed: Sep. 12, 2007

(65) Prior Publication Data

US 2008/0070861 A1 Mar. 20, 2008

Related U.S. Application Data

(62) Division of application No. 10/828,753, filed on Apr. 21, 2004, now Pat. No. 7,429,572.

(60) Provisional application No. 60/474,368, filed on May 30, 2003.

(51) Int. Cl.
| A61K 31/7068 | (2006.01) |
| --- | --- |
| A61K 31/7072 | (2006.01) |
| C07H 19/00 | (2006.01) |
| C07H 19/04 | (2006.01) |
| C07H 19/048 | (2006.01) |
| C07H 19/06 | (2006.01) |
| C07H 19/14 | (2006.01) |
| C07H 19/16 | (2006.01) |

(52) U.S. Cl.
CPC ......... *C07H 19/00* (2013.01); *A61K 31/7068* (2013.01); *A61K 31/7072* (2013.01); *C07H 19/04* (2013.01); *C07H 19/048* (2013.01); *C07H 19/06* (2013.01); *C07H 19/14* (2013.01); *C07H 19/16* (2013.01)

(58) Field of Classification Search
None
See application file for complete search history.

(56) References Cited

U.S. PATENT DOCUMENTS

| | | | |
| --- | --- | --- | --- |
| 3,480,613 | A | 11/1969 | Walton |
| 3,798,209 | A | 3/1974 | Witkowski |
| RE29,835 | E | 11/1978 | Witkowski |
| 4,814,477 | A | 3/1989 | Wijnberg |
| 4,957,924 | A | 9/1990 | Beauchamp |
| 5,026,687 | A | 6/1991 | Yarchoan |
| 5,075,225 | A | 12/1991 | Wong et al. |
| 5,118,820 | A | 6/1992 | Hertel |
| 5,149,794 | A | 9/1992 | Yatvin |
| 5,157,027 | A | 10/1992 | Biller |
| 5,194,654 | A | 3/1993 | Hostetler |
| 5,223,263 | A | 6/1993 | Hostetler |
| 5,256,641 | A | 10/1993 | Yatvin |
| 5,272,152 | A | 12/1993 | Zahler |
| 5,372,808 | A | 12/1994 | Blatt |
| 5,405,598 | A | 4/1995 | Schinazi |
| 5,411,947 | A | 5/1995 | Hostetler |
| 5,420,266 | A | 5/1995 | Britton |
| 5,446,139 | A | 8/1995 | Seela et al. |
| 5,462,724 | A | 10/1995 | Schinazi |
| 5,463,092 | A | 10/1995 | Hostetler |
| 5,496,546 | A | 3/1996 | Wang |
| 5,538,865 | A | 7/1996 | Reyes |
| 5,543,389 | A | 8/1996 | Yatvin |
| 5,543,390 | A | 8/1996 | Yatvin |
| 5,543,391 | A | 8/1996 | Yatvin |
| 5,554,728 | A | 9/1996 | Basava |
| 5,587,362 | A | 12/1996 | Chu |
| 5,610,054 | A | 3/1997 | Draper |
| 5,631,239 | A | 5/1997 | Lin et al. |
| 5,633,358 | A | 5/1997 | Gruetzke |
| 5,633,388 | A | 5/1997 | Diana |
| 5,676,942 | A | 10/1997 | Testa |
| 5,703,058 | A | 12/1997 | Schinazi |
| 5,711,944 | A | 1/1998 | Gilbert |
| 5,725,859 | A | 3/1998 | Omer |
| 5,738,845 | A | 4/1998 | Imakawa |
| 5,738,846 | A | 4/1998 | Greenwald |
| 5,747,646 | A | 5/1998 | Hakimi |
| 5,767,097 | A | 6/1998 | Tam |
| 5,792,834 | A | 8/1998 | Hakimi |
| 5,830,455 | A | 11/1998 | Valtuena |
| 5,830,905 | A | 11/1998 | Diana |
| 5,834,594 | A | 11/1998 | Hakimi |
| 5,837,257 | A | 11/1998 | Tsai |
| 5,846,964 | A | 12/1998 | Ozeki |
| 5,849,696 | A | 12/1998 | Chretien |
| 5,869,253 | A | 2/1999 | Draper |
| 5,891,874 | A | 4/1999 | Colacino |
| 5,905,070 | A | 5/1999 | Schinazi |
| 5,908,621 | A | 6/1999 | Glue |
| 5,922,757 | A | 7/1999 | Chojkier |
| 5,928,636 | A | 7/1999 | Alber |
| 5,942,223 | A | 8/1999 | Bazer |
| 5,977,325 | A | 11/1999 | McCarthy et al. |
| 5,980,884 | A | 11/1999 | Blatt |
| 5,990,276 | A | 11/1999 | Zhang |
| 6,004,933 | A | 12/1999 | Spruce |

(Continued)

FOREIGN PATENT DOCUMENTS

| BR | PI0312286-7 A | 6/2007 |
| --- | --- | --- |
| BR | PI0512104-3 A | 3/2008 |

(Continued)

OTHER PUBLICATIONS

U.S. Appl. No. 60/392,350, filed May 21, 2001, Elek.

(Continued)

*Primary Examiner* — Traviss C McIntosh, III
(74) *Attorney, Agent, or Firm* — Fitzpatrick, Cella, Harper & Scinto

(57) ABSTRACT

The disclosed invention provides compositions and methods of treating a Flaviviridae infection, including hepatitis C virus, West Nile Virus, yellow fever virus, and a rhinovirus infection in a host, including animals, and especially humans, using a (2'R)-2'-deoxy-2'-fluoro-2'-C-methyl nucleosides, or a pharmaceutically acceptable salt or prodrug thereof.

1 Claim, 4 Drawing Sheets

(56) References Cited

U.S. PATENT DOCUMENTS

| | | | |
|---|---|---|---|
| 6,034,134 A | 3/2000 | Gold | |
| 6,043,077 A | 3/2000 | Barber | |
| 6,056,961 A | 5/2000 | Lavie | |
| 6,090,932 A | 7/2000 | McGee | |
| 6,130,326 A | 10/2000 | Ramasamy | |
| 6,156,501 A | 12/2000 | McGall | |
| 6,232,300 B1 | 5/2001 | Schinazi | |
| 6,239,159 B1 | 5/2001 | Brown | |
| 6,326,490 B1 | 12/2001 | Pankiewicz et al. | |
| 6,348,587 B1 | 2/2002 | Schinazi et al. | |
| 6,372,883 B1 | 4/2002 | Attwood | |
| 6,391,859 B1 | 5/2002 | Schinazi | |
| 6,410,531 B1 | 6/2002 | Llinas-Brunet | |
| 6,420,380 B2 | 7/2002 | Llinas-Brunet | |
| 6,455,513 B1 | 9/2002 | McGuigan | |
| 6,455,690 B1 | 9/2002 | Tam | |
| 6,479,463 B1 | 11/2002 | Wang | |
| 6,495,677 B1 | 12/2002 | Ramasamy | |
| 6,509,320 B1 | 1/2003 | Wang | |
| 6,534,523 B1 | 3/2003 | Llinas-Brunet | |
| 6,552,183 B1 | 4/2003 | Ramasamy | |
| 6,555,677 B2 | 4/2003 | Petrillo | |
| 6,573,248 B2 | 6/2003 | Ramasamy | |
| 6,642,206 B2 | 11/2003 | Ramasamy | |
| 6,660,721 B2 | 12/2003 | Devos | |
| 6,677,314 B2 | 1/2004 | Klecker | |
| 6,677,315 B2 | 1/2004 | Klecker | |
| 6,680,303 B2 | 1/2004 | Schinazi | |
| 6,682,715 B2 | 1/2004 | Klecker | |
| 6,683,045 B2 | 1/2004 | Klecker | |
| 6,703,374 B1 | 3/2004 | Klecker | |
| 6,713,623 B2 | 3/2004 | Pankiewicz et al. | |
| 6,753,309 B2 | 6/2004 | Klecker | |
| 6,777,395 B2 | 8/2004 | Bhat | |
| 6,787,305 B1 | 9/2004 | Li | |
| 6,787,526 B1 | 9/2004 | Bryant | |
| 6,812,219 B2 | 11/2004 | Lacolla et al. | |
| 6,815,542 B2 | 11/2004 | Hong | |
| 6,855,821 B2 | 2/2005 | Du et al. | |
| 6,897,201 B2 | 5/2005 | Boyer | |
| 6,908,924 B2 | 6/2005 | Watanabe et al. | |
| 6,914,054 B2 | 7/2005 | Sommadossi | |
| 6,927,291 B2 | 8/2005 | Jin et al. | |
| 6,949,522 B2 | 9/2005 | Otto et al. | |
| 6,962,991 B2 | 11/2005 | Dempcy | |
| 7,018,985 B1 | 3/2006 | Boyer | |
| 7,018,989 B2 | 3/2006 | McGuigan | |
| 7,081,449 B2 | 7/2006 | Pietrzkowski | |
| 7,094,770 B2 | 8/2006 | Watanabe et al. | |
| 7,101,861 B2 | 9/2006 | Sommadossi et al. | |
| 7,105,493 B2 | 9/2006 | Sommadossi et al. | |
| 7,105,499 B2* | 9/2006 | Carroll et al. | 514/49 |
| 7,148,206 B2 | 12/2006 | Sommadossi et al. | |
| 7,157,441 B2 | 1/2007 | Sommadossi et al. | |
| 7,163,929 B2 | 1/2007 | Sommadossi et al. | |
| 7,169,766 B2 | 1/2007 | Sommadossi et al. | |
| 7,192,936 B2 | 3/2007 | Lacolla et al. | |
| 7,211,570 B2 | 5/2007 | Schinazi et al. | |
| 7,365,057 B2 | 4/2008 | Lacolla et al. | |
| 7,384,924 B2 | 6/2008 | Lacolla et al. | |
| 7,429,572 B2* | 9/2008 | Clark | 514/49 |
| 7,547,704 B2 | 6/2009 | Lacolla et al. | |
| 7,601,820 B2 | 10/2009 | Wang et al. | |
| 7,608,597 B2 | 10/2009 | Sommadossi et al. | |
| 7,608,600 B2* | 10/2009 | Storer et al. | 514/45 |
| 7,625,875 B2 | 12/2009 | Gosselin et al. | |
| 7,635,689 B2 | 12/2009 | Lacolla et al. | |
| 7,638,502 B2 | 12/2009 | Schinazi et al. | |
| 7,662,798 B2 | 2/2010 | Lacolla et al. | |
| 7,718,790 B2 | 5/2010 | Stuyver et al. | |
| 7,754,699 B2 | 7/2010 | Chun et al. | |
| 7,772,208 B2 | 8/2010 | Schinazi et al. | |
| RE42,015 E | 12/2010 | Watanabe et al. | |
| 7,919,247 B2 | 4/2011 | Stuyver et al. | |
| 7,964,580 B2 | 6/2011 | Sofia et al. | |
| 8,093,380 B2 | 1/2012 | Wang et al. | |
| 8,114,997 B2 | 2/2012 | Otto et al. | |
| 8,173,621 B2 | 5/2012 | Du et al. | |
| 8,299,038 B2 | 10/2012 | Sommadossi et al. | |
| 8,334,270 B2 | 12/2012 | Sofia et al. | |
| 8,343,937 B2 | 1/2013 | Sommadossi et al. | |
| 8,415,322 B2 | 4/2013 | Clark | |
| 8,481,713 B2 | 7/2013 | Wang et al. | |
| 8,492,539 B2 | 7/2013 | Chun et al. | |
| 8,551,973 B2 | 10/2013 | Bao et al. | |
| 8,569,478 B2 | 10/2013 | Du et al. | |
| 8,580,765 B2 | 11/2013 | Sofia et al. | |
| 8,618,076 B2 | 12/2013 | Ross et al. | |
| 8,629,263 B2 | 1/2014 | Ross et al. | |
| 8,633,309 B2 | 1/2014 | Ross et al. | |
| 8,637,475 B1 | 1/2014 | Storer et al. | |
| 8,716,262 B2 | 5/2014 | Sofia et al. | |
| 8,716,263 B2 | 5/2014 | Chun et al. | |
| 8,735,345 B2 | 5/2014 | Porter et al. | |
| 8,735,372 B2 | 5/2014 | Du et al. | |
| 8,735,569 B2 | 5/2014 | Ross et al. | |
| 8,759,510 B2 | 6/2014 | Du et al. | |
| 8,765,710 B2 | 7/2014 | Sofia et al. | |
| 8,642,756 B2 | 8/2014 | Ross et al. | |
| 8,822,430 B2 | 9/2014 | Bacon et al. | |
| 8,841,275 B2 | 9/2014 | Du et al. | |
| 8,841,278 B2 | 9/2014 | Bacon et al. | |
| 8,859,756 B2 | 10/2014 | Ross et al. | |
| 8,889,159 B2 | 11/2014 | Cleary et al. | |
| 8,895,531 B2 | 11/2014 | Shi | |
| 8,906,880 B2 | 12/2014 | Du et al. | |
| 8,912,321 B2 | 12/2014 | Axt et al. | |
| 8,921,341 B2 | 12/2014 | Bacon et al. | |
| 8,940,718 B2 | 1/2015 | Bacon et al. | |
| 8,957,045 B2 | 2/2015 | Sofia et al. | |
| 8,957,046 B2 | 2/2015 | Du et al. | |
| 8,969,588 B2 | 3/2015 | Scott et al. | |
| 9,045,520 B2 | 6/2015 | Chun et al. | |
| 9,051,340 B2 | 6/2015 | Bacon et al. | |
| 9,056,860 B2 | 6/2015 | Scott et al. | |
| 9,085,573 B2 | 7/2015 | Du et al. | |
| 9,139,570 B2 | 9/2015 | Mogalian et al. | |
| 9,156,823 B2 | 10/2015 | Bacon et al. | |
| 9,206,217 B2 | 12/2015 | Ross et al. | |
| 9,221,833 B2 | 12/2015 | Bacon et al. | |
| 9,284,342 B2 | 3/2016 | Ross et al. | |
| 9,296,777 B2 | 3/2016 | Sofia et al. | |
| 9,340,568 B2 | 5/2016 | Casteel et al. | |
| 9,393,256 B2 | 7/2016 | Ray et al. | |
| 9,394,331 B2 | 7/2016 | Du et al. | |
| 9,409,891 B2 | 8/2016 | Hashash et al. | |
| 9,511,056 B2 | 12/2016 | Bacon et al. | |
| 9,549,941 B2 | 1/2017 | Cleary et al. | |
| 9,585,906 B2 | 3/2017 | Du et al. | |
| 9,624,183 B2 | 4/2017 | Chen et al. | |
| 9,630,972 B2 | 4/2017 | Lapina et al. | |
| 9,637,512 B2 | 5/2017 | Chun et al. | |
| 9,670,187 B2 | 6/2017 | Allan et al. | |
| 9,676,808 B2 | 6/2017 | Du et al. | |
| 9,682,987 B2 | 6/2017 | Mogalian et al. | |
| 9,682,989 B2 | 6/2017 | Bacon et al. | |
| 9,718,807 B2 | 8/2017 | Scott et al. | |
| 9,757,406 B2 | 9/2017 | Gorman et al. | |
| 9,809,600 B2 | 11/2017 | Bacon et al. | |
| 9,845,299 B2 | 12/2017 | Chen et al. | |
| 9,868,745 B2 | 1/2018 | Bacon et al. | |
| 9,884,873 B2 | 2/2018 | Lapina et al. | |
| 9,890,134 B2 | 2/2018 | Allan et al. | |
| 2002/0058635 A1 | 5/2002 | Averett | |
| 2002/0173491 A1 | 11/2002 | Furman | |
| 2002/0198173 A1 | 12/2002 | Schinazi | |
| 2003/0050229 A1 | 3/2003 | Sommadossi | |
| 2003/0060400 A1 | 3/2003 | LaColla | |
| 2003/0120071 A1 | 6/2003 | McGuigan | |
| 2003/0144502 A1 | 7/2003 | Pietrzkowski | |
| 2003/0153744 A1 | 8/2003 | Mekouar | |
| 2004/0006007 A1 | 1/2004 | Gosselin | |
| 2004/0014108 A1 | 1/2004 | Elarup | |
| 2004/0023240 A1 | 2/2004 | Marliere | |

(56) References Cited

U.S. PATENT DOCUMENTS

| | | |
|---|---|---|
| 2004/0023901 A1 | 2/2004 | Cook |
| 2004/0059104 A1 | 3/2004 | Cook |
| 2004/0063622 A1 | 4/2004 | Sommadassi |
| 2004/0067901 A1 | 4/2004 | Bhat |
| 2004/0072788 A1 | 4/2004 | Bhat |
| 2004/0097461 A1 | 5/2004 | Sommadossi |
| 2004/0097462 A1 | 5/2004 | Sommadassi |
| 2004/0101535 A1 | 5/2004 | Sommadossi |
| 2004/0102414 A1 | 5/2004 | Sommadassi |
| 2004/0110717 A1 | 6/2004 | Carroll |
| 2004/0167140 A1 | 8/2004 | Schinazi |
| 2004/0191824 A1 | 9/2004 | Dempcy |
| 2004/0214844 A1 | 10/2004 | Otto |
| 2004/0229839 A1 | 11/2004 | Babu |
| 2004/0248892 A1 | 12/2004 | Wang |
| 2004/0254141 A1 | 12/2004 | Schinazi |
| 2004/0259934 A1 | 12/2004 | Olsen |
| 2004/0265969 A1 | 12/2004 | Li |
| 2004/0266996 A1 | 12/2004 | Rabi |
| 2005/0009737 A1 | 1/2005 | Clark |
| 2005/0026853 A1 | 2/2005 | Mekouar |
| 2005/0031588 A1 | 2/2005 | Sommadassi |
| 2005/0075309 A1 | 4/2005 | Storer |
| 2005/0080034 A1 | 4/2005 | Standring |
| 2005/0090660 A1 | 4/2005 | Watanabe |
| 2005/0124532 A1 | 6/2005 | Sommadossi |
| 2005/0130931 A1 | 6/2005 | Boyer |
| 2005/0137161 A1 | 6/2005 | Sommadossi |
| 2005/0148534 A1 | 7/2005 | Castellino |
| 2005/0164960 A1 | 7/2005 | Olsen |
| 2005/0215513 A1 | 9/2005 | Boojamra |
| 2005/0227947 A1 | 10/2005 | Chan |
| 2005/0261237 A1 | 11/2005 | Boojamra |
| 2006/0003951 A1 | 1/2006 | Mekouar |
| 2006/0014943 A1 | 1/2006 | Dempcy |
| 2006/0035866 A1 | 2/2006 | Cannizzaro |
| 2006/0040944 A1 | 2/2006 | Gosselin |
| 2006/0079478 A1 | 4/2006 | Boojamra |
| 2006/0110727 A9 | 5/2006 | McGall |
| 2006/0122146 A1 | 7/2006 | Chun |
| 2006/0122154 A1 | 7/2006 | Olsen |
| 2006/0142238 A1 | 7/2006 | McGuigan |
| 2006/0144502 A1 | 7/2006 | Weder |
| 2006/0199783 A1 | 9/2006 | Wang et al. |
| 2007/0003777 A1 | 1/2007 | Iwasa et al. |
| 2007/0004299 A1 | 1/2007 | Fitch et al. |
| 2007/0006049 A1 | 1/2007 | Agha et al. |
| 2007/0006054 A1 | 1/2007 | Fiedler |
| 2007/0008796 A1 | 1/2007 | Egerer et al. |
| 2007/0015905 A1 | 1/2007 | Lacolla et al. |
| 2007/0019746 A1 | 1/2007 | Lin et al. |
| 2007/0022524 A1 | 2/2007 | Duarte et al. |
| 2007/0037735 A1 | 2/2007 | Gosselin et al. |
| 2007/0037773 A1 | 2/2007 | Sommadossi et al. |
| 2007/0042939 A1 | 2/2007 | LaColla |
| 2007/0042990 A1 | 2/2007 | Gosselin et al. |
| 2007/0060498 A1 | 3/2007 | Gosselin et al. |
| 2007/0060541 A1 | 3/2007 | Gosselin et al. |
| 2007/0087960 A1 | 4/2007 | Storer et al. |
| 2007/0197463 A1 | 8/2007 | Chun et al. |
| 2007/0225249 A1 | 9/2007 | Shi et al. |
| 2008/0253995 A1 | 10/2008 | Clark |
| 2009/0000413 A1 | 1/2009 | Furhoff et al. |
| 2009/0004135 A1 | 1/2009 | Clark et al. |
| 2009/0017673 A1 | 1/2009 | Chen et al. |
| 2009/0176732 A1 | 7/2009 | Beigelman et al. |
| 2012/0245335 A1 | 9/2012 | Clark |
| 2013/0014928 A1 | 1/2013 | Grayson et al. |
| 2013/0031033 A1 | 1/2013 | Prieditis |
| 2013/0149283 A1 | 6/2013 | Sommadossi et al. |
| 2013/0310336 A1 | 11/2013 | Sommadossi et al. |

FOREIGN PATENT DOCUMENTS

| | | |
|---|---|---|
| CA | 2409613 C | 11/2001 |
| CA | 2490191 C | 1/2004 |
| CN | 1245808 A | 3/2000 |
| CN | 1332747 A | 1/2002 |
| CN | 1761677 A | 4/2006 |
| CN | 104163841 B | 11/2014 |
| DE | 19914474 A1 | 3/1998 |
| DE | 199 14 474 | 10/1999 |
| EP | 180276 A1 | 10/1984 |
| EP | 0285884 A2 | 10/1988 |
| EP | 350287 B1 | 7/1989 |
| EP | 0 350 287 | 1/1990 |
| EP | 0358848 A1 | 1/1990 |
| EP | 0457326 A1 | 11/1991 |
| EP | 0 180 276 | 5/1996 |
| GB | 1209654 A | 10/1970 |
| IN | 343DELNP2005 | 1/2005 |
| JP | 2011190264 A | 9/2011 |
| JP | 2002504558 A | 2/2012 |
| JP | 49581582 B2 | 3/2012 |
| NO | 330755 B1 | 7/2011 |
| WO | WO 89/02733 | 4/1989 |
| WO | WO8902733 A1 | 4/1989 |
| WO | WO9000555 A1 | 6/1989 |
| WO | WO 90/00555 | 1/1990 |
| WO | 1990001036 A1 | 2/1990 |
| WO | WO 91/16920 | 11/1991 |
| WO | WO9116920 A1 | 11/1991 |
| WO | WO 91/18914 | 12/1991 |
| WO | WO 91/19721 | 12/1991 |
| WO | WO9118914 A1 | 12/1991 |
| WO | WO9119721 A1 | 12/1991 |
| WO | WO 93/00910 | 1/1993 |
| WO | WO9300910 A1 | 1/1993 |
| WO | WO 94/26273 | 11/1994 |
| WO | WO9426273 A1 | 11/1994 |
| WO | WO 95/13090 | 5/1995 |
| WO | WO9513090 A1 | 5/1995 |
| WO | WO 95/24185 | 9/1995 |
| WO | 1996013512 A2 | 5/1996 |
| WO | WO 96/15132 | 5/1996 |
| WO | WO9615132 A1 | 5/1996 |
| WO | WO 96/32403 | 10/1996 |
| WO | 97/16456 A1 | 5/1997 |
| WO | WO 97/36554 | 10/1997 |
| WO | WO9736554 A1 | 10/1997 |
| WO | WO 98/16184 | 4/1998 |
| WO | WO 98/17679 | 4/1998 |
| WO | WO9817679 A1 | 4/1998 |
| WO | WO 98/22496 | 5/1998 |
| WO | WO9822496 A2 | 5/1998 |
| WO | WO9822496 A3 | 5/1998 |
| WO | WO 99/07734 | 2/1999 |
| WO | WO9907734 A2 | 2/1999 |
| WO | WO9907734 A3 | 2/1999 |
| WO | WO 99/15194 | 4/1999 |
| WO | WO9915194 A1 | 4/1999 |
| WO | 99/23104 A2 | 5/1999 |
| WO | WO 99/32139 | 7/1999 |
| WO | WO 99/32140 | 7/1999 |
| WO | WO9932139 A1 | 7/1999 |
| WO | WO9932140 A1 | 7/1999 |
| WO | WO 99/43691 | 9/1999 |
| WO | WO9943691 A1 | 9/1999 |
| WO | WO9043691 | 9/1999 |
| WO | WO 99/59621 | 11/1999 |
| WO | WO9959621 A1 | 11/1999 |
| WO | WO 99/64016 | 12/1999 |
| WO | WO9964016 A1 | 12/1999 |
| WO | WO 00/09531 | 2/2000 |
| WO | WO0009531 A2 | 2/2000 |
| WO | WO 00/24355 | 5/2000 |
| WO | WO0024355 A1 | 5/2000 |
| WO | WO 00/37110 | 6/2000 |
| WO | WO0037110 A2 | 6/2000 |
| WO | WO0037110 A3 | 6/2000 |
| WO | WO 01/32153 | 5/2001 |

(56) References Cited

FOREIGN PATENT DOCUMENTS

| | | |
|---|---|---|
| WO | WO0132153 A2 | 5/2001 |
| WO | WO 01/60315 | 8/2001 |
| WO | WO01060315 A3 | 8/2001 |
| WO | WO01060315 R4 | 8/2001 |
| WO | WO 01/079246 | 10/2001 |
| WO | WO0179246 A2 | 10/2001 |
| WO | WO01079246 A3 | 10/2001 |
| WO | WO01079246 R4 | 10/2001 |
| WO | WO 01/81359 | 11/2001 |
| WO | WO 01/90121 | 11/2001 |
| WO | WO0181359 A1 | 11/2001 |
| WO | WO0190121 | 11/2001 |
| WO | WO0190121 A3 | 11/2001 |
| WO | WO0190121 R4 | 11/2001 |
| WO | 2001096353 A3 | 12/2001 |
| WO | WO 01/91737 | 12/2001 |
| WO | WO 01/92282 | 12/2001 |
| WO | WO 01/96353 | 12/2001 |
| WO | WO0191737 A2 | 12/2001 |
| WO | WO0192282 A3 | 12/2001 |
| WO | WO0192282 R4 | 12/2001 |
| WO | WO0196353 A2 | 12/2001 |
| WO | WO0196353 A3 | 12/2001 |
| WO | WO0196353 R4 | 12/2001 |
| WO | WO 02/008187 | 1/2002 |
| WO | WO 02/08198 | 1/2002 |
| WO | WO 02/008251 | 1/2002 |
| WO | WO 02/008256 | 1/2002 |
| WO | WO0208198 A2 | 1/2002 |
| WO | WO0208251 A2 | 1/2002 |
| WO | WO0208256 A2 | 1/2002 |
| WO | WO02008187 A1 | 1/2002 |
| WO | WO02008187 R6 | 1/2002 |
| WO | WO02008198 A3 | 1/2002 |
| WO | WO02008198 R4 | 1/2002 |
| WO | WO02008251 A3 | 1/2002 |
| WO | WO02008251 R4 | 1/2002 |
| WO | 02/18369 A2 | 3/2002 |
| WO | WO 02/18404 | 3/2002 |
| WO | WO 02/032414 | 4/2002 |
| WO | WO 02/32920 | 4/2002 |
| WO | WO0232920 A2 | 4/2002 |
| WO | WO02032414 A3 | 4/2002 |
| WO | WO02032414 R4 | 4/2002 |
| WO | WO2002032920 A3 | 4/2002 |
| WO | WO2002032920 R4 | 4/2002 |
| WO | WO 02/42172 | 6/2002 |
| WO | WO 02/48116 | 6/2002 |
| WO | WO 02/048157 | 6/2002 |
| WO | WO 02/48165 | 6/2002 |
| WO | WO 02/48172 | 6/2002 |
| WO | WO 02/49165 | 6/2002 |
| WO | WO0248116 A2 | 6/2002 |
| WO | WO0248157 A2 | 6/2002 |
| WO | WO0248165 A2 | 6/2002 |
| WO | WO0248172 A2 | 6/2002 |
| WO | WO02048165 A3 | 6/2002 |
| WO | WO02048165 R4 | 6/2002 |
| WO | WO02048165 R5 | 6/2002 |
| WO | WO02048172 A3 | 6/2002 |
| WO | WO02048172 R4 | 6/2002 |
| WO | WO0204815743 R4 | 6/2002 |
| WO | WO 02/057287 | 7/2002 |
| WO | WO 02/057425 | 7/2002 |
| WO | WO02057287 | 7/2002 |
| WO | WO02057425 A2 | 7/2002 |
| WO | WO 02/060926 | 8/2002 |
| WO | WO02060926 A2 | 8/2002 |
| WO | WO02060926 A3 | 8/2002 |
| WO | 02/094289 A1 | 11/2002 |
| WO | WO 02/100415 | 12/2002 |
| WO | WO02100415 A3 | 12/2002 |
| WO | WO02100415 R4 | 12/2002 |
| WO | WO02108415 A2 | 12/2002 |
| WO | WO 03/024461 | 3/2003 |
| WO | WO03024461 A1 | 3/2003 |
| WO | WO 03/051899 | 6/2003 |
| WO | WO 03/053989 | 7/2003 |
| WO | WO 03/061576 | 7/2003 |
| WO | WO 03/062256 | 7/2003 |
| WO | WO 03/068244 | 8/2003 |
| WO | WO 03/105770 | 12/2003 |
| WO | WO 03/106477 | 12/2003 |
| WO | WO 2004/000858 | 12/2003 |
| WO | WO2004000858 A2 | 12/2003 |
| WO | WO2004000858 A3 | 12/2003 |
| WO | WO2004000858 R4 | 12/2003 |
| WO | WO 2004/002422 | 1/2004 |
| WO | WO 2004/002999 | 1/2004 |
| WO | WO 2004/003000 | 1/2004 |
| WO | WO 2004/003138 | 1/2004 |
| WO | WO 2004/007512 | 1/2004 |
| WO | WO 2004/009020 | 1/2004 |
| WO | WO 2004/009610 | 1/2004 |
| WO | WO2004002999 A2 | 1/2004 |
| WO | WO2004002999 A3 | 1/2004 |
| WO | WO2004002999 R4 | 1/2004 |
| WO | WO2004003000 A2 | 1/2004 |
| WO | WO2004003000 A3 | 1/2004 |
| WO | WO2004003000 R4 | 1/2004 |
| WO | WO2004003138 A2 | 1/2004 |
| WO | WO2004007512 | 1/2004 |
| WO | WO 2004/011478 | 2/2004 |
| WO | 2004046331 A2 | 6/2004 |
| WO | 2004046331 A3 | 6/2004 |
| WO | WO 2004/080466 | 9/2004 |
| WO | WO 2004/096234 | 11/2004 |
| WO | WO 2004/096235 | 11/2004 |
| WO | WO 2004/096286 | 11/2004 |
| WO | WO 2004/106356 | 12/2004 |
| WO | WO 2005/002626 | 1/2005 |
| WO | WO 2005/003147 | 1/2005 |
| WO | WO 2005/007810 | 1/2005 |
| WO | WO 200508877 | 1/2005 |
| WO | WO 2005/009418 | 2/2005 |
| WO | WO 2005/012327 | 2/2005 |
| WO | WO 2005/020884 | 3/2005 |
| WO | WO 2005/021568 | 6/2005 |
| WO | WO 2005/072361 | 8/2005 |
| WO | WO 2005/087788 | 9/2005 |
| WO | WO 2006/000922 | 1/2006 |
| WO | WO 2006/012440 | 2/2006 |
| WO | WO 2006/029081 | 3/2006 |
| WO | WO 2006/031725 | 3/2006 |
| WO | WO 2006/037028 | 4/2006 |
| WO | WO 2006/061576 | 6/2006 |
| WO | WO 2006/065335 | 6/2006 |

OTHER PUBLICATIONS

U.S. Appl. No. 60/392,351, filed Jun. 28, 2002, Storer.
Banker, G.S., et al., "Modern Phamaceutics, 3ed.", Marcel Dekker, New York, 1996, pp. 451 and 596.
Battaglia, A.M., et al., Ann. Pharmacother. 34:487-494-2000.
Bhat, et al., (Oral Session V, Hepatitis C Virus, Flaviviridae; 16th International Conference on Antiviral Research (Apr. 27, 2003, Savannah, GA)); p. A75.
Chu, M., et al., Bioorganic and Medicinal Chemistry Letters 9:1949-1952, 1999.
Delambert, et al., J. Med. Chem., 1994, 37:498.
Eldrup, et al., (Oral Session V, Hepatitis C Virus, Flaviviridae; 16th International Conference on Antiviral Research (Apr. 27, 2003, Savannah, GA)).
Eldrup, A., et al., "Structure-Activity Relationship of Purine Ribonucleosides for Inhibition of Hepatitis C Virus RNA-Dependent RNA Polymerase," *J. Med. Chem.*, vol. 47, 2283-2295 (2004).
Farquhar, et al., J. Med. Chem., 1983, 26:1153.
Farquhar et al., J. Med. Chem., 1985, 28:1358.
Freed, et al., Biochem. Pharamac., 1989, 38:3193.

(56) References Cited

OTHER PUBLICATIONS

Hosetler, K.Y., et al., "Synthesis and antiretro-viral activity of phospholipids analogs of azidothymidine and other antiviral nucleosides," 1990, J., Biol. Chem., 265:61127.

Hosteller, K.Y., et al, "Greatly enhanced inhibition of human immunodeficiency virus type 1 replication in CEM and HT4-6 cells by 3'—deoxcythymidine diphosphate dimyristoylglycerol, a lipid prodrug of 3'-deooxythymidine," 1992, Antimicro. Agents Chemother., 36:2025-2029.

Hunston, et al., J. Med. Chem., 1984, 27:440-444.

Jones, R. and Bisehoferger, N., Antiviral Research, 1995 27:1-17.

Khaninei and Torrence, J. Med. Chem., 1996, 39;4109-4115.

Kucera, LS., et al., "Novel membrane-interactive ether lipid analogs that inhibit infectious HIV-1 production and induce defective virus formation," 1990, AIDS Hum. Retro Viruses, 6:491-501.

Meier, et al., Bioorg. Med. Chem. Lett., 1997, 7:99-104.

Olsen, et al., (Oral Session V, Hepatitis C Virus, Flaviviridae; 16$^{th}$ International Conference on Antiviral Research (Apr. 27, 2003, Savannah, GA)); p. A76.

Piantodosi, C., et al., "Synthesis and evaluation of novel either lipid nucleoside conjugates for anti-HIV activity," 1991, J. Med. Chem. 34:1408-1414.

Starrett, et al., J. Med. Chem., 1994, 37:1857-1864.

Stuyver et al., Journal of Virology, 2003, 77, 10689-10694.

Stuyver et al., "Ribonucleoside analogue that blocks replication of bovine viral diarrhea and heptatis C viruses in culture," Antimicrobial Agents and Chemotherapy, 2003, 47:244-254.

Stuyver, L., et al., "Inhibitiion of the Subgenomic Hepatitis C Virus Replicon in Huh-7 Cells by 2'Deoxy-2'-fluorocytidine," Antimicrob. Agents Chemother., vol. 48, No. 2, pp. 651-654 (Feb. 2004).

Zon, Progress in Med. Chem., 1982, 19:205-246.

Wolff, M. , "Burger's Medicinal Chemistry, 5ed, Part I", John Wiley & Sons, 1995, 975-977.

Kruchkov, A.A., et al, "Academy of Sciences of the USSR, Division of Chemical Science," 1987 Plenum Publishing Corporation, vol. 36, No. 6, Part 1, Jun. 1987, 1145-1148.

Li, N.S. and Piccirilli, J., "Synthesis of the Phosphoramidite Derivative of 2'-Deoxy-2'—C-β-methylcytidine", J. Org. Chem., 2003, 68, 6799-6802.

Berenguer, M. et al., "Hepatitis C virus in the transplant setting," Antiviral Therapy. Second International Conference on Therapies for Viral Hepatitis, vol. 3, Supplement 3, pp. 125-136 (1998).

Chu, M. et al., "Structure of Sch 68631: A New Hepatitis C Virus Proteinase Inhibitor from Streptomyces sp.," Tetrahedron Letters, vol. 37, No. 40, pp. 7229-7232 (Sep. 30, 1996).

Clark, J. et al., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, vol. 48, No. 17, pp. 5504-5508 (2005).

Davis, G. L., "Current Therapy for Chronic Hepatitis C," Gastroenterology 118: S104-S114, 2000.

Edmundson et al., "Cyclic Organophophorus Compounds Part 23. Configurational Assignments in the 4-Phenyl-1,3,2 $\lambda^5$-dioxaphosphorinane Series. X-Ray Molecular Structure of cis-2-Benzylamino-4-phenyl-1,3,2-dioxaphosphorinane 2-Oxide," J. Chem. Res. Synop., 1989, 5:122.

Hertel, et al. Synthesis of 2-Deoxy-2,2-difluoro-D-ribose and 2-Deoxy-2,2-difluoro-D-ribofuranosyl Necleosides:, J. Org. Chem. vol. 53, pp. 2406-2409, (1988).

Hostetler, K. et al., "Greatly Enhanced Inhibition of Human Immunodeficiency Virus Type 1 Replication in CEM and HT4-6C Cells by 3'-Deoxythymidine Diphosphate Dimyristoylglycerol, a Lipid Prodrug of 3'-Deoxythymidine," Antimicrob. Agents Chemother., vol. 36, No. 9, pp. 2025-2029 (Sep. 1992).

Hostetler, K. et al., "Synthesis and Antiretroviral Activity of Phospholipid Analogs of Azidothymidine and Other Antiviral Nucleosides," J. Biol. Chem., vol. 265, No. 11, pp. 6112-6117 (Apr. 15, 1990).

International Search Report and Opinion for International Application No. PCT/US05/25916.

Kotra, L.P., "Structure-Activity Relationships of 2'-Deoxy-2',2'-difluoro-L-erythro-pentofuranosyl Nucleosides," J. Med. Chem., vol. 40, pp. 3635-3644, (1997).

Kryuchkov, A. et al., "Influence of Solvent on the Strength of Cyclic Oxygen-Containing Phosphorus Acids," Bulletin of the Academy of Sciences of the USSR. Division of Chemical Science, vol. 36, No. 6, Part 1, pp. 1145-1148 (1987).

Mitchell, A. et al., "Bioreversible Protection for the Phospho Group: Bioactivation of the Di(4-acyloxybenzyl) and Mono(4-acyloxybenzyl) Phosphoesters of Methylphosphonate and Phosphonoacetate," Journal of the Chemical Society, Perkin Transactions 1, No. 18, pp. 2345-2353 (Sep. 21, 1992).

Neidlein, R. et al., "Mild preparation of 1-benzyloxyminoalkylphosphonic dichlorides: Application to the synthesis of cyclic phosphonic diesters and cyclic monoester amides," Heterocycles, vol. 35, No. 2, pp. 1185-1203 (1993).

Nifantyev, E. et al., "Synthesis and structure of some stable phospholane-phospholanes," Phosphorus, Sulfur, and Silicon and the Related Elements, vol. 113, pp. 1-13 (1996).

Shih, Y. et al., "Preparation and Structures of 2-Dimethylamino-4-phenyl-1,3,2-dioxaphosphorinane-2-oxides," Bull. Inst. Chem. Academia Sinica, No. 41, pp. 9-16 (Mar. 1994).

Co-pending U.S. Appl. No. 12/240,342, filed Sep. 29, 2008.

Co-pending U.S. Appl. No. 12/142,536, filed Jun. 19, 2008.

U.S. Appl. No. 10/608,907, filed Jun. 27, 2003.

U.S. Appl. No. 60/466,194, filed Apr. 28, 2003.

U.S. Appl. No. 60/470,949, filed May 14, 2003.

File History for Sommadossi U.S. Appl. No. 12/131,868, filed Jun. 2, 2008-Sep. 20, 2011 Amendment.

Interference No. 105,871, Paper No. 25, Sommadossi Substantive Motion 1, filed Jun. 5, 2012.

Interference No. 105,871, Paper No. 434, Decision on Request for Rehearing, entered Apr. 23, 2013.

Clark, Jeremy L., et al., Synthesis and antiviral activity of 2'-deoxy-2'-fluoro-2'-C-methyl purine nucleosides as inhibitors of hepatitis C virus RNA replication, Bioorganic & Medicinal Chemistry Letters, vol. 16, pp. 1712-1715 (2006).

Clark, Jeremy L., et al., Synthesis of 2-Deoxy-2-Fluoro-2-C- Methyl-D-Ribofuranoses, Journal of Carbohydrate Chemistry, vol. 25, pp. 461-470 (2006).

Condit, R.C., Principles of Virology (Chapter 2), in Knipe, D.M. et al., eds., Fields Virology, Fourth Edition, Philadelphia, Lippincott Williams & Wilkins (2001).

Condit, R.C., Principles of Virology (Chapter 2), in Knipe, D.M. et al., eds., Fields Virology, Fifth Edition, Philadelphia, Lippincott Williams & Wilkins (2007).

Dhanak, D., et al., Identification and Biological Characterization of Heterocyclic Inhibitors of the Hepatitis C Virus RNA-dependent RNA Polymerase, J. Biol. Chem. vol. 277, No. 41, pp. 38322-38327 (2002).

Guo, J.-T., Bichko, V.V., Seeger, C., Effect of Alpha Interferon on the Hepatitis C Virus Replicon, J. Virol., vol. 75, pp. 8516-8523 (2001).

Jeong, Lak S. et al., Unanticipated Retention of Configuration in the DAST Fluorination of Deoxy-4'-thiopyrimidine Nucleosides with "Up" Hydroxyl Groups, Tetrahedron Letters, vol. 35, No. 41, pp. 7569-7572 (1994).

Krieger, Nicole, Enhancement of Hepatitis C Virus RNA Replication by Cell Culture-Adaptive Mutations, J. Virology, vol. 75, No. 10, pp. 4616-4624 (2001).

Lalezari, J., et al., Potent Antiviral Activity of the HCV Nucleoside Polymerase Inhibitor R7128 with PEG-IFN and Ribavirin: Interim Results of R7128 500mg BID for 28 Days, J. Hepatology, vol. 48, Supplement 2, p. S29 (2008).

Lindenbach, B.D. and Rice, C.M., Flaviviridae: The Viruses and Their Replication (Chapter 32) in Knipe, D.M. et al., eds., Fields Virology, 4th ed. Philadelphia, Lippincott Williams & Wilkins (2001).

Lohmann, V., et al., Replication of Subgenomic Hepatitis C Virus RNAs in a Hepatoma Cell Line, Science, vol. 285, pp. 110-113 (1999).

(56) References Cited

OTHER PUBLICATIONS

O'Boyle II, D.R. et al., Development of a cell-based high-throughput specificity screen using a hepatitis C virus-bovine viral diarrhea virus dual replicon assay, Antimicrobial Agents & Chemotherapy, vol. 49, pp. 1346-1353 (2005).
Shim, J. et al., Canonical 3'-deoxyribonucleotides as a chain terminator for HCV NS5B RNA-dependent RNA polymerase, Antiviral Research, vol. 58, pp. 243-251 (2003).
Singh, Rajendra P. and Shreeve, Jean'ne M., Recent Advances in Nucleophilic Fluorination Reactions of Organic Compounds Using Deoxofluor and DAST, Synthesis, No. 17, pp. 2561-2578 (2002).
Stuvyer, L.J. et al., Inhibition of Hepatitis C Replicon RNA Synthesis by β-D-2'-Deoxy-2'-fluoro-2'-C-methylcytidine: A Specific Inhibitor of Hepatitis C Virus Replication, Antimicrobial Agents & Chemotherapy, vol. 17, pp. 79-87 (2006).
Tan, Seng-Lai, et al., Hepatitis C Therapeutics: Current Status and Emerging Strategies, Nature Reviews: Drug Discovery, vol. 1, pp. 867-881 (2002).
Walton, E., et al., Branched-Chain Sugar Nucleosides. A New Type of Biologically Active Nucleoside, Journal of the American Chemical Society, vol. 88, No. 19, pp. 4524-4525 (1966).
Yang, Shu Shu, et al., Synthesis of DL-1-deoxy-fluoro-6-O-methyl-chiro-inositol: confirmation of a structural-DAST fluorination correlation, Carbohydrate Research, vol. 249, pp. 259-263 (1993).
Yi, MinKyung, et al., Subgenomic Hepatitis C Virus Replicons Inducing Expression of a Secreted Enzymatic Reporter Protein, Virology, vol. 304, pp. 197-210 (2002).
Zuck, Paul, et al., A Cell-based β-lactamase Reporter Gene Assay for the Identification of Inhibitors of Hepatitis C Virus Replication, Analytical Biochemistry, vol. 344, pp. 344-355 (2004).
European Search Report for application No. EP 11 15 7832 dated Jun. 8, 2011.
European Search Report for application No. EP 11 15 7939 dated Jun. 8, 2011.
European Search Report for application No. EP 11 15 7942 dated Jun. 8, 2011.
European Search Report for application No. EP 11 15 7954 dated Jun. 8, 2011.
*Storer v. Clark*, U.S. Court of Appeals for the Federal Circuit, Notice re Petition for Writ of Certiorari dated Mar. 9, 2018.
*Storer v. United States*, Petition for a Writ of Certiorari dated Mar. 5, 2018.
Beers, M. H.; et al., Hepatitis, The Merck Manual of Diagnosis and Therapy, 17 ed., 377-386 (1999).
Otto (2006). "Evaluation of nucleoside analogs in the hepatitis C virus replicon system," in Framing the Knowledge of Therapeutics for Viral Hepatitis, R.F. Schinazi & E.R. Schiff. eds., pp. 247-261.
EP Application No. 11157939.7 Third Party Observations dated Apr. 7, 2014.
EP Application No. 11157939.7 Third Party Observations dated May 15, 2013.
EP Application No. 11157942.1 Office Action dated Jun. 16, 2011.
EP Application No. 11157942.1 Office Action dated Jun. 22, 2012.
EP Application No. 11157942.1 Office Action Response dated Jan. 10, 2012.
EP Application No. 11157942.1 Third Party Observations dated Mar. 27, 2012.
EP Application No. 11157942.1 Third Party Observations dated Apr. 30, 2013.
EP Application No. 11157942.1 Third Party Observations dated May 15, 2013.
EP Application No. 11157954.6 Office Action dated May 19, 2016.
EP Application No. 11157954.6 Office Action dated Jun. 16, 2011.
EP Application No. 11157954.6 Office Action dated Jun. 22, 2012.
EP Application No. 11157954.6 Office Action dated Jun. 9, 2015.
EP Application No. 11157954.6 Office Action Response dated Jan. 11, 2012.
EP Application No. 11157954.6 Office Action Response dated Nov. 8, 2013.
EP Application No. 11157954.6 Office Action Response dated Mar. 23, 2016.
EP Application No. 11157954.6 Office Action Response dated Aug. 20, 2013.
EP Application No. 11157954.6 Third Party Observations dated Oct. 16, 2015.
EP Application No. 11157954.6 Third Party Observations dated Nov. 22, 2013.
EP Application No. 11157954.6 Third Party Observations dated Mar. 27, 2012.
EP Application No. 11157954.6 Third Party Observations dated Apr. 30, 2013.
EP Application No. 11157954.6 Third Party Observations dated Apr. 7, 2014.
EP Application No. 11157954.6 Third Party Observations dated May 15, 2013.
EP Application No. 11157954.6 Third Party Observations dated Sep. 8, 2014.
EP Application No. 13152340.9 Communication from Opposition Division dated Feb. 6, 2018.
EP Application No. 13152340.9 EPHA Post-Grant Opposition dated Mar. 27, 2017.
EP Application No. 13152340.9 Gillard Post-Grant Opposition dated Mar. 29, 2017.
EP Application No. 13152340.9 Medecines sans Frontieres Post-Grant Opposition dated Mar. 27, 2017.
EP Application No. 13152340.9 Medecins du Monde Post-Grant Opposition dated Mar. 27, 2017.
EP Application No. 13152340.9 Office Action dated May 16, 2013.
EP Application No. 13152340.9 Office Action dated Jun. 9, 2015.
EP Application No. 13152340.9 Office Action Response dated Dec. 18, 2013.
EP Application No. 13152340.9 Office Action Response dated Dec. 21, 2015.
EP Application No. 13152340.9 Reply to Post-Grant Oppositions dated Sep. 29, 2017.
EP Application No. 13152340.9 Third Party Observations dated Oct. 16, 2015.
EP Application No. 13152340.9 Third Party Observations dated Dec. 20, 2013.
EP Application No. 13152340.9 Third Party Observations dated Apr. 7, 2014.
EP Application No. 13152340.9 Third Party Observations dated Sep. 8, 2014.
EP Application No. 13152340.9, Annex Concerning Formal Priority Entitlement of WO 2004/002999 dated Sep. 29, 2017.
EP Application No. 13152340.9, Annex Concerning Lack of Enabling Disclosure of of WO 2004/002999 dated Sep. 29, 2017.
*Gilead Sciences Europe Ltd. v. Idenix Pharmaceuticals Inc*, Oslo District Court, Norway, Case No. 12-155575TVI-OTIR/01 and 13-170456TVI-OTIR/01, Judgment dated Mar. 21, 2014 (English).
*Gilead Sciences Pty Ltd v. Idenix Pharmaceuticals LLC*, Federal Court of Australia, [2016] FCA 169, File No. NSD 48 of 2013, Judgment dated Mar. 2, 2016.
*Gilead Sciences, Inc. v. Idenix Pharmaceuticals, Inc.*, Federal Court of Canada, Ottawa, Ontario, 2015 FC 1156, Docket T-1156-12, Public Judgment and Reasons dated Nov. 2, 2015.
*Gilead Sciences, Inc. v. Merck & Co., Inc.*, 13-cv-4057-BLF, Joint Pretrial Statement and Order, dated Feb. 25, 2016.
*Gilead Sciences, Inc. v. Merck & Co., Inc.*, 13-cv-4057-BLF, Order Denying Gilead's Motion for Summary Judgment and Granting Merck's Motion for Summary Judgment, dated Feb. 1, 2016.
Employment Agreement between Pharmasset, Inc. and Jeremy L. Clark dated Jul. 23, 2001.
Employment Agreement between Pharmasset, Inc. and Lieven Stuyver dated Apr. 6, 1999.
EP Application No. 03761744.6, Decision Revoking European Patent dated Apr. 18, 2016.
EP Application No. 04775900.6 Extract from the Register of European Patents dated Aug. 18, 2014.
EP Application No. 04775900.6 Office Action dated Jan. 24, 2011.
EP Application No. 04775900.6 Office Action dated Apr. 21, 2017.
EP Application No. 04775900.6 Office Action dated May 19, 2016.

(56) References Cited

OTHER PUBLICATIONS

EP Application No. 04775900.6 Office Action dated Jun. 22, 2012.
EP Application No. 04775900.6 Office Action dated Jun. 9, 2015.
EP Application No. 04775900.6 Office Action Response dated Nov. 8, 2013.
EP Application No. 04775900.6 Office Action Response dated Feb. 9, 2018.
EP Application No. 04775900.6 Office Action Response dated Mar. 23, 2016.
EP Application No. 04775900.6 Office Action Response dated Mar. 23, 2017.
EP Application No. 04775900.6 Office Action Response dated May 24, 2011.
EP Application No. 04775900.6 Office Action Response dated Aug. 20, 2013.
EP Application No. 04775900.6 Third Party Observations dated Nov. 22, 2013.
EP Application No. 04775900.6 Third Party Observations dated Apr. 30, 2013.
EP Application No. 04775900.6 Third Party Observations dated Apr. 7, 2014.
EP Application No. 04775900.6 Third Party Observations dated May 15, 2013.
EP Application No. 04775900.6 Third Party Observations dated Jun. 10, 2011.
EP Application No. 04775900.6 Third Party Observations dated Sep. 3, 2015.
EP Application No. 04775900.6 Third Party Observations dated Sep. 8, 2014.
EP Application No. 11157832.4 Office Action dated May 19, 2016.
EP Application No. 11157832.4 Office Action dated Jun. 16, 2011.
EP Application No. 11157832.4 Office Action dated Jun. 22, 2012.
EP Application No. 11157832.4 Office Action dated Jun. 9, 2015.
EP Application No. 11157832.4 Office Action Response dated Jan. 11, 2012.
EP Application No. 11157832.4 Office Action Response dated Nov. 8, 2013.
EP Application No. 11157832.4 Office Action Response dated Mar. 23, 2016.
EP Application No. 11157832.4 Office Action Response dated Aug. 20, 2013.
EP Application No. 11157832.4 Third Party Observations dated Oct. 16, 2015.
EP Application No. 11157832.4 Third Party Observations dated Nov. 22, 2013.
EP Application No. 11157832.4 Third Party Observations dated Mar. 27, 2012.
EP Application No. 11157832.4 Third Party Observations dated Apr. 30, 2013.
EP Application No. 11157832.4 Third Party Observations dated Apr. 7, 2014.
EP Application No. 11157832.4 Third Party Observations dated May 15, 2013.
EP Application No. 11157832.4 Third Party Observations dated Sep. 8, 2014.
EP Application No. 11157939.7 Office Action dated May 19, 2016.
EP Application No. 11157939.7 Office Action dated Jun. 16, 2011.
EP Application No. 11157939.7 Office Action dated Jun. 26, 2012.
EP Application No. 11157939.7 Office Action dated Jun. 9, 2015.
EP Application No. 11157939.7 Office Action Response dated Nov. 8, 2013.
EP Application No. 11157939.7 Office Action Response dated Mar. 23, 2016.
EP Application No. 11157939.7 Office Action Response dated Aug. 20, 2013.
EP Application No. 04775900.6, 11157832.4, 11157939.7, 11157954.6, and 13152340.9 Reply to Third Party Observations dated Sep. 11, 2014.
EP Application No. 11157939.7 Third Party Observations dated Sep. 8, 2014.
EP Application No. 11157939.7 Third Party Observations dated Oct. 16, 2015.
EP Application No. 11157939.7 Third Party Observations dated Oct. 20, 2011.
EP Application No. 11157939.7 Third Party Observations dated Nov. 22, 2013.
EP Application No. 11157939.7 Third Party Observations dated Apr. 30, 2013.
Appleby, et al., "Structural Basis for RNA Replication by the Hepatitis C Virus Polymerase," Science, 347:771-775 (2015).
AR Application No. 110102356 Office Action dated Sep. 1, 2016.
AR Application No. 110102356 Office Action dated Sep. 1, 2016 (English translation).
AR Application No. 110102358 Office Action dated Sep. 1, 2016.
AR Application No. P040101821 Office Action dated Feb. 11, 2016.
AR Application No. P040101821 Office Action dated Feb. 11, 2016 (English translation).
AR Application No. P04010821 Office Action dated Jun. 16, 2015.
AR Application No. P110102354 Office Action dated Apr. 4, 2016.
AR Application No. P110102354 Office Action dated Apr. 4, 2016 (English).
Asif, et al., "Pharmacokinetics of the Antiviral Agent β-D-2'-Deoxy-2'-C-Methylcytidine in Rhesus Monkeys," Antimicrobial Agents and Chemotherapy 51(8):2877-2882 (2007).
Assignment from Jeremy L. Clark to Pharmasset Ltd. of U.S. Appl. No. 60/474,368 dated Oct. 16, 2003.
Assignment from Lieven J. Stuyver to Pharmasset Ltd. of U.S. Appl. No. 60/474,368 dated Oct. 22, 2003.
Bartenschlager, "Hepatitis C Virus Replicons: Potential Role for Drug Development," Nature Rev. Drug Discovery, 1:911-916 (2002).
Batey, et al., "Tertiary Motifs in RNA Structure and Folding," Angew. Chem. Int. Ed. 38:2326-2328 (1999).
Birch, Hon. Stanley F., Expert Report dated Jul. 31, 2014 from *Idenix Pharmaceuticals, Inc.* v. *Gilead Sciences, Inc.*, High Court of Justice, Chancery Division, Patents Court, Claim No. HP 14D 01069 UK.
CA Application No. 2,733,842 Office Action dated Apr. 29, 2015.
Card, "Synthesis of Fluorinated Carbohydrates," J. Carbohydrate Chem., 4(4):451-487 (1985).
Carroll, et al., "Inhibition of Hepatitis C Virus RNA Replication by 2'-Modified Nucleoside Analogs," J. Biological Chem. 278(14):11979-11984 (2003).
Certificate Merging Pharmasset, Inc. (GA) with and into Pharmasset, Inc. (DE) dated Jul. 23, 2004.
Certificate of Domestication of Pharmasset, Ltd. dated Jun. 8, 2004.
Chabner, et al., "Purification and Properties of Cytidine Deaminase from Normal and Leukemic Granulocytes," J. Clin. Investigation, 53:922-931 (1974).
Chen, A Course of Organic Chemistry, Beijing Normal University Publishing Group, 1st Version, pp. 505-506 (Jun. 1990).
Chen, The Basic Science of Design on Drugs, pp. 159-174 (1995).
CN Application No. ZL200480019148.4 Declaration of Alicia Russo, Esq. dated Oct. 9, 2013.
CN Application No. ZL200480019148.4 Further Supplemental Invalidation Petition dated Nov. 27, 2017.
CN Application No. ZL200480019148.4 Further Supplemental Invalidation Petition dated Nov. 27, 2017 (English).
CN Application No. ZL200480019148.4 Invalidation Petition dated Apr. 19, 2017.
CN Application No. ZL200480019148.4 Invalidation Petition dated Apr. 19, 2017 (English).
CN Application No. ZL200480019148.4 Invalidation Petition dated Apr. 9, 2014 (English).
CN Application No. ZL200480019148.4 Invalidation Petition dated Jul. 29, 2013.
CN Application No. ZL200480019148.4 Invalidation Petition dated Jul. 29, 2013 (English).
CN Application No. ZL200480019148.4 Invalidation Petition dated Aug. 7, 2017.
CN Application No. ZL200480019148.4 Invalidation Petition dated Aug. 7, 2017 (English).
CN Application No. ZL200480019148.4 List of Counter Evidence dated Jun. 12, 2014.

(56) References Cited

OTHER PUBLICATIONS

CN Application No. ZL200480019148.4 List of Counter Evidence dated Jun. 23, 2014 (English).
CN Application No. ZL200480019148.4 Rebuttal re Invalidation Petition dated Feb. 8, 2014 (English).
CN Application No. ZL200480019148.4 Reply dated Jun. 12, 2014.
CN Application No. ZL200480019148.4 Response to Invalidation Petition dated Oct. 10, 2013 (English).
CN Application No. ZL200480019148.4 Response to Invalidation Petition dated Jun. 23, 2014 (English).
CN Application No. ZL200480019148.4 Response to Supplemental Invalidation Petition dated Dec. 14, 2017 (English).
CN Application No. ZL200480019148.4 Response to Supplemental Invalidation Petition dated Jul. 2014 (English).
CN Application No. ZL200480019148.4 Supplemental Invalidation Petition dated May 19, 2017.
CN Application No. ZL200480019148.4 Supplemental Invalidation Petition dated May 19, 2017 (English).
CN Application No. ZL200480019148.4 Supplemental Invalidation Petition dated Jun. 6, 2014 (English).
Consulting Agreement between Novirio Pharmaceuticals, Inc. and J.L. Imbach.
Convention de Cooperation between Novirio SARL, Le Centre National de la Recherche Scientifique, and L'Universite Montpellier II dated Apr. 2002.
Damha, Declaration dated May 2, 2013, Exhibit 1281 in Interference No. 105,871.
De Francesco, et al., "Approaching a New Era for Hepatitis C Virus Therapy: Inhibitors of the NS3-4A Serine Protease and the NS5B RNA-dependent RNA Polymerase," Antiviral Res. 58:1-16 (2003).
De Francesco, et al., "New Therapies on the Horizon for Hepatitis C: Are We Close?," Clin. Liver Dis. 7:211-242 (2003).
Interference No. 105,871, Paper No. 1, Declaration, Entered Feb. 22, 2012.
Interference No. 105,871, Paper No. 2, Standing Order Entered Mar. 8, 2011, Entered Feb. 21, 2012.
Interference No. 105,871, Paper No. 3, Sommadossi Designation of Lead and Back Up Lead Counsel, Filed Mar. 7, 2012.
Interference No. 105,871, Paper No. 4, Sommadossi Clean Copy of Claims, Filed Mar. 7, 2012.
Interference No. 105,871, Paper No. 5, Sommadossi Notice of Real Parties in Interest, Filed Mar. 7, 2012.
Interference No. 105,871, Paper No. 6, Sommadossi Notice of Related Prceedings, Filed Mar. 7, 2012.
Interference No. 105,871, Paper No. 7, Sommadossi File Copy Request, Filed Mar. 7, 2012.
Interference No. 105,871, Paper No. 8, Clark Notice of Real Party-in-Interest, Filed Mar. 7, 2012.
Interference No. 105,871, Paper No. 9, Clark Notice of Lead Counsel and Backup Lead Counsel, Filed Mar. 7, 2012.
Interference No. 105,871, Paper No. 10, Clark Clean Copy of Claims, Filed Mar. 7, 2012.
Interference No. 105,871, Paper No. 11, Clark Request for File Copies, Filed Mar. 7, 2012.
Interference No. 105,871, Paper No. 12, Clark Notice of Related Proceedings, Filed Mar. 7, 2012.
Interference No. 105,871, Paper No. 13, Order—Bd.R. 109(b)—Authorizing Copies of Office Records, Entered Mar. 8, 2012.
Interference No. 105,871, Paper No. 14, Order—Setting Motion Times Bd.R. 104(c), Entered Mar. 26, 2012.
Interference No. 105,871, Paper No. 15, Sommadossi Motions List, Filed Apr. 11, 2012.
Interference No. 105,871, Paper No. 16, Clark List of Intended Motions, Filed Apr. 11, 2012.
Interference No. 105,871, Paper No. 17, Sommadossi Notice of Service of Sommadossi Motions List, Filed Apr. 11, 2012.
Interference No. 105,871, Paper No. 18, Order—Authorizing Motions Motions Phase, Entered Apr. 24, 2012.
Interference No. 105,871, Paper No. 19, Order Large Exhibits, Entered May 17, 2012.
Interference No. 105,871, Paper No. 20, Joint Statement (Settlement Discussions), Filed May 22, 2012.
Interference No. 105,871, Paper No. 21 Notice of Joint Stipulation to Extension of Time, Filed May 24, 2012.
Interference No. 105,871, Paper No. 22, Order—Extending Page Limits, Entered May 25, 2012.
Interference No. 105,871, Paper No. 23, Clark Notice 1 (Regarding Stipulated Extension of Time Period 1), Filed May 31, 2012.
Interference No. 105,871, Paper No. 24, Sommadossi Priority Statement, Filed Jun. 5, 2012.
Interference No. 105,871, Paper No. 25, Sommadossi Substantive Motion 1 (to be Accorded Benefit for Count 1), Filed Jun. 5, 2012.
Interference No. 105,871, Paper No. 26, Sommadossi Substantive Motion 5 (to Substitute Count A or B for Count 1), Filed Jun. 5, 2012.
Interference No. 105,871, Paper No. 27, Sommadossi Notice of Filing Priority Statement, Filed Jun. 5, 2012.
Interference No. 105,871, Paper No. 28, Sommadossi Notice of Service of Exhibits, Filed Jun. 5, 2012.
Interference No. 105,871, Paper No. 29, Sommadossi Exhibit List (as of Jun. 5, 2012) , Filed Jun. 5, 2012.
Interference No. 105,871, Paper No. 30, Clark Notice re Filing of Priority Statement, Filed Jun. 5, 2012.
Interference No. 105,871, Paper No. 31, Clark Priority Statement, Filed Jun. 5, 2012.
Interference No. 105,871, Paper No. 32, Clark Substantive Motion 1 (for Benefit of Clark U.S. Appl. No. 60/474,368), filed Jun. 5, 2012.
Interference No. 105,871, Paper No. 33, Clark Substantive Motion 2 (to Attack Benefit of Sommadossi U.S. Appl. No. 10/608,908), filed Jun. 5, 2012.
Interference No. 105,871, Paper No. 34, Clark Substantive Motion 3 (for Judgment Based on 35 U.S.C. §§ 135(b)(1) and 135(b)(2)), Filed Jun. 5, 2012.
Interference No. 105,871, Paper No. 35, Clark Substantive Motion 6 (for Judgment Based on Lack of Utility, Enablement, and Written Description), Filed Jun. 5, 2012.
Interference No. 105,871, Paper No. 36, Sommadossi Notice of Service of Priority Statement, Filed Jun. 5, 2012.
Interference No. 105,871, Paper No. 37, Order—Authorizing Responsive Motion, Entered Jun. 18, 2012.
Interference No. 105,871, Paper No. 38, Notice of Joint Stipulation to Extension of Time, Filed Jun. 18, 2012.
Interference No. 105,871, Paper No. 39, Notice re Sommadossi Substantive Motion 5, Filed Jun. 22, 2012.
Interference No. 105,871, Paper No. 40, Sommadossi Notice of Service of Exhibits, Filed Jun. 22, 2012.
Interference No. 105,871, Paper No. 41, Sommadossi Substantive Motion 18 (to Substitute Count C or D for Count 1), Filed Jun. 22, 2012.
Interference No. 105,871, Paper No. 42, Declaration of Masad J. Damha, Ph.D., Filed Jun. 28, 2012.
Interference No. 105,871, Paper No. 43, Declaration of Barry M. Trost, Ph.D., Filed Jun. 28, 2012.
Interference No. 105,871, Paper No. 44, Declaration of Stanley M. Lemon, M.D., Filed Jun. 28, 2012.
Interference No. 105,871, Paper No. 45, Declaration of Jeffrey S. Glenn, Md., Ph.D., Filed Jun. 28, 2012.
Interference No. 105,871, Paper No. 46, Clark Submission of Sommadossi Declarations (for Jun. 28 2012 Telephone conference), Filed Jun. 28, 2012.
Interference No. 105,871, Paper No. 47, Sommadossi Submission of Clark Declarations, Filed Jun. 28, 2012.
Interference No. 105,871, Paper No. 50, Sommadossi Notice of Service of Supplemental Evidence 1, Filed Jun. 29, 2012.
Interference No. 105,871, Paper No. 51, Clark Notice of Service of Supplemental Evidence 1, Filed Jun. 29, 2012.
Interference No. 105,871, Paper No. 52, Order—Cross-Examination of Witnesses, Entered Jul. 5, 2012.
*Gilead Sciences, Inc.* v. *Merck & Co., Inc.*, 13-cv-4057-BLF, Stipulation and Order, dated Mar. 14, 2016.
*Gilead Sciences, Inc.* v. *Merck & Co., Inc.*, 13-cv-4057-BLF, Verdict Form Phase Two, dated Mar. 24, 2016.

(56) References Cited

OTHER PUBLICATIONS

*Gilead Sciences, Inc. v. Merck & Co., Inc.*, 13-cv-4057-BLF, Verdict Form, dated Mar. 22, 2016.
Griffon, Substitute Declaration, Interference No. 105,871 Exhibit 1471.
GU, Chemistry Dictionary, pp. 445, 601 (1989).
Gumina, et al., "Synthesis and Potent Anti-HIV Activity of L-3'-Fluoro-2',3'-Unsaturated Cytidine," Organic Letters, 3 (26):4177-4180 (2001).
Harada, et al., "Nucleosides. 139. Synthesis and Anticytomegalovirus and Antiherpes Simplex Virus Activity of 5'-Modified Analogues of 2'-Fluoroarabinosylpyrimidine Nucleosides," J. Med. Chem. 30:226-229 (1987).
Harry-O'Kuru, et al., "2'-C-Alkylribonucleosides: Design, Synthesis, and Conformation," Nucleosides, Nucleotides & Nucleic Acids, 16:1457-1460 (1997).
Hayakawa, et al., "Diethylaminosulfur Trifluoride (DAST) as a Fluorinating Agent of Pyrimidine Nucleosides Having a 2',3'-Vicinal Diol System," Chem. Pharm. Bull., 38(5):1136-1139 (1990).
Herdewijn, et al., "Synthesis and Anti-HIV Activity of Various 2'- and 3'-Substituted 2',3'-Dideoxyadenosines: A Structure-Activity Analysis," J. Med. Chem., 30:2131-2137 (1987).
Herdewijn, et al., "Synthesis of 2',3'-Disubstituted 3'-Deoxythymidine Derivatives," Bull. Soc. Chim. Belg., 98 (12):943-947 (1989).
*Idenix Pharmaceuticals Inc v. Gilead Sciences Inc.*, UK Court of Appeal (Civil Division), Case No. A3/2015/0450, [2016] EWCA Civ 1089, Judgment dated Nov. 8, 2016.
*Idenix Pharmaceuticals LLC v. Gilead Sciences Europe Ltd.*, Borgarting Court of Appeal, Norway, Judgment dated Apr. 14, 2016 (English).
*Idenix Pharmaceuticals, Inc. v. Gilead Pharmasset LLC*, Federal Court of Appeal, Canada, Ontario, 2017 FCA 161, Docket A-483-15, Reasons for Judgment dated Jul. 24, 2017.
*Idenix Pharmaceuticals, Inc. v. Gilead Sciences, Inc.*, UK High Court of Justice, Chancery Division, Patents Court, Claim No. HP 14D 01069, [2014] EWHC 3916 (Pat), Judgment dated Dec. 1, 2014.
*Idenix Pharmaceuticals, Inc. v. Gilead Sciences, Inc.*, UK High Court of Justice, Chancery Division, Patents Court, Claim No. HP 14D 01069, Agreed Statement on Foreign Law.
*Idenix Pharmaceuticals, Inc. v. Gilead Sciences, Inc.*, UK High Court of Justice, Chancery Division, Patents Court, Claim No. HP 14D 01069, Principles of Foreign Law.
Idenix Pharmaceuticals, S-1/A dated May 17, 2002.
*Idenix SARL v. Gilead Sciences Inc.*, Regional Court Dusseldorf, Germany, Order dated Mar. 12, 2015 (English).
Iino, et al., "Nucleosides and Nucleotides 139. Stereoselective Synthesis of (2'S)-2'-C-Alkyl-2'-Deoxyuridines," Nucleosides & Nucleotides, 15(1-3):169-181 (1996).
Ikeda, et al., The Effect of Two Antipodal Fluorine-Induced Sugar Puckers on the Conformation and Stability of the Dickerson-Drew Dodecamer Duplex [d(CGCGAATTCGCG)]2, Nucleic Acid Research, 26:2237-2244 (1998).
IN Application No. 1870/DELNP/2011 Office Action dated Feb. 12, 2015.
IN Application No. 1871/DELNP/2011 Office Action dated Feb. 12, 2015.
IN Application No. 2079/DELNP/2011 Office Action dated Feb. 12, 2015.
IN Application No. 6087/DELNP/2005 Amended Claims dated Aug. 7, 2015.
IN Application No. 6087/DELNP/2005 BDR Pre-Grant Opposition dated Jan. 30, 2015.
IN Application No. 6087/DELNP/2005 DNP+/I-MAK Letter dated Apr. 6, 2016.
IN Application No. 6087/DELNP/2005 DNP+/I-MAK Pre-Grant Opposition dated Mar. 17, 2014.
IN Application No. 6087/DELNP/2005 Natco Pre-Grant Opposition dated Mar. 13, 2014.
IN Application No. 6087/DELNP/2005 Optimus Pre-Grant Opposition dated Mar. 20, 2015.
IN Application No. 6087/DELNP/2005 Rejoinder Statement of Sankalp dated Oct. 12, 2015.
IN Application No. 6087/DELNP/2005 Reply to BDR Pre-Grant Opposition dated Aug. 7, 2015.
IN Application No. 6087/DELNP/2005 Reply to DNP+/I-MAK Pre-Grant Opposition dated Aug. 7, 2015.
IN Application No. 6087/DELNP/2005 Reply to Natco Pre-Grant Opposition dated Aug. 7, 2015.
IN Application No. 6087/DELNP/2005 Reply to Optimus Pre-Grant Opposition dated Aug. 7, 2015.
IN Application No. 6087/DELNP/2005 Reply to Sankalp Pre-Grant Opposition dated Aug. 7, 2015.
IN Application No. 6087/DELNP/2005 Sankalp Pre-Grant Opposition dated Jan. 30, 2015.
IN Application No. 6087/DELNP/2005 Written Arguments of DNP+ and I-MAK dated Mar. 10, 2016.
IN Application No. 6087/DELNP/2005 Written Arguments of Sankalp Rehabilitation Trust, Optimus Pharma Ltd., and India Cares dated Mar. 11, 2016.
IN Application No. 6087/DELNP/2005 Written Arguments/Submission of BDR dated Mar. 11, 2016.
IN Application No. 6087/DELNP/2005 Written Note on Argument (BDR Opposition) dated Mar. 11, 2016.
IN Application No. 6087/DELNP/2005 Written Note on Argument (DNP+/I-MAK Opposition) dated Mar. 11, 2016.
IN Application No. 6087/DELNP/2005 Written Note on Argument (Optimus, India Cares, and Sankalp Oppositions) dated Mar. 11, 2016.
IN Application No. 6087/DELNP/2005, Form 1 dated Dec. 27, 2005.
IN Application No. 6087/DELNP/2005, Form 3 dated Dec. 27, 2005.
IN Application No. 6087/DELNP/2005, Form 3 dated May 13, 2014.
IN Application No. 6087/DELNP/2005, Form 3 dated Jun. 24, 2014.
Interference No. 105,871 Decision on Motions dated Mar. 22, 2013.
Interference No. 105,871 Exhibit 1260.
Interference No. 105,871 Exhibit 1275.
Interference No. 105,871, Paper No. 53, Clark Notice of Change in Related Proceedings, Filed Jul. 6, 2012.
Interference No. 105,871, Paper No. 54, Clark Notice of Service of Supplemental Evidence 2, Filed Jul. 12, 2012.
Interference No. 105,871, Paper No. 55, Notice of Stipulated Extension of Time, Filed Jul. 16, 2012.
Interference No. 105,871, Paper No. 56, Order—Authorizing Miscellaneous Motion, Entered Jul. 16, 2012.
Interference No. 105,871, Paper No. 57, Clark Notice of Second Backup Lead Counsel, Filed Jul. 16, 2012.
Interference No. 105,871, Paper No. 58, Sommadossi Miscellaneous Motion 19, Filed Jul. 18, 2012.
Interference No. 105,871, Paper No. 59, Sommadossi Notice of Service of Exhibits, Filed Jul. 18, 2012.
Interference No. 105,871, Paper No. 60, Sommadossi Notice of Service of Supplemental Evidence 2, Filed Jul. 18, 2012.
Interference No. 105,871, Paper No. 61, Order—Limited Admission Pro Hac Vice, Entered Jul. 23, 2012.
Interference No. 105,871, Paper No. 62, Clark Opposition 19 (Opposing Request to Amend Specification to Insert Missing 35 U.S.C. § 120 Cross-Reference), Filed Jul. 25, 2012.
Interference No. 105,871, Paper No. 63, Sommadossi Reply 19, Filed Jul. 30, 2012.
Interference No. 105,871, Paper No. 64, Sommadossi Notice of Service Exhibit 1165, Filed Jul. 30, 2012.
Interference No. 105,871, Paper No. 65, Clark Notice 2 (Regarding Stipulated Extension of Time Period 3), Filed Aug. 14, 2012.
Interference 2012 No. 105,871, Paper No. 66, Order—Re: Miscellaneous Motion and Motion Numbering, Entered Aug. 16, 2012.
Interference No. 105,871, Paper No. 67, Sommadossi Notice of Service of Exhibits, Filed Aug. 17, 2012.
Interference No. 105,871, Paper No. 68 , Sommadossi Opposition 1, Filed Aug. 17, 2012.

(56) References Cited

OTHER PUBLICATIONS

Interference No. 105,871, Paper No. 69, Sommadossi Opposition 2, Filed Aug. 17, 2012.
Interference No. 105,871, Paper No. 70, Sommadossi Opposition 3, Filed Aug. 17, 2012.
Interference No. 105,871, Paper No. 71, Sommadossi Opposition 6, Filed Aug. 17, 2012.
Interference No. 105,871, Paper No. 72, Clark Opposition 1 (Opposing Requested Benefit of Sommadossi U.S. Appl. No. 60/393,350), Filed Aug. 17, 2012.
Interference No. 105,871, Paper No. 73, Clark Opposition 6 (Opposing Request to Substitute Proposed Counts C or D for Count 1), Filed Aug. 17, 2012.
Interference No. 105,871, Paper No. 74, Clark Notice of Service of Supplemental Evidence 3, Filed Sep. 10, 2012.
Interference No. 105,871, Paper No. 75, Sommadossi Notice of Service of Supplemental Evidence 3, Filed Sep. 10, 2012.
Interference No. 105,871, Paper No. 76, Notice of Stipulated Extension of Time (Regarding Stipulated Extension of Time Period 4), Filed Sep. 24, 2012.
Interference No. 105,871, Paper No. 77, Order—Cross Examination of Marquez, Entered Sep. 27, 2012.
Interference No. 105,871, Paper No. 78, Sommadossi Notice of Service of Exhibits, Filed Oct. 11, 2012.
Interference No. 105,871, Paper No. 79, Sommadossi Reply 1, Filed Oct. 11, 2012.
Interference No. 105,871, Paper No. 80, Sommadossi Reply 6, Filed Oct. 11, 2012.
Interference No. 105,871, Paper No. 81, Clark Reply 1, Filed Oct. 11, 2012.
Interference No. 105,871, Paper No. 82, Clark Reply 2, Filed Oct. 11, 2012.
Interference No. 105,871, Paper No. 83, Clark Reply 3, Filed Oct. 11, 2012.
Interference No. 105,871, Paper No. 84, Clark Reply 6, Filed Oct. 11, 2012.
Interference No. 105,871, Paper No. 85, Clark Corrected Reply 1, Filed Oct. 11, 2012.
Interference No. 105,871, Paper No. 86, Clark Corrected Reply 6, Filed Oct. 11, 2012.
Interference No. 105,871, Paper No. 87, Clark Submission of Corrected Clark Replies 1 and 6, Filed Oct. 11, 2012.
Interference No. 105,871, Paper No. 88, Sommadossi Responses to Clark's Material Facts of Clark Corrected Reply 1, Filed Oct. 18, 2012.
Interference Oct. 18, No. 105,871, Paper No. 89, Sommadossi Responses to Clark's Material Facts of Clark Reply 2, Filed Oct. 18, 2012.
Interference No. 105,871, Paper No. 90, Sommadossi Responses to Clark's Material Facts of Clark Reply 3, Filed Oct. 18, 2012.
Interference No. 105,871, Paper No. 91, Sommadossi Responses to Clark's Material Facts of Clark Corrected Reply 6, Filed Oct. 18, 2012.
Interference No. 105,871, Paper No. 92, Sommadossi Notice of Service of Exhibits, Filed Oct. 23, 2012.
Interference No. 105,871, Paper No. 93, Sommadossi Miscellaneous Motion 8 (to Exclude Evidence), Filed Oct. 23, 2012.
Interference No. 105,871, Paper No. 94, Sommadossi Request for Oral Argument, Filed Oct. 23, 2012.
Interference No. 105,871, Paper No. 95, Clark Miscellaneous Motion 7 (to Exclude Evidence), Filed Oct. 23, 2012.
Interference No. 105,871, Paper No. 96, Clark Request for Oral Argument, Filed Oct. 23, 2012.
Interference No. 105,871, Paper No. 97, Sommadossi Opposition 7, Filed Nov. 13, 2012.
Interference No. 105,871, Paper No. 98, Sommadossi Notice of Service of Exhibits, Filed Nov. 13, 2012.
Interference No. 105,871, Paper No. 99, Clark Opposition 8, Filed Nov. 13, 2012.
Interference No. 105,871, Paper No. 100, Order—Denying Requests for Oral Argument, Entered Nov. 16, 2012.
Interference No. 105,871, Paper No. 101, Sommadossi Reply 8, Filed Nov. 19, 2012.
Interference No. 105,871, Paper No. 102, Clark Reply 7, Filed Nov. 19, 2012.
Interference No. 105,981, Exhibit No. 2094, C1 File History—May 30, 2003 Clark Provisional Appln. Cover Sheet, Filed Sep. 18, 2014.
Interference No. 105,981, Exhibit No. 2183, Patent Assignment Abstract of Title for U.S. Pat. No. 8,198,426 B2 Printed on Jun. 17, 2014, Filed Sep. 18, 2014.
Interference No. 105,981, Exhibit No. 2179, p. 21 of Exhibit 2145 Annotated by Stanislaw F. Wnuk, Ph.D. During Jun. 12, 2014 Deposition, Filed Sep. 18, 2014.
Interference No. 105,981, Exhibit No. 2169, E-mail from Thomas E. Friebel to Anthony Zupcic, et al., sent Feb. 11, 2014, Filed Sep. 18, 2014.
Interference No. 105,981, Exhibit No. 2113, Interference No. 105,871, Paper No. 506, Idenix Exhibit 1239 (entitled (by Idenix): "Substitute Declaration of George Fleet, signed May 31, 2013"), Filed Sep. 18, 2014.
Interference No. 105,981, Exhibit No. 2019, Matsuda, A., et al., Alkyl Addition Reaction of Pyrimidine 2'-Ketonucleosides: Synthesis of 2'-Branched-Chain Sugar Pyrimidine Nucleosides (Nucleosides and Nucleotides. LXXXI), Chem. Pharm Bull., No. 36(3), pp. 945-953 (1988), Filed May 23, 2014.
Interference No. 105,981, Exhibit No. 2163, Cui, L., et al., Cellular and Molecular Events Leading to Mitochondrial Toxicity of 1-(2-Deoxy-2-Fluoro-1-β-D-Arabinofuranosyl)-5-lodouracil in Human Liver Cells, Journal of Clinical Investigation, vol. 95, pp. 555-563 (1995), Filed Sep. 18, 2014.
Interference No. 105,981, Exhibit No. 2159, Malo, N., et. al., Statistical Practice in High-Throughput Screening Data Analysis, Nature Biotechnology, vol. 24, No. 2, pp. 167-175 (2006), Filed Sep. 18, 2014.
Interference No. 105,981, Exhibit No. 2158, Howe, A.Y.M., et. al., C Virus RNA-Dependent RNA Polymerase Novel Nonnucleoside Inhibitor of Hepatitis, Antimicrobial Agents and Chemotherapy, vol. 48, No. 12, pp. 4813-21 (2004), Filed Sep. 18, 2014.
Interference No. 105,981, Exhibit No. 2006, Interference No. 105,871, Paper No. 434, Decision on Request for Rehearing, Entered Apr. 23, 2013, Filed Mar. 10, 2014.
Interference No. 105,981, Exhibit No. 2064, Stuyver, L.J., et al., Inhibition of hepatitis C replicon RNA synthesis by β-D-2'-deoxy-2'-C-methylcytidine: a specific inhibitor of hepatitis C virus replication, Antiviral Chem & Chemotherapy 17:79-87 (2006), Filed Mar. 10, 2014.
Interference No. 105,981, Exhibit No. 2137-1, Swarbrick, J. and Boylan, J.C., eds., Encyclopedia of Pharmaceutical Technology, vol. 13, Marcel Dekker, Inc. (1996), Filed Sep. 18, 2014.
Interference No. 105,981, Exhibit No. 2110-22, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2137-3, Swarbrick, J. and Boylan, J.C., eds., Encyclopedia of Pharmaceutical Technology, vol. 13, Marcel Dekker, Inc. (1996), Filed Sep. 18, 2014.
Interference No. 105,981, Exhibit No. 2137-2, Swarbrick, J. and Boylan, J.C., eds., Encyclopedia of Pharmaceutical Technology, vol. 13, Marcel Dekker, Inc. (1996), Filed Sep. 18, 2014.
Interference No. 105,981, Exhibit No. 2110-1, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2110-19, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2111, Interference No. 105,871, Paper No. 993, Sommadossi Opposition 10, Filed Sep. 18, 2014.
Interference No. 105,981, Exhibit No. 2079, Storer U.S. Appl. No. 10/608,907 ("S4") file history—May 25, 2006 Amendment and Response to Office Action, Filed Mar. 10, 2014.

(56) References Cited

OTHER PUBLICATIONS

Interference No. 105,981, Exhibit No. 2066, Stuyver, L.J., et al., Ribonucleoside Analogue That Blocks Replication of Bovine Viral Diarrhea and Hepatitis C Viruses in Culture, Antimicrob Agents & Chemother 47(1):244-254 (2003), Filed Mar. 10, 2014.
Interference No. 105,981, Exhibit No. 2039, Interference No. 105,871, Paper No. 571, Idenix Exhibit 1304 (entitled (by Idenix): "Report on fluorination Scientific Update Training Course"), Filed Mar. 10, 2014.
Interference No. 105,981, Exhibit No. 2180, U.S. Pat. No. 6,383,768 B1, Filed Sep. 18, 2014.
Interference No. 105,981, Exhibit No. 2110-20, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2110-11, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2110-21, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2092, U.S. Appl. No. 11/005,446 file history—May 7, 2007 Amendment and Response, Filed Sep. 18, 2014.
Interference No. 105,981, Exhibit No. 2155, Interference No. 105,871, Paper No. 755, Idenix Exhibit 1489 (entitled (by Idenix): "Curriculum Vitae of Dr Sarah Jenkinson"), Filed May 23, 2014.
Interference No. 105,981, Exhibit No. 2070, Zuck, P., et al., A cell-based β-lactamase reporter gene assay for the Identification of inhibitors of hepatitis C virus replication, Anal Biochem 334: 344-355 (2004), Filed Sep. 18, 2014.
Interference No. 105,981, Exhibit No. 2058, Krieger, N., et al., Enhancement of Hepatitis C Virus RNA Replications by Cell Culture-Adaptive Mutations, J. Virol 75:4614-4624 (2001), Filed Sep. 18, 2014.
Interference No. 105,981, Exhibit No. 2084, U.S. Pat. No. 7,662,798 (U.S. Appl. No. 10/609,298) file history—Feb. 25, 2008 Amendment and Response, Filed Mar. 10, 2014.
Interference No. 105,981, Exhibit No. 2037, Interference No. 105,871, Paper No. 577, Idenix Exhibit 1310 (entitled (by Idenix): "Idenix memorandum for meeting held on Jul. 31, 2003"), Filed Mar. 10, 2014.
Interference No. 105,981, Exhibit No. 2177, Storer U.S. Appl. No. 14/146,520 ("S8") file history—Office Action dated Feb. 26, 2014, Filed Sep. 18, 2014.
Interference No. 105,981, Exhibit No. 2110-18, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2110-27, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2105, Interference No. 105,871, Paper No. 15, Sommadossi Motions List, Filed Apr. 11, 2012, Filed Mar. 10, 2014.
Interference No. 105,981, Exhibit No. 2020, Storer U.S. Appl. No. 12/131,868 ("S5") file history—Sep. 20, 2011 Amendment and Response Under 37 C.F.R. § 1.111, Filed Sep. 18, 2014.
Interference No. 105,981, Exhibit No. 2073, Eldrup, A. B., et al., Structure-Activity Relationship of Purine Ribonucleosides for Inhibition of Hepatitis C Virus RNA-Dependent RNA Polymerase, J. Med. Chem., vol. 47, pp. 2283-2295 (2004), Filed Mar. 10, 2014.
Interference No. 105,981, Exhibit No. 2008, Interference No. 105,871, Paper No. 1, Declaration, Entered Feb. 22, 2012, Filed Mar. 10, 2014.
Interference No. 105,981, Exhibit No. 2187, Transcript of Deposition of Stanislaw F. Wnuk, Ph.D., taken Jun. 12, 2014, Filed Sep. 18, 2014.
Interference No. 105,981, Exhibit No. 2089, Interference No. 105,871, Paper No. 403, Idenix Exhibit 1189, Transcript of Deposition of Stanley Moncrief Lemon, M.D., taken Jul. 31, 2012, Filed Sep. 18, 2014.
Interference No. 105,981, Exhibit No. 2131, Interference No. 105,871, Paper No. 925, Idenix Exhibit 1644 (entitled (by Idenix): "Deposition Transcript of Richard Storer, Ph.D. dated Jun. 14, 2013 (with errata sheet)"), Filed Sep. 18, 2014.
Interference No. 105,981, Exhibit No. 2110-15, Declaration of Prof. Dr. Chris Meier, signed Aug. 31, 2013 (with axhibits) (filed by Idenix in Oslo District Court case 12-155575TVI-OTIR/01) Filed Sep. 18, 2014.
Interference No. 105,981, Exhibit No. 2082, U.S. Pat. No. 7,625,875 (U.S. Appl. No. 11/005,444) file history—Apr. 6, 2009 Amendment and Response, Filed Sep. 18, 2014.
Interference No. 105,981, Exhibit No. 2081, U.S. Appl. No. 11/005,469 file history—Apr. 5, 2007 Amendment and Response, Filed Sep. 18, 2014.
Interference No. 105,981, Exhibit No. 2166, Interference No. 105,871, Paper No. 517, Idenix Exhibit 1250 (entitled (by Idenix)= "Novirio Chemistry Meeting Agenda"), Filed Sep. 18, 2014.
Interference No. 105,981, Exhibit No. 2161, De Clercq, E, Milestones in the Discovery of Antiviral Agents: Nucleoside and Nucleotides, Acta Pharmaceutica Sinica B, vol. 2, No. 6, pp. 535-548 (2012), Filed Sep. 18, 2014.
Interference No. 105,981, Exhibit No. 2071, Bhat, B., et al., Slides presented at the oral session on the 16th International Conference on Antiviral Research (Apr. 27, 2003, Savannah, Ga.) (Exhibit 97 to the Aug. 31, 2013 Declaration of Prof. Dr. Chris Meier, filed by Idenix in Oslo District Court case 12-155575TVI-OTIR/01), Filed Mar. 10, 2014.
Interference No. 105,981, Exhibit No. 2132, Interference No. 105,871, Paper No. 905, Idenix Exhibit 1646 (entitled (by Idenix): "Deposition Transcript of Jean-Francois Griffon dated Jun. 25, 2013 (with errata sheet)"), Filed Sep. 18, 2014.
Interference No. 105,981, Exhibit No. 2134, Interference No. 105,871, Paper No. 909, Idenix Exhibit 1651 (entitled (by Idenix): "Deposition Transcript of George Fleet dated Jul. 9, 2013 (with errata sheet)"), Filed Sep. 18, 2014.
Interference No. 105,981, Exhibit No. 2110-28, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Pradere et al., "Synthesis of Nucleoside Phosphate and Phosphonate Prodrugs," Chem. Rev. 114:9154-9218 (2014).
Joubert, Synthese et Evaluation de Nouveaux Nucleosides Ciblant l'Hepatite C dans un Systeme Replicon, Autre, Universite d'Orleans, Francais (2006).
Leisvuori, Prodrug Strategies of Antiviral Nucleotides: Studies on Enzymatically and Thermally Removable Phosphate Protecting Groups (2015).
English Translation of French Passages in EP Application No. 13152340.9, Written Submission Before Oral Proceedings in the Opposition Against Patent EP2604620 from Medecins du Monde, Medici Senza Frontiere Onlus, and European Public Health Alliance dated Jul. 12, 2018.
EP Application No. 03761744.6 (EP Patent 1523489) Idenix Comments on Gilead Sciences, Inc. Opposition date Jun. 2, 2015.
EP Application No. 03761744.6 (EP Patent 1523489) Idenix Grounds of Appeal dated Aug. 26, 2016.
EP Application No. 03761744.6 (EP Patent 1523489) Decision Revoking European Patent dated Apr. 26, 2018.
EP Application No. 13152340.9, Gilead Pharmasset LLC Written Submissions in Advance of Oral Proceedings dated Jul. 13, 2018.
EP Application No. 13152340.9, Main Request and Auxiliary Requests 1-2 Claims dated Jul. 13, 2018.
EP Application No. 10183144.4 (EP Patent 2332852) Decision Revoking European Patent dated Apr. 26, 2018.

(56) References Cited

OTHER PUBLICATIONS

EP Application No. 13152340.9, Submission Discussing the Relevance of the UK Judgment to Gilead's Applications dated Sep. 29, 2017.
European Commission, Commission Implementing Decision of Jan. 16, 2014 granting marketing authorisation under Regulation (EC) No. 726/2004 of the European Parliament and of the Council for "Sovaldi—sofosbuvir", a medicinal product for human use (Jan. 16, 2014).
Brox, Studies on the Growth Inhibition and Metabolism of 2'-Deoxy-2'-fluorocytidine in Cultured Human Lymphoblasts, Cancer Research 34:1838-1842 (1974).
ChemIDplus, Substance Name: GS-461203, Registry No. 1015073-42-3 (Jun. 19, 2017).
Interference No. 105,981, Exhibit No. 2146, Interference No. 105,871, Paper No. 300, Idenix Exhibit 1101 (entitled (by Idenix): "Declaration of Masad J. Damha, Ph.D., signed Jun. 2, 2012"), Filed May 23, 2014.
Interference No. 105,981, Exhibit No. 2137-7, Swarbrick, J. and Boylan, J.C., eds., Encyclopedia of Pharmaceutical Technology, vol. 13, Marcel Dekker, Inc. (1996), Filed Sep. 18, 2014.
Interference No. 105,981, Exhibit No. 2147, Interference No. 105,871, Paper No. 361, Idenix Exhibit 1147 (entitled (by Idenix): "Second Declaration of Masad J. Damha, Ph.D., signed Jun. 28, 2012"), Filed May 23, 2014.
Interference No. 105,981, Exhibit No. 2143, Milne, H. Bayard and Peng, Chi-Hsieh, The Use of Benzylsulfonyl Chloride in Peptide Syntheses, J. Am. Chem. Soc., vol. 79, pp. 639-644 (1956), Filed Sep. 18, 2014.
Interference No. 105,981, Exhibit No. 2142, Awad, Laila Fathy, et al., A Synthesis of Methyl 3-O-(β-D-Mannopyranosyl)-α-mannopyranoside from Sulfonate Intermediates, Bull. Chem. Soc. Jpn., vol. 59, pp. 1587-1592 (1986), Filed Sep. 18, 2014.
Interference No. 105,981, Exhibit No. 2059, Lalezari, J., et al., Potent Antiviral Activity of the HCV Nucleoside Polymerase Inhibitor R7128 with PEG-IFN and Ribavirin: Interim Results of R7128 500mg BID for 28 Days, J. Hepatology, vol. 48, Supplement 2, p. S29 (2008), Filed Mar. 10, 2014.
Interference No. 105,981, Exhibit No. 2023, Middleton, W.J., New Fluorinating Reagents. Dialkylaminosulfur Fluorides, J. Org. Chem., vol. 40, No. 5, pp. 574-578 (1975), Filed Mar. 10, 2014.
Interference No. 105,981, Exhibit No. 2110-3, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2149, Interference No. 105,871, Paper No. 366, Idenix Exhibit 1152 (entitled (by Idenix): "Substitute Declaration of Barry M. Trost, Ph.D."), Filed May 23, 2014.
Interference No. 105,981, Exhibit No. 2110-8, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2171, Substitute 2nd Declaration of Christoph Seeger, Ph.D., Filed Sep. 18, 2014.
Interference No. 105,981, Exhibit No. 2072, Declaration of Prof. Dr. Chris Meier, signed Aug. 31, 2013 (without exhibits) (filed by Idenix in Oslo District Court case 12-155575TVI-OTIR/01), Filed Mar. 10, 2014.
Interference No. 105,981, Exhibit No. 2054, Dhanak, D., et al., Identification and Biological Characterization of Heterocyclic Inhibitors of the Hepatitis C Virus RNA-dependent RNA Polymerase, J Biol Chem 277(41):38322-38327 (2002), Filed Mar. 10, 2014.
Interference No. 105,981, Exhibit No. 2136, Baginski, S.G. et al., Mechanism of Action of a Pestivirus Antiviral Compound, PNAS, vol. 97, No. 14, pp. 7981-7986 (2000), Filed Mar. 31, 2014.
Interference No. 105,981, Exhibit No. 2164, Lewis W., et al., Fialuridine and Its Metabolites Inhibit DNA Polymerase y at Sites of Multiple Adjacent Analog Incorporation, Decrease mtDNA Abundance, and Cause Mitochondrial Structural Defects in Cultured Hepatoblasts, PNAS, vol. 93, pp. 3592-3597 (1996), Filed Sep. 18, 2014.
Interference No. 105,981, Exhibit No. 2162, Hertel, L.W., et al., Evaluation of the Antitumor Activity of Gemcitabine (2', 2'-Difluoro-2'-deoxycitidine, Cancer Research, vol. 50, pp. 4417-4422 (1990), Filed Sep. 18, 2014.
Interference No. 105,981, Exhibit No. 2086, U.S. Pat. No. 7,608,597 (U.S. Appl. No. 10/602,691) file history—May 4, 2007 Amendment and Response, Filed Mar. 10, 2014.
Interference No. 105,981, Exhibit No. 2044, Interference No. 105,871, Paper No. 603, Idenix Exhibit 1336 (entitled (by Idenix): "Email from Dr Stewart to Dr. Storer dated Nov. 11, 2004"), Filed Mar. 10, 2014.
Interference No. 105,981, Exhibit No. 2033, Interference No. 105,871, Paper No. 586, Idenix Exhibit 1319 (entitled (by Idenix): "Summary of May 10, 2004 Idenix meeting in Cambridge, MA"), Filed Mar. 10, 2014.
Interference No. 105,981, Exhibit No. 2176, Storer U.S. Appl. No. 14/146,520 ("S8") file history—Jan. 3, 2014 Preliminary Amendment, Filed Sep. 18, 2014.
Interference No. 105,981, Exhibit No. 2110-26, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2110-2, Declaration of Prof. Dr Chris Meier, signed Aug. 31, 2013 (with exhibits) (filed by Idenix in Oslo District Court case 12-155575TVI-OTIR/01), Filed Sep. 18, 2014.
Interference No. 105,981, Idenix in Exhibit No. 2110-9, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2145 (Substitute), Substitute 2nd Declaration of Stanislaw F. Wnuk, Ph.D., Filed Jun. 10, 2014.
Interference No. 105,981, Exhibit No. 2145, Substitute 2nd Declaration of Stanislaw F. Wnuk, Ph.D., Filed May 23, 2014.
Interference No. 105,981, Exhibit No. 2110-25, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2110-24, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2013, U.S. Patent Appln. Pub. No. 2005/0009737 A1, published Jan. 13, 2005 ("C2-Pub"), Filed Mar. 10, 2014.
Interference No. 105,981, Exhibit No. 2110-29, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2093, Clark U.S. Appl. No. 11/854,218 ("C3") file history—Sep. 12, 2007 Preliminary Amendment, Filed Sep. 18, 2014.
Interference No. 105,981, Exhibit No. 2046, Hacksell, U., et al., Stereocontrolled Palladium(II)-Mediated Coupling of Furanoid Glycals with a Pyrimidinylmercuric Salt. Facile C-Nucleoside Syntheses, J. Org. Chem., vol. 48, No. 17, pp. 2870-2876 (1983), Filed Sep. 18, 2014.
Interference No. 105,981, Exhibit No. 2004, Christoph Seeger, Ph.D. curriculum vitae, Filed Sep. 18, 2014.
Interference No. 105,981, Exhibit No. 2085, U.S. Pat. No. 7,608,597 (U.S. Appl. No. 10/602,691) file history—Oct. 31, 2007 Request for Continued Examination and Amendment and Response, Filed Mar. 10, 2014.
Interference No. 105,981, Exhibit No. 2018, Pankiewicz, K.W., et al., A Synthesis of 9-(2-Deoxy-2-fluoro-β-D-arabinofuranosyl) adenine and Hypoxanthine. An Effect of C3'-Endo to C2'-Endo Conformational Shift on the Reaction Course of 2'-Hydroxyl Group with DAST, J. Org. Chem., vol. 57, No. 2, pp. 553-559 (1992), Filed Mar. 10, 2014.
Interference No. 105,981, Exhibit No. 2190, Clark Objections 3 served May 30, 2014, Filed Sep. 18, 2014.
Interference No. 105,981, Exhibit No. 2051, Storer U.S. Appl. No. 60/470,949 ("S3") as filed May 14, 2003, Filed Mar. 10, 2014.

(56) References Cited

OTHER PUBLICATIONS

Interference No. 105,981, Exhibit No. 2110-16, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2110-13, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2135, Interference No. 105,871, Paper No. 913, Idenix Exhibit 1655 (entitled (by Idenix): "Deposition Transcript of Elodie Pecheux dated Jul. 12, 2013 (with errata sheet)"), Filed Sep. 18, 2014.
Interference No. 105,981, Exhibit No. 2110-17, Declaration of Prof. Dr. Chris Meier, signed Aug. 31, 2013 (with ehibits) (filed by Idenix in Oslo District Court case 12-155575TVI-OTIR/01), Filed Sep. 18, 2014.
Interference No. 105,981, Exhibit No. 2110-5, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2140, Storer U.S. Appl. No. 14/220,534 ("S9") file history—Mar. 21, 2014 Preliminary Amendment, Filed May 23, 2014.
Interference No. 105,981, Exhibit No. 2104, Clark U.S. Appl. No. 10/828,753 ("C2") file history—Sep. 5, 2006 Restriction Requirement, Filed Sep. 18, 2014.
Interference No. 105,981, Exhibit No. 2063, Shim, J., et al., Canonical 3'-deoxyribonucleotides as a chain terminator for HCV NS5B RNA-dependent RNA polymerase, Antiviral Res 58:243-251 (2003), Filed Mar. 10, 2014.
Interference No. 105,981, Exhibit No. 2055, Guo, J.-T., et al., Effect of Alpha Interferon on the Hepatitis C Virus Replicon, J. Viral 75:8516-8523 (2001), Filed Mar. 10, 2014.
Interference No. 105,981, Exhibit No. 2034, Interference No. 105,871, Paper No. 602, Idenix Exhibit 1335 (entitled (by Idenix): "Prioritized Summary of Idenix Meeting with Professor Fleet on May 10, 2004"), Filed Mar. 10, 2014.
Interference No. 105,981, Exhibit No. 2062, O'Boyle II, D.R., et al., Development of a Cell-Based High-Throughput Specificity Screen Using a Hepatitis C Virus-Bovine Viral Diarrhea Virus Dual Replicon Assay, Antimicrob Agents Chemother 49:1346-1353 (2005), Filed Sep. 18, 2014.
Interference No. 105,981, Exhibit No. 2185, Horscroft, N., et al., Establishment of a Subgenomic Replicon for Bovine Viral Diarrhea Virus in Huh-7 Cells and Modulation of Interferon-Regulated Factor 3-Mediated Antiviral Response, Journal of Virology, vol. 79, No. 5, pp. 2788-2796 (2005), Filed Sep. 18, 2014.
Interference No. 105,981, Exhibit No. 2173, Interference No. 105,871, Paper No. 16, Clark List of Intended Motions, Filed Apr. 11, 2012, Filed Sep. 18, 2014.
Interference No. 105,981, Exhibit No. 2003, Substitute Declaration of Christoph Seeger, Ph.D., Filed Mar. 10, 2014.
BR Application No. PI0419343-1 ANVISA 1st Opinion (English translation) dated Oct. 26, 2016.
BR Application No. PI0419343-1 Office Action (English translation) dated Oct. 10, 2017.
BR Application No. PI0410846-9 ANVISA 1st Opinion (English translation) dated Oct. 21, 2016.
BR Application No. PI0410846-9 Office Action (English translation) dated Oct. 10, 2017.
BR Application No. PI0419342-3 ANVISA 1st Opinion (English translation) dated Oct. 26, 2016.
BR Application No. PI0419342-3 Office Action (English translation) dated Oct. 10, 2017.
BR Application No. PI0419344-0 ANVISA 1st Opinion (English translation) dated Oct. 26, 2016.
BR Application No. PI0419344-0 Office Action (English translation) dated Oct. 10, 2017.
BR Application No. PI0419345-8 Anvisa 1st Opinion (English translation) dated Oct. 26, 2016.
BR Application No. PI0419345-8 Office Action (English translation) dated Oct. 10, 2017.
BR Application No. PI0419345-8 Office Action (English translation) dated Jan. 29, 2018.
HU Case No. S1600062/5, registration E029877, Order dated Mar. 2, 2017.
LV Ref. No. C/LV2016/0044/z Office Action dated Nov. 21, 2017.
LV Ref. No. C/LV2016/0044/z Office Action dated Nov. 21, 2017 (English translation).
SE SPC Application No. 1690055-6 Office Action dated Oct. 5, 2017 (English translation).
CN Application No. ZL200480019148.4 Patentee's Response to Invalidation Petition (English translation) dated Jul. 21, 2017.
CN Application No. ZL200480019148.4 Petitioner's Rebuttal dated Dec. 14, 2017.
CN Application No. ZL200480019148.4 Petitioner's Rebuttal dated Dec. 14, 2017 (English translation).
CN Application No. ZL200480019148.4 Patentee's Further Response (English translation) dated Jan. 16, 2018.
CN Application No. ZL200480019148.4 Patentee's Response to Invalidation Petition (English translation) dated Oct. 9, 2017.
CN Application No. ZL200480019148.4 Petitioner's Response dated Oct. 30, 2017.
CN Application No. ZL200480019148.4 Petitioner's Response dated Oct. 30, 2017 (English translation).
CN Application No. ZL200480019148.4 Patentee's Further Response (English translation) dated Dec. 27, 2017.
ID Application No. W00201101419 Office Action dated Jun. 2, 2017.
ID Application No. W00201101420 Office Action dated May 24, 2017.
ID Application No. W00201101421 Office Action dated May 24, 2017.
ID Application No. W00201101422 Office Action dated May 24, 2017.
AR Application No. P040101821 Office Action dated Jun. 16, 2015 (English translation).
AR Application No. PI 10102354 Office Action dated Jan. 26, 2015 (English translation).
AR Application No. PI 10102358 Office Action dated Sep. 1, 2016 (English translation).
Chen, A Course in Organic Chemistry, pp. 505-506 (1990) (English translation).
Chen, Basic Science of Design on Drugs, pp. 159-174 (1995) (English translation).
Gu, Chemistry Dictionary (1989) (English translation).
ID Application No. W00201101419 Office Action dated Jun. 2, 2017 (English translation).
ID Application No. W00201101420 Office Action dated May 24, 2017 (English translation).
ID Application No. W00201101421 Office Action dated May 24, 2017 (English translation).
ID Application No. W00201101422 Office Action dated May 24, 2017 (English translation).
BR Application No. PI0410846-9 Blanver Opposition.
ES Certificate of Protection No. 201630081 Office Action dated Oct. 25, 2017.
FR Certificate of Protection No. 16 C0045 Office Action dated Aug. 17, 2017.
Tan, English-Chinese Dictionary of Biochemistry & Molecular Biology, p. 805 (2000) (English translation).
AR Application No. 20040101821 Office Action dated May 24, 2018.
AR Application No. 20040101821 Office Action dated May 24, 2018 (English translation).
TH Application No. 0401001521 Office Action Response with Attachments dated Feb. 7, 2018.
TH Application No. 0401001521 Office Action dated Jun. 20, 2018.
BR Application No. PI0419345-8 Blanver Third Party Observation dated Mar. 26, 2018 (English translation).

(56) References Cited

OTHER PUBLICATIONS

BR Application No. PI0419345-8 Office Action Response dated May 7, 2018.
BR Application No. PI0419345-8 Office Action Response dated May 7, 2018 (English translation).
BR Application No. PI0419345-8 Office Action dated Jun. 5, 2018 (English translation).
BR Application No. PI0419345-8 Blanver Third Party Observation dated Jul. 3, 2018 (English translation).
CN Application No. 200480019148.4, Patent Reexamination Board Decision on IMAK Invalidation Request (Aug. 3, 2018).
CN Application No. 200480019148.4, Patent Reexamination Board Decision on Fujian Invalidation Request (Aug. 3, 2018).
CN Application No. 200480019148.4, English Translation of Patent Reexamination Board Decisions on IMAK and Fujian Invalidation Requests (Aug. 3, 2018).
EP Application No. 04775900.6 Communication of Intent to Grant European Patent (Apr. 30, 2018).
Interference No. 105,981, Exhibit No. 1161, W.J. Middleton, 1975, J. Org. Chem. 40(5): 574-578, Filed Mar. 10, 2014.
Interference No. 105,981, Exhibit No. 1122, Clark et al., "Design, Synthesis, and Antiviral Activity of 2'-Deoxy-2'-fluoro-2'-C-methylcytidine, a Potent Inhibitor of Hepatitis C Virus" J. Med. Chem. 2005, 48, 5504-5508, Filed Sep. 16, 2014.
Interference No. 105,981, Exhibit No. 1186, Preliminary Amendment, filed Jun. 24, 2011, from the file history of Storer et al., in U.S. Appl. No. 13/168,895, filed Jun. 24, 2011, Filed Sep. 16, 2014.
Interference No. 105,981, Exhibit No. 1215, Buckwold et al., 2003, "Synergistic In Vitro Interactions between Alpha Interferon and Ribavirin against Bovine Viral Diarrhea Virus and Yellow Fever Virus as Surrogate Models of Hepatitis C Virus Replication," Antimicrob. Agents Chemother. 47: 2293-98, Filed Sep. 17, 2014.
Interference No. 105,981, Exhibit No. 1048, Kolykhalov et al., 1997, "Transmission of Hepatitis C by Intrahepatic Inoculation with Transcribed RNA," Science 277: 570-74, Filed Mar. 10, 2014.
Interference No. 105,981, Exhibit No. 12/783,680, 1202, Ross et al., U.S. Pat. No. 8,642,756 B2, which issued Feb. 4, 2014 from U.S. Appl. No. 12/783,680, filed May 20, 2010, Filed Sep. 17, 2014.
Interference No. 105,981, Exhibit No. 1201, Second Declaration of Dr. Raffaele De Francesco, Ph.D., Filed Sep. 16, 2014.
Interference No. 105,981, Exhibit No. 1003-7, Sommadossi et al., U.S. Appl. No. 60/392,350, filed Jun. 28, 2002, Filed Mar. 10, 2014.
Interference No. 105,981, Exhibit No. 2002, Filed 1003-6 (Part 1), Sommadossi et al., U.S. Appl. No. 60/392,350, filed Jun. 28, 2002, Filed Mar. 10, 2014.
Interference No. 105,981, Exhibit No. 2002, Filed 1003-6 (Part 2), Sommadossi et al., U.S. Appl. No. 60/392,350, filed Jun. 28, 2002, Filed Mar. 10, 2014.
Interference No. 105,981, Exhibit No. 1003-5, Sommadossi et al., U.S. Appl. No. 60/392,350, filed Jun. 28, 2002, Filed Mar. 10, 2014.
Interference No. 105,981, Exhibit No. 1003-4, Sommadossi et al., U.S. Appl. No. 60/392,350, filed Jun. 28, 2002, Filed Mar. 10, 2014.
Interference No. 105,981, Exhibit No. 1003-3, Sommadossi et al., U.S. Appl. No. 60/392,350, filed Jun. 28, 2001, Filed Mar. 10, 2014.
Interference No. 105,981, Exhibit No. 1003-2 (Part 1), Sommadossi et al., U.S. Appl. No. 60/392,350, filed Jun. 28, 2002, Filed Mar. 10, 2014.
Interference No. 105,981, Exhibit No. 1003-2 (Part 2), Sommadossi et al., U.S. Appl. No. 60/392,350, filed Jun. 28, 2002, Filed Mar. 10, 2014.
Interference No. 105,981, Exhibit No. 1003-1, Sommadossi et al., U.S. Appl. No. 60/392,350, filed Jun. 28, 2002, Filed Mar. 10, 2014.
Interference No. 105,981, Exhibit No. 1124, Request for Declaration of Interference, dated Aug. 30, 2013 from the File History of Clark, U.S. Appl. No. 11/854,218, filed Sep. 12, 2007, Filed Mar. 10, 2014.
Interference No. 105,981, Exhibit No. 1158, Herdewijn et al., 1987, J. Med. Chem. 30(11): 2131-2137, Filed Mar. 10, 2014.
Interference No. 105,981, Exhibit No. 1150, Herdewijn et al., 1989, Bull. Soc. Chim. Belg. 98(12): 943-947, Filed Mar. 10, 2014.
Interference No. 105,981, Exhibit No. 1143, Harry-O'kuru et al., J .Org. Chem., 1997, 62: 1754-1759, Filed Mar. 10, 2014.
Interference No. 105,981, Exhibit No. 1141, Matsuda et al., J. Med. Chem., 1991, 34: 234-239, Filed Mar. 10, 2014.
Interference No. 105,981, Exhibit No. 1131, Executed Declaration and Power of Attorney, filed Jan. 12, 2004, from the File History of Sommadossi et al., U.S. Appl. No. 10/608,907, filed Jun. 27, 2003, Filed Mar. 10, 2014.
Interference No. 105,981, Exhibit No. 1099, Ferrari et al., 1999, "Characterization of Soluble Hepatitis C Virus RNA-Dependent RNA Polymerase Expressed in *Escherichia coli*," J. Virol. 73: 1649-54, Filed Mar. 10, 2014.
Interference No. 105,981, Exhibit No. 1091, Bishop & Hwang, 1992, BioTechniques 12: 326-30, Filed Mar. 10, 2014.
Interference No. 105,981, Exhibit No. 1090, Martell et al., 1999, J. Clin. Microbiol. 37: 327-32, Filed Mar. 10, 2014.
Interference No. 105,981, Exhibit No. 1251, Clark Objections 3, served May 30, 2014, Filed Sep. 17, 2014.
Interference No. 105,981, Exhibit No. 1231, Jingyang Wang Notebook 73, pp. 115-118, Filed Sep. 17, 2014.
IInterference No. 105,981, Exhibit No. 1054, Cohen, 1999, "The Scientific Challenge of Hepatitis C," Science 285: 26-30, Filed Mar. 10, 2014.
Interference No. 105,981, Exhibit No. 1025, Migliaccio et al., 2003, "Characterization of Resistance to Non-obligate Chainterminating Ribonucleoside Analogs That Inhibit Hepatitis C Virus Replication in Vitro," J. Biol. Chem. 278: 49164-70, Filed Mar. 10, 2014.
Interference No. 105,981, Exhibit No. 1197, Robins et al., "Nucleic Acid Related Compounds. 88. Efficient Conversions of Ribonucleosides into Their 2',3'-Anhydro, 2'(and 3')-Deoxy, 2',3'-Didehydro-2',3'-didoexy, and 2',3'-Dideoxynucleoside Analogues1," J. Org. Chem. 1995, 60, 7902-7908, Filed Sep. 17, 2014.
Interference No. 105,981, Exhibit No. 1073, Pflugheber et al., Apr. 2002, "Regulation of PKR and IRF-1 during hepatitis C virus RNA replication," Proc. Natl. Acad. Sci. USA 99: 4650-55, Filed Mar. 10, 2014.
Interference No. 105,981, Exhibit No. 1178, Storer et al., U.S. Pat. No. 8,637,475, issued Jan. 28, 2014, Filed Sep. 16, 2014.
Interference No. 105,981, Exhibit No. 1159, Van Aerschot et al., 1989, J. Med. Chem. 32(8): 1743-1749, Filed Sep. 16, 2014.
Interference No. 105,981, Exhibit No. 1136, Damha et al., 2003, Nucleosides, Nucleotides & Nucleic Acids 22: 1343-1346, Filed Mar. 10, 2014.
Interference No. 105,981, Exhibit No. 1120, Office Action, dated Sep. 5, 2006, from the File History of Clark, U.S Appl. No. 10/828,753, filed Apr. 21, 2004, Filed Mar. 10, 2014.
Interference No. 105,981, Exhibit No. 1106, Carroll et al., 2011, "Antiviral Efficacy upon Administration of a HepDirect Prodrug of 2'-C-Methylcytidine to Hepatitis C Virus-Infected Chimpanzees," Antimicrob. Agents Chemother. 55: 3854-60, Filed Mar. 10, 2014.
Interference No. 105,981, Exhibit No. 1097, Yamashita et al., 1998, "RNA-dependent RNA Polymerase Activity of the Soluble Recombinant Hepatitis C Virus NS5B Protein Truncated at the C-terminal Region," J. Biol. Chem. 273: 15479-86, Filed Mar. 10, 2014.
Interference No. 105,981, Exhibit No. 1086, Dhanak et al., 2002 (received for publication on Jun. 5, 2002, "Identification and Biological Characterization of Heterocyclic Inhibitors of the Hepatitis C Virus RNA-dependent RNA Polymerase," J. Biol. Chem. 277: 38322-27, Filed Mar. 10, 2014.
Interference No. 105,981, Exhibit No. 1081, Randall and Rice, 2001, "Hepatitis C virus cell culture replication systems: their potential use for the development of antiviral therapies," Curr. Opin. Infect. Dis. 14: 743-47, Filed Mar. 10, 2014.
Interference No. 105,981, Exhibit No. 1026, Tomei et al., 2003, "Mechanism of Action and Antiviral Activity of Benzimidazole-Based Allosteric Inhibitors of the Hepatitis C Virus RNA-Dependent RNA Polymerase," J. Virol. 77: 13225-31, Filed Mar. 10, 2014.
Interference No. 105,981, Exhibit No. 1224, Van Aerschot et al., 1989, Bull. Soc. Chim. Belg. 98: 937-941, Filed Sep. 17, 2014.
Interference No. 105,981, Exhibit No. 1223, Robins et al., 1992, J. Org. Chem. 57: 2357-2364, Filed Sep. 17, 2014.

(56) References Cited

OTHER PUBLICATIONS

Interference No. 105,981, Exhibit No. 1182, Utility Patent Application Transmittal and Executed Declaration and Power of Attorney, filed Jun. 2, 2008, from the File History of Sommadossi et al., U.S. Appl. No. 12/131,868, filed Jun. 2, 2008, Filed Sep. 16, 2014.
Interference No. 105,981, Exhibit No. 1167, Office Action, dated Aug. 16, 2011, from the File History of Sommadossi et al., U.S. Appl. No. 12/131,868, filed Jun. 2, 2008, Filed Sep. 16, 2014.
Interference No. 105,981, Exhibit No. 1018, Cerretani et al., 1999, "A High-Throughput Radiometric Assay for Hepatitis C Virus NS3 Protease," Anal. Biochem. 266: 192-97, Filed Mar. 10, 2014.
Interference No. 105,981, Exhibit No. 1055, Di Bisceglie and Bacon, Oct. 1999, "The Unmet Challenges of Hepatitis C," Sci. Am. 281: 80-85, Filed Mar. 10, 2014.
Interference No. 105,981, Exhibit No. 1027, Pace et al., 2004, "The monoethyl ester of meconic acid is an active site Inhibitor of HCV NS5B RNA-dependent RNA polymerase," Bioorg. Med. Chem. Lett. 14: 3257-61, Filed Mar. 10, 2014.
Interference No. 105,981, Exhibit No. 1022, Carroll et al., 2003, "Inhibition of Hepatitis C Virus RNA Replication by 2'-Modified Nucleoside Analogs," J. Biol. Chem. 278: 11979-84, Filed Mar. 10, 2014.
Interference No. 105,981, Exhibit No. 1177, Madam Prothonotary Mireille Tabib's Order, dated Jan. 9, 2014, in Canada Federal Court, Docket T-1156-12, *Gilead Sciences, Inc. and Gilead Sciences Canada, Inc. v. Idenix Pharmaceuticals, Inc.*, Universita Degli Studi di Cagliari, L'Universite Montpellier II and Centre National de la Recherche Scientifique, Filed Mar. 10, 2014.
Interference No. 105,981, Exhibit No. 1239, Zhang et al., 2000, J. Comb. Chem. 2: 259-265, Filed Sep. 17, 2014.
Interference No. 105,871, Exhibit No. 1440, Certification of the English Translation of the Declaration of Tony Bouisset, signed May 6, 2013, Filed Nov. 6, 2013.
Interference No. 105,871, Exhibit No. 1438, Certification of the English Translation of the Declaration of Edith Badel, signed May 5, 2013, Filed Nov. 6, 2013.
Interference No. 105,871, Exhibit No. 1381, Email from Reference Services to Dr. Stewart dated Jun. 2, 2004., Filed Nov. 6, 2013.
Interference No. 105,871, Exhibit No. 1354, Email from Dr. Stewart to Professor Fleet and Dr. Jenkinson dated Feb. 8, 2005, Filed Nov. 6, 2013.
Interference No. 105,871, Exhibit No. 1353, Email from Dr. Stewart to Dr. Storer dated Feb. 3, 2005, Filed Nov. 6, 2013.
Interference No. 105,871, Exhibit No. 1352, Email attachment of Ex 1351, Filed Nov. 6, 2013.
Interference No. 105,871, Exhibit No. 1351, Email from Dr. Stewart to Dr. Jenkinson dated Feb. 2, 2005, Filed Nov. 6, 2013.
Interference No. 105,871, Exhibit No. 1350, Email from Dr. Stewart to Dr. Jenkinson dated Feb. 1, 2005, Filed Nov. 6, 2013.
Interference No. 105,871, Exhibit No. 1349, Email from Dr. Jenkinson to Dr. Stewart dated Jan. 28, 2005, Filed Nov. 6, 2013.
Interference No. 105,871, Exhibit No. 1347, Email from Dr. Jenkinson to Dr. Stewart dated Jan. 26, 2005, Filed Nov. 6, 2013.
Interference No. 105,871, Exhibit No. 1344, Email from Dr. Stewart to Dr. Jenkinson dated Jan. 12, 2005, Filed Nov. 6, 2013.
Interference No. 105,871, Exhibit No. 1342, Email from Dr. Jenkinson to Dr. Stewart dated Dec. 7, 2004, Filed Nov. 6, 2013.
Interference No. 105,871, Exhibit No. 1341, Email from Dr. Stewart to Dr. Jenkinson dated Dec. 7, 2004, Filed Nov. 6, 2013.
Interference No. 105,871, Exhibit No. 1340, Email from Dr. Stewart to Professor Fleet and Dr. Storer dated Nov 30, 2004, Filed Nov. 6, 2013.
Interference No. 105,871, Exhibit No. 1339, Email attachment of Ex 1338, Filed Nov. 6, 2013.
Interference No. 105,871, Exhibit No. 1338, Email from Dr. Stewart to Professor Fleet dated Nov. 29, 2004, Filed Nov. 6, 2013.
Interference No. 105,871, Exhibit No. 1322, Filed Nov. 6, 2013 Email correspondence between George Fleet and Alistair Stewart dated May 9, 2004, Filed Nov. 6, 2013.
Interference No. 105,871, Exhibit No. 1321, Email correspondence between George Fleet and Alistair Stewart dated May 12, 2004, Filed Nov. 6, 2013.
Interference No. 105,871, Exhibit No. 1268, Printed copy of NMR analysis dated May 24, 2004, Filed Nov. 6, 2013.
Interference No. 105,871, Exhibit No. 1254, English version of Resume of Audrey Chappe-Dumas, Filed Nov. 6, 2013.
Interference No. 105,871, Exhibit No. 1253, Resume of Audrey Chappe-Dumas, Filed Nov. 6, 2013.
Interference No. 105,871, Exhibit No. 1243, English translation of Resume of Edith Badel, Filed Nov. 6, 2013.
Interference No. 105,871, Exhibit No. 1242, Resume of Edith Badel, Filed Nov. 6, 2013.
Interference No. 105,871, Exhibit No. 1640, Excerpt from Notebook No. 2, p. 143 of Jean-Francois Griffon, Filed Nov. 6, 2013.
Interference No. 105,871, Exhibit No. 1598, NMR spectrum of Alistair Stewart dated Jan. 21, 2005, Filed Nov. 6, 2013.
Interference No. 105,871, Exhibit No. 1597, NMR spectrum of Alistair Stewart dated Jan. 21, 2005, Filed Nov. 6, 2013.
Interference No. 105,871, Exhibit No. 1596, NMR spectrum of Alistair Stewart dated Jan. 24, 2005, Filed Nov. 6, 2013.
Interference No. 105,871, Exhibit No. 1595, NMR spectrum of Alistair Stewart dated Jan. 18, 2005, Filed Nov. 6, 2013.
Interference No. 105,871, Exhibit No. 1594, NMR spectrum of Alistair Stewart dated Jan. 21, 2005, Filed Nov. 6, 2013.
Interference No. 105,871, Exhibit No. 1593, NMR spectrum of Alistair Stewart dated Jan. 18, 2005, Filed Nov. 6, 2013.
Interference No. 105,871, Exhibit No. 1592, NMR spectrum of Alistair Stewart dated Jan. 18, 2005, Filed Nov. 6, 2013.
Interference No. 105,871, Exhibit No. 1591, NMR spectrum of Alistair Stewart dated Jan. 21, 2005, Filed Nov. 6, 2013.
Interference No. 105,871, Exhibit No. 1590, NMR spectrum of Alistair Stewart dated Dec. 20, 2004, Filed Nov. 6, 2013.
Interference No. 105,871, Exhibit No. 1589, NMR spectrum of Alistair Stewart dated Dec. 20, 2004, Filed Nov. 6, 2013.
Interference No. 105,871, Exhibit No. 1588, NMR spectrum of Alistair Stewart dated Dec. 22, 2004, Filed Nov. 6, 2013.
Interference No. 105,871, Exhibit No. 1587, NMR spectrum of Alistair Stewart dated Dec. 22, 2004, Filed Nov. 6, 2013.
Interference No. 105,871, Exhibit No. 1586, NMR spectrum of Alistair Stewart dated Jan. 4, 2005, Filed Nov 6, 2013.
Interference No. 105,871, Exhibit No. 1585, NMR spectrum of Alistair Stewart dated Dec. 13, 2004, Filed Nov. 6, 2013.
Interference No. 105,871, Exhibit No. 1584, NMR spectrum of Alistair Stewart dated Dec. 13, 2004, Filed Nov. 6, 2013.
Interference No. 105,871, Exhibit No. 1583, NMR spectrum of Alistair Stewart labeled "Idenix/AS-081-024-01-Fr-28-42", Filed Nov. 6, 2013.
Interference No. 105,871, Exhibit No. 1582, NMR spectrum of Alistair Stewart labeled "Idenix/AS-081-024-01-Fr-8-16", Filed Nov. 6, 2013.
Interference No. 105,871, Exhibit No. 1581, NMR spectrum of Alistair Stewart dated Dec. 13, 2004., Filed Nov. 6, 2013.
Interference No. 105,871, Exhibit No. 1580, NMR spectrum of Alistair Stewart dated Dec. 13, 2004, Filed Nov. 6, 2013.
Interference No. 105,871, Exhibit No. 1579, NMR spectrum of Alistair Stewart dated Dec. 13, 2004, Filed Nov. 6, 2013.
Interference No. 105,871, Exhibit No. 1578, NMR spectrum of Alistair Stewart dated Dec. 7, 2004, Filed Nov. 6, 2013.
Interference No. 105,871, Exhibit No. 1577, NMR spectrum of Alistair Stewart dated Dec. 7, 2004, Filed Nov. 6, 2013.
Interference No. 105,871, Exhibit No. 1576, NMR spectrum of Alistair Stewart dated Dec. 7, 2004, Filed Nov. 6, 2013.
Interference No. 105,871, Exhibit No. 1575, NMR spectrum of Alistair Stewart dated Dec. 7, 2004, Filed Nov. 6, 2013.
Interference No. 105,871, Exhibit No. 1574, NMR spectrum of Alistair Stewart dated Dec. 7, 2004, Filed Nov. 6, 2013.
Interference No. 105,871, Exhibit No. 1573, NMR spectrum of Alistair Stewart dated Dec. 7, 2004, Filed Nov. 6, 2013.
BR Application No. PI 0410846-9 Blanver Third Party Observation dated Apr. 26, 2018.
BR Application No. PI 0410846-9 Blanver Third Party Observation dated Apr. 26, 2018 (English translation).

(56) References Cited

OTHER PUBLICATIONS

BR Application No. PI 0410846-9 Abifina Third Party Observation dated May 24, 2018 (English translation).
BR Application No. PI 0410846-9 Abia Third Party Observation dated Jun. 26, 2018.
BR Application No. PI 0410846-9 Office Action dated Apr. 12, 2018 (English translation).
BR Application No. PI 0410846-9 Abia Third Party Observation dated Jun. 26, 2018 (English translation).
BR Application No. PI 0410846-9 Office Action Response dated Jul. 16, 2018 with Attachments.
*Initiative for Medicines, Access & Knowledge (I-MAK), Inc. v. Gilead Pharmasset LLC*, IPR2018-00123, Petition for Inter Partes Review dated Nov. 9, 2017.
*Initiative for Medicines, Access & Knowledge (I-MAK), Inc. v. Gilead Pharmasset LLC*, IPR2018-00123, Declaration of Joseph M. Fortunak, Ph.D. dated Nov. 9, 2017.
*Initiative for Medicines, Access & Knowledge (I-MAK), Inc. v. Gilead Pharmasset LLC*, IPR2018-00125, Petition for Inter Partes Review dated Oct. 30, 2017.
*Initiative for Medicines, Access & Knowledge (I-MAK), Inc. v. Gilead Pharmasset LLC*, IPR2018-00125, Declaration of Joseph M. Fortunak, Ph.D. dated Oct. 30, 2017.
*Initiative for Medicines, Access & Knowledge (I-MAK), Inc. v. Gilead Pharmasset LLC*, IPR2018-00126, Petition for Inter Partes Review dated Nov. 2, 2017.
*Initiative for Medicines, Access & Knowledge (I-MAK), Inc. v. Gilead Pharmasset LLC*, IPR2018-00126, Declaration of Joseph M. Fortunak, Ph.D. dated Nov. 2, 2017.
Congiatu et al., "Novel Potential Anticancer Naphthyl Phosphoramidates of BVdU: Separation of Diastereoisomers and Assignment of the Absolute Configuration of the Phosphorus Center," J. Med. Chem. 49:452-455 (2006).
McGuigan et al., "Nucleoside Analogues Previously Found to Be Inactive Against HIV May Be Activated by Simple Chemical Phosphorylation," FEBS 322:249-252 (1993).
McGuigan et al., "Certain Phosphoramidate Derivatives of Dideoxy Uridine (ddU) Are Active Against HIV and Successfully By-pass Thymidine Kinase," FEBS 351:11-14 (1994).
Codington et al., "Nucleosides. XIV. Synthesis of 2'-Deoxy-2'-Fluorouridine," J. Am. Chem. Soc. 83:5030-5031 (1961).
EP Application No. 13152340.9 Claims Granted Jun. 29, 2016.
EP Application No. 13152340.9 (EP Patent No. 2604620) Opposition by European Public Health Alliance (EPHA) et al. dated Mar. 27, 2017.
EP Application No. 13152340.9 (EP Patent No. 2604620) Opposition by Medecins du Monde et al. dated Mar. 27, 2017.
EP Application No. 13152340.9 (EP Patent No. 2604620) Opposition by Medici Senza Frontiere Onlus et al. dated Mar. 27, 2017.
EP Application No. 13152340.9 (EP Patent No. 2604620) Opposition by Richard Gillard dated Mar. 29, 2017.
AR Application No. P110102354 Office Action dated Jan. 26, 2015.
Bennua-Skalmowski et al., "A New Simple Nucleoside Synthesis," Tetrahedron Letters 36(43):7845-7848 (1995).
Martin et al., "Synthesis and Antiviral Activity of Monofluoro and Difluoro Analogues of Pyrimidine Deoxyribonucleosides Against Human Immunodeficiency Virus (HIV-1)," J. Med. Chem. 33:2137-2145 (1990).
Codington et al., "Nucleosides. XVIII. Synthesis of 2'-Fluorothymidine, 2'-Fluorodeoxyuridine, and Other 2'-Halogeno-2'-Deoxy Nucleosides," J. Org. Chem. 29:558-564 (1964).
Wright et al., "Nucleosides. LX. Fluorocarbohydrates. XXII. Synthesis of 2-Deoxy-2-fluoro-D-arabinose and 9-(2-Deoxy-2-fluoro-alpha- and -beta-D-arabinofuranosyl)adenines," J. Org. Chem. 34:2632-2636 (1969).
Ranganathan, "Modification of the 2'-Position of Purine Nucleosides: Synthesis of 2'-alpha-Substituted-2'-deoxyadenosine Analogs," Tetrahedron Letters 15:1291-1294 (1977).

Watanabe et al., "Nucleosides. 123. Synthesis of Antiviral Nucleosides: 5-Substituted 1-(2-Deoxy-2-halogeno-beta-D-arabinofuranosyl)cytosines and -uracils. Some Structure-Activity Relationships," J. Med. Chem. 26:152-156 (1983).
Ma et al., "Structure-Activity Relationships of 1-(2-Deoxy-2-fluoro-beta-L-arabino-furanosyl)pyrimidine Nucleosides as Anti-Hepatitis B Virus Agents," J. Med. Chem. 39:2835-2843 (1996).
Noble & Goa, "Adis Drug Evaluation: Gemcitabine: A Review of Its Pharmacology and Clinical Potential in Non-Small Cell Lung Cancer and Pancreatic Cancer," Drugs 54(3):447-472 (1997).
Soares et al., "Estrategias para a Sintese de Desoxinucleosideos," Quim. Nova 24:206-219 (2001).
CN Application No. 200480019148.4, Invalidation Request by Fujian Cosunter Pharmaceutical Co., Ltd. dated Aug. 25, 2017, including English translation.
CN Application No. 200480019148.4, Gilead Pharmasset LLC Observations re Invalidation Request by Fujian Cosunter Pharmaceutical Co., Ltd. dated Oct. 9, 2017, including English translation.
CN Application No. 200480019148.4, Supplemental Invalidation Request by Fujian Cosunter Pharmaceutical Co., Ltd. dated Oct. 30, 2017, including English translation.
CN Application No. 200480019148.4, Fujian Cosunter Pharmaceutical Co., Gilead Pharmasset LLC Supplemental Observations re Invalidation Request by Ltd. dated 112/14/2017, including English translation.
CN Application No. 200480019148.4, Gilead Pharmasset LLC Post-Hearing Brief re Invalidation Request by Fujian Cosunter Pharmaceutical Co., Ltd. dated Feb. 13, 2018, including English translation.
CN Application No. 200480019148.4, Pharmaceutical Co., Ltd. (English) Final Amended Claims re Invalidation Request by Fujian Cosunter.
CN Application No. 200480019148.4, Invalidation Request by I-MAK dated May 4, 2017, including English translation.
CN Application No. 200480019148.4, First Supplemental Invalidation Request by I-MAK dated May 27, 2017, including English translation.
CN Application No. 200480019148.4, Gilead Pharmasset LLC Observations re Invalidation Request by I-MAK dated May 19, 2017, including English translation.
CN Application No. 200480019148.4, Second Supplemental Invalidation Request by I-MAK dated Aug. 11, 2017, including English translation.
CN Application No. 200480019148.4, Gilead Pharmasset LLC Second Observations re Invalidation Request by I-MAK dated Sep. 26, 2017, including English translation.
CN Application No. 200480019148.4, Third Supplemental Invalidation Request by I-MAK dated Dec. 14, 2017, including English translation.
CN Application No. 200480019148.4, Gilead Pharmasset LLC Post-Hearing Brief re Invalidation Request by I-MAK dated Feb. 13, 2018, including English translation.
CN Application No. 200480019148.4, Final Amended Claims re Invalidation Request by I-MAK (English).
Curriculum Vitae of Dr. Richard L. Mackman, CChem MRSC.
Curriculum Vitae of Eisuke Murakami.
EP Application No. 13152340.9, Written Submission Before Oral Proceedings in the Opposition Against Patent EP2604620 from Medecins du Monde, Medici Senza Frontiere Onlus, and European Public Health Alliance dated Jul. 12, 2018.
EP Application No. 13152340.9, Written Submission Before Oral Proceedings in the Opposition Against Patent EP2604620 from Re. Gillard dated Jul. 13, 2018.
Interference No. 105,981, Exhibit No. 2069, Yi, M., et al., Subgenomic Hepatitis C Virus Replicons Inducing Expression of a Secreted Enzymatic Reporter Protein, Virol 304:197-210 (2002), Filed Sep. 18, 2014.
Interference No. 105,981, Exhibit No. 2127, Interference No. 105,871, Paper No. 713, Idenix Exhibit 1447 (entitled (by Idenix): "Substitute Certified English Translation of the Declaration of Elodie Pecheux, signed May 29, 2013"), Filed Sep. 18, 2014.

(56) References Cited

OTHER PUBLICATIONS

Interference No. 105,981, Exhibit No. 2083, U.S. Pat. No. 8,299,038 (U.S. Appl. No. 12/504,601) file history—Apr. 25, 2011 Response Under 37 C.F.R. § 1.111, Filed Mar. 10, 2014.
Interference No. 105,981, Exhibit No. 2078, Interference No. 105,871, Paper No. 926, Idenix Exhibit 1645, Deposition Transcript of Dr. Alistair Stewart dated Jun. 19, 2013 (with errata sheet), Filed Mar. 10, 2014.
Interference No. 105,981, Exhibit No. 2170, Interference No. 105,871, Paper No. 404, Idenix Exhibit 1190 (entitled (by Idenix): "Deposition Transcript of Jeffrey Scott Glenn, M.D., Ph.D., dated Jul. 31, 2012 (with errata sheet), executed Aug. 31, 2012"), Filed Sep. 18, 2014.
Interference No. 105,981, Exhibit No. 2001, Declaration of Stanislaw F. Wnuk, Ph.D., Filed Mar. 10, 2014.
Interference No. 105,981, Exhibit No. 2001, Substitute Declaration of Stanislaw F. Wnuk, Ph.D., Filed Mar. 31, 2014.
Interference No. 105,981, Exhibit No. 2125, Interference No. 105,871, Paper No. 695, Idenix Exhibit 1428 (entitled (by Idenix): "Substitute Declaration of Adel Moussa, signed Jun. 3, 2013"), Filed May 23, 2014.
Interference No. 105,981, Exhibit No. 2097, Storer U.S. Appl. No. 10/608,907 ("S4") file history—Aug. 20, 2007 Amendment and Response, Filed May 23, 2014.
Interference No. 105,981, Exhibit No. 2067, Tan, S.-L, et al., Hepatitis C Therapeutics: Current Status and Emerging Strategies, Nat Rev Drug Discov 1:867-881 (2002), Filed Mar. 31, 2014.
Interference No. 105,981, Exhibit No. 2124, Interference No. 105,871, Paper No. 691, Idenix Exhibit 1424 (entitled (by Idenix): "Substitute Declaration of Elodie Pecheux, signed May 29, 2013"), Filed Sep. 18, 2014.
Interference No. 105,981, Exhibit No. 2188, Transcript of Deposition of Christoph Seeger, Ph.D., taken Jun. 25, 2014, Filed Sep. 18, 2014.
Interference No. 105,981, Exhibit No. 2157, Galmarini, C.M., et al., Nucleoside Analogues: Mechanisms of Drug Resistance and Reversal Strategies, Leukemia, vol. 15, pp. 875-890 (2001), Filed Sep. 18, 2014.
Interference No. 105,981, Exhibit No. 2002, Stanislaw F. Wnuk, Ph.D. curriculum vitae, Filed Sep. 18, 2014.
Interference No. 105,981, Exhibit No. 2038, Interference No. 105,871, Paper No. 685, Idenix Exhibit 1418 (entitled (by Idenix): "Reply from Paul Coe to Dick Storer"), Filed Mar. 10, 2014.
Interference No. 105,981, Exhibit No. 2174, Interference No. 105,871, Paper No. 18, Order-Authorizing Motions, Entered Apr. 24, 2012, Filed Sep. 18, 2014.
Interference No. 105,981, Exhibit No. 2139, Transcript of Deposition of Stanislaw F. Wnuk, Ph.D., taken May 9, 2014, Filed May 23, 2014.
Interference No. 105,981, Exhibit No. 2110-14, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2126, Interference No. 105,871, Paper No. 696, Idenix Exhibit 1429 (entitled (by Idenix): "Substitute Declaration of Richard Storer, D.Phil., signed May 31, 2013"), Filed May 23, 2014.
Interference No. 105,981, Exhibit No. 2016, Singh, R. P. & Shreeve, J. M., Recent Advances in Nucleophilic Fluorination Reactions of Organic Compounds Using Deoxofluor and DAST, Synthesis, No. 17, pp. 2561-2578 (2002), Filed Mar. 10, 2014.
Interference No. 105,981, Exhibit No. 2068, Walton, E, et al., Branched-Chain Sugar Nucleosides. A New Type of Biologically Active Nucleoside, J Amer Chem Soc 88:4524 (1966), Filed May 23, 2014.
Interference No. 105,981, Exhibit No. 2154, Interference No. 105,871, Paper No. 718, Idenix Exhibit 1452 (entitled (by Idenix): "Brief Resume/Biography of Adel Moussa"), Filed May 23, 2014.
Interference No. 105,981, Exhibit No. 2121, Clark Exhibit 2121, Filed Sep. 18, 2014.
Interference No. 105,981, Exhibit No. 2120, Clark Exhibit 2120, Filed Sep. 18, 2014.
Interference No. 105,981, Exhibit No. 2119, Clark Exhibit 2119, Filed Sep. 18, 2014.
Interference No. 105,981, Exhibit No. 2041, Clark Exhibit 2041, Filed Mar. 10, 2014.
Interference No. 105,981, Exhibit No. 2040, Clark Exhibit 2040, Filed Mar. 10, 2014.
Interference No. 105,981, Exhibit No. 2024, Clark Exhibit 2024, Filed Mar. 10, 2014.
Interference No. 105,981, Exhibit No. 2181, Clark Exhibit 2181, Filed Sep. 18, 2014.
Interference No. 105,981, Exhibit No. 2087, Clark Exhibit 2087, Filed May 23, 2014.
Interference No. 105,981, Exhibit No. 2021, Clark Exhibit 2021, Filed Mar. 10, 2014.
Interference No. 105,981, Exhibit No. 2090, Clark Exhibit 2090, Filed Sep. 18, 2014.
Interference No. 105,981, Exhibit No. 2075, Clark Exhibit 2075, Filed Mar. 10, 2014.
Interference No. 105,981, Exhibit No. 2047, Berge, S.M., et al., Pharmaceutical Salts, J. Pharmaceutical Sciences, vol. 36, No. 1, pp. 1-19 (1977), Filed Mar. 10, 2014.
Interference No. 105,981, Exhibit No. 2172, Interference No. 105,871, Paper No. 405, Idenix Exhibit 1191 (entitled (by Idenix): "Deposition Transcript of Barry M. Trost, Ph.D., dated Aug. 2, 2012 (with errata sheet), executed Aug. 31, 2012"), Filed May 23, 2014.
Interference No. 105,981, Exhibit No. 2011, Clark U.S. Appl. No. 11/854,218 ("C3") as filed Sep. 12, 2007, Filed Mar. 10, 2014.
Interference No. 105,981, Exhibit No. 2010, Clark U.S. Appl. No. 10/828,753 ("C2") as filed Apr. 21, 2004, Filed Mar. 10, 2014.
Interference No. 105,981, Exhibit No. 2109, Lalezari, J., et al., Potent Antiviral Activity of the HCV Nucleoside Polymerase Inhibitor, R7128, in Combination with PEG-IFN α-2a and Ribavirin, 43rd Annual Meeting of EASL, Milan, Italy, Apr. 23-27, 2008, Filed Mar. 10, 2014.
Interference No. 105,981, Exhibit No. 2076, Eldrup, A.B., et al., Structure Activity Relationship of 2' Modified Nucleosides for Inhibition of Hepatitis C Virus, Oral Session V, Hepatitis C Virus, Flaviviridae; 16th International Conference on Antiviral Research (Apr. 27, 2003, Savannah, Ga.) (Exhibit 96 to the Aug. 31, 2013 Declaration of Prof. Dr. Chris Meier, filed by Idenix in Oslo District Court case 12-155575TVI-OTIR/01), Filed Mar. 10, 2014.
Interference No. 105,981, Exhibit No. 2057, International Patent Publication No. WO 02/18404 A2, Filed Mar. 10, 2014.
Interference No. 105,981, Exhibit No. 2129, Interference No. 105,871, Paper No. 804, Idenix Exhibit 1540 (entitled (by Idenix): "Substitute Certified English Translation of the Declaration of Audrey Chappe- Dumas, signed May 30, 2013"), Filed Sep. 18, 2014.
Interference No. 105,981, Exhibit No. 2091, U.S. Pat. No. 7,625,875 (U.S. Appl. No. 11/005,444) file history—Apr. 4, 2008 Response, Filed Sep. 18, 2014.
Interference No. 105,981, Exhibit No. 2122, Interference No. 105,871, Paper No. 669, Idenix Exhibit 1402 (entitled (by Idenix): "Substitute Declaration of Audrey Chappe-Dumas, signed May 30, 2013"), Filed Sep. 18, 2014.
Interference No. 105,981, Exhibit No. 2077, Walker, M.P., et. al., Hepatitis C virus therapies: current treatments, targets and future perspectives, Antiviral Chemistry & Chemotherapy, vol. 14, No. 1, pp. 1-21 (Jan. 2003), Filed Mar. 10, 2014.
Interference No. 105,981, Exhibit No. 2080, Interference No. 105,871, Paper No. 454, Substitute Sommadossi Motion 8 [sic, 9], Filed Jul. 18, 2013, Filed Sep. 18, 2014.
Interference No. 105,981, Exhibit No. 2099-10, Storer U.S. Appl. No. 10/608,907 ("S4") as filed Jun. 27, 2003, Filed Mar. 10, 2014.
Interference No. 105,981, Exhibit No. 2099-9, Storer U.S. Appl. No. 10/608,907 ("S4") as filed Jun. 27, 2003, Filed Mar. 10, 2014.
Interference No. 105,981, Exhibit No. 2099-8, Storer U.S. Appl. No. 10/608,907 ("S4") as filed Jun. 27, 2003, Filed Mar. 10, 2014.
Interference No. 105,981, Exhibit No. 2099-7, Storer U.S. Appl. No. 10/608,907 ("S4") as filed Jun. 27, 2003, Filed Mar. 10, 2014.
Interference No. 105,981, Exhibit No. 2099-6, Storer U.S. Appl. No. 10/608,907 ("S4") as filed Jun. 27, 2003, Filed Mar. 10, 2014.

(56) References Cited

OTHER PUBLICATIONS

Interference No. 105,871, Exhibit No. 1487, Certification of the English Translation of Notebook 7 of Jerome Peyronnet, Filed Nov. 6, 2013.
Interference No. 105,871, Exhibit No. 1486, Certification of the English Translation of Notebook 7 of Edith Badel, Filed Nov. 6, 2013.
Interference No. 105,871, Exhibit No. 1485, Certification of the English Translation of Notebook 6 of Edith Badel, Filed Nov. 6, 2013.
Interference No. 105,871, Exhibit No. 1484, Certification of the English Translation of Notebook 4 of Tony Bouisset, Filed Nov. 6, 2013.
Interference No. 105,871, Exhibit No. 1483, Certification of the English Translation of Notebook 4 of Audrey Chappe-Dumas, Filed Nov. 6, 2013.
Interference No. 105,871, Exhibit No. 1482, Certification of the English Translation of Notebook 3 of Tony Bouisset, Filed Nov. 6, 2013.
Interference No. 105,871, Exhibit No. 1481, Certification of the English Translation of Notebook 3 of Clement Counor, Filed Nov. 6, 2013.
Interference No. 105,871, Exhibit No. 1404, Jul. 23, 2002 Email from Gilles Gosselin to Dick Storer, Filed Nov. 6, 2013.
Interference No. 105,871, Exhibit No. 1401, English Translation of French Legal Code Establishing Public Holidays, Filed Nov. 6, 2013.
Interference No. 105,871, Exhibit No. 1400, French Legal Code Establishing Public Holidays, Filed Nov. 6, 2013.
Interference No. 105,871, Exhibit No. 1393, Email from Reference Services to Dr. Stewart dated Jan. 24, 2004, Filed Nov. 6, 2013.
Interference No. 105,871, Exhibit No. 1391, Email from Reference Services to Dr. Stewart dated Nov. 18, 2004, Filed Nov. 6, 2013.
Interference No. 105,871, Exhibit No. 1389, Email from Reference Services to Dr. Stewart dated Nov. 17, 2004, Filed Nov. 6, 2013.
Interference No. 105,871, Exhibit No. 1387, Email from Reference Services to Dr. Stewart dated Nov. 16, 2004, Filed Nov. 6, 2013.
Interference No. 105,871, Exhibit No. 1385, Email from Reference Services to Dr. Stewart dated Nov. 10, 2004, Filed Nov. 6, 2013.
Interference No. 105,871, Exhibit No. 1383, Email from Reference Services to Dr. Stewart dated Sep. 1, 2004, Filed Nov. 6, 2013.
Interference No. 105,871, Exhibit No. 1379, Email from Dr. Jenkinson to Dr. Stewart dated Apr. 15, 2005, Filed Nov. 6, 2013.
Interference No. 105,871, Exhibit No. 1356, Email attachment of Ex 1354, Filed Nov. 6, 2013.
Interference No. 105,871, Exhibit No. 1602, NMR spectrum of Alistair Stewart dated Jan. 6, 2005, Filed Nov. 6, 2013.
Interference No. 105,871, Exhibit No. 1601, NMR spectrum of Alistair Stewart labeled "AS-081-051-01", Filed Nov. 6, 2013.
Interference No. 105,871, Exhibit No. 1600, NMR spectrum of Alistair Stewart dated Jan. 24, 2005, Filed Nov. 6, 2013.
Interference No. 105,871, Exhibit No. 1515, NMR spectrum of compound 29 of Scheme C acquired on Nov. 12, 2004, Filed Nov. 6, 2013.
Interference No. 105,871, Exhibit No. 1514, NMR spectrum of compound 7 of Scheme B acquired on Nov. 6, 2004, Filed Nov. 6, 2013.
Interference No. 105,871, Exhibit No. 1513, NMR spectrum of compound 10 of Scheme B acquired on Oct. 27, 2004, Filed Nov. 6, 2013.
Interference No. 105,871, Exhibit No. 1512, NMR spectrum of compound 10 of Scheme B acquired on Oct. 26, 2004, Filed Nov. 6, 2013.
Interference No. 105,871, Exhibit No. 1511, IR spectrum of compound 14 of Scheme B acquired on Oct. 26, 2004, Filed Nov. 6, 2013.
Interference No. 105,871, Exhibit No. 1510, IR spectrum of compound 10 of Scheme B acquired on Oct. 25, 2004, Filed Nov. 6, 2013.
Interference No. 105,871, Exhibit No. 1509, NMR spectrum of compound 20 of Scheme B acquired on Oct. 19, 2004, Filed Nov. 6, 2013.
Interference No. 105,871, Exhibit No. 1508, NMR spectrum of compound 20 of Scheme B acquired on Oct. 6, 2004, Filed Nov. 6, 2013.
Interference No. 105,871, Exhibit No. 1507, NMR spectrum of compound 7 of Scheme B acquired on Sep. 17, 2004, Filed Nov. 6, 2013.
Interference No. 105,871, Exhibit No. 1506, NMR spectrum of compound 14 of Scheme B acquired on Sep. 9, 2004, Filed Nov. 6, 2013.
Interference No. 105,871, Exhibit No. 1505, NMR spectrum of compound 14 of Scheme B acquired on Sep. 1, 2004, Filed Nov. 6, 2013.
Interference No. 105,871, Exhibit No. 1504, NMR spectrum of compound 14 of Scheme B acquired on Aug. 14, 2004, Filed Nov. 6, 2013.
Interference No. 105,871, Exhibit No. 1503, NMR spectrum of compound 5 of Scheme G2 acquired on Aug. 10, 2004, Filed Nov. 6, 2013.
Interference No. 105,871, Exhibit No. 1502, NMR spectrum of compound 6 of Scheme G2 acquired on Jul. 23, 2004, Filed Nov. 6, 2013.
Interference No. 105,871, Exhibit No. 1480, Certification of the English Translation of Notebook 3 of Audrey Chappe-Dumas, Filed Nov. 6, 2013.
Interference No. 105,871, Exhibit No. 1479, Certification of the English Translation of Notebook 2 of Jean François Griffon, Filed Nov. 6, 2013.
Interference No. 105,871, Exhibit No. 1478, Certification of the English Translation of Notebook 2 of Audrey Chappe-Dumas, Filed Nov. 6, 2013.
Interference No. 105,871, Exhibit No. 1477, Certification of the English Translation of Notebook 1 of Jean-François Griffon, Filed Nov. 6, 2013.
Interference No. 105,871, Exhibit No. 1476, Certification of the English Translation of the Curriculum Vitae of Tony Bouisset, Filed Nov. 6, 2013.
Interference No. 105,871, Exhibit No. 1475, Certification of the English Translation of the Curriculum Vitae of Elodie Pecheux, Filed Nov. 6, 2013.
Interference No. 105,871, Exhibit No. 1474, Certification of the English Translation of the Curriculum Vitae of Edith Badel, Filed Nov. 6, 2013.
Interference No. 105,871, Exhibit No. 1473, Certification of the English Translation of the Curriculum Vitae of Clement Counor, Filed Nov. 6, 2013.
Interference No. 105,871, Exhibit No. 1472, Certification of the English Translation of the Declaration of Jean-François Griffon, signed May 3, 2013, Filed Nov. 6, 2013.
Interference No. 105,871, Exhibit No. 1467, Jan. 6, 2005 shipping form from the Laboratoire de Chimie Organique Biomoleculaire de Synthese at Laboratoire Cooperatif Idenix-CNRS-UL II to Adel Moussa, Filed Nov. 6, 2013.
Interference No. 105,871, Exhibit No. 1466, Dec. 10, 2004 shipping form from the Laboratoire de Chimie Drganique Biomoleculaire de Synthese at Laboratoire Cooperatif Idenix-CNRS-UL II to Adel Moussa, Filed Nov. 6, 2013.
Interference No. 105,871, Exhibit No. 1450, Certification of the English Translation of the Declaration of Jerome Peyronnet, signed May 6, 2013, Filed Nov. 6, 2013.
Interference No. 105,871, Exhibit No. 1448, Certification of the English Translation of the Declaration of Jerome Peyronnet, signed May 6, 2013, Filed Nov. 6, 2013.
Interference No. 105,871, Exhibit No. 1444, Certification of the English Translation of the Declaration of Gilles Lhenry, signed May 6, 2013, Filed Nov. 6, 2013.
Interference No. 105,871, Exhibit No. 1442, Certification of the English Translation of the Declaration of Clement Counor, signed May 2, 2013, Filed Nov. 6, 2013.
Interference No. 105,871, Exhibit No. 1355, Email attachment of Ex 1354, Filed Nov. 6, 2013.

(56) References Cited

OTHER PUBLICATIONS

Interference No. 105,871, Exhibit No. 1328, Email correspondence between George Fleet, Richard Storer and Alistair Stewart dated Dec. 12, 2004, Filed Nov. 6, 2013.
Interference No. 105,871, Exhibit No. 1325, Email correspondence between George Fleet, Sarah Jenkinson and Richard Storer dated Oct. 22, 2004, Filed Nov. 6, 2013.
Interference No. 105,871, Exhibit No. 1324, Letter from Adel Moussa to George Fleet dated Jul. 9, 2004, Filed Nov. 6, 2013.
Interference No. 105,871, Exhibit No. 1323, Email correspondence between George Fleet and Richard Storer dated Jun. 18 and 20, 2004, Filed Nov. 6, 2013.
Interference No. 105,871, Exhibit No. 1274, Resume of Jean-François Griffon, Filed Nov. 6, 2013.
Interference No. 105,871, Exhibit No. 1626, Declaration of Dylan Blaney, signed Jun. 3, 2013, Filed Nov. 6, 2013.
Interference No. 105,871, Exhibit No. 1664, Handwritten notes from Clark's attorneys, Erica Norey and Gabrielle Markeson, on Jun. 14, 2013, Filed Nov. 6, 2013.
Interference No. 105,871, Exhibit No. 1568, NMR spectra of Jingyang Wang dated Apr. 6, 2005, Filed Nov. 6, 2013.
Interference No. 105,871, Exhibit No. 1373, Email from Dr. Stewart to Dr. Jenkinson dated Mar. 24, 2005, Filed Nov. 6, 2013.
Interference No. 105,871, Exhibit No. 1360, Email attachment of Ex 1357, Filed Nov. 6, 2013.
Interference No. 105,871, Exhibit No. 1358, Email attachment of Ex 1357, Filed Nov. 6, 2013.
Interference No. 105,871, Exhibit No. 1228, English Translation of Notebook 7 of Jerome Peyronnet, Filed Nov. 6, 2013.
Interference No. 105,871, Exhibit No. 1227, Notebook 7 of Jerome Peyronnet, Filed Nov. 6, 2013.
Interference No. 105,871, Exhibit No. 1064, Husson van Vilet, 1990, Biologicals 18: 25-27, Filed Nov. 6, 2013.
Interference No. 105,871, Exhibit No. 1048, Marshall, 2000, Science 290: 1870-71, Filed Nov. 6, 2013.
Interference No. 105,871, Exhibit No. 1007, Corrected Filing Receipt, dated Jan. 17, 2008, from the File History of Sommadossi et al., U.S. Appl. No. 60/392,350, filed Jun. 28, 2002, Filed Nov. 6, 2013.
Interference No. 105,871, Exhibit No. 1009, Filing Receipt, dated Jul. 17, 2008, from the File History of Sommadossi et al., U.S. Appl. No. 12/131,868, filed Jun. 2, 2008, Filed Nov. 6, 2013.
Interference No. 105,871, Exhibit No. 1158, Corrected Filing Receipt, dated May 22, 2009, from the File History of Sommadossi et al., U.S. Appl. No. 12/131,868, filed Jun. 2, 2008, Filed Nov. 6, 2013.
Interference No. 105,871, Exhibit No. 1157, Updated Filing Receipt, dated Sep. 25, 2008, from the File History of Sommadossi et al., U.S. Appl. No. 12/131,868, filed Jun. 2, 2008, Filed Nov. 6, 2013.
Interference No. 105,871, Exhibit No. 1209, Sommadossi Objections to Evidence 1, served Jun. 13, 2012, Filed Nov. 6, 2013.
Interference No. 105,871, Exhibit No. 1150, Szuromi (ed.), "Exploring HCV Replication," 1999, Science 285: 9, Filed Nov. 6, 2013.
Interference No. 105,871, Exhibit No. 1106, Cox et al., 1993, Principles of Biochemistry, p. 330, Filed Nov. 6, 2013.
Interference No. 105,871, Exhibit No. 1105, The Merck Index, 2001, 13th ed., 4401, Filed Nov. 6, 2013.
Interference No. 105,871, Exhibit No. 1161, Stryer, 1981, Biochemistry (W.H Freeman & Co., New York), Chapter 22:Biosynthesis of Nucleotides, pp. 511-538, Filed Nov. 6, 2013.
Interference No. 105,871, Exhibit No. 1017, Sommadossi et al., International Patent Application Publication No. WO 01/92282, published Dec. 6, 2001, Filed Nov. 6, 2013.
Interference No. 105,871, Exhibit No. 1172, filed Apr. 21, 2004, Office Action, dated Mar. 30, 2007, from the File History of Clark U.S. Appl. No. 10/828,753, Filed Nov. 6, 2013.
Interference No. 105,871, Exhibit No. 1248, Herdewijn et al., 1989, Nucleosides Nucleotides 8: 65-96, Filed Nov. 6, 2013.
Interference No. 105,871, Exhibit No. 1171, Second Preliminary Amendment, dated Feb. 26, 2007, from the File History of Clark U.S. Appl. No. 10/828,753, filed Apr. 21, 2004, Filed Nov. 6, 2013.

Interference No. 105,871, Exhibit No. 1648, Deposition Transcript of Audrey Chappe-Dumas dated Jul. 2, 2013 (with errata sheet), Filed Nov. 6, 2013.
Interference No. 105,871, Exhibit No. 1187, Chu, C. K; Baker, D. C., Eds., 1993, Nucleosides and Nucleotides as Antitumor and Antiviral Agents (Plenum Press, New York), pp. 23-53, Filed Nov. 6, 2013.
Interference No. 105,871, Exhibit No. 1650, Deposition Transcript of Jerome Peyronnet dated Jul. 3, 2013 (with errata sheet), Filed Nov. 6, 2013.
Interference No. 105,871, Exhibit No. 1464, Nov. 18, 2004 email correspondence between Adel Moussa, Alistair Stewart and Ben Mayes, Filed Nov. 6, 2013.
Interference No. 105,871, Exhibit No. 1240, Substitute Declaration of Sarah Jenkinson, signed May 30, 2013, Filed Nov. 6, 2013.
Interference No. 105,871, Exhibit No. 1179, Harnden, M. R., 1985, Approaches to Antiviral Agents pp. 57-82 and 94-99, Filed Nov. 6, 2013.
Interference No. 105,871, Exhibit No. 1163, Hudlicky and Pavlath (eds.), 1995, Chemistry of Organic Fluorine Compounds II, "Replacement of Oxygen by Fluorine," pp. 199-262, Filed Nov. 6, 2013.
Interference No. 105,871, Exhibit No. 1658, Deposition Transcript of Jean-Francois Griffon dated Jul. 12, 2013 (with errata sheet), Filed Nov. 6, 2013.
Interference No. 105,871, Exhibit No. 1137, Amendment dated Jun. 21, 2012, including Exhibits A-C, from the File History of Sommadossi et al., U.S. Appl. No. 12/131,868, filed Jun. 2, 2008, Filed Nov. 6, 2013.
Interference No. 105,871, Exhibit No. 1154, Clark Objections 2, served Jun. 29, 2012, Filed Nov. 6, 2013.
Interference No. 105,871, Exhibit No. 1380, Timesheets for Dr. Alistair Stewart, Filed Nov. 6, 2013.
Interference No. 105,871, Exhibit No. 1003, Curriculum Vitae of Stanley M. Lemon, Md., Filed Nov. 6, 2013.
Interference No. 105,871, Exhibit No. 1312, Notice for Idenix Discovery Research Retreat on Oct. 6-7, 2003, Filed Nov. 6, 2013.
Interference No. 105,871, Exhibit No. 1311, Email from Jean-François Griffon to Dick Storer dated Aug. 28, 2003 with attached Jul.-Aug. 2003 progress report, Filed Nov. 6, 2013.
Interference No. 105,871, Exhibit No. 1308, Email from Jean-François Griffon to Dick Storer dated Jun. 3, 2003 with attached May 2003 progress report, Filed Nov. 6, 2013.
Interference No. 105,871, Exhibit No. 1302, Email from Jean-François Griffon to Dick Storer dated Feb. 3, 2003 with attached Jan. 2003 progress report, Filed Nov. 6, 2013.
Interference No. 105,871, Exhibit No. 1296, Notice of Idenix Discovery Research Retreat, Filed Nov. 6, 2013.
Interference No. 105,871, Exhibit No. 1288, [Substitute] Printed copy of mass spectrometry data dated Feb. 25-26, 2004, Filed Nov. 6, 2013.
Interference No. 105,871, Exhibit No. 1285, [Substitute] Printed copy of mass spectrometry analysis dated May 7, 2003, Filed Nov. 6, 2013.
Interference No. 105,871, Exhibit No. 1555, NMR spectra of Jingyang Wang dated Mar. 4, 2005, Filed Nov. 6, 2013.
Interference No. 105,871, Exhibit No. 1554, NMR spectra of Jingyang Wang dated Mar. 4, 2005, Filed Nov. 6, 2013.
Wu, Modern Organic Synthetic Chemistry, pp. 19-57 (2006).
Wu, Modern Organic Synthetic Chemistry, Section 3.3, pp. 26-35 (2006) (English Translation).
Interference No. 105,871, Exhibit No. 2086, U.S. Appl. No. 11/005,469 file history—Dec. 14, 2007 Amendment, Filed Nov. 28, 2012.
Interference No. 105,871, Exhibit No. 2052, U.S. Pat. No. 7,591,789 (U.S. Appl. No. 12/005,937) file history—Oct. 11, 2010 Request for Continued Examination and Amendmen, Filed Nov. 28, 2012.
Interference No. 105,871, Exhibit No. 2030, Lal, G. Sankar, et al., Electrophilic NF Fluorinating Agents, Chem. Rev., vol. 96, pp. 1737-1755 (1996), Filed Nov. 28, 2012.
Interference No. 105,871, Exhibit No. 2148, Transcript of Deposition of Victor E Marquez, Ph.D., taken Jul. 15, 2013, Filed Nov. 7, 2013.
Interference No. 105,871, Exhibit No. 2133, 3rd Declaration of Victor E Marquez, Ph.D., Filed Nov. 7, 2013.

(56) References Cited

OTHER PUBLICATIONS

Interference No. 105,871, Exhibit No. 2025, Lalezari, J., et al., Potent Antiviral Activity of the HCV Nucleoside Polymerase Inhibitor, R7128, in Combination with PEG-IFN α-2a and Ribavirin, 43rd Annual Meeting of Easl, Milan, Italy, Apr. 23-27, 2008, Filed Nov. 28, 2012.
Interference No. 105,871, Exhibit No. 2073, U.S. Pat. No. 7,601,820 B2, Filed Nov. 28, 2012.
Interference No. 105,871, Exhibit No. 2146, Transcript of Deposition of Michael J. Otto, Ph.D., taken Jul. 11, 2013, Filed Nov. 7, 2013.
Interference No. 105,871, Exhibit No. 2044, International Pub. No. WO 02/18404 A2, Filed Nov. 28, 2012.
Interference No. 105,871, Exhibit No. 2065, Transcript of Deposition of Victor E Marquez, Ph.D., taken Jul. 27, 2012, Filed Nov. 28, 2012.
Interference No. 105,871, Exhibit No. 2088, U.S. Appl. No. 11/005,444 file history—Apr. 4, 2008 Amendment, Filed Nov. 28, 2012.
Interference No. 105,871, Exhibit No. 2141, International Pub. No. WO 2010/101967 A2, Filed Nov. 7, 2013.
Interference No. 105,871, Exhibit No. 2067, 2nd Declaration of Christoph Seeger, Ph.D., Filed Nov. 28, 2012.
Interference No. 105,871, Exhibit No. 2152, 4th Declaration of Victor E. Marquez, Ph.D., Filed Nov. 7, 2013.
Interference No. 105,871, Exhibit No. 2007, C1 File History—Jul. 11, 2005 Petition to Correct Inventorship, Filed Nov. 28, 2012.
Interference No. 105,871, Exhibit No. 2093, 2012 Transcript of Deposition of Victor E Marquez, Ph.D., taken Sep. 26, 2012, Filed Nov. 28, 2012.
Interference No. 105,871, Exhibit No. 2095, U.S. Pat. No. 5,118,672, Filed Nov. 28, 2012.
Interference No. 105,871, Exhibit No. 2028, International Pub. No. WO 01/90121 A2, Filed Nov. 28, 2012.
Interference No. 105,871, Exhibit No. 2157, Clark Objections 8 served Sep. 13, 2013, Filed Nov. 7, 2013.
Interference No. 105,871, Exhibit No. 2120, Declaration of Christina Schwarz, Filed Nov. 7, 2013.
Interference No. 105,871, Exhibit No. 2119, Declaration of Erica L Norey, Filed Nov. 7, 2013.
Interference No. 105,871, Exhibit No. 2118, Declaration of Steven C. Kline, Filed Nov. 7, 2013.
Interference No. 105,871, Exhibit No. 2115, Assignment from Jeremy Clark to Pharmasset, Ltd. dated May 6, 2004, Recorded at Reel 018067, Frame 0977, Filed Nov. 7, 2013.
Interference No. 105,871, Exhibit No. 2056, European Patent Appln. No. 03761744 file history—Apr. 16, 2012 Office Action, Filed Nov. 28, 2012.
Interference No. 105,871, Exhibit No. 2050, Walton, E., et al., Branched-Chain Sugar Nucleosides. A New Type of Bologically Active Nucleoside, Journal of the American Chemical Society, vol. 88, No. 19, pp. 4524-4525 (1966), Filed Nov. 28, 2012.
Interference No. 105,871, Exhibit No. 2061, Dec. 1, 2010 Mutual Non-Disclosure Agreement, Filed Nov. 28, 2012.
Interference No. 105,871, Exhibit No. 2029, International Pub. No. WO 01/92282 A2, Filed Nov. 28, 2012.
Interference No. 105,871, Exhibit No. 2041, Condit, R.C., Principles of Virology (Chapter 2), in Knipe, D.M. et al., eds., Fields Virology, Fifth Edition, Philadelphia, Lippincott Williams & Wilkins (2007), Filed Nov. 28, 2012.
Interference No. 105,871, Exhibit No. 2049, Stuyver, L.J., et al., Inhibition of the Subgenomic Hepatitis C Virus Replicon in Huh-7 Cells by 2'-deoxy-2'-fluorocytidine, Antimicrobial Agents and Chemotherapy, vol. 48, No. 2, pp. 351-654 (2004), Filed Nov. 28, 2012.
Interference No. 105,871, Exhibit No. 2099, Clark Objections 2 served Jun. 29, 2012, Filed Nov. 28, 2012.
Interference No. 105,871, Exhibit No. 2134, Hertel, Lw., et al., Synthesis of 2-Deoxy-2,2-difluoro-D-ribose and 2-Deoxy-2,2-difluoro-D-ribofuranosyl Nucleosides, J. Org. Chem., vol. 53, pp. 2406-2409 (1988), Filed Nov. 7, 2013.
Interference No. 105,871, Exhibit No. 2117, Certificate of Domestication of Pharmasset, Ltd. to Pharmasset, Inc. (a Delaware corporation) dated Jun. 8, 2004, Recorded at Reel 015833, Frame 0430, Filed Nov. 7, 2013.
Interference No. 105,871, Exhibit No. 2116, Assignment from Jeremy Clark to Pharmasset, Ltd. dated May 13, 2004, Recorded at Reel 015833, Frame 0267, Filed Nov. 7, 2013.
Interference No. 105,871, Exhibit No. 2103, Jeremy Clark Notebook No. 1058, pp. 25, 26, Filed Nov. 7 2013.
Interference No. 105,871, Exhibit No. 2085, Sommadossi S5 file history, Filed Nov. 28, 2012.
Interference No. 105,871, Exhibit No. 2055, S5 File History, Filed Nov. 28, 2012.
Interference No. 105,871, Exhibit No. 2100, Clark Objections 5 served Oct. 18, 2012, Filed Nov. 28, 2012.
Interference No. 105,871, Exhibit No. 2075, Briot, Anne, et al., Benzylsulfonyl: A Valuable Protecting and Deactivating Group in Phenol Chemistry, Tetrahedron Letters, vol. 44, pp. 965-967 (2003), Filed Nov. 28, 2012.
Interference No. 105,871, Exhibit No. 2063, Goldman, Bruce, Potential New Class of Drugs to Combat Hepatitis C Identified by Scientists, Stanford School of Medicine, http://med.stanford.edu/ism/2010/january/glenn.html (Jan. 20, 2010), Filed Nov. 28, 2012.
Interference No. 105,871, Exhibit No. 2035, Clark, Jeremy L., et al., Synthesis and antiviral activity of 2'-deoxy-2'-fluoro-2'-Cmethyl purine nucleosides as inhibitors of hepatitis C virus RNA replication,Bioorganic & Medicinal chemistry Letters, vol. 16, pp. 1712-1715 (2006), Filed Nov. 28, 2012.
Interference No. 105,871, Exhibit No. 2032, Jeong, Lak S. et al., Unanticipated Retention of Configuration in the DAST Fluorination of Deoxy-4'-thiopyrimidine Nucleosides with "Up" Hydroxyl Groups, Tetrahedron Letters, vol. 35, No. 41, pp. 7569-7572 (1994), Filed Nov. 28, 2012.
Interference No. 105,871, Exhibit No. 2005, Clark U.S. Appl. No. 60/474,368 ("C1") as filed May 30, 2003, Filed Nov. 28, 2012.
Interference No. 105,871, Exhibit No. 2010, Sommadossi U.S. Appl. No. 60/466,194 ("S2") as filed Apr. 28, 2003, Filed Nov. 28, 2012.
Interference No. 105,871, Exhibit No. 2043, International Pub. No. WO 02/18369 A2, Filed Nov. 28, 2012.
Interference No. 105,871, Exhibit No. 2009, Clark U.S. Pat. No. 7,429,572 B2 ( "Clark Patent"), Filed Nov. 28, 2012.
Interference No. 105,871, Exhibit No. 2142, Sommadossi Exhibit 1319 Annotated by George Fleet, PhD. During Jul. 9, 2013 Deposition, Filed Nov. 7, 2013.
Interference No. 105,871, Exhibit No. 2139, Certificate of Conversion and Name Change of Pharmasset, Inc. (a Delaware corporation) to Gilead Pharmasset LLC (a Delaware limited liability company) dated Feb. 10, 2012, Recorded at Reel 027757, Frame 0273, Filed Nov. 7, 2013.
Interference No. 105,871, Exhibit No. 2154, Van Robays, Marc, et al., Preparation and Determination of Configuration of 3-Halogeno-3-methyl-5α-cholestane Epimers, J. Chem. Soc. Perkin Trans., pp. 251-254 (1986), Filed Nov. 7, 2013.
Interference No. 105,871, Exhibit No. 2091, The Journal of the American Chemical Society, Table of Contents, vol. 79, No. 3 (1957), Filed Nov. 28, 2012.
Interference No. 105,871, Exhibit No. 2090, Interference No. 105,871—printout of interference web portal file contents, Filed Nov. 28, 2012.
Matsuda, et al., "Radical Deoxygenation of tert-Alcohols in 2'-Branched-Chain Sugar Pyrimidine Nucleosides: Synthesis and Antileukemic Activity of 2'-Deoxy-2' (S)-Methylcytidine," Chem. Pharm. Bull., 35(9):3967-3970 (1987).
Maybridge MedChem: Bioisosteres in Medicinal Chemistry.
Mcatee, et al., "A Complete Diastereoselective Electrophilic Fluorination of a Chiral, Noncarbohydrate Sugar Ring Precursor: Application to the Synthesis of Several Novel 2'-Fluoronucleosides," J. Org. Chem., 63:2161-2167 (1998).
Meier, Expert Opinion dated Aug. 31, 2013 in Oslo District Court Case 12-1555757TVI-0TIR/01.
Middleton, "New Fluorinating Reagents. Dialkylaminosulfur Fluorides," J. Org. Chem., 40(5), pp. 574-578 (1975).

(56) References Cited

OTHER PUBLICATIONS

Mills, et al., "Cytosine and Orotic Acid in Urine of Immunodeficient Children," Clin. Chem., 25(3):419-424 (1979).
Moffatt, "A General Synthesis of Nucleoside-5' Triphosphates," Canadian J. Chemistry, 42:599-604 (1964).
Moradpour, et al., "Functional Properties of a Monoclonal Antibody Inhibiting the Hepatitis C Virus RNA-dependent RNA Polymerase," J. Biol. Chem., 277(1):593-601 (2002).
Moussa, Substitute Declaration dated Jun. 3, 2013, Exhibit 1428 in Interference No. 105,871.
Murakami, et al., "Mechanism of Action of β-D-2'-Deoxy-2'-Fluoro-2'-C-Methylcytidine Involves a Second Metabolic Pathway Leading to β-D-2'-Deoxy-2'-Fluoro-2'-C-Methyluridine 5'-Triphosphate, a Potent Inhibitor of the Hepatitis C Virus RNA-Dependent RNA Polymerase," Antimicrobial Agents and Chemotherapy 52(2):458-464 (2008).
Murakami, et al., "Mechanism of Activation of β-D-2'-Deoxy-2'-Fluoro-2'-C-Methylcytidine and Inhibition of Hepatitis C Virus NS5B RNA Polymerase," Antimicrobial Agents and Chemotherapy 51(2):503-509 (2007).
Nakabayashi, et al., "Growth of Human Hepatoma Cell Lines with Differentiated Functions in Chemically Defined Medium," Cancer Res. 42:3858-3863 (1982).
Olah, et al., "Synthetic Methods and Reactions. 63. Pyridinium Poly(hydrogen fluoride) (30% Pyridine-70% Hydrogen Fluoride): A Convenient Reagent for Organic Fluorination Reactions," J. Org. Chem., 44(22):3872-3881 (1979).
Olsen, et al., "Study of a Hammerhead Ribozyme Containing 2'-Modified Adenosine Residues," Biochemistry, 30:9735-9741 (1991).
OM Application No. 112/2005 Office Action dated Feb. 7, 2016 (English translation).
Pankiewicz, "Fluorinated Nucleosides," Carbohydrate Research, 327:87-105 (2000).
Pankiewicz, et al., "A Synthesis of 9-(2-Deoxy-2-fluoro-β-D-arabinofuranosyl)adenine and Hypoxanthine. An Effect of C3'-Endo to C2'-Endo Conformational Shift on the Reaction Course of 2'-Hydoxyl Group with DAST," J. Org. Chem., 57:553-559 (1992).
Park, et al., "Effects of Fluorine Substitution on Drug Metabolism: Pharmacological and Toxicological Implications," Drug Metabolism Rev., 26(3):605-643 (1994).
Park, et al., "Metabolism of Fluorine-Containing Drugs," Annu. Rev. Pharmacol. Toxicol., 41:443-470 (2001).
PCT/US04/12472 Request dated Apr. 21, 2004.
Perlman, et al., "Nucleosides. 133. Synthesis of 5-Alkenyl-1-(2-deoxy-2-fluoro-β-D-arabinofuranosyl)cytosines and Related Pyrimidine Nucleosides as Potential Antiviral Agents," J. Med. Chem., 28:741-748 (1985).
Perrone, "Application of the Phosphoramidate ProTide Approach to 4'-Azidouridine Confers Sub-micromolar Potency versus Hepatitis C Virus on an Inactive Nucleoside," J. Med. Chem., 50:1840-1849 (2007).
Pierra, et al., "Synthesis and Pharmacokinetics of Valopicitabine (NM283), an Efficient Prodrug of the Potent Anti-HCV Agent 7-C-Methylcytidine," J. Med. Chem., 49:6614-6620 (2006).
Program and Abstracts, 16th International Conference on Antiviral Research, Savannah, Ga., USA, Apr. 27-May 1, 2003, Abstract 119 (Eldrup, et al.), Abstract 120 (Bhat, et al.), Abstract 121 (Olsen, et al.).
Rane, Declaration re IN Application No. 6087/DELNP/2005 Optimus Pre-Grant Opposition dated Mar. 17, 2015.
Research and Development Agreement between Pharmasset, Ltd. And Pharmasset, Inc., draft dated Dec. 9, 1999.
Roberts, Bryce Allen, First Witness Statement dated Jul. 10, 2014 from *Idenix Pharmaceuticals, Inc.* v. *Gilead Sciences, Inc.*, UK High Court of Justice, Chancery Division, Patents Court, Claim No. HP 14D 01069.
Roemer, Alan Sloane, Declaration dated Jul. 31, 2013.
Sangarappan, Declaration re IN Patent No. 273003 Vector Post-Grant Opposition dated May 9, 2017.

Schinazi, et al., "DPC 817: A Cytidine Nucleoside Analog with Activity against Zidovudine- and Lamivudine-Resistant Viral Variants," Antimicrobial Agents & Chemotherapy, 46(5):1394-1401 (2002).
Schinazi, Raymond F., Declaration dated Jul. 24, 2013.
Sengupta, et al., "Evaluation of Anticancer Activity of Some 1,3,4-Oxadiazole Derivatives," Indian J. Chem., 47B:460-462 (2008).
Standring, et al., "NM 283 Has Potent Antiviral Activity Against Genotype 1 Chronic Hepatitis C Virus (HCV-1) Infection in the Chimpanzee," Abstract 3, J. Hepatology, 38(Suppl. 2):3 (2003).
Stella, "Prodrugs as Therapeutics," Expert Opin. Ther. Patents 14(3):277-280 (2004).
Stewart, Deposition Transcript dated Jun. 19, 2013, Exhibit 1645 in Interference No. 105,871.
Stewart, Substitute Declaration dated May 30, 2013, Exhibit 1241 in Interference No. 105,871.
Stewart, Testimony dated Oct. 9, 2014, pp. 468-469, from *Idenix Pharmaceuticals, Inc.* v. *Gilead Sciences, Inc.*, UK High Court of Justice, Chancery Division, Patents Court, Claim No. HP 14D 01069.
*Storer* v. *Clark*, U.S. Court of Appeals for the Federal Circuit, Decision dated Jun. 21, 2017.
Storer, Substitute Declaration dated May 31, 2013, Exhibit 1429 in Interference No. 105,871.
Tan et al., English-Chinese Dictionary of Biochemistry and Molecular Biology, p. 805 (2000).
Thomas, Prof. John R., Expert Report dated Jul. 31, 2014 from *Idenix Pharmaceuticals, Inc.* v. *Gilead Sciences, Inc.*, UK High Court of Justice, Chancery Division, Patents Court, Claim No. HP 14D 01069.
U.S. Appl. No. 60/474,368, Assent of Assignee to Correct Inventorship dated Jul. 12, 2005.
Van Aerschot, et al., "2,3'-Difluoro and 3'-Azido-2'-Fluoro Substituted Dideoxypyrimidines as Potential Anti-HIV Agents," Bull. Soc. Chim. Belg., 98(12):937-941 (1989).
Van Aerschot, et al., "3'-Fluoro-2',3'-dideoxy-5-chlorouridine: Most Selective Anti-HIV-1 Agent Among a Series of New 2'-and 3'-Fluorinated 2',3'-Dideoxynucleoside Analogues," J. Med. Chem., 32(8):1743-1749 (1989).
Van Robays, et al., "Preparation and Determination of Configuration of 3-Halogeno-3-methyl-5α-cholestane Epimers," J. Chem. Soc. Perkin Trans. I, 251-254 (1986).
Van Rompay, et al., "Phosphorylation of Nucleosides and Nucleoside Analogs by Mammalian Nucleoside Monophosphate Kinases," Pharmacology & Therapeutics, 87:189-198 (2000).
Van Rompay, et al., "Phosphorylation of Uridine and Cytidine Nucleoside Analogs by Two Human Uridine-Cytidine Kinases," Mol. Pharmacology, 59:1181-1186 (2001).
Verri, et al., "Relaxed Enantioselectivity of Human Mitochondrial Thymidine Kinase and Chemotherapeutic Uses of L-Nucleoside Analogues," Biochem. J., 328:317-320 (1997).
Von Janta-Lipinski et al., "Newly Synthesized L-Enantiomers of 3'-Fluoro-Modified β-2'-Deoxyribonucleoside 5'-Triphosphates Inhibit Hepatitis B DNA Polymerases But Not the Five Cellular DNA Polymerases α, β, γ, σ, ε Nor HIV-1 Reverse Transcriptase," J. Med. Chem. 41:2040-2046 (1998).
Wachtmeister, et al., "Synthesis of 4-Substituted Carbocyclic 2,3-Dideoxy-3-C-hydroxymethyl Nucleoside Analogues as Potential Anti-viral Agents," Tetrahedron, 55:10761-10770 (1999).
Interference No. 105,981, Exhibit No. 2099-5, Storer U.S. Appl. No. 10/608,907 ("S4") as filed Jun. 27, 2003, Filed Mar. 10, 2014.
Interference No. 105,981, Exhibit No. 2099-4, Storer U.S. Appl. No. 10/608,907 ("S4") as filed Jun. 27, 2003, Filed Mar. 10, 2014.
Interference No. 105,981, Exhibit No. 2099-3, Storer U.S. Appl. No. 10/608,907 ("S4") as filed Jun. 27, 2003, Filed Mar. 10, 2014.
Interference No. 105,981, Exhibit No. 2099-2, Storer U.S. Appl. No. 10/608,907 ("S4") as filed Jun. 27, 2003, Filed Mar. 10, 2014.
Interference No. 105,981, Exhibit No. 2099-1, Storer U.S. Appl. No. 10/608,907 ("S4") as filed Jun. 27, 2003, Filed Mar. 10, 2014.
Interference No. 105,981, Exhibit No. 2099-11, Storer U.S. Appl. No. 10/608,907 ("S4") as filed Jun. 27, 2003, Filed Mar. 10, 2014.

(56) References Cited

OTHER PUBLICATIONS

Interference No. 105,981, Exhibit No. 2148, Interference No. 105,871, Paper No. 548, Idenix Exhibit 1281 (entitled (by Idenix): "Declaration of Masad J. Damha, Ph.D., signed May 2, 2013"), Filed May 23, 2014.
Interference No. 105,981, Exhibit No. 2049-12, Storer U.S. Appl. No. 60/392,350 ("S1") as filed Jun. 28, 2002, Filed Mar. 10, 2014.
Interference No. 105,981, Exhibit No. 2049-19, Storer U.S. Appl. No. 60/392,350 ("S1") as filed Jun. 28, 2002, Filed Mar. 10, 2014.
Interference No. 105,981, Exhibit No. 2049-18, Storer U.S. Appl. No. 60/392,350 ("S1") as filed Jun. 28, 2002, Filed Mar. 10, 2014.
Interference No. 105,981, Exhibit No. 2049-17, Storer U.S. Appl. No. 60/392,350 ("S1") as filed Jun. 28, 2002, Filed Mar. 10, 2014.
Interference No. 105,981, Exhibit No. 2049-16, Storer U.S. Appl. No. 60/392,350 ("S1") as filed Jun. 28, 2002, Filed Mar. 10, 2014.
Interference No. 105,981, Exhibit No. 2049-15, Storer U.S. Appl. No. 60/392,350 ("S1") as filed Jun. 28, 2002, Filed Mar. 10, 2014.
Interference No. 105,981, Exhibit No. 2049-14, Storer U.S. Appl. No. 60/392,350 ("S1") as filed Jun. 28, 2002, Filed Mar. 10, 2014.
Interference No. 105,981, Exhibit No. 2049-13, Storer U.S. Appl. No. 60/392,350 ("S1") as filed Jun. 28, 2002, Filed Mar. 10, 2014.
Interference No. 105,981, Exhibit No. 2049-11, Storer U.S. Appl. No. 60/392,350 ("S1") as filed Jun. 28, 2002, Filed Mar. 10, 2014.
Interference No. 105,981, Exhibit No. 2049-10, Storer U.S. Appl. No. 60/392,350 ("S1") as filed Jun. 28, 2002, Filed Mar. 10, 2014.
Interference No. 105,981, Exhibit No. 2049-9, Storer U.S. Appl. No. 60/392,350 ("S1") as filed Jun. 28, 2002, Filed Mar. 10, 2014.
Interference No. 105,981, Exhibit No. 2049-7, Storer U.S. Appl. No. 60/392,350 ("S1") as filed Jun. 28, 2002, Filed Mar. 10, 2014.
Interference No. 105,981, Exhibit No. 2049-8, Storer U.S. Appl. No. 60/392,350 ("S1") as filed Jun. 28, 2002, Filed Mar. 10, 2014.
Interference No. 105,981, Exhibit No. 2049-6, Storer U.S. Appl. No. 60/392,350 ("S1") as filed Jun. 28, 2002, Filed Mar. 10, 2014.
Interference No. 105,981, Exhibit No. 2049-5, Storer U.S. Appl. No. 60/392,350 ("S1") as filed Jun. 28, 2002, Filed Mar. 10, 2014.
Interference No. 105,981, Exhibit No. 2049-4, Storer U.S. Appl. No. 60/392,350 ("51") as filed Jun. 28, 2002, Filed Mar. 10, 2014.
Interference No. 105,981, Exhibit No. 2049-3, Storer U.S. Appl. No. 60/392,350 ("S1") as filed Jun. 28, 2002, Filed Mar. 10, 2014.
Interference No. 105,981, Exhibit No. 2049-2, Storer U.S. Appl. No. 60/392,350 ("S1") as filed Jun. 28, 2002, Filed Mar. 10, 2014.
Interference No. 105,981, Exhibit No. 2049-1, Storer U.S. Appl. No. 60/392,350 ("S1") as filed Jun. 28, 2002, Filed Mar. 10, 2014.
Interference No. 105,981, Exhibit No. 2095, C1 File History—Jul. 11, 2005 Petition to Correct Inventorship, Filed Sep. 18, 2014.
Interference No. 105,981, Exhibit No. 2007, Interference No. 105,871, Paper No. 1007, Decision—Priority, Entered Jan. 29, 2014, Filed Mar. 10, 2014.
Interference No. 105,981, Exhibit No. 2048, Bighley, L.D., et al., Salt Forms of Drugs and Absorption, in Swarbrick, J. and Boylan, J.C., eds., Encyclopedia of Pharmaceutical Technology, vol. 13, Marcel Dekker, Inc. (1996), Filed Mar. 10, 2014.
Interference No. 105,981, Exhibit No. 2049-20, Storer U.S. Appl. No. 60/392,350 ("S1") as filed Jun. 28, 2002, Filed Mar. 10, 2014.
Interference No. 105,981, Exhibit No. 2115, Interference No. 105,871, Paper No. 526, Idenix Exhibit 1259 (entitled (by Idenix): "Notebook 4 of Audrey Chappe-Dumas"), Filed Sep. 18, 2014.
Interference No. 105,981, Exhibit No. 2043, Interference No. 105,871, Paper No. 527, Idenix Exhibit 1260 (entitled (by Idenix): "English translation of Notebook 4 of Audrey Chappe-Dumas"), Filed Mar. 10, 2014.
Interference No. 105,981, Exhibit No. 2153, Interference No. 105,871, Paper No. 583, Idenix Exhibit 1316 (entitled Idenix): "Curriculum Vitae of George (by Fleet"), Filed May 23, 2014.
Interference No. 105,981, Exhibit No. 2123, Interference No. 105,871, Paper No. 677, Idenix Exhibit 1410 (entitled (by Idenix): "Report on the Individual Meeting with Dick Storer, Gilles Gosselin and George Fleet, dated Dec. 31, 2002"), Filed Sep. 18, 2014.

Interference No. 105,981, Exhibit No. 2117, Interference No. 105,871, Paper No. 561, Idenix Exhibit 1294 (entitled (by Idenix): "Report summarizing meeting of Dec. 2, 2002"), Filed Sep. 18, 2014.
Interference No. 105,981, Exhibit No. 2141, Briot, Anne, et al., Benzylsulfonyl: A Valuable Protecting and Deactivating Group in Phenol Chemistry, Tetrahedron Letters, vol. 44, pp. 965-967 (2003), Filed Sep. 18, 2014.
Interference No. 105,981, Exhibit No. 2096, Clark U.S. Appl. No. 11/854,218 ("C3") file history—Dec. 12, 2007 Filing Receipt, Filed Mar. 10, 2014.
Interference No. 105,981, Exhibit No. 2032, Interference No. 105,871, Paper No. 585, Idenix Exhibit 1318 (entitled (by Idenix): "Report meeting in Montpellier, France"), Filed Mar. 10, 2014.
Interference No. 105,981, Exhibit No. 2017, Tewson, T.J., et al., New Approaches to the Synthesis of 3-Deoxy-3-fluoro-Dglucose, J. Org. Chem., vol. 43, No. 6, pp. 1090-1092 (1978), Filed Mar. 10, 2014.
Interference No. 105,981, Exhibit No. 2189, Clark Objections 2 served Mar. 17, 2014, Filed Sep. 18, 2014.
Interference No. 105,981, Exhibit No. 2151, Interference No. 105,871, Paper No. 516, Idenix Exhibit 1249 (entitled (by Idenix): "Curriculum Vitae of Richard Storer, D. Phil."), Filed May 23, 2014.
Interference No. 105,981, Exhibit No. 2184, International Patent Publication No. WO 2006/021449 Al, Filed Sep. 18, 2014.
Interference No. 105,981, Exhibit No. 2005, Interference No. 105,871, Paper No. 426, Decision on Motions, Entered Mar. 22, 2013, Filed Mar. 10, 2014.
Interference No. 105,981, Exhibit No. 2022, Interference No. 105,871, Paper No. 515, Idenix Exhibit 1248 (entitled (by Idenix): "Herdewijn et al., 1989, NucleosidesNucleotides 8: 65-96"), Filed Mar. 10, 2014.
Interference No. 105,981, Exhibit No. 2133, Interference No. 105,871, Paper No. 906, Idenix Exhibit 1648 (entitled (by Idenix): "Deposition Transcript of Audrey Chappe-Dumas dated Jul. 2, 2013 (with errata sheet)"), Filed Sep. 18, 2014.
Interference No. 105,981, Exhibit No. 2053, Condit, R.C., Principles of Virology (Chapter 2), in Knipe, D.M. et al., eds., Fields Virology, 5th ed. Philadelphia, Lippincott Williams & Wilkins (2007), Filed May 23, 2014.
Interference No. 105,981, Exhibit No. 2182, U.S. Pat. No. 8,198,426 B2, Filed Sep. 18, 2014.
Interference No. 105,981, Exhibit No. 2052, Condit, R.C., Principles of Virology (Chapter 2), in Knipe, D.M. et al., eds., Fields Virology, 4th ed. Philadelphia, Lippincott Williams & Wilkins (2001), Filed May 23, 2014.
Interference No. 105,981, Exhibit No. 2150, Interference No. 105,871, Paper No. 507, Idenix Exhibit 1240 (entitled (by Idenix): "Substitute Declaration of Sarah Jenkinson, signed May 30, 2013"), Filed May 23, 2014.
Interference No. 105,981, Exhibit No. 2045, Interference No. 105,871, Paper No. 991, Sommadossi List of Exhibits (as of Nov. 8, 2013), Filed Mar. 10, 2014.
Interference No. 105,871, Paper No. 108, Sommadossi Filing of the Record, Filed Nov. 28, 2012.
Interference No. 105,871, Paper No. 109, Clark Final Exhibit List (Clark Exhibit List 8), Filed Nov. 28, 2012.
Interference No. 105,871, Paper No. 110, Clark Submission of Record, Filed Nov. 28, 2012.
Interference No. 105,871, Paper No. 426, Decision on Motions, Entered Mar. 22, 2013.
Interference No. 105,871, Paper No. 427, Redeclaration, Entered Mar. 22, 2013.
Interference No. 105,871, Paper No. 428, Order—Time for Taking Action in Priority Phase, Entered Mar. 22, 2013.
Interference No. 105,871, Paper No. 429, Order Regarding Conference Call of Apr. 2, 2013, Entered Apr. 3, 2013.
Interference No. 105,871, Paper No. 430, Order—Transferring Interference Bd. R. 104(a), Entered Apr. 4, 2013.
Interference No. 105,871, Paper No. 431, Sommadossi Request for Rehearing, Filed Apr. 5, 2013.
Interference No. 105,871, Paper No. 432, Sommadossi Notice of Related Litigations, Filed Apr. 11, 2013.

(56) References Cited

OTHER PUBLICATIONS

Interference No. 105,871, Paper No. 433, Clark Notice of Related Proceedings 2, Filed Apr. 11, 2013.
Interference No. 105,871, Paper No. 434, Decision on Request for Hearing, Entered Apr. 23, 2013.
Interference No. 105,871, Paper No. 435, Order—Schedule Bd.R. 104(a), Entered Apr. 23, 2013.
Interference No. 105,871, Paper No. 436, Order—Schedule Bd.R. 104(a), Entered May 1, 2013.
Interference No. 105,871, Paper No. 437, Sommadossi Substantive Motion 8 (for Judgment Based on Priority), Filed May 10, 2013.
Interference No. 105,871, Paper No. 438, Sommadossi Notice of Service of Exhibits, Filed May 10, 2013.
Interference No. 105,871, Paper No. 439, Joint Statement Regarding Settlement Discussions, Filed May 22, 2013.
Interference No. 105,871, Paper No. 440, Sommadossi Notice of Service of Supplemental Evidence 4, Filed Jun. 3, 2013.
Interference No. 105,871, Paper No. 441, Order—Pro Hac Vice, Entered Jun. 10, 2013.
Interference No. Filed 105,871, Paper No. 442, Clark Miscellaneous Motion 8 (for Pro Hac Vice Admission for Priority Phase Deposition), Filed Jun. 10, 2013.
Interference No. 105,871, Paper No. 443, Clark Exhibit List 9, Filed Jun. 10, 2013.
Interference No. 105,871, Paper No. 447, Order—Limited Admission Pro Hac Vice, Entered Jun. 10, 2013.
Interference No. 105,871, Paper No. 448, Clark Substantive Motion 9 (for Judgment Based on Priority), Filed Jun. 28, 2013.
Interference No. 105,871, Paper No. 448.001, Order—Miscellaneous—Bd. R.104(a), Entered Jul. 1, 2013.
Interference No. 105,871, Paper No. 449, Order—Miscellaneous—Bd. R. 104(a), Entered Jul. 2, 2013.
Interference No. 105,871, Paper No. 450, Clark Notice of Service of Supplemental Evidence 4, Filed Jul. 10, 2013.
Interference No. 105,871, Paper No. 451, Clark Notice of service of Supplemental Evidence 5, Filed Jul. 12, 2013.
Interference No. 105,871, Paper No. 452, Order—Evidence Matters—Bd. R. 104(a), Entered Jul. 15, 2013.
Interference No. 105,871, Paper No. 453, Clark Notice of Service of Supplemental Evidence 4, Filed Jul. 17, 2013.
Interference No. 105,871, Paper No. 454, Substitute Sommadossi Substantive Motion 8 (for Judgment Based on Priority), Filed Jul. 18, 2013.
Interference No. 105,871, Paper No. 455, Sommadossi List of Exhibits Containing Testimony of Edith Badel, Filed Jul. 18, 2013.
Interference No. 105,871, Paper No. 456, Clark Notice Re Exhibit 2136, Filed Jul. 22, 2013.
Interference No. 105,871, Paper No. 456.001, Email Communication, Entered Jul. 22, 2013.
Interference No. 105,871, Paper No. 457, Substitute Clark Substantive Motion 9 (for Judgment Based on Priority), Filed Jul. 22, 2013.
Interference No. 105,871, Paper No. 458, Sommadossi Opposition 9, Filed Jul. 26, 2013.
Interference No. 105,871, Paper No. 459, Sommadossi Notice of Service of Exhibits, Filed Jul. 26, 2013.
Interference No. 105,871, Paper No. 460, Clark Opposition 9 (Opposing Sommadossi's Prority Motion Misnumbered "8"), Filed Jul. 26, 2013.
Interference No. 105,871, Paper No. 461, Sommadossi Supplemental Notice of Service of Exhibits, Filed Jul. 26, 2013.
Interference No. 105,871, Paper No. 462, Order—Miscellaneous—Bd.R. 104(a), Filed Aug. 1, 2013.
Interference No. 105,871, Paper No. 463, Sommadossi Notice of Service of Exhibits, Filed Aug. 16, 2013.
Interference No. 105,871, Paper No. 464, Sommadossi Reply 9, Filed Sep. 6, 2013.
Interference No. 105,871, Paper No. 465, Sommadossi Notice of Service of Exhibits, Filed Sep. 6, 2013.
Interference No. 105,871, Paper No. 466, Clark Reply 9, Filed Sep. 6, 2013.
Interference No. 105,871, Paper No. 467, Order—Miscellaneous—Bd.R. 104(a), Entered Sep. 11, 2013.
Interference No. 105,871, Paper No. 468, Sommadossi Supplemental Notice of Related Proceedings, Filed Sep. 17, 2013.
Interference No. 105,871, Paper No. 469, Sommadossi Responses to Clark's Material Facts of Clark Reply 9, Filed Sep. 17, 2013.
Interference No. 105,871, Paper No. 470, Clark Response to Sommadossi Reply 9 Alleged Material Facts, Filed Sep. 17, 2013.
Interference No. 105,871, Paper No. 471, Order—Miscellaneous—Bd.R. 104(a), Entered Sep. 18, 2013.
Interference No. 105,871, Paper No. 472, Order—Page Limits—Bd.R. 104(a), Entered Sep. 26, 2013.
Interference No. 105,871, Paper No. 473, Sommadossi Miscellaneous Motion 10 (to Exhibit Evidence), Filed Oct. 18, 2013.
Interference No. 105,871, Exhibit No. 1120, Wachtmeister et al., 1999, Tetrahedron 55: 10761-10770, Filed Nov. 6, 2013.
Interference No. 105,871, Exhibit No. 1267, English translation of Trainee Notebook 1 of Elodie Pecheux, cover page and pp. 30-89, Filed Nov. 6, 2013.
Interference No. 105,871, Exhibit No. 1657, Deposition Transcript of Robert Albon dated Jul. 16, 2013 (with errata sheet), Filed Nov. 6, 2013.
Interference No. 105,871, Exhibit No. 1170, Response to Restriction Requirement and Preliminary Amendment, dated Jan. 4, 2007, from the File History of Clark U.S. Appl. No. 10/828,753, filed Apr. 21, 2004, Filed Nov. 6, 2013.
Interference No. 105,871, Exhibit No. 1014, Schinazi et al., International Patent Application Publication No. WO 99/43691, published Sep. 2, 1999, Filed Nov. 6, 2013.
Interference No. 105,871, Exhibit No. 1310, Idenix memorandum for meeting held on Jul. 31, 2003, Filed Nov. 6, 2013.
Interference No. 105,871, Exhibit No. 1307, Idenix memorandum for meeting held on May 22, 2003, Filed Nov. 6, 2013.
Interference No. 105,871, Exhibit No. 1279, Printed copy of mass spectrometry analysis dated Dec. 18, 2002, =Filed Nov. 6, 2013.
Interference No. 105,871, Exhibit No. 1528, Supplemental Amendment, dated Oct. 30, 2007, from the File History of Sommadossi et al., U.S. Appl. No. 10/608,907, filed Jun. 27, 2003, Filed Nov. 6, 2013.
Interference No. 105,871, Exhibit No. 1489, Curriculum Vitae of Dr. Sarah Jenkinson, Filed Nov. 6, 2013.
Interference No. 105,871, Exhibit No. 1437, Certified English Translation of the Declaration of Edith Badel, signed May 3, 2013, Filed Nov. 6, 2013.
Interference No. 105,871, Exhibit No. 1457, Jun. 9, 2003 email correspondence between Adel Moussa and Richard Storer, Filed Nov. 6, 2013.
Interference No. 105,871, Exhibit No. 1423, Declaration of Edith Badel, signed May 5, 2013, Filed Nov. 6, 2013.
Interference No. 105,871, Exhibit No. 1078, Office Action, dated Jun. 8, 2011, from the File History of Clark, U.S. Appl. No. 12/878,262, filed Sep. 9, 2010, Filed Nov. 6, 2013.
Interference No. 105,871, Exhibit No. 1060, Lohmann et al., 1998, Virology 249: 108-18, Filed Nov. 6, 2013.
Interference No. 105,871, Exhibit No. 1039, Frese et al., Apr. 2001, J. Gen. Virol. 82: 723-33, Filed Nov. 6, 2013.
Interference No. 105,871, Exhibit No. 1038, Friebe et al., Dec. 2001 (accepted for publication Sep. 2001), J. Virol. 75: 12047-57, Filed Nov. 6, 2013.
Interference No. 105,871, Exhibit No. 1037, Krieger et al., May 2001, J. Virol. 75: 4614-24, Filed Nov. 6, 2013.
Interference No. 105,871, Exhibit No. 1096, Wilds and Damha, 2000, Nucleic Acids Res. 28(18): 3625-3635, Filed Nov. 6, 2013.
Interference No. 105,871, Exhibit No. 1129, McGuigan et al, 2001, Antiviral Chem. & Chemother. 12: 293-300, Filed Nov. 6, 2013.
Interference No. 105,871, Exhibit No. 1200, Guo et al., J. Virol. 77: 10769-79 (2003), Filed Nov. 6, 2013.
Interference No. 105,871, Exhibit No. 1195, File Certified Copy of Pending Claims and Communication Pursuant to Article 94(3) EPC, dated May 6, 2011, from the File History of Idenix Pharmaceuticals, Inc., EP03761744.6, Filed Nov. 6, 2013.

(56) References Cited

OTHER PUBLICATIONS

Interference No. 105,871, Exhibit No. 1162, Marquez et al., U.S. Pat. No. 5,817,799, issued Oct. 6, 1998 from United States application 556,713, filed Jul. 23, 1990, Filed Nov. 6, 2013.
Interference No. 105,871, Exhibit No. 1010, Storer et al., U.S. Pat. No. 7,608,600 B2, which issued Oct. 27, 2009 from U.S. Appl. No. 10/608,907, filed Jun. 27, 2003, Filed Nov. 6, 2013.
Interference No. 105,871, Exhibit No. 1652, Deposition Transcript of Sarah Jenkinson dated Jul. 9, 2013 (with errata sheet), Filed Nov. 6, 2013.
Interference No. 105,871, Exhibit No. 1301, Copy of bibliographic search by Jean-François Griffon, Filed Nov. 6, 2013.
Interference No. 105,871, Exhibit No. 1399, BVDV Cell Protection Assay: Determination of Antiviral Potency and Cytotoxicity of Novirio Compounds in BVDV-Infected MDBK Cells, Standard Operating Procedure, Version 1.0, Aug. 28, 2001, Author: Meredith Cope Fisher, Filed Nov. 6, 2013.
Interference No. 105,871, Exhibit No. 1247, English translation of Notebook 7 of Edith Badel, Filed Nov. 6, 2013.
Interference No. 105,871, Exhibit No. 1246, Notebook 7 of Edith Badel, Filed Nov. 6, 2013.
Interference No. 105,871, Exhibit No. 1433, Tanabe et al., 2004, J. Infect. Dis. 189(7): 1129-1139, Filed Nov. 6, 2013.
Interference No. 105,871, Exhibit No. 1408, Filed Nov. 6, 2013 Idenix Pharmaceuticals Laboratory Notebook No. 102 (Michele M. Tausek), pages, Filed Nov. 6, 2013.
Interference No. 105,871, Exhibit No. 1026, Yanagi et al., 1998, Virology 244: 161-72, Filed Nov. 6, 2013.
Interference No. 105,871, Exhibit No. 1021, Behrens et al., 1996, Embo J. 15: 12-22, Filed Nov. 6, 2013.
Interference No. 105,871, Exhibit No. 1082, Murakami et al., 2010, J. Biol. Chem. 285: 34337-34347, Filed Nov. 6, 2013.
Interference No. 105,871, Exhibit No. 1123, Yi et al., 2006, Proc. Nat'l Acad. Sci. U.S.A. 103:2310-5, Filed Nov. 6, 2013.
Interference No. 105,871, Exhibit No. 1121, Shimakami et al., 2012, Proc. Nat'l. Acad. Sci U.S.A. 109:941-6, Filed Nov. 6, 2013.
Interference No. 105,871, Exhibit No. 1211, Clark Exhibit List 6, served Oct. 11, 2012, Filed Nov. 6, 2013.
Interference No. 105,871, Exhibit No. 1210, Clark Exhibits List 4, served Aug. 17, 2012, Filed Nov. 6, 2013.
Interference No. 105,871, Exhibit No. 1166, Deposition Transcript of Stanley Moncrief Lemon, M.D., dated Jul. 31, 2012 (with errata sheet), Filed Nov. 6, 2013.
Interference No. 105,871, Exhibit No. 1398, Screenshots of Select XLfitTM Spreadsheets with Data and Calculations Recorded by Massimiliano La Colla, Ph.D., Filed Nov. 6, 2013.
Interference No. 105,871, Exhibit No. 1446, Substitute Third Declaration of Jeffrey S. Glenn, M.D., Ph.D., signed May 31, 2013, Filed Nov. 6, 2013.
Interference No. 105,871, Exhibit No. 1250, Novirio Chemistry Meeting Agenda, Filed Nov. 6, 2013.
Interference No. 105,871, Exhibit No. 1451, Pages from Light Cycler Data Analysis binder of Michele M. Tausek, Filed Nov. 6, 2013.
Interference No. 105,871, Exhibit No. 1056, Lohmann et al. 1997, J. Virol. 71: 8416-28, Filed Nov. 6, 2013.
Interference No. 105,871, Exhibit No. 1050, Mottola et al., 2002 (accepted for publication Oct. 11, 2001), Virology 293: 31-43, Filed Nov. 6, 2013.
Interference No. 105,871, Exhibit No. 1042, Pietschmann et al., Feb. 2001, J. Virol. 75: 1252-64, Filed Nov. 3, 2013.
Interference No. 105,871, Exhibit No. 1041, Lohmann et al., Feb. 2001, J. Virol. 75: 1437-49, Filed Nov. 6, 2013.
Interference No. 105,871, Exhibit No. 1030, Di Bisceglie and Bacon, Oct. 1999, Sci. Am. 281: 80-85, Filed Nov. 6, 2013.
Interference No. 105,871, Exhibit No. 1015, Clarke, 2000, Bailliere's Clin. Gastroenterol. 14: 293-305, Filed Nov. 3, 2013.
Interference No. 105,871, Exhibit No. 1002, Curriculum Vitae of Masad Jose Damha, Ph.D., F.C.I.C., Filed Nov. 3, 2013.
Interference No. 105,871, Exhibit No. 1045, Shi and Lai, Aug. 2001, Cell. Mol. Life Sci. 58: 1276-95, Filed Nov. 6, 2013.
Interference No. 105,871, Exhibit No. 1164, Marquez, 1996, Research Monograph Series (National Institute on Drug Abuse), Drugs of Abuse: Chemistry, Pharmacology, Immunology and AIDS, "Effect of Fluorine Substitution on Anti-HIV Activity of Dideoxynucleosides," pp. 61-79, Filed Nov. 6, 2013.
Interference No. 105,871, Exhibit No. 1191, Deposition Transcript of Barry M. Trost, Ph.D., dated Aug. 2, 2012 (with errata sheet), executed Aug. 31, 2012, Filed Nov. 6, 2013.
Interference No. 105,871, Exhibit No. 1538, Sommadossi, et al., International Patent Application Publication No. WO 2004/002999, published Jan. 8, 2004, Filed Nov. 6, 2013.
Interference No. 105,871, Exhibit No. 1169, Deposition Transcript of Masad Damha, Ph.D., dated Aug. 2, 2012 (with errata sheet), Filed Nov. 6, 2013.
Interference No. 105,871, Exhibit No. 1192, Deposition Transcript of Masad Damha, Ph.D., dated Aug. 2, 2012 (with errata sheet), executed Sep. 7, 2012, Filed Nov. 6, 2013.
Interference No. 105,871, Exhibit No. 1006, *Genentech, Inc. v. Chiron Corp.*, Interference 105,048, Paper 258 (BPAI Nov. 30, 2004) (non-precedential), Filed Nov. 6, 2013.
Interference No. 105,871, Exhibit No. 1430, Idenix Management Report—Mar. 2005, dated Apr. 15, 2005 from Guy Macdonald to Jean-Pierre Sommadossi, Ph.D., Filed Nov. 6, 2013.
Interference No. 105,871, Exhibit No. 1134, Schinazi et al., U.S. Pat. No. 6,071,922, issued Jun. 6, 2000, Filed Nov. 6, 2013.
Interference No. 105,871, Exhibit No. 1070, Clark, U.S. Appl. No. 11/854,218, filed Sep. 12, 2007, Filed Nov. 6, 2013.
Interference No. 105,871, Exhibit No. 1540, Substitute Certified English Translation of the Declaration of Audrey Chappe-Dumas, signed May 30, 2013, Filed Nov. 6, 2013.
Interference No. 105,871, Exhibit No. 1219, Marquez et al., Nucleosides and Nucleotides as Antitumor and Antiviral Agent 265-284 (Chu et al. eds, 1993), Filed Nov. 6, 2013.
Interference No. 105,871, Exhibit No. 1079, Response to Non-Final Office Action, dated Sep. 1, 2011, from the File History of Clark, U.S. Appl. No. 12/878,262, filed Sep. 9, 2010, Filed Nov. 6, 2013.
Interference No. 105,871, Exhibit No. 1075, Response to Non-Final Office Action, dated Oct. 11, 2010, from the File History of Clark, U.S. Appl. No. 11/854,218, filed Sep. 12, 2007, Filed Nov. 6, 2013.
Interference No. 105,871, Exhibit No. 1114, Greene and Wuts, 1999, Protective Groups in Organic Synthesis (3rd ed.): 76-81, 95-96, 102-106, 150, 173-176 and 197-198, Filed Nov. 6, 2013.
Interference No. 105,871, Exhibit No. 1402, Substitute Declaration of Audrey Chappe-Dumas, signed May 30, 2013, Filed Nov. 6, 2013.
Interference No. 105,871, Exhibit No. 1127, Cramer and Pfleiderer, 1996, Helvetica Chimica Acta 79: 2114-2136, Filed Nov. 6, 2013.
Interference No. 105,871, Exhibit No. 1204, Carroll et al., International Patent Application Publication No. WO 02/057425, published Jul. 25, 2002, Filed Nov. 6, 2013.
Interference No. 105,871, Exhibit No. 1281, Declaration of Masad J. Damha, Ph.D., signed May 2, 2013, Filed Nov. 6, 2013.
Interference No. 105,871, Exhibit No. 1498, Sarah Jenkinson Notebook 2, Filed Nov. 6, 2013.
Interference No. 105,871, Exhibit No. 1076, Response to Final Office Action, dated Jun. 20, 2011, from the File History of Clark, U.S. Appl. No. 11/854,218, filed Sep. 12, 2007, Filed Nov. 6, 2013.
Interference No. 105,871, Exhibit No. 1148, Greene and Wuts, 1999, Protective Groups in Organic Synthesis (3rd ed.): xi-xxi, 17-25 and 28-245, Filed Nov. 6, 2013.
Interference No. 105,871, Exhibit No. 1238, English translation of Notebook 3 of Clement Counor, Filed Nov. 6, 2013.
Interference No. 105,871, Exhibit No. 1237, Notebook 3 of Clement Counor, Filed Nov. 6, 2013.
Interference No. 105,871, Exhibit No. 1432, Substitute Declaration of Jingyang Wang, signed Jun. 3, 2013, Filed Nov. 6, 2013.
Interference No. 105,871, Exhibit No. 1181, Simons, C., 2001, Nucleoside Mimetics, Chapter 6, pp. 117-136, Filed Nov. 6, 2013.
Interference No. 105,871, Exhibit No. 1407, Idenix Pharmaceuticals Laboratory Notebook No. 076 (Michele M. Tausek), pages, Filed Nov. 6, 2013.

(56) References Cited

OTHER PUBLICATIONS

Interference No. 105,871, Exhibit No. 1188, Chu, C. K; Baker, D. C., Eds., 1993, Nucleosides and Nucleotides as Antitumor and Antiviral Agents (Plenum Press, New York), pp. 177-201, Filed Nov. 6, 2013.
Interference No. 105,871, Exhibit No. 1260, English translation of Notebook 4 of Audrey Chappe-Dumas, Filed Nov. 6, 2013.
Interference No. 105,871, Exhibit No. 1259, Notebook 4 of Audrey Chappe-Dumas, Filed Nov. 6, 2013.
Interference No. 105,871, Exhibit No. 1207, Deposition Transcript of Victor E. Marquez, Ph.D., dated Sep. 26, 2012 (without errata sheet), Filed Nov. 6, 2013.
Interference No. 105,871, Exhibit No. 1249, Curriculum Vitae of Richard Storer, D.Phil., Filed Nov. 6, 2013.
Interference No. 105,871, Exhibit No. 1091, *Calif. Inst. of Technol. v. Enzo Life Sciences, Inc.*, Interference 105,496, Paper 120 (BPAI Sep. 22, 2010), Filed Nov. 6, 2013.
Interference No. 105,871, Exhibit No. 1095, Sommadossi et al., International Patent Application Publication No. WO 0190121, published Nov. 29, 2001, Filed Nov. 6, 2013.
Interference No. 105,871, Exhibit No. 1661, Sommadossi Objections to Evidence 4, served Aug. 2, 2013, Filed Nov. 6, 2013.
Interference No. 105,871, Exhibit No. 1306, Email from Jean-François Griffon to Dick Storer dated May 6, 2003 with attached Apr. 2003 progress report, Filed Nov. 6, 2013.
Interference No. 105,871, Exhibit No. 1305, Filed Email from Jean-François Griffon to Dick Storer dated Apr. 8, 2003 with attached Mar. 2003 progress report, Filed Nov. 6, 2013.
Interference No. 105,871, Exhibit No. 1303, Email from Jean-François Griffon to Dick Storer dated Mar. 4, 2003 with attached Feb. 2003 progress report, Filed Nov. 6, 2013.
Interference No. 105,871, Exhibit No. 1300, Dec. 2002 progress report prepared by Jean-François Griffon, Filed Nov. 6, 2013.
Interference No. 105,871, Exhibit No. 1297, Copy of email from Jean-François Griffon to Dick Storer dated Dec. 9, 2002, Filed Nov. 6, 2013.
Interference No. 105,871, Exhibit No. 1275, English language version of resume of Jean-François Griffon, Filed Nov. 6, 2013.
Interference No. 105,871, Exhibit No. 1550, NMR spectra of Jingyang Wang dated Mar. 2, 2005, Filed Nov. 6, 2013.
Interference No. 105,871, Exhibit No. 1549, NMR spectra of Jingyang Wang dated Mar. 2, 2005, Filed Nov. 6, 2013.
Interference No. 105,871, Exhibit No. 1264, [Substitute] Resume of Elodie Pecheux, Filed Nov. 6, 2013.
Interference No. 105,871, Exhibit No. 1496, Email correspondence between Sarah Jenkinson, George Fleet and Alana Davies dated Sep. 28 and Oct. 5, 2004, Filed Nov. 6, 2013.
Interference No. 105,871, Exhibit No. 1495, Visitor's contract between Sarah Jenkinson and University of Oxford, Filed Nov. 6, 2013.
Interference No. 105,871, Exhibit No. 1491, Visitor's contract between Sarah Jenkinson and University of Oxford, Filed Nov. 6, 2013.
Interference No. 105,871, Exhibit No. 1490, Mar. 19, 2004 and Apr. 1, 2004 email correspondence between George Fleet and Sarah Jenkinson, Filed Nov. 6, 2013.
Interference No. 105,871, Exhibit No. 1406, Resume of Michele M. Tausek, Filed Nov. 6, 2013.
Interference No. 105,871, Exhibit No. 1500, Email correspondence between George Fleet, Sarah Jenkinson and Francesco Punzo dated Dec. 3, 2004 with attachment, Filed Nov. 6, 2013.
Interference No. 105,981, Paper No. 411, Storer Reply 15, Filed Jul. 9, 2014.
Interference No. 105,981, Paper No. 412, Storer List of Exhibits (as of Jul. 9, 2014), Filed Jul. 9, 2014.
Interference No. 105,981, Paper No. 413, Clark Reply 5, Filed Jul. 9, 2014.
Interference No. 105,981, Paper No. 414, Clark Reply 7, Filed Jul. 9, 2014.
Interference No. 105,981, Paper No. 415, Clark Reply 8, Filed Jul. 9, 2014.
Interference No. 105,981, Paper No. 416, Storer Notice of Service of Supplemental Evidence 4, Filed Jul. 23, 2014.
Interference No. 105,981, Paper No. 417, Storer List of Exhibits (as of Jul. 23, 2014), Filed Jul. 23, 2014.
Interference No. 105,981, Paper No. 418, Storer Fourth Supplemental Notice of Related Proceedings, Filed Jul. 23, 2014.
Interference No. 105,981, Paper No. 419, Clark Reply 1, Filed Aug. 1, 2014.
Interference No. 105,981, Paper No. 420, Clark Reply 2, Filed Aug. 1, 2014.
Interference No. 105,981, Paper No. 421, Clark Reply 3, Filed Aug. 1, 2014.
Interference No. 105,981, Paper No. 422, Clark Reply 10, Filed Aug. 1, 2014.
Interference No. 105,981, Paper No. 423, Order Motion Times BD.R. 104(c), Filed Aug. 14, 2014.
Interference No. 105,981, Paper No. 424, Storer Request for Oral Argument and List of Issues, Filed Aug. 15, 2014.
Interference No. 105,981, Paper No. 425, Storer Miscellaneous Motion 16, Filed Aug. 15, 2014.
Interference No. 105,981, Paper No. 426, Clark Request for Oral Argument and List of Issues, Filed Aug. 15, 2014.
Interference No. 105,981, Paper No. 427, Clark Miscellaneous Motion 18, Filed Aug. 15, 2014.
Interference No. 105,981, Paper No. 428, Order BD.R. 124 Oral Argument, Filed Sep. 2, 2014.
Interference No. 105,981, Paper No. 429, Storer Opposition 18, Filed Sep. 5, 2014.
Interference No. 105,981, Paper No. 430, Clark Opposition 16, Filed Sep. 5, 2014.
Interference No. 105,981, Paper No. 680, Storer Reply 16, Filed Sep. 19, 2014.
Interference No. 105,981, Paper No. 681, Clark Final Exhibit List, Filed Sep. 19, 2014.
Interference No. 105,981, Paper No. 682, Clark Submission of Evidence 3, Filed Sep. 19, 2014.
Interference No. 105,981, Paper No. 683, Clark Reply 18, Filed Sep. 19, 2014.
Interference No. 105,981, Paper No. 684, Storer Final List of Exhibits, Filed Sep. 19, 2014.
Interference No. 105,981, Paper No. 685, Order BD.R. 104(a)Miscellaneous Order, Filed Oct. 3, 2014.
Interference No. 105,981, Paper No. 686, Order BD.R. 104(a)Miscellaneous Order, Filed Oct. 9, 2014.
Interference No. 105,981, Paper No. 687, Decision on Motions BD.R. 125, Filed Jan. 16, 2015.
Interference No. 105,981, Paper No. 688, Redeclaration BD.R. 203(c), Filed Jan. 16, 2015.
Interference No. 105,981, Paper No. 689, Order Priority Times BD.R. 104(c), Filed Jan. 16, 2015.
Interference No. 105,981, Paper No. 690, Order to Show Cause BD.R. 104(a), Filed Jan. 16, 2015.
Interference No. 105,981, Paper No. 691, Storer Response to Order to Show Cause, Filed Feb. 20, 2015.
Interference No. 105,981, Paper No. 692, Miscellaneous Order BD.R. 104, Filed Mar. 30, 2015.
Interference No. 105,981, Paper No. 693, Order Motion Times BD.R. 104(c), Filed Mar. 10, 2015.
Interference No. 105,981, Paper No. 694, Judgment—Request for Adverse—BD.R. 127(b)(4), Filed Mar. 23, 2015.
Interference No. 105,981, Paper No. 695, Storer Notice of Judicial Review, Filed May 22, 2015.
Interference No. 105,981, Paper No. 696, Storer Second Notice of Judicial Review, Filed May 28, 2015.
Interference No. 105,981, Paper No. 697, Cafc Decision, Filed Jun. 17, 2017.
Interference No. 105,981, Paper No. 698, Mandate, Filed Nov. 13, 2017.
Interference No. 105,871, Exhibit No. 1329, Notebook pp. 8—192 of A. Stewart Notebook 81, Filed Nov. 6, 2013.

(56) References Cited

OTHER PUBLICATIONS

Interference No. 105,871, Exhibit No. 1289, Summary of literature search results for 3'fluoro-3'-methyl nucleosides, Filed Nov. 6, 2013.
Interference No. 105,871, Exhibit No. 1283, English translation of Notebook 2 of Jean-François Griffon, Filed Nov. 6, 2013.
Interference No. 105,871, Exhibit No. 1636, Pankiewicz, 2000, Carbohydrate Research 327: 87-105, Filed Nov. 6, 2013.
Interference No. 105,871, Exhibit No. 1386, Email attachment of Ex 1385, Filed Nov. 6, 2013.
Interference No. 105,871, Exhibit No. 1097, Damha et al., 2002, Curr. Protocols in Nucleic Acid Chem: 1.7.1-1.7.19, Filed Nov. 6, 2013.
Interference No. 105,871, Exhibit No. 1206, Deposition Transcript of Christoph Seeger, Ph.D., dated Sep. 28, 2012 (without errata sheet), Filed Nov. 6, 2013.
Interference No. 105,871, Exhibit No. 1168, Deposition Transcript of Barry M. Trost, Ph.D., dated Aug. 2, 2012 (without errata sheet), Filed Nov. 6, 2013.
Interference No. 105,871, Exhibit No. 1318, Report of Dec. 2, 2002 Idenix meeting in Montpellier, France, Filed Nov. 6, 2013.
Interference No. 105,871, Exhibit No. 1316, Curriculum Vitae of George Fleet, Filed Nov. 6, 2013.
Interference No. 105,871, Exhibit No. 1313, Correspondence from Jean-François Griffon to Adel Moussa dated Dec. 7-8, 2004, Filed Nov. 6, 2013.
Interference No. 105,871, Exhibit No. 1294, Report summarizing meeting of Dec. 2, 2002, Filed Nov. 6, 2013.
Interference No. 105,871, Exhibit No. 1291, [Substitute] Printed copy of NMR data dated May 24, 2004, Filed Nov. 6, 2013.
Interference No. 105,871, Exhibit No. 1290, Printed copy of NMR data dated Apr. 28, 2004, Filed Nov. 6, 2013.
Interference No. 105,871, Exhibit No. 1541, Certification of the English Translation of the Declaration of Audrey Chappe-Dumas, signed May 6, 2013, Filed Nov. 6, 2013.
Interference No. 105,871, Exhibit No. 1345, Email attachment of Ex 1344, Filed Nov. 6, 2013.
Interference No. 105,871, Exhibit No. 1624, NMR spectrum of Alistair Stewart dated Apr. 28, 2005, Filed Nov. 6, 2013.
Interference No. 105,871, Exhibit No. 1607, NMR spectrum of Alistair Stewart dated Jan. 21, 2005, Filed Nov. 6, 2013.
Interference No. 105,871, Exhibit No. 1606, NMR spectrum of Alistair Stewart dated Jan. 21, 2005, Filed Nov. 6, 2013.
Interference No. 105,871, Exhibit No. 1599, NMR spectrum of Alistair Stewart dated Jan. 22, 2005, Filed Nov. 6, 2013.
Interference No. 105,871, Exhibit No. 1501, Email correspondence between Francesco Punzo and Sarah Jenkinson dated Dec. 6, 2004 with attachment, Filed Nov. 6, 2013.
Interference No. 105,871, Exhibit No. 1348, Email from Dr. Stewart to Dr. Jenkinson dated Jan. 27, 2005, Filed Nov. 6, 2013.
Interference No. 105,871, Exhibit No. 1346, Email from Dr. Stewart to Dr. Jenkinson dated Jan. 25, 2005, Filed Nov. 6, 2013.
Interference No. 105,871, Exhibit No. 1343, Email from Dr. Stewart to Dr. Jenkinson dated Jan. 11, 2005, Filed Nov. 6, 2013.
Interference No. 105,871, Exhibit No. 1337, Email from Professor Fleet to Dr. Stewart dated Nov. 29, 2004, Filed Nov. 6, 2013.
Interference No. 105,871, Exhibit No. 1327, Email correspondence between George Fleet and Alistair Stewart dated Nov. 29, 2004, Filed Nov. 6, 2013.
Interference No. 105,871, Exhibit No. 1270, Certification of the English Translation of the Declaration of David Dukhan, signed May 3, 2013, Filed Nov. 6, 2013.
Interference No. 105,871, Exhibit No. 1663, Email communications dated Jun. 12, 2013 from Alicia A. Russo at Fitzpatrick, Cella, Harper & Scinto to Thomas Friebel and Anthony Insogna at Jones Day, Filed Nov. 6, 2013.
Interference No. 105,871, Exhibit No. 1572, NMR spectra of Jingyang Wang dated Apr. 4, 2005, Filed Nov. 6, 2013.
Interference No. 105,871, Exhibit No. 1563, NMR spectrum of Jingyang Wang dated Mar. 17, 2005, Filed Nov. 6, 2013.
Interference No. 105,871, Exhibit No. 1454, Jan. 3, 2003 email correspondence between Adel Moussa and George Fleet, Filed Nov. 6, 2013.
Interference No. 105,871, Exhibit No. 1453, Dec. 16, 2002 email correspondence between Adel Moussa and George Fleet, Filed Nov. 6, 2013.
Interference No. 105,871, Exhibit No. 1410, Report on the Individual Meeting with Dick Storer, Gilles Gosselin and George Fleet, dated Dec. 31, 2002, Filed Nov. 6, 2013.
Interference No. 105,871, Exhibit No. 1378, Email from Dr. Jenkinson to Dr. Stewart dated Apr. 14, 2005, Filed Nov. 6, 2013.
Interference No. 105,871, Exhibit No. 1375, Email from Dr. Jenkinson to Dr. Stewart dated Apr. 7, 2005, Filed Nov. 6, 2013.
Interference No. 105,871, Exhibit No. 1374, Email from Dr. Jenkinson to Dr. Stewart dated Apr. 5, 2005, Filed Nov. 6, 2013.
Interference No. 105,871, Exhibit No. 1371, Email from Dr. Jenkinson to Dr. Stewart dated Mar. 23, 2005, Filed Nov. 6, 2013.
Interference No. 105,871, Exhibit No. 1366, Email from Dr. Stewart to Dr. Jenkinson dated Mar. 14, 2005, Filed Nov. 6, 2013.
Interference No. 105,871, Exhibit No. 1364, Email from Dr. Stewart to Dr. Jenkinson dated Feb. 14, 2005, Filed Nov. 6, 2013.
Interference No. 105,871, Exhibit No. 1226, Trainee Notebook 1 of Elodie Pecheux, cover page and pp. 30-89, Filed Nov. 6, 2013.
Interference No. 105,871, Exhibit No. 1044, Wu, Jun. 2001, Hepatology 33: 1550-51, Filed Nov. 6, 2013.
Interference No. 105,871, Exhibit No. 1035, Apath.com webpage at http://www.apath.com/Blazing_Blight_7.htm, Filed Nov. 6, 2013.
Interference No. 105,871, Exhibit No. 1156, Manual of Patent Examining Procedure, Eighth Edition, Revision 8 (Jul. 2010), Section 201.11(V), Filed Nov. 6, 2013.
Interference No. 105,871, Exhibit No. 1132, Kuroboshi et al., 1995, Synlett 987-988, Filed Nov. 6, 2013.
Interference No. 105,871, Exhibit No. 1131, Taguchi et al., 1974, J. of the American Chemical Society 96: 3010-3011, Filed Nov. 6, 2013.
Interference No. 105,871, Exhibit No. 1205, Email from A. Zupcic to K. Flanagan, A. Katula and L. Banks, dated Jun. 27, 2012, 12:36 p.m., Filed Nov. 6, 2013.
Interference No. 105,871, Exhibit No. 1202, Bhat et al. Hepatitis C Virus, Flaviviruses, Abstract 120, Program and Abstract, The Sixteenth International Conference on Antiviral Research, Apr. 27, 2003-May 1, 2003, Savannah, Ga., USA, p. A75, Filed Nov. 6, 2013.
Interference No. 105,871, Exhibit No. 1153, Notice to File Corrected Application Papers, dated Jul. 17, 2008, from the File History of Sommadossi et al., U.S. Appl. No. 12/131,868, filed Jun. 2, 2008, Filed Nov. 6, 2013.
Interference No. 105,871, Exhibit No. 1151, Sofia et al., Abstracts of Papers, 238th ACS National Meeting, Washington, DC, United States, Aug. 16-20, 2009, Abstract MEDI-101 (including cover page of Abstract book), Filed Nov. 6, 2013.
Interference No. 105,871, Exhibit No. 1086, Granted Claims of U.S. Pat. No. 7,608,600 B2, Filed Nov. 6, 2013.
Interference No. 105,871, Exhibit No. 1085, Furman et al., 2011, Antiviral Res. 91: 120-132, Filed Nov. 6, 2013.
Interference No. 105,871, Exhibit No. 1160, Locatelli et al., 2001, J. Mol. Biol. 313: 683-94, Filed Nov. 6, 2013.
Interference No. 105,871, Exhibit No. 1117, Matsuda et al., 1988, Chem. Pharm. Bull. 36(3): 945-953 and 3967-3970, Filed Nov. 6, 2013.
Interference No. 105,871, Exhibit No. 1104, Walton, Great Britain Patent 1,209,654, published Oct. 21, 1970, Filed Nov. 6, 2013.
Interference No. 105,871, Exhibit No. 1087, Amendment and Response Under 37 C.F.R. § 1.111, dated Sep. 20, 2011, from the File History of U.S. Appl. No. 12/131,868, filed Jun. 2, 2008, Filed Nov. 6, 2013.
Interference No. 105,871, Exhibit No. 1189, Deposition Transcript of Stanley Moncrief Lemon, M.D., dated Jul. 31, 2012 (with errata sheet), executed Sep. 6, 2012, Filed Nov. 6, 2013.
Interference No. 105,871, Exhibit No. 1647, Deposition Transcript of Jingyang Wang dated Jul. 2, 2013 (with errata sheet), Filed Nov. 6, 2013.
Interference No. 105,871, Exhibit No. 1092, Visser v. Hofvander, Interference 103,579, Final Decision (BPAI), Filed Nov. 6, 2013.

(56) References Cited

OTHER PUBLICATIONS

Interference No. 105,871, Exhibit No. 1644, Deposition Transcript of Richard Storer, Ph.D. dated Jun. 14, 2013 (with errata sheet), Filed Nov. 6, 2013.
Interference No. 105,871, Exhibit No. 1447, Substitute Certified English Translation of the Declaration of Elodie Pecheux, signed May 29, 2013, Filed Nov. 6, 2013.
Interference No. 105,871, Exhibit No. 1445, Substitute Declaration of David Standring, Ph.D., signed May 31, 2013, Filed Nov. 6, 2013.
Interference No. 105,871, Exhibit No. 1049, Yi et al., 2002, Virology 304: 197-210, Filed Nov. 6, 2013.
Interference No. 105,871, Exhibit No. 1047, Rosenberg, Oct. 2001, J. Mol. Biol. 313:451-64, Filed Nov. 6, 2013.
Interference No. 105,871, Exhibit No. 1020, Prusoff, 1963, Cancer Res. 23: 1246-59, Filed Nov. 6, 2013.
Interference No. 105,871, Exhibit No. 1130, Hudziak v. Ring, Interference 105,266, 2005 WL 3694322 (BPAI 2005), Filed Nov. 6, 2013.
Interference No. 105,871, Exhibit No. 1646, Deposition Transcript of Jean-Francois Griffon dated Jun. 25, 2013 (with errata sheet), Filed Nov. 6, 2013.
Interference No. 105,871, Exhibit No. 1651, Deposition Transcript of George Fleet dated Jul. 9, 2013 (with errata sheet), Filed Nov. 6, 2013.
Interference No. 105,871, Exhibit No. 1167, Deposition Transcript of Jeffrey Scott Glenn, M.D., Ph.D., dated Jul. 31, 2012 (with errata sheet), Filed Nov. 6, 2013.
Interference No. 105,871, Exhibit No. 1645, Deposition Transcript of Dr. Alistair Stewart dated Jun. 19, 2013 (with errata sheet), Filed Nov. 6, 2013.
Interference No. 105,871, Exhibit No. 1190, Deposition Transcript of Jeffrey Scott Glenn, M.D., Ph.D., dated Jul. 31, 2012 (with errata sheet), executed Aug. 30, 2012, Filed Nov. 6, 2013.
Interference No. 105,871, Exhibit No. 1637, Clark Exhibit List 11, served Jun. 28, 2013, Filed Nov. 6, 2013.
Interference No. 105,871, Exhibit No. 1395, Substitute Declaration of Massimiliano La Colla, Ph.D., signed May 30, 2013, Filed Nov. 6, 2013.
Interference No. 105,871, Exhibit No. 1428, Substitute Declaration of Adel Moussa, signed Jun. 3, 2013, Filed Nov. 6, 2013.
Interference No. 105,871, Exhibit No. 1424, Substitute Declaration of Elodie Pecheux, signed May 29, 2013, Filed Nov. 6, 2013.
Interference No. 105,871, Exhibit No. 1422, Curriculum Vitae of David Standring, Ph.D., Filed Nov. 6, 2013.
Interference No. 105,871, Exhibit No. 1001, Curriculum Vitae of Jeffrey S. Glenn, M.D., Ph.D., Filed Nov. 6, 2013.
Interference No. 105,871, Exhibit No. 1178, Jeong et al., 1993, J. Med. Chem. 36: 181-195, Filed Nov. 6, 2013.
Interference No. 105,871, Exhibit No. 1174, Office Action, dated Feb. 26, 2008, from the File History of Clark U.S. Appl. No. 10/828,753, filed Apr. 21, 2004, Filed Nov. 6, 2013.
Interference No. 105,871, Exhibit No. 1634, Deposition Transcript of David Standring, dated Jun. 11, 2013 (with errata sheets), Filed Nov. 6, 2013.
Interference No. 105,871, Exhibit No. 1660, Clark Exhibit List 16, served Jul. 26, 2013, Filed Nov. 6, 2013.
Interference No. 105,871, Exhibit No. 1535, Amendment and Response, dated Aug. 20, 2007, from the File History of Sommadossi et al., U.S. Appl. No. 10/608,907, filed Jun. 27, 2003, Filed Nov. 6, 2013.
Interference No. 105,871, Exhibit No. 1397, Idenix Pharmaceuticals Laboratory Notebook No. 064 (Massimiliano La Colla, Ph.D.), cover pages and pp. 152-155, 157-160 and 162-166, Filed Nov. 6, 2013.
Interference No. 105,871, Exhibit No. 1418, Reply from Paul Coe to Dick Storer, Filed Nov. 6, 2013.
Interference No. 105,871, Exhibit No. 1019, Leyssen et al., 2000, Clin. Microbiol. Rev. 13: 67-82, Filed Nov. 6, 2013.
Interference No. 105,871, Exhibit No. 1100, Watts and Damha, 2008, Can. J. Chem., 86: 641-656, Filed Nov. 6, 2013.
Interference No. 105,871, Exhibit No. 1080, Carroll and LaFemina, Antiviral Research: Strategies in Antiviral Drug Discovery 153-166 (Robert L. LaFemina, Ph.D., ed., 2009), Filed Nov. 6, 2013.
Interference No. 105,871, Exhibit No. 1112, Hirooka et al., 2001, Bull. Chem. Soc. Jpn. 74(9): 1679-1694, Filed Nov. 6, 2013.
Interference No. 105,871, Exhibit No. 1110, Bryant et al., International Patent Publication No. WO 01/96353, published Dec. 20, 2001, Filed Nov. 6, 2013.
Interference No. 105,871, Exhibit No. 1405, Substitute Declaration of Michele M. Tausek, signed May 31, 2013, Filed Nov. 6, 2013.
Interference No. 105,871, Exhibit No. 1429, Substitute Declaration of Richard Storer, D.Phil., signed May 31, 2013, Filed Nov. 6, 2013.
Interference No. 105,871, Exhibit No. 1052, Bartenschlager and Lohmann, Oct. 2001, Antiviral Res. 52: 1-17, Filed Nov. 6, 2013.
Interference No. 105,871, Exhibit No. 1028, Commentary in 1999, Science 285: 9, Filed Nov. 6, 2013.
Interference No. 105,871, Exhibit No. 1102, Sofia et al., 2010, J. Med. Chem. 53: 7202-7218, Filed Nov. 6, 2013.
Interference No. 105,871, Exhibit No. 1182, Franchetti et al., 1994, Nucleosides & Nucleotides 13: 1739-55, Filed Nov. 6, 2013.
Interference No. 105,871, Exhibit No. 1107, De Clercq, 2001, J. Clin. Virology 22: 73-89, Filed Nov. 6, 2013.
Interference No. 105,871, Exhibit No. 1016, Watanabe et al., International Patent Application Publication No. WO 01/79246, published Oct. 25, 2001, Filed Nov. 6, 2013.
Interference No. 105,871, Exhibit No. 1282, Notebook 2 of Jean-François Griffon, Filed Nov. 6, 2013.
Interference No. 105,871, Exhibit No. 1277, English translation of Notebook 1 of Jean-François Griffon, Filed Nov. 6, 2013.
Interference No. 105,871, Exhibit No. 1276, Notebook 1 of Jean-François Griffon, Filed Nov. 6, 2013.
Interference No. 105,871, Exhibit No. 1011, Notebook 1 of Jean-François Griffon, Filed Nov. 6, 2013.
Interference No. 105,871, Exhibit No. 1527, Certified English Translation of Apr. 14, 2003 Email from Dick Storer to Gilles Gosselin, Filed Nov. 6, 2013.
Interference No. 105,871, Exhibit No. 1525, IR spectrum of compound 17 of Scheme B acquired on Apr. 11, 2004, Filed Nov. 6, 2013.
Interference No. 105,871, Exhibit No. 1524, NMR spectrum of compound 33 of Scheme C acquired on Mar. 7, 2004, Filed Nov. 6, 2013.
Interference No. 105,871, Exhibit No. 1523, NMR spectrum of compound 25 of Scheme B acquired on Feb. 21, 2004, Filed Nov. 6, 2013.
Interference No. 105,871, Exhibit No. 1522, NMR spectrum of compound 25 of Scheme B acquired on Feb. 17, 2004, Filed Nov. 6, 2013.
Interference No. 105,871, Exhibit No. 1521, NMR spectrum of compound 19 of Scheme B acquired on Feb. 14, 2004, Filed Nov. 6, 2013.
Interference No. 105,871, Exhibit No. 1520, NMR spectrum of compound 14 of Scheme B acquired on Jan. 25, 2004, Filed Nov. 6, 2013.
Interference No. 105,871, Exhibit No. 1519, NMR spectrum of compound 5 of Scheme G2 acquired on Jan. 6, 2004, Filed Nov. 6, 2013.
Interference No. 105,871, Exhibit No. 1518, NMR spectrum of compound 28 of Scheme C acquired on Dec. 2, 2004, Filed Nov. 6, 2013.
Interference No. 105,871, Exhibit No. 1517, NMR spectrum of compound 7 of Scheme B acquired on Nov. 30, 2004, Filed Nov. 6, 2013.
Interference No. 105,871, Exhibit No. 1516, NMR spectrum of compound 13 of Scheme B acquired on Nov. 17, 2004, Filed Nov. 6, 2013.
Interference No. 105,871, Exhibit No. 1261, Schedule of vacation days, sick days and holidays at Idenix, Filed Nov. 6, 2013.
Interference No. 105,871, Exhibit No. 1539, Certification of the English Translation of the Memorandum announcing closure of analytical laboratories at University of Montpellier II from Jul. 25, 2003-Sep. 1, 2003, Filed Nov. 6, 2013.

(56) References Cited

OTHER PUBLICATIONS

Interference No. 105,871, Exhibit No. 1334, Email from Dr. Stewart to Dr. Mayes dated Jun. 28, 2004, Filed Nov. 6, 2013.
Interference No. 105,871, Exhibit No. 1333, Email from Professor Fleet to Dr. Stewart dated May 9, 2004, Filed Nov. 6, 2013.
Interference No. 105,871, Exhibit No. 1331, Email from Professor Fleet to Dr. Stewart dated May 12, 2004, Filed Nov. 6, 2013.
Interference No. 105,871, Exhibit No. 1236, English Translation of Resume of Clement Counor, Filed Nov. 6, 2013.
Interference No. 105,871, Exhibit No. 1235, Resume of Clement Counor, Filed Nov. 6, 2013.
Interference No. 105,871, Exhibit No. 1230, English translation of Resume of Tony Bouisset, Filed Nov. 6, 2013.
Interference No. 105,871, Exhibit No. 1639, Excerpt from Notebook No. 2, p. 142 of Jean-Francois Griffon, Filed Nov. 6, 2013.
Interference No. 105,871, Exhibit No. 1638, Excerpt from Notebook No. 2, p. 132 of Jean-Francois Griffon, Filed Nov. 6, 2013.
Interference No. 105,871, Exhibit No. 1635, Excerpt from Notebook No. 2, p. 127 of Jean-Francois Griffon, Filed Nov. 6, 2013.
Interference No. 105,871, Exhibit No. 1633, Excerpt from Notebook No. 2, p. 124 of Jean-Francois Griffon, Filed Nov. 6, 2013.
Interference No. 105,871, Exhibit No. 1632, Excerpt from Notebook No. 2, p. 110 of Jean-Francois Griffon, Filed Nov. 6, 2013.
Interference No. 105,871, Exhibit No. 1631, Excerpt from Notebook No. 2, p. 56 of Jean-Francois Griffon, Filed Nov. 6, 2013.
Interference No. 105,871, Exhibit No. 1630, Excerpt from Notebook 2, p. 46 of Jean-Francois Griffon, Filed Nov. 6, 2013.
Interference No. 105,871, Exhibit No. 1625, NMR spectrum of Alistair Stewart dated Apr. 27 2005, Filed Nov. 6, 2013.
Interference No. 105,871, Exhibit No. 1623, NMR spectrum of Alistair Stewart dated Apr. 13, 2005, Filed Nov. 6, 2013.
Interference No. 105,871, Exhibit No. 1622, NMR spectrum of Alistair Stewart dated Apr. 12, 2005, Filed Nov. 6, 2013.
Interference No. 105,871, Exhibit No. 1621, NMR spectrum of Alistair Stewart dated Apr. 1, 2005, Filed Nov. 6, 2013.
Interference No. 105,871, Exhibit No. 1620, NMR spectrum of Alistair Stewart dated Mar. 29, 2005, Filed Nov. 6, 2013.
Interference No. 105,871, Exhibit No. 1619, NMR spectrum of Alistair Stewart dated Mar. 29, 2005, Filed Nov. 6, 2013.
Interference No. 105,871, Exhibit No. 1618, NMR spectrum of Alistair Stewart dated Mar. 22, 2005, Filed Nov. 6, 2013.
Interference No. 105,871, Exhibit No. 1617, NMR spectrum of Alistair Stewart dated Mar. 21, 2005, Filed Nov. 6, 2013.
Interference No. 105,871, Exhibit No. 1616, NMR spectrum of Alistair Stewart dated Mar. 21, 2005, Filed Nov. 6, 2013.
Interference No. 105,871, Exhibit No. 1615, NMR spectrum of Alistair Stewart dated Mar. 21, 2005, Filed Nov. 6, 2013.
Interference No. 105,871, Exhibit No. 1614, NMR spectrum of Alistair Stewart dated Mar. 17, 2005, Filed Nov. 6, 2013.
Interference No. 105,871, Exhibit No. 1613, NMR spectrum of Alistair Stewart dated Mar. 15, 2005, Filed Nov. 6, 2013.
Interference No. 105,871, Exhibit No. 1612, NMR spectrum of Alistair Stewart dated Jan. 21, 2005, Filed Nov. 6, 2013.
Interference No. 105,871, Exhibit No. 1611, NMR spectrum of Alistair Stewart dated Jan. 18, 2005, Filed Nov. 6, 2013.
Interference No. 105,871, Exhibit No. 1610, NMR spectrum of Alistair Stewart dated Jan. 27, 2005, Filed Nov. 6, 2013.
Interference No. 105,871, Exhibit No. 1609, NMR spectrum of Alistair Stewart dated Jan. 21, 2005, Filed Nov. 6, 2013.
Interference No. 105,871, Exhibit No. 1608, NMR spectrum of Alistair Stewart dated Jan. 27, 2005, Filed Nov. 6, 2013.
Interference No. 105,871, Exhibit No. 1605, NMR spectrum of Alistair Stewart dated Jan. 21, 2005, Filed Nov. 6, 2013.
Interference No. 105,871, Exhibit No. 1604, NMR spectrum of Alistair Stewart dated Jan. 6, 2005, Filed Nov. 6, 2013.
Interference No. 105,871, Exhibit No. 1603, NMR spectrum of Alistair Stewart dated Jan. 6, 2005, Filed Nov. 6, 2013.
Interference No. 105,871, Exhibit No. 1499, Email correspondence between Sarah Jenkinson and Francesco Punzo dated Oct. 20, 2004, Filed Nov. 6, 2013.
Interference No. 105,871, Exhibit No. 1493, Jul. 27, 2004 email correspondence between Michael Parker and Sarah Jenkinson, Filed Nov. 6, 2013.
Interference No. 105,871, Exhibit No. 1492, Jul. 6, 2004 email correspondence between George Fleet and Sarah Jenkinson, Filed Nov. 6, 2013.
Interference No. 105,871, Exhibit No. 1488, Certification of the English Translation of Notebook 1 of Elodie Pecheux, cover page and pp. 30-89, Filed Nov. 6, 2013.
Interference No. 105,981, Exhibit No. 1118 (Substitute), Cerretani et al., 1999, "A High-Throughput Radiometric Assay for Hepatitis C Virus NS3 Protease," Anal. Biochem. 266: 192-97, Filed Mar. 31, 2014.
Interference No. 105,981, Exhibit No. 1123, Gottlieb et al., "NMR Chemical Shifts of Common Laboratory Solvents as Trace Impurities," J. Org. Chem. 1997, 62, 7512-7515, Filed Sep. 16, 2014.
Interference No. 105,981, Exhibit No. 1192, Tang et al., Mar. 29-Apr. 2, 1998, "Synthesis of 2'-C-[beta sign]-fluoromethyl, difluoromethyl, and trifluoromethyl substituted ribonucleosides," Book of Abstracts, 215th jACS National Meeting, American Chemical Society, Dallas, TX, Abstract 046, Filed Sep. 16, 2014.
Interference No. 105,981, Exhibit No. 1095, De Francesco et al., International Patent Application Publication No. WO 96/37619, published Nov. 28, 1996, Filed Mar. 10, 2014.
Interference No. 105,981, Exhibit No. 1166-4, Storer et al., U.S. Appl. No. 13/168,895, filed Jun. 24, 2011, Filed Sep. 16, 2014.
Interference No. 105,981, Exhibit No. 1166-3, Storer et al., U.S. Appl. No. 13/168,895, filed Jun. 24, 2011, Filed Sep. 16, 2014.
Interference No. 105,981, Exhibit No. 1166-2, Storer et al., U.S. Appl. No. 13/168,895, filed Jun. 24, 2011, Filed Sep. 16, 2014.
Interference No. 105,981, Exhibit No. 1166-1, Storer et al., U.S. Appl. No. 13/168,895, filed Jun. 24, 2011, Filed Sep. 16, 2014.
Interference No. 105,981, Exhibit No. 1165-4, Storer et al., U.S. Appl. No. 13/958,463, filed Aug. 2, 2013, Filed Sep. 16, 2014.
Interference No. 105,981, Exhibit No. 1165-3, Storer et al., U.S. Appl. No. 13/958,463, filed Aug. 2, 2013, Filed Sep. 16, 2014.
Interference No. 105,981, Exhibit No. 1164-4, Storer et al., U.S. Appl. No. 14/220,534, filed Mar. 20, 2014, Filed Sep. 16, 2014.
Interference No. 105,981, Exhibit No. 1164-3, Storer et al., U.S. Appl. No. 14/220,534, filed Mar. 20, 2014, Filed Sep. 16, 2014.
Interference No. 105,981, Exhibit No. 1164-2, Storer et al., U.S. Appl. No. 14/220,534, filed Mar. 20, 2014, Filed Sep. 16, 2014.
Interference No. 105,981, Exhibit No. 1164-1, Storer et al., U.S. Appl. No. 14/220,534, filed Mar. 20, 2014, Filed Sep. 16, 2014.
Interference No. 105,981, Exhibit No. 1165-2, Storer et al., U.S. Appl. No. 13/958,463, filed Aug. 2, 2013, Filed Sep. 16, 2014.
Interference No. 105,981, Exhibit No. 1165-1, Storer et al., U.S. Appl. No. 13/958,463, filed Aug. 2, 2013, Filed Sep. 16, 2014.
Interference No. 105,981, Exhibit No. 1185-2, Substitute Specification (marked-up version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1185-3, Substitute Specification (marked-up version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1185-4, Substitute Specification (marked-up version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1185-1, Substitute Specification (marked-up version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1011, Declaration of Dr. Raffaele De Francesco, Filed Mar. 10, 2014.
Interference No. 105,981, Exhibit No. 1001-2, Storer et al., U.S. Pat. No. 7,608,600 B2, which issued Oct. 27, 2009 from U.S. Appl. No. 10/608,907, filed Jun. 27, 2003, Filed Mar. 10, 2014.
Interference No. 105,981, Exhibit No. 1001-1, Storer et al., U.S. Pat. No. 7,608,600 B2, which issued Oct. 27, 2009 from U.S. Appl. No. 10/608,907, filed Jun. 27, 2003, Filed Mar. 10, 2014.

(56) References Cited

OTHER PUBLICATIONS

Interference No. 105,981, Exhibit No. 1205, Koonin, 1993, "Evolution and Taxonomy of Positive-Strand RNA Viruses: Implications of Comparative Analysis of Amino Acid Sequences," Critical Rev. Biochem. Mol. Biol. 28: 375-430, Filed Sep. 17, 2014.
Interference No. 105,981, Exhibit No. 1139, Lehninger, Nelson and Cox (Editors), 1993, Principles of Biochemistry (2nd ed.), Chapter 12, "Nucleotides and Nucleic Acids," pp. 324-357, Filed Sep. 16, 2014.
Interference No. 105,981, Exhibit No. 1238, Stuyver, International Publication WO 03/068164 A2, published Aug. 21, 2003, Filed Sep. 17, 2014.
Interference No. 105,981, Exhibit No. 1034, Lindenbach and Rice, 2001, Flaviviridae: The Viruses and Their Replication (Chapter 32) in Knipe et al., eds., Fields Virology, 4th ed. Philadelphia, Lippincott Williams & Wilkins, pp. 391-1041, Filed Mar. 10, 2014.
Interference No. 105,981, Exhibit No. 1029, Summa et al., 2004, "HCV NS5b RNA-Dependent RNA Polymerase Inhibitors: From ?, γ-Diketoacids to 4,5-Dihydroxypyrimidine- or 3-Methyl-5-hydroxypyrimidinonecarboxylic Acids. Design and Synthesis," J. Med. Chem. 47: 5336-39, Filed Mar. 10, 2014.
Interference No. 105,981, Exhibit No. 1028, Summa et al., 2004, "Discovery of α,γ-Diketo Acids as Potent Selective and Reversible Inhibitors of Hepatitis C Virus NS5b RNA-Dependent RNA Polymerase," J. Med. Chem. 47: 14-17, Filed Mar. 10, 2014.
Interference No. 105,981, Exhibit No. 1163, Notice of Allowance, dated Apr. 7, 2009, from the File History of U.S. Pat. No. 7,608,600 B2, Filed Sep. 16, 2014.
Interference No. 105,981, Exhibit No. 1241, Maag et al., 2001, J. Biol. Chem. 276: 46094-46098, Filed Sep. 17, 2014.
Interference No. 105,981, Exhibit No. 1185-5, Codington et al., 1961, J. Am. Chem. Soc. 83: 5030-5031, Filed Sep. 16, 2014.
Interference No. 105,981, Exhibit No. 1165-5, Storer et al., U.S. Appl. No. 13/958,463, filed Aug. 2, 2013, Filed Sep. 16, 2014.
Interference No. 105,981, Exhibit No. 1164-5, Storer et al., U.S. Appl. No. 14/220,534, filed Mar. 20, 2014, Filed Sep. 16, 2014.
Interference No. 105,981, Exhibit No. 1166-5, Storer et al., U.S. Appl. No. 13/168,895, filed Jun. 24, 2011, Filed Sep. 16, 2014.
Interference No. 105,981, Exhibit No. 1002-1, Storer et al., U.S. Appl. No. 10/608,907, filed Jun. 27, 2003, Filed Mar. 10, 2014.
Interference No. 105,981, Exhibit No. 1002-3 (Part 1), Storer et al., U.S. Appl. No. 10/608,907, filed Jun. 27, 2003, Filed Mar. 10, 2014.
Interference No. 105,981, Exhibit No. 1002-3 (Part 2), Storer et al., U.S. Appl. No. 10/608,907, filed Jun. 27, 2003, Filed Mar. 10, 2014.
Interference No. 105,981, Exhibit No. 1002-2 (Part 1), Storer et al., U.S. Appl. No. 10/608,907, filed Jun. 27, 2003, Filed Mar. 10, 2014.
Interference No. 105,981, Exhibit No. 1002-2 (Part 2), Storer et al., U.S. Appl. No. 10/608,907, filed Jun. 27, 2003, Filed Mar. 10, 2014.
Interference No. 105,981, Exhibit No. 1002-4 (Part 1), Storer et al., U.S. Appl. No. 10/608,907, filed Jun. 27, 2003, Filed Mar. 10, 2014.
Interference No. 105,981, Exhibit No. 1002-4 (Part 2), Storer et al., U.S. Appl. No. 10/608,907, filed Jun. 27, 2003, Filed Mar. 10, 2014.
Interference No. 105,981, Exhibit No. 1162, Paper 80, Interference 105,871, *Clark v. Sommadossi*, Sommadossi Reply 3, filed Oct. 11, 2012, Filed Sep. 16, 2014.
Interference No. 105,981, Exhibit No. 1074, De Francesco et al., International Patent Application Publication No. WO 02/059321 A2, published Aug. 1, 2002, filed Jan. 16, 2002, Filed Mar. 10, 2014.
Interference No. 105,981, Exhibit No. 1137, Damha et al., 2006, J. Org. Chem. 71(3): 921-925, Filed Mar. 10, 2014.
Interference No. 105,981, Exhibit No. 1077, Bhat et al., Feb. 2003 "Synthesis and Pharmacokinetic Properties of Nucleoside Analogs as Possible Inhibitors of HCV RNA Replication," Hepatitis C Virus, Flaviviruses, Abstract 120, Program and Abstract, The Sixteenth International Conference on Antiviral Research, Apr. 27, 2003-May 1, 2003, Savannah, GA., USA, p. A75, Filed Mar. 10, 2014.
Interference No. 105,981, Exhibit No. 1211, Zitzmann et al., 1999 "Imino sugars inhibit the formation and secretion of povine viral diarrhea virus, a pestivirus model of hepatitis C virus: Implications for the development of broad spectrum anti-hepatitis virus agents," Proc. Natl. Acad. Sci. USA 96: 11878-82, Filed Sep. 17, 2014.

Interference No. 105,981, Exhibit No. 1057, Blight et al., 2000, "Efficient Initiation of HCV RNA Replication in Cell Culture," Science 290: 1972-74, Filed Mar. 10, 2014.
Interference No. 105,981, Exhibit No. 1052, Lohmann et al., 1999, "Replication of Subgenomic Hepatitis C Virus RNAs im a Hepatoma Cell Line," Science 285: 110-13, Filed Mar. 10, 2014.
Interference No. 105,981, Exhibit No. 1017, Van Aerschot et al., 1989, Bull. Soc. Chim. Belg. 98(12): 937-941 [Substitute], Filed Mar. 10, 2014.
Interference No. 105,981, Exhibit No. 2138, De Francesco, J., Anti-HCV Drug Discovery: Preclinical Studies, First International Course of Translational Hepatology, Florence, 2011 (Presentation) with Page Numbering Inserted, Filed Sep. 18, 2014.
Interference No. 105,981, Exhibit No. 2152, Interference No. 105,871, Paper No. 542, Idenix Exhibit 1275 (entitled (by Idenix): "English Language Version of Resume of Jean-François Griffon"), Filed May 23, 2014.
Interference No. 105,981, Exhibit No. 2065, Stuyver, L.J., et al., Inhibition of the Subgenomic Hepatitis C Virus Replicon in Huh-7 Cells by 2'-Deoxy-2'-Fluorocytidine, Antimicrob Agents & Chemotherapy 48(2):651-654 (2004), Filed Mar. 31, 2014.
Interference No. 105,981, Exhibit No. 2112, Interference No. 105,871, Paper No. 1001, Sommadossi Filing of Its Priority Record, Filed Sep. 18, 2014.
Interference No. 105,981, Exhibit No. 2160, DeLong, D.C., et al., Antiviral Activity of 2', 2'-Difluorocytidine, Abstracts of the Annual Meeting of the American Society of Microbiology, T-55 (1986) with Page Numbering Inserted, Filed Sep. 18, 2014.
Interference No. 105,981, Exhibit No. 2156, Storer U.S. Appl. No. 14/146,520 ("S8") file history—Jan. 15, 2014 Filing Receipt, Filed Sep. 18, 2014.
Interference No. 105,981, Exhibit No. 2012, Clark U.S. Appl. No. 11/854,218 ("C3") file history—Aug. 30, 2013 Preliminary Amendment, Filed Mar. 10, 2014.
Interference No. 105,981, Exhibit No. 2101, U.S. Pat. No. 5,637,688, Filed Mar. 10, 2014.
Interference No. 105,981, Exhibit No. 2042, Interference No. 105,871, Paper No. 622, Idenix Exhibit 1355 (entitled (by Idenix): "Email attachment of Ex 1354"), Filed Mar. 10, 2014.
Interference No. 105,981, Exhibit No. 2029, Interference No. 105,871, Paper No. 570, Idenix Exhibit 1303 (entitled (by Idenix): "Email from Jean-François Griffon to Dick Storer dated Mar. 4, 2003 with attached Feb. 2003 progress report"), Filed Mar. 10, 2014.
Interference No. 105,981, Exhibit No. 2027, Interference No. 105,871, Paper No. 567, Idenix Exhibit 1300 (entitled (by Idenix): "Dec. 2002 progress report prepared by Jean-François Griffon"), Filed Mar. 10, 2014.
Interference No. 105,981, Exhibit No. 2026, Interference No. 105,871, Paper No. 564, Idenix Exhibit 1297 (entitled (by Idenix): "Copy of email from Jean-François Griffon to Dick Storer dated Dec. 9, 2002"), Filed Mar. 10, 2014.
Interference No. 105,981, Exhibit No. 2025, Van Robays, M., et al., Preparation and Determination of Configuration of 3- Halogeno-3-methyl-5α-cholestane Epimers, J. Chem. Soc. Perkin Trans., pp. 251- 254 (1986), Filed Mar. 10, 2014.
Interference No. 105,981, Exhibit No. 2015, Jeong, L.S., et al., Unanticipated Retention of Configuration in the DAST Fluorination of Deoxy-4'-thiopyrimidine Nucleosides with "Up" Hydroxyl Groups, Tetrahedron Letters, vol. 35, No. 41, pp. 7569-7572 (1994), Filed Mar. 10, 2014.
Interference No. 105,981, Exhibit No. 2128, Interference No. 105,871, Paper No. 737, Idenix Exhibit 1471 (entitled (by Idenix): "Substitute Certified English Translation of the Declaration of Jean-François Griffon, signed May 31, 2013"), Filed May 23, 2014.
Interference No. 105,981, Exhibit No. 2168, Interference No. 105,871, Paper No. 271, Idenix Exhibit 1088 (entitled (by Idenix): "Declaration of Jeffrey S. Glenn, M.D., Ph.D., signed Jun. 2, 2012"), Filed Sep. 18, 2014.
Interference No. 105,981, Exhibit No. 2178, U.S. Patent Appln. Pub. No. 2008/0070861 A1, published Mar. 20, 2008 "C3- Pub"), Filed Sep. 18, 2014.

(56) References Cited

OTHER PUBLICATIONS

Interference No. 105,981, Exhibit No. 2050, Interference No. 105,871, Paper No. 507, Idenix Exhibit 1240 (entitled (by Idenix): "Substitute Declaration of Sarah Jenkinson, signed May 30, 2013"), Filed Mar. 10, 2014.
Interference No. 105,981, Exhibit No. 2009, Clark U.S. Appl. No. 60/474,368 ("C1") as filed May 30, 2003, Filed Mar. 10, 2014.
Interference No. 105,981, Exhibit No. 2056, International Patent Publication No. WO 02/18369 A2, Filed Mar. 10, 2014.
Interference No. 105,981, Exhibit No. 2118, Interference No. 105,871, Paper No. 565, Idenix Exhibit 1298 (entitled (by Idenix): "Substitute Declaration of Jean-François Griffon, signed May 31, 2013"), Filed Sep. 18, 2014.
Interference No. 105,981, Exhibit No. 2107, Interference No. 105,871, Paper No. 25, Sommadossi Substantive Motion 1, Filed Jun. 5, 2012, Filed Mar. 10, 2014.
Interference No. 105,981, Exhibit No. 2167, Interference No. 105,871, Paper No. 171, Idenix Exhibit 1013 (entitled (by Idenix): "Declaration of Stanley M. Lemon, M.D., signed Jun. 4, 2012"), Filed Sep. 18, 2014.
Interference No. 105,981, Exhibit No. 2036, Interference No. 105,871, Paper No. 891, Idenix Exhibit 1627 (entitled (by Idenix): "English Translation of Internship Report of Elodie Pecheux"), Filed Mar. 10, 2014.
Interference No. 105,981, Exhibit No. 2116, Interference No. 105,871, Paper No. 536, Idenix Exhibit 1269 (entitled (by Idenix): "Internship Report of Elodie Pecheux"), Filed Sep. 18, 2014.
Interference No. 105,981, Exhibit No. 2106, Interference No. 105,871, Paper No. 427, Redeclaration, Entered Mar. 22, 2013, Filed Mar. 10, 2014.
Interference No. 105,981, Exhibit No. 2061, Lohmann, V., et al., Replication of Subgenomic Hepatitis C Virus RNAs in a Hepatoma Cell Line, Science 285:110-113 (1999), Filed Mar. 31, 2014.
Interference No. 105,981, Exhibit No. 2100, European Patent Appln. No. 03761744 file history—Oct. 29, 2013 Result of Consultation by Telephone/In Person with Certification Cover Sheet and Page Numbering Inserted, Filed Sep. 18, 2014.
Interference No. 105,981, Exhibit No. 2165, Kaufman, H.E, et al., Use of 5-Iodo-2'-Deoxyuridine (IDU) in Treatment of Herpes Simplex Keratitis, Arch Ophthalmol., vol. 68, No. 2, pp. 235-239 (1962), Filed Sep. 18, 2014.
Interference No. 105,981, Exhibit No. 2144, The Journal of the American Chemical Society, Table of Contents, vol. 79, No. 3 (1957), Filed Sep. 18, 2014.
Interference No. 105,981, Exhibit No. 2035, Interference No. 105,871, Paper No. 734, Idenix Exhibit 1468 (entitled (by Idenix): "Jan. 7, 2005 email correspondence between Adel Moussa and Alistair Stewart"), Filed Mar. 10, 2014.
Interference No. 105,981, Exhibit No. 2031, Interference No. 105,871, Paper No. 578, Idenix Exhibit 1311 (entitled (by Idenix): "Email from Jean-François Griffon to Dick Storer dated Aug. 28, 2003 with attached Jul.-Aug. 2003 progress report"), Filed Mar. 10, 2014.
Interference No. 105,981, Exhibit No. 2030, Interference No. 105,871, Paper No. 575, Idenix Exhibit 1308 (entitled (by Idenix): "Email from Jean-François Griffon to Dick Storer dated Jun. 3, 2003 with attached May 2003 progress report"), filed Mar. 10, 2014.
Interference No. 105,981, Exhibit No. 2028, Interference No. 105,871, Paper No. 569, Idenix Exhibit 1302 (entitled (by Idenix): "Email from Jean-François Griffon to Dick Storer dated Feb. 3, 2003 with attached Jan. 2003 progress report"), Filed Mar. 10, 2014.
Interference No. 105,981, Exhibit No. 2014, Yang, S.S., et al., Synthesis of DL-1-deoxy-1-fluoro-6-O-methyl-chiro-inositol: confirmation of a structural-DAST fluorination correlation, Carbohydrate Research, vol. 249, pp. 259-263 (1993), Filed Mar. 10, 2014.
Interference No. 105,981, Exhibit No. 2175, Storer U.S. Appl. No. 13/958,463 ("S7") file history—Aug. 5, 2013 Preliminary Amendment, Filed Sep. 18, 2014.
Interference No. 105,981, Exhibit No. 2088, Paper No. 41, Affidavit Exhibit No. 1—Declaration and Curriculum Vitae of Jean-Pierre Sommadossi, Ph.D., Interference No. 103,906, Apr. 3, 1998, Filed Sep. 18, 2014.
Interference No. 105,981, Exhibit No. 2137-4, Swarbrick, J. and Boylan, J.C., eds., Encyclopedia of Pharmaceutical Technology, vol. 13, Marcel Dekker, Inc. (1996), Filed Sep. 18, 2014.
Interference No. 105,981, Exhibit No. 2110-6, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2137-5, Swarbrick, J. and Boylan, J.C., eds., Encyclopedia of Pharmaceutical Technology, vol. 13, Marcel Dekker, Inc. (1996), Filed Sep. 18, 2014.
Interference No. 105,981, Exhibit No. 2186, U.S. Pat. No. 8,742,101 B2, Filed Sep. 18, 2014.
Interference No. 105,981, Exhibit No. 2110-7, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2110-10, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 2074, Lindenbach, B.D., et al., Flaviviridae: The Viruses and Their Replication (Chapter 33), in Knipe, D.M. et al., eds., Fields Virology, 5th ed. Philadelphia, Lippincott Williams & Wilkins (2007), Filed Mar. 10, 2014.
Interference No. 105,981, Exhibit No. 2060, Lindenbach, B.D. and Rice, C.M., Flaviviridae: The Viruses and Their Replication (Chapter 32) in Knipe, D.M. et al., eds., Fields Virology, 4th ed. Philadelphia, Lippincott Williams & Wilkins 2001), Filed Mar. 10, 2014.
Interference No. 105,981, Exhibit No. 2110-4, Clark U.S. Appl. No. 10/828,753 ("C2") as filed Apr. 21, 2004, Filed Sep. 18, 2014.
Interference No. 105,981, Exhibit No. 2108, Transcript of Conference Call for Interference No. 105,981, held Jan. 10, 2014, Filed Sep. 18, 2014.
Interference No. 105,981, Exhibit No. 2103, Interference No. 105,871, Paper No. 69, Sommadossi Opposition 2, Filed Aug. 17, 2012, Filed Sep. 18, 2014.
Interference No. 105,981, Exhibit No. 2102, Interference No. 105,871, Paper No. 466, Sommadossi Reply 9, Filed Sep. 6, 2013, Filed Sep. 18, 2014.
Interference No. 105,981, Exhibit No. 2110-12, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,871 Exhibit 1276.
Interference No. 105,871 Exhibit 1282.
Interference No. 105,871 Exhibit 1289.
Interference No. 105,871 Exhibit 1294.
Interference No. 105,871 Exhibit 1295.
Interference No. 105,871 Exhibit 1297.
Interference No. 105,871 Exhibit 1300.
Interference No. 105,871 Exhibit 1302.
Interference No. 105,871 Exhibit 1303.
Interference No. 105,871 Exhibit 1304.
Interference No. 105,871 Exhibit 1308.
Interference No. 105,871 Exhibit 1311.
Interference No. 105,871 Exhibit 1318.
Interference No. 105,871 Exhibit 1319.
Interference No. 105,871 Exhibit 1335.
Interference No. 105,871 Exhibit 1418.
Interference No. 105,871 Exhibit 1468.
Interference No. 105,871, Clark Opposition 9 dated Jul. 26, 2013.
Interference No. 105,871, Decision—Priority dated Jan. 29, 2014.
Interference No. 105,871, Decision on Request for Rehearing dated Apr. 23, 2013.
Interference No. 105,871, Exhibit 1336.
Interference No. 105,871, Exhibit 1416.
Interference No. 105,871, Substitute Sommadossi Substantive Motion 8 dated Jul. 18, 2013.

(56) References Cited

OTHER PUBLICATIONS

Interference No. 105,981, Decision on Motions dated Jan. 16, 2015.
Interference No. 105,981, Judgment—Request for Adverse dated Mar. 23, 2015.
Invention and Non-Disclosure Agreement between Novirio Pharmaceuticals, Inc. and Jean-Pierre Sommadossi dated Nov. 1, 2000.
Invention and Non-Disclosure Agreement between Novirio Pharmaceuticals, Inc. and Richard Storer dated Nov. 20, 2001.
Jung, et al., "Synthesis of Methylene-Expanded Oxetanocin Isonucleosides in Both Enantiomeric Forms," J. Org. Chem., 63:347-355 (1998).
Kuhl, Memo to Board of Directors of Pharmasset, Ltd. dated Nov. 18, 2003.
Kuhl, Weldell Craig, First Witness Statement dated Jul. 10, 2014 from *Idenix Pharmaceuticals, Inc.* v. *Gilead Sciences, Inc.*, UK High Court of Justice, Chancery Division, Patents Court, Claim No. HP 14D 01069.
Laliberte, et al., "Human Cytidine Deaminase: Purification of Enzyme, Cloning, and Expression of Its complementary DNA," Cancer Res. 54:5401-5407 (1994).
Lam, et al., "PSI-7851, a Pronucleotide of β-D-2'-Deoxy-2'-Fluoro-2'-C-Methyluridine Monophosphate, Is a Potent and Pan-Genotype Inhibitor of Hepatitis C Virus Replication," Antimicrobial Agents & Chemotherapy, 54(8):3187-3196 (2010).
Lavanchy, "Evolving Epidemiology of Hepatitis C Virus," Clinical Microbiology and Infection, 17(2):107-115 (2011).
Limbach, et al., "Summary: The Modified Nucleosides of RNA," Nucleic Acids Research, 22:2183-2196 (1994).
Lin, et al., "Design and Synthesis of 2',3'-Dideoxy-2',3'-Didehydro-β-L-Cytidine (β-L-d4C) and 2',3'-Dideoxy-2',3'-Didehydro-β-L-5-Fluorocytidine (β-L-Fd4C), Two Exceptionally Potent Inhibitors of Human Hepatitis B Virus (HBV) and Potent Inhibitors of Human Immunodeficiency Virus (HIV) in Vitro," J. Med. Chem. 39(9):1757-1759 (1996).
Lin, et al., "Synthesis of Several Pyrimidine L-Nucleoside Analogues as Potent Antiviral Agents," Tetrahedron Lett. 51 (4):1055-1068 (1995).
Locatelli, et al., "Hepatitis C Virus NS3 NTPase/Helicase: Different Stereoselectivity in Nucleoside Triphosphate Utilisation Suggests that NTPase and Helicase Activities are Coupled by a Nucleotide-dependent Rate Limiting Step," J. Mol. Biol. 313:683-694 (2001).
Lohmann, et al. "Biochemical and Kinetic Analysis of NS5B RNA-Dependent RNA Polymerase of the Hepatitis C Virus," Virology, 249:108-118 (1998).
Ma, et al., "Characterization of the Metabolic Activation of Hepatitis C Virus Nucleoside Inhibitor β-D-2'-Deoxy-2'fluoro-2'-C-methylcytidine (PSI-6130) and Identification of a Novel Active 5'-Triphosphate Species," Journal of Biological Chemistry 282(41):29812-29820 (2007).
Mangner, et al. "Synthesis of 2'-Deoxy-2'[18F]fluoro-β-D-arabinofuranosyl Nucleosides, [18F]FAU, [18F]FMAU, [18F]FBAU and [18F]FIAU, as Potential PET Agents for Imaging Cellular Proliferation," Nuclear Medicine & Biologiy 30:215-224 (2003).
Manoharan, et al. "2-O- and 3'-O-Pyrimidine Aminoether-Containing Oligonucleotides: Synthesis and Conjugation Chemistry," Tetrahedron Letters, 36(21):3647-3650 (1995).
Mansour, et al., "Stereochemical Aspects of the Anti-HCMV Activity of Cytidine Nucleoside Analogues," Antiviral chemistry & Chemotherapy, 6(3):138-142 (1995).
Marchand, et al., "Stereospecific Synthesis of Unnatural β-L-Enantiomers of 2-Chloroadenine Pentofuranonucleoside Derivatives," J. Chem. Soc. Perkin Trans 1, pp. 2249-2254 (1999).
Marquez, 4th Declaration dated Jul. 25, 2013, Exhibit 2152 in Interference No. 105871.
Marquez, Deposition Transcript dated Jul. 15, 2013, Exhibit 2148 in Interference No. 105,871.
Marquez, Expert Opinion in Opposition to EP Patent No. 1523489 dated Nov. 26, 2014.
Marquez, Expert Opinion in Opposition to EP Patent No. 1523489, Declaration 2, dated Nov. 26, 2014.
Marquez, Substitute 2nd Declaration dated Sep. 6, 2012, Exhibit 2066 in Interference No. 105,871.
Marquez, Substitute Declaration dated Jun. 29, 2012, Exhibit 2001 in Interference No. 105,871.
Matsude, et al., "Alkyl Addition Reaction of Pyrimidine 2'-Ketonucleosides: Synthesis of 2'-Branched-Chain Sugar Pyrimidine Nucleosides (Nucleosides and Nucleotides. LXXXI)," Chem. Pharm. Bull, 36(3):945-953 (1988).
Interference No. 105,981, Exhibit No. 1219, Markland et al., 2000, "Broad-Spectrum Antiviral Activity of the IMP Dehydrogenase Inhibitor VX-497: a Comparison with Ribavirin and Demonstration of Antiviral Additivity with Alpha Interferon," Antimicrob. Agents Chemother. 44: 859-66, Filed Sep. 17, 2014.
Interference No. 105,981, Exhibit No. 1208, Wolters et al. 2001, "Nucleoside analogues for chronic hepatitis B," Eur. J. Gastroenterol. Hepatol. 13: 1499-1506, Filed Sep. 17, 2014.
Interference No. 105,981, Exhibit No. 1071, Marshall, 2000, "New 'Replicon' Yields Viral Proteins," Science 290: 1870-71 Filed Mar. 10, 2014.
Interference No. 105,871, Paper No. 474, Sommadossi Request for Oral Argument, Filed Oct. 18, 2013.
Interference No. 105,871, Paper No. 475, Sommadossi Notice of Service of Exhibits, Filed Oct. 18, 2013.
Interference No. 105,871, Paper No. 476, Clark Miscellaneous Motion 10 (to Exclude Evidence), Filed Oct. 18, 2013.
Interference No. 105,871, Paper No. 477, Clark Request for Oral Argument 2 and List of Issues to be Considered, Filed Oct. 18, 2013.
Interference No. 105,871, Paper No. 478, Sommadossi List of Issues, Filed Oct. 18, 2013.
Interference No. 105,871, Paper No. 986, Clark Final Exhibit List-Priority Phase (Clark Exhibit List 18), Filed Nov. 7, 2013.
Interference No. 105,871, Paper No. 987, Clark Submission of Priority Phase Exhibits, Filed Nov. 7, 2013.
Interference No. 105,871, Paper No. 990, Sommadossi Notice of Service of Exhibits, Filed Nov. 8, 2013.
Interference No. 105,871, Paper No. 991, Sommadossi List of Exhibits (as of Nov. 8, 2013), Filed Nov. 8, 2013.
Interference No. 105,871, Paper No. 992, Sommadossi Submission of Priority Phase Exhibits, Filed Nov. 8, 2013.
Interference No. 105,871, Paper No. 993, Sommadossi Opposition 10, Filed Nov. 8, 2013.
Interference No. 105,871, Paper No. 994, Clark Opposition 10 (Opposing Sommadossi Motion to Exclude Evidence), Filed Nov. 8, 2013.
Interference No. 105,871, Paper No. 995, Order—Oral Argument—Bd.R. 124, Entered Nov. 21, 2013.
Interference No. 105,871, Paper No. 996, Sommadossi Reply 10, Filed Nov. 22, 2013.
Interference No. 105,871, Paper No. 997, Clark Reply 10, Filed Nov. 22, 2013.
Interference No. 105,871, Paper No. 998, Order—Miscellaneous—Bd.R. 104(a), Entered Nov. 26, 2013.
Interference No. 105,871, Paper No. 999, Clark Exhibit List for Priority Record (Clark Exhibit List 19), Filed Dec. 4, 2013.
Interference No. 105,871, Paper No. 1000, Clark Submission of Record 2, Filed Dec. 4, 2013.
Interference No. 105,871, Paper No. 1001, Sommadossi Filing of its Priority Record, Filed Dec. 4, 2013.
Interference No. 105,871, Paper No. 1002, Clark Submissions of DVD Containing Clark Submission of Record 2, Filed Dec. 23, 2013.
Interference No. 105,871, Paper No. 1003, Sommadossi Filing of Demonstrative Exhibits, Filed Dec. 30, 2013.
Interference No. 105,871, Paper No. 1004, Clark Filing of Demonstrative Exhibits (for Jan. 3, 2014 Oral Argument), Filed Jan. 3, 2014.
Interference No. 105,871, Paper No. 1005, Appearance Record, Entered Jan. 7, 2014.
Interference No. 105,871, Paper No. 1006, Order—Inappropriate Communication—Bd.R. 104(a), Entered Jan. 16, 2014.
Interference No. 105,871, Paper No. 1007, Decision—Priority—Bd.R. 125(a), Entered Jan. 29, 2014.

(56) References Cited

OTHER PUBLICATIONS

Interference No. 105,871, Paper No. 1008, Judgment—Bd.R. 127, Entered Jan. 29, 2014.
Interference No. 105,871, Paper No. 1009, Oral Hearing Held Jan. 7, 2014, Entered Jan. 29, 2014.
Interference No. 105,871, Paper No. 1010, Sommadossi Notice of Judicial Review, Filed Feb. 6, 2014.
Interference No. 105,871, Paper No. 1011, Clark Notice of Judicial Review (under 35 U.S.C.§ 146), Filed Mar. 31, 2014.
Interference No. 105,871, Exhibit No. 2143, E-mail from Masad Damha to Victor Marquez, et al., sent Jun. 7, 2012, Filed Nov. 7, 2013.
Interference No. 105,871, Exhibit No. 2151, Handwritten Document Entitled "Errata" Provided by Sarah Jenkinson, Ph. During Jul. 9, 2013 Deposition, Filed Nov. 7, 2013.
Interference No. 105,871, Exhibit No. 2150, Drawing Prepared by Tony Bouisset During Jul. 2, 2013 Deposition Clark Exhibit, Filed Nov. 7, 2013.
Interference No. 105,871, Exhibit No. 2145, Handwritten Document Prepared by Erica L. Norey During Jul. 16, 2013 Deposition of Robert Albon, Filed Nov. 7, 2013.
Interference No. 105,871, Exhibit No. 2140, Drawing Prepared by Jean-François Griffon, Ph.D. During Jun. 25, 2013 Deposition, Filed Nov. 7, 2013.
Interference No. 105,871, Exhibit No. 2137, E-mail from Kyoichi A. Watanabe to Byoung-Kwon Chun, et al., sent Jan. 15, 2003, Filed Nov. 7, 2013.
Interference No. 105,871, Exhibit No. 2130, Overhead Transparency labeled "Jeremy Clark: Mar. 28, 2003", Filed Nov. 7, 2013.
Interference No. 105,871, Exhibit No. 2128, E-mail from Ann J. Hobbs to Abdalla Hassan, et al., sent Apr. 8, 2003 attaching Pharmasset Chemistry Meeting Minutes dated Mar. 28, 2003, Filed Nov. 7, 2013.
Interference No. 105,871, Exhibit No. 2123, Attachment to Sommadossi Exhibit 1454 (per Representation of John Kinton, Esq.), Filed Nov. 7, 2013.
Interference No. 105,871, Exhibit No. 2121, Drawing Prepared by David Standring, Ph.D. During Jun. 11, 2013 Deposition, Filed Nov. 7, 2013.
Interference No. 105,871, Exhibit No. 2111, E-mail from Ann J. Hobbs to Alan Roemer, et al., sent May 30, 2003 attaching Pharmasset Chemistry Meeting Minutes dated May 23, 2003 (Ex 2112), Filed Nov. 7, 2013.
Interference No. 105,871, Exhibit No. 2109, E-mail from Amanda Beard to Raymond Schinazi, et al., sent May 23, 2003 attaching Pharmasset Biology Meeting Minutes dated May 20, 2003 (Ex 2110), Filed Nov. 7, 2013.
Interference No. 105,871, Exhibit No. 2107, E-mail from Alan S. Roemer to Raymond Schinazi, et al., sent Feb. 7, 2003 attaching Pharmasset Chemistry Progress Report dated Jan. 31, 2003 (Ex 2108), Filed Nov. 7, 2013.
Interference No. 105,871, Exhibit No. 2105, E-mail from Ann J. Hobbs to Abdalla Hassan, et al., sent Feb. 10, 2003 attaching Pharmasset Chemistry Meeting Minutes dated Jan. 31, 2003 (Ex 2106), Filed Nov. 7, 2013.
Interference No. 105,871, Exhibit No. 2006, C1 File History—May 30, 2003 Clark Provisional Appln. Cover Sheet, Filed Nov. 28, 2012.
Interference No. 105,871, Exhibit No. 2101, E-mail from Anthony M. Zupcic to Thomas E. Friebel on Oct. 10, 2012, Filed Nov. 28, 2012.
Interference No. 105,871, Exhibit No. 2019, Sommadossi S5 file history—Sep. 17, 2008 Response to Notice to File Corrected Appln. Papers, Filed Nov. 28, 2012.
Interference No. 105,871, Exhibit No. 2131, Substitute Declaration of Suguna Rachakonda, Ph.D., Filed Nov. 7, 2013.
Interference No. 105,871, Exhibit No. 2108, Pharmasset Chemistry Progress Report dated Jan. 31, 2003, Filed Nov. 7, 2013.
Interference No. 105,871, Exhibit No. 2026, Stuvyer, L.J. et al., Inhibition of Hepatitis C Replicon RNA Synthesis by β-D-2'-Deoxy-2'-fluoro-2'-C-methylcytidine: A Specific Inhibitor of Hepatitis C Virus Replication, Antimicrobial Agents & Chemotherapy, vol. 17, pp. 79-87 (2006), Filed Nov. 28, 2012.
Interference No. 105,871, Exhibit No. 2023, Sommadossi S5 file history—Aug. 16, 2011 Office Action, Filed Nov. 28, 2012.
Interference No. 105,871, Exhibit No. 2062, Feb. 9, 2011 Material Transfer Agreement, Filed Nov. 28, 2012.
Interference No. 105,871, Exhibit No. 2017, Sommadossi S4 file history—Jan. 20, 2009 Amendment, Filed Nov. 28, 2012.
Interference No. 105,871, Exhibit No. 2016, Sommadossi S4 file history—Jul. 24, 2008 Amendment, Filed Nov. 28, 2012.
Interference No. 105,871, Exhibit No. 2114, Employment Agreement between Jeremy L Clark and Pharmasset, Inc. (a Georgia corporation) dated Jul. 23, 2001, Recorded at Reel 015833, Frame 0438, Filed Nov. 7, 2013.
Interference No. 105,871, Exhibit No. 2078, Trost, Barry M. and Kallander, Lara S., A Versatile Enantioselective Strategy Toward L-C-Nucleosides: A Total Synthesis of L-Showdomycin, J. Org. Chem., vol. 64, No. 15, pp. 5427-5435 (1999), Filed Nov. 28, 2012.
Interference No. 105,871, Exhibit No. 2057, Clark, Jeremy L., et al., Synthesis of 2-Deoxy-2-Fluoro-2-C- Methyl-DRibofuranoses, Journal of Carbohydrate Chemistry, vol. 25, pp. 461-470 (2006), Filed Nov. 28, 2012.
Interference No. 105,871, Exhibit No. 2048, Stuvyer, L.J., et al., Ribonucleoside Analogue That Blocks Replication of Bovine Viral Diarrhea and Hepatitis C Viruses in Culture, Antimicrobial Agents and Chemotherapy, vol. 47, No. 1, pp. 244-254 (2003), Filed Nov. 28, 2012.
Interference No. 105,871, Exhibit No. 2022, Sommadossi S5 file history—May 27, 2011 Amendment, Filed Nov. 28, 2012.
Interference No. 105,871, Exhibit No. 2015, Sommadossi S4 file history—Oct. 30, 2007 Supplemental Amendment, Filed Nov. 28, 2012.
Interference No. 105,871, Exhibit No. 2155, Clark Objections 6 served May 17, 2013, Filed Nov. 7, 2013.
Interference No. 105,871, Exhibit No. 2092, Zuck, Paul, et al., A Cell-based β-lactamase Reporter Gene Assay for the Identification of Inhibitors of Hepatitis C Virus Replication, Analytical Biochemistry, vol. 344, pp. 344-355 (2004), Filed Nov. 28, 2012.
Interference No. 105,871, Exhibit No. 2089, 9 U.S. Appl. No. 11/005,446 file history—May 7, 2007 Amendment, Filed Nov. 28, 2012.
Interference No. 105,871, Exhibit No. 2072, Trost, Barry M., et al., Asymmetric Synthesis of Oxygen Heterocycles via PdCatalyzed Dynamic Kinetic Asymmetric Transformations: Application to Nucleosides, Chem Eur. J., vol. 9, pp. 4442-4451 (2003), Filed Nov. 28, 2012.
Interference No. 105,871, Exhibit No. 2036, Oxtoby, David W., et al., Principles of Modern Chemistry, Fourth Edition, pp. A.41-A.49 (1999), Filed Nov. 28, 2012.
Interference No. 105,871, Exhibit No. 2012, Sommadossi U.S. Appl. No. 10/608,907 ("S4") file history—May 25, 2006 Amendment, Filed Nov. 28, 2012.
Interference No. 105,871, Exhibit No. 3005, Sommadossi S5 file history—Sep. 17, 2008 Substitute Specification (clean version), Filed Nov. 28, 2012.
Interference No. 105,871, Exhibit No. 2122, Sommadossi Exhibit 1250 Annotated With Page Numbers by David Standring, PhD. During Jun. 11, 2013 Depositio, Filed Nov. 7, 2013.
Interference No. 105,871, Exhibit No. 2084, U.S. Appl. No. 11/005,469 file history—Apr. 5, 2007 Amendment, Filed Nov. 28, 20121.
Interference No. 105,871, Exhibit No. 2024, Sommadossi S5 file history—Sep. 20, 2011 Amendment, Filed Nov. 28, 2012.
Interference No. 105,871, Exhibit No. 2071, U.S. Pat. No. 5,149,794, Filed Nov. 28, 2012.
Interference No. 105,871, Exhibit No. 2070, Song, Xueqin, et al., Amino Acid Ester Prodrugs of the Anticancer Agent Gemcitabine: Synthesis, Bioconversion, Metabolic Bioevasion, and hPEPT1-Mediated Transport, Molecular Pharmaceutics, vol. 2, No. 2, pp. 157-167 (2004), Filed Nov. 28, 2012.

(56) References Cited

OTHER PUBLICATIONS

Interference No. 105,871, Exhibit No. 2127, Ann J. Hobbs Notebook No. 1013, pp. 148, 149, 151, 153, 155, 157, 160, 161-164, 184, Filed Nov. 7, 2013.
Interference No. 105,871, Exhibit No. 2087, U.S. Appl. No. 11/005,444 file history—Apr. 6, 2009 Amendment, Filed Nov. 28, 2012.
Interference No. 105,871, Exhibit No. 2066, Substitute 2nd Declaration of Victor E. Marquez, Ph.D., Filed Nov. 28, 2012.
Interference No. 105,871, Exhibit No. 3001, Sommadossi U.S. Appl. No. 60/392,350 ("S1") as filed Jun. 28, 2002, Filed Nov. 28, 2012.
Interference No. 105,871, Exhibit No. 2126, Substitute Declaration of Ann J. Hobbs, Filed Nov. 7, 2013.
Interference No. 105,871, Exhibit No. 2081, Yi, MinKyung, et al., Subgenomic Hepatitis C Virus Replicons Inducing Expression of a Secreted Enzymatic Reporter Protein, Virology, vol. 304, pp. 197-210 (2002), Filed Nov. 28, 2012.
Interference No. 105,871, Exhibit No. 2069, Limbach, Patrick A., et al., Summary: The Modified Nucleosides of RNA, Nucleic Acids Research, vol. 22, No. 12, pp. 2183-2196 (1994), Filed Nov. 28, 2012.
Interference No. 105,871, Exhibit No. 2020, Sommadossi S5 file history—Dec. 14, 2010 Response to Restriction Requirement, Filed Nov. 28, 2012
Interference No. 105,871, Exhibit No. 2064, Transcript of Deposition of Christoph Seeger, Ph.D., taken Jul. 25, 2012, Filed Nov. 28, 2012.
Interference No. 105,871, Exhibit No. 2102, Substitute Declaration of Michael J. Otto, Ph.D., Filed Nov. 7, 2013.
Interference No. 105,871, Exhibit No. 2053, U.S. Pat. No. 7,902,202 (U.S. Appl. No. 12/150,327) file history—Nov. 16, 2010 Amendment, Filed Nov. 28, 2012.
Interference No. 105,871, Exhibit No. 2014, Sommadossi S4 file history—Aug. 20, 2007 Amendment, Filed Nov. 28, 2012.
Interference No. 105,871, Exhibit No. 2001, Substitute Declaration of Victor E. Marquez, Ph.D, Filed Nov. 28, 2012.
Interference No. 105,871, Exhibit No. 3002, 2 Sommadossi U.S. Appl. No. 10/608,907 ("S4") as filed Jun. 27, 2003, Filed Nov. 28, 2012.
Interference No. 105,871, Exhibit No. 2097, U.S. Pat. No. 5,455,339, Filed Nov. 28, 2012.
Interference No. 105,871, Exhibit No. 2033, Singh, Rajendra P. and Shreeve, Jean'ne M., Recent Advances in Nucleophilic Fluorination Reactions of Organic Compounds Using Deoxofluor and DAST, Synthesis, No. 17, pp. 2561-2578 (2002), Filed Nov. 28, 2012.
Interference No. 105,871, Exhibit No. 2018, Sommadossi U.S. Appl. No. 12/131,868 ("S5") file history—Jun. 2, 2008 Preliminary Amendment, Filed Nov. 28, 2012.
Interference No. 105,871, Exhibit No. 3003, Sommadossi U.S. Appl. No. 12/131,868 ("S5") as filed Jun. 2, 2008, Filed Nov. 28, 2012.
Interference No. 105,871, Exhibit No. 2135, Vorbruggen, Helmut & Ruh-Pohlenz, Carmen, Handbook of Nucleoside Synthesis, pp. 10-24 (Wiley 2001), Filed Nov. 7, 2013.
Interference No. 105,871, Exhibit No. 2147, Transcript of Deposition of Suguna Rachakonda, Ph.D., taken Jul. 13, 2013, Filed Nov. 7, 2013.
Interference No. 105,871, Exhibit No. 2094, Transcript of Deposition of Christoph Seeger, Ph.D., taken Sep. 28, 2012, Filed Nov. 28, 2012.
Interference No. 105,871, Exhibit No. 2153, Yang, Shu Shu, et al., Synthesis of 25-Fluorovitamin D3, Tetrahedron Lett., No. 27, pp. 2315-2316 (1977), Filed Nov. 7, 2013.
Interference No. 105,871, Exhibit No. 2132, Suguna Rachakonda's Handwritten Notes dated Jan. 15, 2003, Filed Nov. 7, 2013.
Interference No. 105,871, Exhibit No. 2129, Pharmasset Chemistry Meeting Minutes dated Mar. 28, 2003, Filed Nov. 7, 2013.
Interference No. 105,871, Exhibit No. 2112, Pharmasset Chemistry Meeting Minutes dated May 23, 2003 (redacted), Filed Nov. 7, 2013.
Interference No. 105,871, Exhibit No. 2110, Pharmasset Biology Meeting Minutes dated May 20, 2003 (redacted), Filed Nov. 7, 2013.
Interference No. 105,871, Exhibit No. 2106, Pharmasset Chemistry Meeting Minutes dated Jan. 31, 2003, Filed Nov. 7, 2013.
Interference No. 105,871, Exhibit No. 2104, Pharmasset Notebook Policy, Revised May 22, 2000, Filed Nov. 7, 2013.
Interference No. 105,871, Exhibit No. 3004, Sommadossi S5 file history—Sep. 17, 2008 Substitute Specification (marked-up version), Filed Nov. 7, 2013.
Interference No. 105,981, Paper No. 1, Declaration BD.R. 203, Filed Dec. 3, 2013.
Interference No. 105,981, Paper No. 2, Standing Order, Filed Dec. 3, 2013.
Interference No. 105,981, Paper No. 3, Storer Designation of Lead and Backup Lead Counsel, Filed Dec. 17, 2013.
Interference No. 105,981, Paper No. 4, Clark Notice of Real Party-In-Interest, Filed Dec. 17, 2013.
Interference No. 105,981, Paper No. 5, Clark Clean Copy of Claims, Filed Dec. 17, 2013.
Interference No. 105,981, Paper No. 6, Clark Notice of Lead Counsel and Backup Lead Counsel, Filed Dec. 17, 2013.
Interference No. 105,981, Paper No. 7, Clark Request for File Copies, Filed Dec. 17, 2013.
Interference No. 105,981, Paper No. 8, Clark Notice of Related Proceedings, Filed Dec. 17, 2013.
Interference No. 105,981, Paper No. 9, Storer Notice of Real Parties in Interest, Filed Dec. 17, 2013.
Interference No. 105,981, Paper No. 10, Storer Clean Copy of Claims, Filed Dec. 17, 2013.
Interference No. 105,981, Paper No. 11, Storer File Copy Request, Filed Dec. 17, 2013.
Interference No. 105,981, Paper No. 12, Storer Notice of Related Proceedings, Filed Dec. 17, 2013.
Interference No. 105,981, Paper No. 13, Storer Designation of Lead and Back Up Lead Counsel, Filed Dec. 17, 2013.
Interference No. 105,981, Paper No. 14, Order Bd.R. 109(b)Authorizing Copies of Office Records, Filed Dec. 18, 2013.
Interference No. 105,981, Paper No. 15, Storer Motions List, Filed Jan. 7, 2014.
Interference No. 105,981, Paper No. 16, Clark List of Intended Motions, Entered Jan. 7, 2014.
Interference No. 105,981, Paper No. 17, Storer Supplemental Notice of Related Proceedings, Filed Jan. 13, 2014.
Interference No. 105,981, Paper No. 18, Miscellaneous Order Bd.R. 104(a), Filed Jan. 16, 2014.
Interference No. 105,981, Paper No. 19, Order Motion Times Bd.R. 104(c), Filed Jan. 21, 2014.
Interference No. 105,981, Paper No. 20, Storer Request for Panel Rehearing, Filed Feb. 4, 2014.
Interference No. 105,981, Paper No. 20.001, Order-Bd.R. 104(a), Filed Jan. 28, 2014.
Interference No. 105,981, Paper No. 21, Storer Second Supplemental Notice of Related Proceedings, Filed Feb. 5, 2014.
Interference No. 105,981, Paper No. 21.001, Order Miscellaneous BD.R. 104(a); 127(a), Filed Feb. 5, 2014.
Interference No. 105,981, Paper No. 22, Order Miscellaneous BD.R. 104(a), Filed Feb. 12, 2014.
Interference No. 105,981, Paper No. 23, Storer Miscellaneous Motion 13, Filed Feb. 21, 2014.
Interference No. 105,981, Paper No. 24, Storer Notice of Service of Exhibits, Filed Feb. 21, 2014.
Interference No. 105,981, Paper No. 25, Storer Corrected Clean Copy of Claims, Filed Feb. 21, 2014.
Interference No. 105,981, Paper No. 26, Storer Notice of Stipulation of Extension of Time, Filed Feb. 21, 2014.
Interference No. 105,981, Paper No. 27, Order Request for Panel Rehearing Bd.R. 125(c)(5), Filed Feb. 27, 2014.
Interference No. 105,981, Paper No. 28, Clark Notice of Filing of Terminal Disclaimer, Filed Feb. 28, 2014.
Interference No. 105,981, Paper No. 29, Joint Statement Regarding Settlement Discussions, Filed Mar. 3, 2014.

(56) References Cited

OTHER PUBLICATIONS

Interference No. 105,981, Paper No. 30, Order Miscellaneous Bd.R 104(a), Filed Mar. 3, 2014.
Interference No. 105,981, Paper No. 31, Clark Notice Regarding Stipulated Extension of Time 1, Filed Mar. 4, 2014.
Interference No. 105,981, Paper No. 32, Storer Notice of Service of Supplemental Evidence 1, Filed Mar. 5, 2014.
Interference No. 105,981, Paper No. 33, Storer Response to Order to Show Cause, Filed Mar. 10, 2014.
Interference No. 105,981, Paper No. 98, Clark Priority Statement, Filed Mar. 10, 2014.
Interference No. 105,981, Paper No. 99, Clark Notice Re Filing of Priority Statement, Filed Mar. 10, 2014.
Interference No. 105,981, Paper No. 100, Clark Exhibit List 1, Filed Mar. 10, 2014.
Interference No. 105,981, Paper No. 101, Clark Submission of Evidence for Motion 5, Filed Mar. 10, 2014.
Interference No. 105,981, Paper No. 154, Clark Substantive Motion 7, Filed Mar. 10, 2014.
Interference No. 105,981, Paper No. 155, Clark Substantive Motion 8, Filed Mar. 10, 2014.
Interference No. 105,981, Paper No. 156, Clark Substantive Motion 9, Filed Mar. 10, 2014.
Interference No. 105,981, Paper No. 157, Storer Substantive Motion 5, Filed Mar. 10, 2014.
Interference No. 105,981, Paper No. 158, Storer Substantive Motion 11, Filed Mar. 10, 2014.
Interference No. 105,981, Paper No. 159, Storer Notice of Service of Exhibits, Filed Mar. 10, 2014.
Interference No. 105,981, Paper No. 160, Storer Notice of Filing Priority Statement, Filed Mar. 10, 2014.
Interference No. 105,981, Paper No. 161, Storer Priority Statement, Filed Mar. 10, 2014.
Interference No. 105,981, Paper No. 162, Clark Substantive Motion 5, Filed Mar. 10, 2014.
Interference No. 105,981, Paper No. 324, Storer Notice of Service of Priority Statement, Filed Mar. 11, 2014.
Interference No. 105,981, Paper 325, Clark Notice Re Service of Priority Statement, Filed Mar. 11, 2014.
Interference No. 105,981, Exhibit No. 1037, Clarke, 2000, "New drugs for hepatitis C virus (HCV)," Baillière's Clin. Gastroenterol. 14: 293-305, U.S. Appl. No. 12/131,868, filed Jun. 2, 2008, Filed Mar. 10, 2014.
Interference No. 105,981, Exhibit No. 1007, Amendment and Response, dated Aug. 20, 2007, from the File History of Storer et al., U.S. Appl. No. 10/608,907, filed Jun. 27, 2003, Filed Sep. 17, 2014.
Interference No. 105,981, Exhibit No. 1214, Buckwold et al., 2003, "Bovine viral diarrhea virus as a surrogate model of hepatitis C virus for the evaluation of antiviral agents," Antiviral Res. 60: 1-15, Filed Sep. 17, 2014.
Interference No. 105,981, Exhibit No. 1070, Rosenberg, 2001, "Recent Advances in the Molecular Biology of Hepatitis C Virus," J. Mol. Biol. 313: 451-64, J. Virol. 75: 12047-57, Filed Mar. 10, 2014.
Interference No. 105,981, Exhibit No. 1195, Transcript of Deposition of Raffaele De Francesco on Thursday, Apr. 17, 2014 (with errata sheet), Filed Sep. 16, 2014.
Interference No. 105,981, Exhibit No. 1103, Watanabe et al., International Patent Application Publication No. WO 01/79246, published Oct. 25, 2001, Filed Mar. 10, 2014.
Interference No. 105,981, Exhibit No. 1117, Lawitz et al., 2009, Abstract 102, Global Antiviral J. 5: 96, Filed Mar. 10, 2014.
Interference No. 105,981, Exhibit No. 1144, Delang et al., 2013, Curr. Top. Microbiol. Immunol. 369: 289-320, Filed Mar. 10, 2014.
Interference No. 105,981, Exhibit No. 1102, Moradpour et al., Jan. 2002 (published online Oct. 2001), "Functional Properties of a Monoclonal Antibody Inhibiting the Hepatitis C Virus RNA-dependent RNA Polymerase," J. Biol. Chem. 277: 593-601, Filed Mar. 10, 2014.
Interference No. 105,981, Exhibit No. 1183, Preliminary Amendment, filed Jun. 2, 2008, from the file history of Sommadossi et al., in U.S. Appl. No. 12/131,868, filed Jun. 2, 2008, Filed Sep. 16, 2014.
Interference No. 105,981, Exhibit No. 1188, Sommadossi Miscellaneous Motion 7 (Paper 58), Interference 105,871, *Clark v. Sommadossi*, (previously designated as Sommadossi Miscellaneous Motion 19), Filed Sep. 16, 2014.
Interference No. 105,981, Exhibit No. 1041, Bartenschlager, 1997, "Candidate Targets for Hepatitis C Virus-Specific Antiviral Therapy," Intervirology 40: 378-93, Filed Mar. 10, 2014.
Interference No. 105,981, Exhibit No. 1138, Damha et al. [sic, Watts and Damha], 2008, Can. J. Chem. 86: 641-656, Filed Mar. 10, 2014.
Interference No. 105,981, Exhibit No. 1066, Kim et al., Jan. 2002, "Domains I and II in the 5' Nontranslated Region of the HCV Genome Are Required for RNA Replication," Biochem. Biophys. Res. Commun. 290: 105-12, Filed Mar. 10, 2014.
Interference No. 105,981, Exhibit No. 1087, Email from R. De Francesco to R. Bartenschlager, dated Oct. 20, 2000; and Email from R. Bartenschlager to R. De Francesco, dated Oct. 23, 2000, Filed Mar. 10, 2014.
Interference No. 105,981, Exhibit No. 1056, Apath.com webpage at http://www.apath.com/Blazing_Blight_7.htm, Filed Mar. 10, 2014.
Interference No. 105,981, Exhibit No. 1176, Thomas E. Friebel Jan. 14, 2014 email to Patent Trial and Appeal Board raising inequitable conduct issue, Filed Mar. 10, 2014.
Interference No. 105,981, Exhibit No. 1116, Sofia et al., 2010, J. Med. Chem. 53: 7202-7218, Filed Mar. 10, 2014.
Interference No. 105,981, Exhibit No. 1082, De Francesco, 2000, "Strategies for New HCV Antiviral Therapy," 7th International Symposium on Hepatitis C Virus and Related Viruses, Gold Coast, Queensland, Australia, Filed Mar. 10, 2014.
Interference No. 105,981, Exhibit No. 1080, Bartenschlager and Lohmann, 2001, "Novel cell culture systems for the hepatitis C virus," Antiviral Res. 52: 1-17, Filed Mar. 10, 2014.
Interference No. 105,981, Exhibit No. 1035, De Clercq, 2001, "Antiviral drugs: current state of the art," J. Clin. Virology 22: 73-89, Filed Mar. 10, 2014.
Interference No. 105,981, Exhibit No. 1019, De Francesco et al., 2000, "Biochemical and Immunologic Properties of the Nonstructural Proteins of the Hepatitis C Virus: Implications for Development of Antiviral Agents and Vaccines," Semin. Liver Dis. 20: 69-83, Filed Mar. 10, 2014.
Interference No. 105,981, Exhibit No. 1184-6, Substitute Specification (clean version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1184-5, Substitute Specification (clean version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1184-4, Substitute Specification (clean version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1184-3, Substitute Specification (clean version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1184-2, Substitute Specification (clean version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1184-12, Substitute Specification (clean version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1184-11, Substitute Specification (clean version), filed Sep. 17, 2008, from the file history of Sommadossi et al., in U.S. Appl. No. 12/131,868, filed Jun. 2, 2008, Filed Sep. 16, 2014.

(56) References Cited

OTHER PUBLICATIONS

Interference No. 105,981, Exhibit No. 1184-10, Substitute Specification (clean version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1184-9, Substitute Specification (clean version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1184-8, Substitute Specification (clean version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1184-7, Substitute Specification (clean version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1004, Sommadossi et al., International Patent Application Publication No. WO 2004/02999 A2, published Jan. 8, 2004, Filed Sep. 17, 2014.
Interference No. 105,981, Exhibit No. 1244, Transcript of Deposition of Masad J. Damha, Ph.D. on Friday, Jun. 20, 2014, (with errata sheet), signed Jul. 21, 2014, Filed Sep. 17, 2014.
Interference No. 105,981, Exhibit No. 1024, De Francesco et al., 2003, "Approaching a new era for hepatitis C virus therapy: inhibitors of the NS3-4A serine protease and the NS5B RNA-dependent RNA polymerase," Antiviral Res. 58: 1-16, Filed Mar. 10, 2014.
Interference No. 105,981, Exhibit No. 1040, Leyssen et al., 2000, "Perspectives for the Treatment of Infections with Flavivindae," Clin. Microbiol. Rev. 13:67-82, Filed Mar. 10, 2014.
Interference No. 105,981, Exhibit No. 1068, Shi and Lai, 2001, "Hepatitis C viral RNA: challenges and promises," Cell. Mol. Life Sci. 58: 1276-95, Filed Mar. 10, 2014.
Interference No. 105,981, Exhibit No. 1245, Clark Exhibit 2148, Interference 105,871, Transcript of Deposition of Victor E. Marquez, Ph.D., taken Jul. 15, 2013, Filed Sep. 17, 2014.
Interference No. 105,981, Exhibit No. 1005, Clark U.S. Appl. No. 11/854,218, filed on Sep. 12, 2007, Filed Mar. 10, 2014.
Interference No. 105,981, Exhibit No. 1156, Marquez et al., Nucleosides and Nucleotides as Antitumor and Antiviral Agent 265-284 (Chu et al. eds, 1993), Filed Mar. 10, 2014.
Interference No. 105,981, Exhibit No. 1045, Pankiewicz, 2000, "Fluorinated nucleosides," Carbohydrate Research 327: 87-105, Filed Mar. 10, 2014.
Interference No. 105,981, Exhibit No. 1194, Transcript of Deposition of Masad J. Damha, PhD. on Tuesday, Apr. 15, 2014, Filed Sep. 16, 2014.
Interference No. 105,981, Exhibit No. 1085, Devos et al., International Patent Application Publication No. WO 02/18404 A2, published Mar. 7, 2002, Filed Mar. 10, 2014.
Interference No. 105,981, Exhibit No. 1246, Clark Exhibit 2146, Interference 105,871, Transcript of Deposition of Michael J. Otto, Ph.D., taken Jul. 11, 2013, Filed Sep. 17, 2014.
Interference No. 105,981, Exhibit No. 1092, Hornbeck, 2001, Curr. Protoc. lmmunol. Chapter 2, Unit 2.1, published on-line at doi:: 10.1002/0471142735.im0201s01, Filed Mar. 10, 2014.
Interference No. 105,981, Exhibit No. 1036, De Clercq (Editor), 1993, Advances in Antiviral Drug Design, vol. 1, Chapter 2 (Robins & Revankar, "Design and Synthesis of β-D-Ribofuranosyl Nucleosides Active Against RNA Viral Infections"), Chapter 3 (Johansson, "Structure, Antiviral Activity, and Chemistry of Acyclic Nucleoside Analogues"), and Chapter 5 (Herdewijn et al., "2',3'-Dideoxynucleoside Analogues as Anti-HIV Agents"), Filed Mar. 10, 2014.
Interference No. 105,981, Exhibit No. 1190, Transcript of Deposition of Victor E Marquez, Ph.D. on Friday, Jul. 27, 2012, Filed Sep. 16, 2014.
Interference No. 105,981, Exhibit No. 1078, Walker et al., 2003, "Hepatitis C virus therapies: current treatments, argets and future perspectives," Antiviral Chemistry & Chemotherapy 14: 1-21, Filed Sep. 17, 2014.
Interference No. 105,981, Exhibit No. 1044, IMarquez, 1996, Research Monograph Series (National Institute on Drug Abuse), Drugs of Abuse: Chemistry, Pharmacology, Immunology and Aids, "Effect of Fluorine Substitution on Anti-HIV Activity of Dideoxynucleosides," pp. 61-79, Filed Mar. 10, 2014.
Interference No. 105,871, Exhibit No. 1465, Dec. 7 and 8, 2004 email correspondence between Adel Moussa and Jean-Francois Griffon, Filed Nov. 6, 2013.
Interference No. 105,871, Exhibit No. 1463, Aug. 9, 2004 letter from Adel Moussa to Gilles Gosselin, Filed Nov. 6, 2013.
Interference No. 105,871, Exhibit No. 1461, Feb. 19, 2004 letter from Adel Moussa to Gilles Gosselin, Filed Nov. 6, 2013.
Interference No. 105,871, Exhibit No. 1460, Dec. 2, 2003 letter from Adel Moussa to Gilles Gosselin, Filed Nov. 6, 2013.
Interference No. 105,871, Exhibit No. 1459, Sep. 19, 2003 letter from Adel Moussa to Gilles Gosselin, Filed Nov. 6, 2013.
Interference No. 105,871, Exhibit No. 1458, Jun. 26, 2003 letter from Adel Moussa to Gilles Gosselin, Filed Nov. 6, 2013.
Interference No. 105,871, Exhibit No. 1456, Jun. 9, 2003 email correspondence between Adel Moussa and Richard Storer, Filed Nov. 6, 2013.
Interference No. 105,871, Exhibit No. 1452, Brief Resume/Biography of Adel Moussa, Filed Nov. 6, 2013.
Interference No. 105,871, Exhibit No. 1431, Email from Guy Macdonald, dated Apr. 19, 2005 forwarding "Management Report Mar. 2005.doc" Standring and others, Filed Nov. 6, 2013.
Interference No. 105,871, Exhibit No. 1419, Apr. 14, 2003 Email from Dick Storer to Gilles Gosselin, Filed Nov. 6, 2013.
Interference No. 105,871, Exhibit No. 1417, Feb. 13, 2003 Email from Dick Storer to Gilles Gosselin, Filed Nov. 6, 2013.
Interference No. 105,871, Exhibit No. 1415, Feb. 7, 2003 Email from Dick Storer to Gilles Gosselin, Filed Nov. 6, 2013.
Interference No. 105,871, Exhibit No. 1414, Feb. 1, 2003 Email from Dick Storer to Gilles Gosselin, Filed Nov. 6, 2013.
Interference No. 105,871, Exhibit No. 1413, Email from Dick Storer to Adel Moussa, Narayan Chaudhuri, Steven Mathieu, Jingyang Wang, Filed Nov. 6, 2013.
Interference No. 105,871, Exhibit No. 1412, Dec. 13, 2002 Email from Dick Storer to Diane Coe, Filed Nov. 6, 2013.
Interference No. 105,871, Exhibit No. 1377, Email from Dr. Stewart to Dr. Jenkinson dated Apr. 13, 2005, Filed Nov. 6, 2013.
Interference No. 105,871, Exhibit No. 1376, Email from Dr. Stewart to Dr. Moussa dated Apr. 11, 2005, Filed Nov. 6, 2013.
Interference No. 105,871, Exhibit No. 1372, Email from Dr. Jenkinson to Dr. Stewart dated Mar. 24, 2005, Filed Nov. 6, 2013.
Interference No. 105,871, Exhibit No. 1370, Email from Dr. Stewart to Dr. Moussa dated Mar. 21, 2005, Filed Nov. 6, 2013.
Interference No. 105,871, Exhibit No. 1368, Email from Dr. Jenkinson to Dr. Stewart dated Mar. 15, 2005, Filed Nov. 6, 2013.
Interference No. 105,871, Exhibit No. 1365, Email from Dr. Jenkinson to Dr. Stewart dated Feb. 16, 2005, Filed Nov. 6, 2013.
Interference No. 105,871, Exhibit No. 1362, Email attachment of Ex 1357, Filed Nov. 6, 2013.
Interference No. 105,871, Exhibit No. 1361, Email attachment of Ex 1357, Filed Nov. 6, 2013.
Interference No. 105,871, Exhibit No. 1359, Email attachment of Ex 1357, Filed Nov. 6, 2013.
Interference No. 105,871, Exhibit No. 1357, Email from Dr. Stewart to Dr. Jenkinson dated Feb. 11, 2005, Filed Nov. 6, 2013.
Interference No. 105,871, Exhibit No. 1229, Resume of Tony Bouisset, Filed Nov. 6, 2013.
Interference No. 105,871, Exhibit No. 1103, Lawitz et al., Abstract 102, Global Antiviral J. 5: 96, Filed Nov. 6, 2013.
Interference No. 105,871, Exhibit No. 1081, Sofia et al., Abstracts of Papers, 238th ACS National Meeting, Washington, DC, United States, Aug. 16-20, 2009), MEDI-101, Filed Nov. 6, 2013.
Interference No. 105,871, Exhibit No. 1008, BIB Data Sheet, from the File History of Sommadossi et al., U.S. Appl. No. 10/608,907, filed Jun. 27, Filed Nov. 6, 2013.

(56) References Cited

OTHER PUBLICATIONS

Interference No. 105,871, Exhibit No. 1128, Lawitz et al., 2012, Abstract 7, J. Hepatol. 56: S4, Filed Nov. 6, 2013.
Interference No. 105,871, Exhibit No. 1196, Peters et al., Aug. 5-9, 2012, "Flexible Nucleotides As Antivirals," Presented at the 20th International Round Table of Nucleosides, Nucleotides and Nucleic Acids, Montreal, Quebec, Canada, Filed Nov. 6, 2013.
Interference No. 105,871, Exhibit No. 1165, Notice of Publication from the File History of Sommadossi et al., U.S. Appl. No. 10/608,907, filed Jun. 27, 2003, Filed Nov. 6, 2013.
Interference No. 105,871, Exhibit No. 1108, News & Analysis, 2011, Nature Reviews 10: 891, Filed Nov. 6, 2013.
Interference No. 105,871, Exhibit No. 1317, Consulting Agreement between Idenix and George Fleet dated Jan. 18, 2002, Filed Nov. 6, 2013.
Interference No. 105,871, Exhibit No. 1304, Report on fluorination Scientific Update Training Course, Filed Nov. 6, 2013.
Interference No. 105,871, Exhibit No. 1284, Printed copy of mass spectrometry analysis dated Feb. 26, 2003, Filed Nov. 6, 2013.
Interference No. 105,871, Exhibit No. 1526, Slides presented by Sarah Jenkinson on Nov. 22, 2004, Filed Nov. 6, 2013.
Interference No. 105,871, Exhibit No. 1641, Ex. 4 to "Jeremy Clark's Reply to Raymond Schinazi's Response on Motion to Appoint Special Prosecutor" filed on Dec. 29, 2011, in *Clark v. Schinazi*, (N.D. Ala.) containing Minutes of Pharmasset Chemistry Meetings dated Jun. 27, 2003, Jul. 25, 2013 and Nov. 21, 2003, Filed Nov. 6, 2013.
Interference No. 105,871, Exhibit No. 1537, Office Action, dated Jan. 11, 2006, from the File History of Sommadossi et al., U.S. Appl. No. 10/608,907, filed Jun. 27, 2003, Filed Nov. 6, 2013.
Interference No. 105,871, Exhibit No. 1536, Amendment and Response, dated Jul. 24, 2008, from the File History of Sommadossi et al., U.S. Appl. No. 10/608,907, filed Jun. 27, 2003, Filed Nov. 6, 2013.
Interference No. 105,871, Exhibit No. 1420, Report on fluorination Scientific Update Training Course, Filed Nov. 6, 2013.
Interference No. 105,871, Exhibit No. 1409, Consulting Agreement between Idenix and George Fleet dated Jan. 18, 2002, Filed Nov. 6, 2013.
Interference No. 105,871, Exhibit No. 1220, Meier et al., 1999, J. Med. Chem. 42(9): 1615-1624, Filed Nov. 6, 2013.
Interference No. 105,871, Exhibit No. 1066, Diamond et al., 2000, J. Virol. 74:4957-66, Filed Nov. 6, 2013.
Interference No. 105,871, Exhibit No. 1040, Frese et al., 2002 (accepted for publication Dec. 7, 2001), Hepatology 35: 694-703, Filed Nov. 6, 2013.
Interference No. 105,871, Exhibit No. 1031, Ikeda et al., 2002 (received Oct. 3, 2001, accepted for publication Dec. 20, 2001), J. Virol. 76: 2997-3006, Filed Nov. 6, 2013.
Interference No. 105,871, Exhibit No. 1093, Stuyver et al., 2006, Antiviral Chem. and Chemother. 17: 79-87, Filed Nov. 6, 2013.
Interference No. 105,871, Exhibit No. 1084, Lam et al., 2011, Antimicrob. Agents Chemother. 55: 2566-2575, Filed Nov. 6, 2013.
Interference No. 105,871, Exhibit No. 1083, Lam et al., 2010, Antimicrob. Agents Chemother. 54: 3187-3196, Filed Nov. 6, 2013.
Interference No. 105,871, Exhibit No. 1139, Wohlrab et al., 1985, Biochim. Biophys. Acta, 824: 233-42, Filed Nov. 6, 2013.
Interference No. 105,981, Paper No. 326, Order Responsive Motion Bd.R. 41.121(a)(2), Filed Mar. 21, 2014.
Interference No. 105,981, Paper No. 327, Storer Contingent Responsive Motion 14, Filed Mar. 28, 2014.
Interference No. 105,981, Paper No. 328, Storer Contingent Miscellaneous Motion 15, Filed Mar. 28, 2014.
Interference No. 105,981, Paper No. 329, Storer Notice of Service of Exhibits, Filed Mar. 28, 2014.
Interference No. 105,981, Paper No. 337, Clark Exhibit List 2, Filed Mar. 31, 2014.
Interference No. 105,981, Paper No. 338, Clark Notice of Service of Supplemental Evidence 1, Filed Mar. 31, 2014.
Interference No. 105,981, Paper No. 339, Clark Submission of Supplemental Evidence for Motion 5, Filed Mar. 31, 2014.
Interference No. 105,981, Paper No. 340, Storer Third Supplemental Notice of Related Proceedings, Filed Mar. 31, 2014.
Interference No. 105,981, Paper No. 341, Storer Notice of Service of Supplemental Evidence 2, Filed Mar. 31, 2014.
Interference No. 105,981, Paper No. 342, Storer List of Exhibits (as of Mar. 31, 2014), Filed Mar. 31, 2014.
Interference No. 105,981, Paper No. 347, Order Miscellanoeus Bd.R. 104(a), Filed Apr. 1, 2014.
Interference No. 105,981, Paper No. 347.001, Joint Statement Regarding Settlement Discussions, Filed Apr. 1, 2014.
Interference No. 105,981, Paper No. 348, Storer Notice of Intent to Video-Record Cross-Examination, Filed Apr. 7, 2014.
Interference No. 105,981, Paper No. 349, Clark Notice of Related Proceedings 2, Filed Apr. 9, 2014.
Interference No. 105,981, Paper No. 350, Decision on Storer Response to Order to Show Cause Revised Motion Times Order BD.R. 104(a);127(a);104(c), Filed Apr. 11, 2014.
Interference No. 105,981, Paper No. 351, Miscellaneous Order-Bd. R. 41.203(c), 41.121, Filed Apr. 17, 2014.
Interference No. 105,981, Paper No. 352, Errata, Filed Apr. 23, 2014.
Interference No. 105,981, Paper No. 353, Clark Request for Rehearing 1, Filed Apr. 25, 2014.
Interference No. 105,981, Paper No. 354, Clark Request for Rehearing 2, Filed May 1, 2014.
Interference No. 105,981, Paper No. 355, Storer Notice of Intent to Video-Record Cross-Examination, Filed May 5, 2014.
Interference No. 105,981, Paper No. 356, Order Miscellaneous Bd.R. 104(a), Filed May 9, 2014.
Interference No. 105,981, Paper No. 357, Order Request for Panel Rehearing Bd.R. 125(c)(5), Filed May 16, 2014.
Interference No. 105,981, Paper No. 382, Clark Opposition 5, Filed May 23, 2014.
Interference No. 105,981, Paper No. 383, Clark Opposition 11, Filed May 23, 2014.
Interference No. 105,981, Paper No. 384, Clark Opposition 14, Filed May 23, 2014.
Interference No. 105,981, Paper No. 385, Clark Opposition 15, Filed May 23, 2014.
Interference No. 105,981, Paper No. 386, Clark Exhibit List 4, Filed May 23, 2014.
Interference No. 105,981, Paper No. 387, Clark Submission of Evidence for Clark Motions 1, 2, 3, 10, Filed May 23, 2014.
Interference No. 105,981, Paper No. 388, Storer Notice of Service of Exhibits, Filed May 23, 2014.
Interference No. 105,981, Paper No. 389, Clark Substantive Motion 1, Filed May 23, 2014.
Interference No. 105,981, Paper No. 390, Clark Substantive Motion 2, Filed May 23, 2014.
Interference No. 105,981, Paper No. 391, Clark Substantive Motion 3, Filed May 23, 2014.
Interference No. 105,981, Paper No. 392, Clark Substantive Motion 10, Filed May 23, 2014.
Interference No. 105,981, Paper No. 393, Storer Opposition 7, Filed May 23, 2014.
Interference No. 105,981, Paper No. 394, Storer Opposition 8, Filed May 23, 2014.
Interference No. 105,981, Paper No. 395, Storer Opposition 5, Filed May 23, 2014.
Interference No. 105,981, Paper No. 396, Storer Notice of Service of Supplemental Evidence 3, Filed Jun. 10, 2014.
Interference No. 105,981, Paper No. 397, Storer List of Exhibits (as of Jun. 10, 2014), Filed Jun. 10, 2014.
Interference No. 105,981, Paper No. 398, Clark Exhibit List 5, Filed Jun. 10, 2014.
Interference No. 105,981, Paper No. 399, Clark Notice of Service of Supplemental Evidence 2, Filed Jun. 10, 2014.
Interference No. 105,981, Paper No. 401, Clark Submission of Suppl Evidence for Motions 1, 2, 3, 10, Filed Jun. 10, 2014.
Interference No. 105,981, Paper No. 402, Storer Opposition 1, Filed Jun. 27, 2014.
Interference No. 105,981, Paper No. 403, Storer Opposition 2, Filed Jun. 27, 2014.

(56) References Cited

OTHER PUBLICATIONS

Interference No. 105,981, Paper No. 404, Storer Opposition 3, Filed Jun. 27, 2014.
Interference No. 105,981, Paper No. 405, Storer Opposition 10, Filed Jun. 27, 2014.
Interference No. 105,981, Paper No. 406, Storer Notice of Service of Exhibits, Filed Jun. 27, 2014.
Interference No. 105,981, Paper No. 407, Clark Notice Regarding Stipulated Extension of Time 2, Filed Jul. 2, 2014.
Interference No. 105,981, Paper No. 408, Storer Reply 5, Filed Jul. 9, 2014.
Interference No. 105,981, Paper No. 409, Storer Reply 11, Filed Jul. 9, 2014.
Interference No. 105,981, Paper No. 410, Storer Reply 14, Filed Jul. 9, 2014.
Interference No. 105,871, Exhibit No. 2059, European Patent Appln. No. 03761744 file history—Apr. 16, 2012 Office Action (certified copy), Filed Nov. 28, 2012.
Interference No. 105,871, Exhibit No. 2042, Stuyver, L.J., et al., Inhibition of the Subgenomic Hepatitis C Virus Replicon in Huh-7 Cells by 2'-deoxy-2'-fluorocytidine, Antimicrobial Agents and Chemotherapy, vol. 48, No. 2, pp. 351-654 (2004), Filed Nov. 28, 2012.
Interference No. 105,871, Exhibit No. 2040, Lohmann, V., et al., Replication of Subgenomic Hepatitis C Virus RNAs in a Hepatoma Cell Line, Science, vol. 285, pp. 110-113 (1999), Filed Nov. 28, 2012.
Interference No. 105,871, Exhibit No. 2034, Clark, J.L. et al., Design, Synthesis, and Antiviral Activity of 2'-Deoxy-2'fluoro2'-C-methylcytidine, a Potent Inhibitor of Hepatitis C Virus Replication, J. Med. Chem., vol. 48, pp. 5504-5508 (2005), Filed Nov. 28, 2012.
Interference No. 105,871, Exhibit No. 2054, Paper No. 41, Affidavit Exhibit No. 1—Declaration and Curriculum Vitae of JeanPierre Sommadossi, Ph.D., Interference No. 103,906, Apr. 3, 1998, Filed Nov. 28, 2012.
Interference No. 105,871, Exhibit No. 2051, Sofia, Michael J., et al., Nucleoside, Nucleotide, and Non-Nucleoside Inhibitors of Hepatitis C Virus NS5B RNA-Dependent RNA-Polymerase, J. Med. Chem., vol. 55, pp. 2481-2531 (2012), filed Nov. 28, 2012.
Interference No. 105,871, Exhibit No. 2039, Lindenbach, B.D. and Rice, C.M., Flaviviridae: The Viruses and Their Replication (Chapter 32) in Knipe, D.M. et al., eds., Fields Virology, 4th ed. Philadelphia, Lippincott Williams & Wilkins (2001), Filed Nov. 28, 2012.
Interference No. 105,871, Exhibit No. 2096, U.S. Patent Appln. Pub. No. 2002/0120129 A1, Filed Nov. 28, 2012.
Interference No. 105,871, Exhibit No. 2138, Merger of Pharmasset, Inc. (a Georgia corporation) into Pharmasset, Inc. (a Delaware corporation) dated Jul. 23, 2004, Recorded at Reel 027941, Frame 0605, Filed Nov. 7, 2013.
Interference No. 105,871, Exhibit No. 2113, Overhead Transparencies labeled "Jerm C: May 23, 2003" and "Lieven Stuyver: May 23, 2003", Filed Nov. 7, 2013.
Interference No. 105,871, Exhibit No. 2079, Harrison, Steadman D., et al., Therapeutic Synergism of Tiazofurin and Selected Antitumor Drugs against Sensitive and Resistant P388 Leukemia in Mice, Cancer Research, vol. 46, pp. 3396-3400 (1986), Filed Nov. 28, 2012.
Interference No. 105,871, Exhibit No. 2077, Milne, H. Bayard and Peng, Chi-Hsieh, The Use of Benzylsulfonyl Chloride in Peptide Syntheses, J. Am. Chem. Soc., vol. 79, pp. 639-644 (1956), Filed Nov. 28, 2012.
Interference No. 105,871, Exhibit No. 2076, Awad, Laila Fathy, et al., A Synthesis of Methyl 3-O-(β-D-Mannopyranosyl)-α-Dmannopyranoside from Sulfonate Intermediates, Bull. Chem. Soc. Jpn., vol. 59, pp. 1587-1592 (1986), Filed Nov. 28, 2012.
Interference No. 105,871, Exhibit No. 2058, Lalezari, J., et al., Potent Antiviral Activity of the HCV Nucleoside Inhibitor R7128 with PEG-IFN and Ribavirin: Interim Results of R7128 500mg BID for 28 Days, J. Hepatology, vol. 48, Supplement 2, p. S29 (2008), Filed Nov. 28, 2012.

Interference No. 105,871, Exhibit No. 2031, 1 Yang, Shu Shu, et al., Synthesis of DL-1-deoxy-fluoro-6-O-methyl-chiro-inositol: confirmation of a structural-DAST fluorination correlation, Carbohydrate Research, vol. 249, pp. 259-263 (1993), Filed Nov. 28, 2012.
Interference No. 105,871, Exhibit No. 2003, Substitute Declaration of Christoph Seeger, Ph.D., Filed Nov. 28, 2012.
Interference No. 105,871, Exhibit No. 2002, Victor E. Marquez, Ph.D. curriculum vitae, Filed Nov. 28, 2012.
Interference No. 105,871, Exhibit No. 2098, Clark Objections 1 served Jun. 12, 2012, Filed Nov. 26, 2012.
Interference No. 105,871, Exhibit No. 2125, Pierra, Claire, et al., Synthesis and Pharmacokinetics of Valopicitabine (NM283), an Efficient Prodrug of the Potent Anti-HCV Agent 2'-C-Methylcytidine, J. Med. Chem., vol. 49, No. 22, pp. 3614-6620 (2006), Filed Nov. 7, 2013.
Interference No. 105,871, Exhibit No. 2083, 3 Bourne, Nigel, et al., Screening for Hepatitis C Virus Antiviral Sctivity With a Cell-based Secreted Alkaline Phosphatase Reporter Replicon System, Antiviral Research, vol. 67, pp. 76-82 (2005), Filed Nov. 28, 2012.
Interference No. 105,871, Exhibit No. 2080, Wang, Peiyuan, et al., An Efficient and Diastereoselective Synthesis of PSI-6130: A Clinically Efficacious Inhibitor of HCV NS5B Polymerase, J. Org. Chem., vol. 74, No. 17, pp. 6819-6824 (2009), Filed Nov. 28, 2012.
Interference No. 105,871, Exhibit No. 2045, Dhanak, D., et al., Identification and Biological Characterization of Heterocyclic Inhibitors of the Hepatitis C Virus RNA-dependent RNA Polymerase, J. Biol. Chem. vol. 277, No. 41, pp. 38322-38327 (2002), Filed Nov. 28, 2012.
Interference No. 105,871, Exhibit No. 2027, Harry-O'kuru, Rogers E., et al., A Short, Flexible Route toward 2'-C-Branched Ribonucleosides, J. Org. Chem., vol. 62, pp. 1754-1759 (1997), Filed Nov. 28, 2012.
Interference No. 105,871, Exhibit No. 2021, 21 Sommadossi S5 file history—Mar. 3, 2011 Office Action, Filed Nov. 28, 2012.
Interference No. 105,871, Exhibit No. 2068, Hostetler, Karl Y., et al., Synthesis and Antiretroviral Activity of Phospholipid Analogs of Azidothymidine and Other Antiviral Nucelosides, The Journal of Biological Chemistry, vol. 265, No. 11, pp. 6112-6117 (1990), Filed Nov. 28, 2012.
Interference No. 105,871, Exhibit No. 2008, Clark U.S. Patent Appln. Pub. No. 2005/0009737 A1 ("Clark Publication"), Filed Nov. 28, 2012.
Interference No. 105,871, Exhibit No. 2156, The Oxford Hachette French Dictionary, Oxford University Press, 1994, pp. 446, 447, 453, 720, 1351 (renumbered 4 through 8.), Filed Nov. 7, 2013.
Interference No. 105,871, Exhibit No. 2082, McKenzie, Robin, M.D., et al., Hepatic Failure and Lactic Acidosis Due to Fialuridine (FIAU), an Investigational Nucleoside Analogue for Chronic Hepatitis B, The New England Journal of Medicine, vol. 333, No. 17, pp. 1099-1105 (1995), Filed Nov. 28, 2012.
Interference No. 105,871, Exhibit No. 2047, Wakita, T., et al., Production of infectious hepatitis C virus in tissue culture from a cloned viral genome, Nature Medicine, vol. 11, pp. 791-796 (2005), Filed Nov. 28, 2012.
Interference No. 105,871, Exhibit No. 2004, Christoph Seeger, Ph.D. curriculum vitae, Filed Nov. 28, 2012.
Interference No. 105,871, Exhibit No. 2013, 3 Sommadossi S4 file history—Feb. 15, 2007 Amendment, Filed Nov. 28, 2012.
Interference No. 105,871, Exhibit No. 2011, Sommadossi U.S. Appl. No. 60/470,949 ("S3") as filed May 14, 2003, Filed Nov. 28, 2012.
Interference No. 105,871, Exhibit No. 2046, Shim, J. et al., Canonical 3'-deoxyribonucleotides as a chain terminator for HCV NS5B RNA-dependent RNA polymerase, Antiviral Research, vol. 58, pp. 243-251 (2003), Filed Nov. 28, 2012.
Interference No. 105,871, Exhibit No. 2074, Beauchamp, L.M., et al., Amino Acid Ester Prodrugs of Acyclovir, Antiviral Chemistry & Chemotherapy, vol. 3, No. 3, pp. 157-164 (1992), Filed Nov. 28, 2012.
Interference No. 105,871, Exhibit No. 2060, Dec. 15, 2005 Consulting Agreement, Filed Nov. 28, 2012.

(56) References Cited

OTHER PUBLICATIONS

Interference No. 105,871, Exhibit No. 2038, Guo, J.-T., Bichko, V.V., Seeger, C., Effect of Alpha Interferon on the Hepatitis C Virus Replicon, J. Virol., vol. 75, pp. 8516-8523 (2001), Filed Nov. 28, 2012.
Interference No. 105,871, Exhibit No. 2037, Choi, Yongseok, et al., A Conformationally Locked Analogue of the Anti-HIV Agent Stavudine. An Important Correlation between Pseudorotation and Maximum Amplitude, J. Med. Chem., vol. 46, pp. 3292-3299 (2003), Filed Nov. 28, 2012.
Interference No. 105,871, Exhibit No. 2124, U.S. Patent Appln. Pub. No. 2010/0316594 A1, Filed Nov. 7, 2013.
Interference No. 105,871, Exhibit No. 2149, Transcript of Deposition of Ann J. Hobbs, taken Jul. 19, 2013, Filed Nov. 7, 2013.
Interference No. 105,871, Exhibit No. 1320, Email correspondence between George Fleet and Alistair Stewart dated May 11, 2004, Filed Nov. 7, 2013.
Interference No. 105,871, Exhibit No. 1315, Certified English Translation of Feb. 13, 2003 Email from Dick Storer to Gilles Gosselin, Filed Nov. 7, 2013.
Interference No. 105,871, Exhibit No. 1314, Certified English Translation of Jul. 23, 2002 Email from Gilles Gosselin to Dick Storer, Filed Nov. 7, 2013.
Interference No. 105,871, Exhibit No. 1309, Email from Jean-François Griffon to Adel Moussa dated Jun. 30, 2003, Filed Nov. 7, 2013.
Interference No. 105,871, Exhibit No. 1299, Email from Jean-François Griffon to Dick Storer dated Jan. 9, 2003 with attached Dec. 2002 progress report, Filed Nov. 7, 2013.
Interference No. 105,871, Exhibit No. 1293, English translation of memorandum announcing closure of analytical laboratories at University of Montpellier II in Jul. 2004, Filed Nov. 7, 2013.
Interference No. 105,871, Exhibit No. 1292, Memorandum announcing closure of analytical laboratories at University of Montpellier II in Jul. 2004, Filed Nov. 7, 2013.
Interference No. 105,871, Exhibit No. 1287, Certified English translation of the Memorandum announcing closure of analytical laboratories at University of Montpellier II from Jul. 25, 2003-Sep. 1, 2003, Filed Nov. 7, 2013.
Interference No. 105,871, Exhibit No. 1286, Memorandum announcing closure of analytical laboratories at University of Montpellier II from Jul. 25, 2003-Sep. 1, 2003, Filed Nov. 7, 2013.
Interference No. 105,871, Exhibit No. 1280, Memorandum announcing closure dates of Idenix laboratories and offices, Filed Nov. 7, 2013.
Interference No. 105,871, Exhibit No. 1642, Drawing by Victor Marquez, Ph.D. created and marked at his deposition dated Jul. 15, 2013, Filed Nov. 7, 2013.
Interference No. 105,871, Paper No. 442, Clark Miscellaneous Motion 8 (for Pro Hac Vice Admission for Priority Phase Deposition), Filed Jun. 10, 2013.
*Jeremy Clark v. Gilead Sciences, Inc.*, et al., American Arbitration Association Case No. 30 160 141 12 (Atlanta, Georgia), Deposition Transcript of Jeremy Clark dated Mar. 18, 2013 (412 pages).
In re Application of Idenix Pharmaceuticals, Inc., Case No. 2:13-cv-1069-LSC (N.D. Ala.), Deposition Transcript of Jeremy Clark dated Oct. 25, 2013, pp. 1-75, 189-368 (255 pages).
In re Application of Idenix Pharmaceuticals, Inc., Case No. 2:13-cv-1069-LSC (N.D. Ala.), Deposition Transcript of Jeremy Clark dated Oct. 25, 2013, pp. 76-188 (129 pages).
*Idenix Pharmaceuticals, Inc., et al. v. Gilead Sciences, Inc.*, et al., Case No. 13-1987-LPS (D. Del.), Deposition Transcript of Jeremy Clark dated Nov. 18, 2015 (63 pages).
*Idenix Pharmaceuticals, Inc., et al. v. Gilead Sciences, Inc.*, et al., Case No. 13-1987-LPS (D. Del.), Deposition Transcript of Raymond F. Schinazi dated Jan. 29, 2016 (117 pages).
Interference No. 105,981, Exhibit No. 1232, Idenix Exhibit 1432, Interference 105,871, Substitute Declaration of Jingyang Wang, signed Jun. 3, 2014 [substituted for original Exhibit 1232], Filed Sep. 17, 2014.
Interference No. 105,981, Exhibit No. 1184-1, Substitute Specification (clean version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1226, Simons, Nucleoside Mimetics, 117-136 (2001), Filed Sep. 18, 2014.
Interference No. 105,981, Exhibit No. 1125 (Part 1), Sommadossi et al., U.S. Appl. No. 12/131,868, filed Jun. 2, 2008, Filed Mar. 10, 2014.
Interference No. 105,981, Exhibit No. 1125 (Part 2), Sommadossi et al., U.S. Appl. No. 12/131,868, filed Jun. 2, 2008, Filed Mar. 10, 2014.
Interference No. 105,981, Exhibit No. 1125 (Part 3), Sommadossi et al., U.S. Appl. No. 12/131,868, filed Jun. 2, 2008, Filed Mar. 10, 2014.
Interference No. 105,981, Exhibit No. 1172, Decision—Priority Bd. R. 125(a) (Paper 1007), Interference 105,871, *Clark v. Sommadossi*, Filed Mar. 10, 2014.
Interference No. 105,981, Exhibit No. 1135, Damha et al., 2002, Curr. Protocols in Nucleic Acid Chem: 1.7.1-1.7.19, Filed Mar. 10, 2014.
Interference No. 105,981, Exhibit No. 1132, Declaration of Masad J. Damha, Ph.D., Filed Sep. 18, 2014.
Interference No. 105,981, Exhibit No. 1115, Sommadossi et al., International Patent Application Publication No. WO 01/90121, published Nov. 29, 2001, Filed Mar. 10, 2014.
Interference No. 105,981, Exhibit No. 1129, Corrected Filing Receipt, dated Jan. 17, 2008, from the File History of Sommadossi et al., U.S. Appl. No. 60/392,350, filed Jun. 28, 2002, Filed Mar. 10, 2014.
Interference No. 105,981, Exhibit No. 1180, Preliminary Amendment, filed Mar. 20, 2014 from the file history of Storer et al., U.S. Appl. No. 14/220,534, filed Mar. 20, 2014, Filed Sep. 16, 2014.
Interference No. 105,981, Exhibit No. 1170, Filing Receipt, dated Sep. 19, 2011, from the File History of Storer et al., U.S. Appl. No. 13/168,895, filed Jun. 24, 2011, Filed Sep. 16, 2014.
Interference No. 105,981, Exhibit No. 1053, Commentary in 1999, "Exploring HCV Replication," Science 285: 9, Filed Mar. 10, 2014.
Interference No. 105,981, Exhibit No. 1174, Order—Inappropriate Communications Bd. R. 104(a) (Paper 1006), Interference 105,871, *Clark v. Sommadossi*, Filed Mar. 10, 2014.
Interference No. 105,981, Exhibit No. 1173, Judgment Bd. R. 127 (Paper 1008), Interference 105,871, *Clark v. Sommadossi*, Filed Mar. 10, 2014.
Interference No. 105,981, Exhibit No. 1032, Claims of Storer et al. U.S. Pat. No. 7,608,600, filed Jun. 27, 2003, Filed Mar. 10, 2014.
Interference No. 105,981, Exhibit No. 1236, Biggadike and Borthwick, 1990, J. Chem. Soc. Chem. Commun. 1380-82, Filed Sep. 17, 2014.
Interference No. 105,981, Exhibit No. 1187, Preliminary Amendment, filed Aug. 2, 2013, from the file history of Storer et al., in U.S. Appl. No. 13/958,463, filed Aug. 2, 2013, Filed Sep. 16, 2014.
Interference No. 105,981, Exhibit No. 1169, Filing Receipt, dated Jul. 17, 2008, from the File History of Sommadossi et al., U.S. Appl. No. 12/131,868, filed Jun. 2, 2008, Filed Sep. 16, 2014.
Interference No. 105,981, Exhibit No. 1076, Carroll et al., 2002, "Nucleoside analogues as inhibitors of HCV RNA polymerase," Antiviral Ther. 7: L103, Abstract 32, Filed Mar. 10, 2014.
Interference No. 105,981, Exhibit No. 1075, Olsen et al., 2003, "2'-Modified Nucleoside Analogs as Inhibitors of Hepatitis C RNA Replication," Antiviral Res. 57: Abstract 121, Filed Mar. 10, 2014.
Interference No. 105,981, Exhibit No. 1119, Altamura et al., U.S. Patent Application Publication No. 2003/0176503, published Sep. 18, 2003, filed Apr. 19, 2002, provisional application to which priority is claimed filed Apr. 20, 2001, Filed Mar. 10, 2014.
Interference No. 105,981, Exhibit No. 1193, Gao et al., U.S. Pat. No. 7,195,885 B2, which issued Mar. 27, 2007 from U.S. Appl. No. 10/639,150, Aug. 12, 2003 Filed Sep. 16, 2014.
Interference No. 105,981, Exhibit No. 1043, Sommadossi et al., International Patent Application Publication No. WO 01/92282, published Dec. 6, 2001, Filed Mar. 10, 2014.
Interference No. 105,981, Exhibit No. 1128, Decision on Motions (Paper 426), Interference 105,871, *Clark v. Sommadossi*, Filed Mar. 10, 2014.

(56) References Cited

OTHER PUBLICATIONS

Interference No. 105,981, Exhibit No. 1160, Herdewijn et al., 1989, Nucleosides Nucleotides 8: 65-96, Filed Mar. 10, 2014.
Interference No. 105,981, Exhibit No. 1114, Delang et al., 2013, Curr. Top. Microbiol. lmmunol. 369: 289-320, Filed Mar. 10, 2014.
Interference No. 105,981, Exhibit No. 1023, De Francesco & Rice, 2003, "New therapies on the horizon for hepatitis C: are we close?," Clin. Liver Dis. 7: 211-42, Filed Mar. 10, 2014.
Interference No. 105,981, Exhibit No. 1189, Amendment dated Jun. 21, 2012, including Exhibits A-C, from the file history of Sommadossi et al., in U.S. Appl. No. 12/131,868, filed Jun. 2, 2008, Filed Sep. 16, 2014.
Interference No. 105,981, Exhibit No. 1142, Matsuda et al., Nucleosides & Nucleotides, 1992, 11(2-4): 197-226, Filed Mar. 20, 2014.
Interference No. 105,981, Exhibit No. 1147, Codington et al., 1961, J. Am. Chem. Soc. 83: 5030-5031, Filed Mar. 10, 2014.
Interference No. 105,981, Exhibit No. 1108, Sofia et al., "Structure-activity relationships of 2'-C-methyl modified nucleosides as anti-HCV agents," Abstracts of Papers, 238th ACS National Meeting, Washington, DC, United States, Aug. 16-20, 2009), MEDI-101, Filed Mar. 10, 2014.
Interference No. 105,981, Exhibit No. 1199, Larock, 1999, Comprehensive Organic Transformations: A Guide to Functional Group Preparations (2nd ed.), Chapter 8, "Halogenation of Alcohols," pp. 689-690, Filed Sep. 17, 2014.
Interference No. 105,981, Exhibit No. 1171, Filing Receipt, dated Aug. 26, 2013, from the File History of Storer et al., U.S. Appl. No. 13/958,463, filed Aug. 2, 2013, Filed Sep. 16, 2014.
Interference No. 105,981, Exhibit No. 1042, Bhat et al., 2002, "Nucleoside analogues inhibit HCV replication in cells," Antiviral Ther. 7: L103, Abstract 33, Filed Mar. 10, 2014.
Interference No. 105,981, Exhibit No. 1242, Borthwick et al., 1993, Bioorg. Med. Chem. Lett. 12: 2577-2580, Filed Sep. 17, 2014.
Interference No. 105,981, Exhibit No. 1209, Xu et al., 2014, "Synthesis and anti-BVDV activity of novel σ-sultones in vitro: Implications for HCV therapies," Bioorg. Med. Chem. Lett. 24: 2388-91, Filed Sep. 17, 2014.
Interference No. 105,981, Exhibit No. 1191, Li et al., 2001, "2'-C-Branched Ribonucleosides. 2. Synthesis of 2'-C-β-Trifluoromethyl Pyrimidine Ribonucleosides," Org. Lett. 3: 1025-28, Filed Sep. 16, 2014.
Interference No. 105,981, Exhibit No. 1067, Wu, 2001, "Beefing Up Replication of the Hepatitis C Virus," Hepatology 33: 1550-51, Filed Mar. 10, 2014.
Interference No. 105,981, Exhibit No. 1200, Second Declaration of Masad J. Damha, Ph.D., Filed Sep. 17, 2014.
Interference No. 105,981, Exhibit No. 1084, Babine et al., International Patent Application Publication No. WO 02/18369 A2, published Mar. 7, 2002, Filed Mar. 10, 2014.
Interference No. 105,981, Exhibit No. 1146, Schinazi et al., U.S. Pat. No. 6,348,587, issued Feb. 19, 2002, Filed Mar. 10, 2014.
Interference No. 105,981, Exhibit No. 1109, Clark, U.S. Pat. No. 7,429,572, issued Sep. 30, 2008 from U.S. Appl. No. 10/828,753, filed Apr. 21, 2004, Filed Sep. 17, 2014.
Interference No. 105,981, Exhibit No. 1225, S. Bohm, Of Oxygen Substituents Having a C—O Bond, in Organo-Fluorine Compounds, Workbench Edition, E10b/Part 1: 82-118 (B. Baasner ed., 2000), Filed Sep. 17, 2014.
Interference No. 105,981, Exhibit No. 1151, Van Aerschot et al., 1989, Bull. Soc. Chim. Belg. 98(12): 937-941 [Substitute], Filed Mar. 10, 2014.
Interference No. 105,981, Exhibit No. 1033, Claims 164 and 165 of Clark U.S. Appl. No. 11/854,218, Filed Mar. 10, 2014.
Interference No. 105,981, Exhibit No. 1249, Clark Objections 4, served Jul. 9, 2014, Filed Sep. 17, 2014.
Interference No. 105,981, Exhibit No. 1175, Anthony Zupcic Jan. 13, 2014 email to Patent Trial and Appeal Board raising inequitable conduct issue, Filed Mar. 10, 2014.
Interference No. 105,981, Exhibit No. 1151 (Substitute), Van Aerschot et al., 1989, Bull. Soc. Chim. Belg. 98(12): 937-941 [Substitute], Filed Mar. 31, 2014.
Interference No. 105,981, Exhibit No. 1127, Amendment and Response Under 37 C.F.R. § 1.111, dated Sep. 20, 2011, from the file history of Sommadossi et al., U.S. Appl. No. 12/131,868, filed Jun. 2, 2008, Filed Mar. 10, 2014.
Interference No. 105,981, Exhibit No. 1126, Declaration (Paper 1), Interference 105,871, *Sommadossi* v. *Clark*, Filed Mar. 10, 2014.
Interference No. 105,981, Exhibit No. 1111, Lam et al., 2010, "PSI-7851, a Pronucleotide of β-D-2'-Deoxy-2'-Fluoro-2'-CMethyluridine Monophosphate, Is a Potent and Pan-Genotype Inhibitor of Hepatitis C Virus Replication," Antimicrob. Agents Chemother. 54: 3187-96, Filed Mar. 10, 2014.
Interference No. 105,981, Exhibit No. 1061, Friebe et al., 2001, "Sequences in the 5' Nontranslated Region of Hepatitis C Virus Required for RNA Replication," J. Virol. 75: 12047-57, Filed Mar. 10, 2014.
Interference No. 105,981, Exhibit No. 1021, Bressanelli et al., Apr. 2002, "Structural Analysis of the Hepatitis C Virus RNA Polymerase in Complex with Ribonucleotides," J. Virol. 76: 3482-92, Filed Mar. 10, 2014.
Interference No. 105,981, Exhibit No. 1031, Harper et al., 2005, "Potent Inhibitors of Subgenomic Hepatitis C Virus RNA Replication through Optimization of Indole-N-Acetamide Allosteric Inhibitors of the Viral NS5B Polymerase," J. Med. Chem. 48: 4547-57, Filed Mar. 10, 2014.
Interference No. 105,981, Exhibit No. 1206, Ago et al., 1999, "Crystal structure of the RNA-dependent RNA polymerase of hepatitis C virus," Structure 7: 1417-26, Filed Sep. 17, 2014.
Interference No. 105,981, Exhibit No. 1058, Ikeda et al., Mar. 2002 (received Oct. 3, 2001, accepted for publication Dec. 20, 2001), "Selectable Subgenomic and Genome-Length Dicistronic RNAs Derived from an Infectious Molecular Clone of the HCV-N Strain of Hepatitis C Virus Replicate Efficiently in Cultured Huh7 Cells," J. Viral. 76: 2997-3006, Filed Mar. 10, 2014.
Interference No. 105,981, Exhibit No. 1121, Sommadossi Notice of Judicial Review (Paper 1010), Interference 105,871, *Clark* v. *Sommadossi*, Filed Mar. 10, 2014.
Interference No. 105,981, Exhibit No. 1148 (Substitute), Wachtmeister et al., 1999, Tetrahedron 55: 10761-10770 [Substitute], Filed Mar. 31, 2014.
Interference No. 105,981, Exhibit No. 1221, Chapel et al., 2007, "Reduction of the infectivity of hepatitis C virus pseudoparticles by incorporation of misfolded glycoproteins induced by glucosidase inhibitors," J. Gen. Virol. 88: 1133-43, Filed Sep. 17, 2014.
Interference No. 105,981, Exhibit No. 1216, Seio et al., 2004, "Synthesis of Benzodithiol-2-yl-Substituted Nucleoside Derivatives as Lead Compounds Having Anti-Bovine Viral Diarrhea Virus Activity," J. Med. Chem. 47: 5265-75, Filed Sep. 17, 2014.
Interference No. 105,981, Exhibit No. 1213, Ouzounov et al., 2002 (accepted for publication May 7, 2002), "The combination of interferon α-2b and n-butyl deoxynojirimycin has a greater than additive antiviral effect upon production of infectious bovine viral diarrhea virus (BVDV) in vitro: implications for hepatitis C virus (HCV) therapy," Antiviral Res. 55: 425-35, Filed Sep. 17, 2014.
Interference No. 105,981, Exhibit No. 1228, Transcript of Deposition of Stanley Moncrief Lemon on Tuesday, Jul. 31, 2012, Filed Sep. 17, 2014.
Interference No. 105,981, Exhibit No. 1248, Transcript of Deposition of Stanislaw F. Wnuk, Ph.D. On Thursday, Jun. 12, 2014 [Copy of Clark Exhibit 2187], Filed Sep. 17, 2014.
Interference No. 105,981, Exhibit No. 1233, Idenix Exhibit 1647, Interference 105,871, Deposition Transcript of Jingyang Wang dated Jul. 2, 2013 (with errata sheet) [substituted for original Exhibit 1233], Filed Sep. 17, 2014.
Interference No. 105,981, Exhibit No. 1113, Aghemo et al., 2013, Hepatology 58: 428-38, Filed Mar. 10, 2014.
Interference No. 105,981, Exhibit No. 1100, Lohmann et al., 1998, "Biochemical and Kinetic Analyses of NS5B RNADependent RNA Polymerase of the Hepatitis C Virus," Virology 249: 108-18, Filed Mar. 10, 2014.

(56) References Cited

OTHER PUBLICATIONS

Interference No. 105,981, Exhibit No. 1093, Mendoza et al., 1999, "High-Throughput Microarray-Based Enzyme-Linked mmunosorbent Assay (ELISA)," BioTechniques 27: 778-88, Filed Mar. 10, 2014.
Interference No. 105,981, Exhibit No. 1083, Di Bisceglie, Jan. 2002, "New Therapeutic Strategies for Hepatitis C," Hepatology 35: 224-31, Filed Mar. 10, 2014.
Interference No. 105,981, Exhibit No. 1062, Frese et al., 2001, "Interferon-α inhibits hepatitis C virus subgenomic RNA replication by an MxA-independent pathway," J. Gen. Virol. 82: 723-33, Filed Mar. 10, 2014.
Interference No. 105,981, Exhibit No. 1212, Durantel et al., 2001, "Study of the Mechanism of Antiviral Action of Iminosugar Derivatives against Bovine Viral Diarrhea Virus," J. Virol. 75: 8987-98, Filed Sep. 17, 2014.
Interference No. 105,981, Exhibit No. 1168, Office Action, dated Feb. 27, 2014, from the File History of Storer et al., U.S. Appl. No. 13/958,463, filed Aug. 2, 2013, Filed Sep. 16, 2014.
Interference No. 105,981, Exhibit No. 1060, Krieger et al., 2001, "Enhancement of Hepatitis C Virus RNA Replication by Cell Culture-Adaptive Mutations," J. Virol. 75: 4614-24, Filed Mar. 10, 2014.
Interference No. 105,981, Exhibit No. 1050, Yanagi et al., 1997, "Transcripts from a single full-length cDNA clone of hepatitis C virus are infectious when directly transfected into the liver of a chimpanzee," Proc. Natl. Acad. Sci. USA 94: 8738-43 Filed Mar. 10, 2014.
Interference No. 105,981, Exhibit No. 1015, De Francesco et al., 1996, "RNA-Dependent RNA Polymerase of Hepatitis C Virus," Methods Enzymol. 275: 58-67 [Substitute], Filed Mar. 31, 2014.
Interference No. 105,981, Exhibit No. 1240, Lanford et al., 2003, J. Virol. 77: 1092-1104, Filed Sep. 17, 2014.
Interference No. 105,981, Exhibit No. 1218, Luscombe et al., 2010, "A novel Hepatitis C virus p7 ion channel inhibitor, BIT225, inhibits bovine viral diarrhea virus in vitro and shows synergism with recombinant interferon-α-2b and nucleoside analogues," Antiviral Res. 86: 144-53, Filed Sep. 17, 2014.
Interference No. 105,981, Exhibit No. 1012, Curriculum Vitae of Dr. Raffaele De Francesco, Filed Mar. 10, 2014.
Interference No. 105,981, Exhibit No. 1243, Sommadossi et al., International Patent Application Publication No. WO 01/92282, published Dec. 6, 2001, Filed Sep. 17, 2014.
Interference No. 105,981, Exhibit No. 1229, Transcript of Deposition of Jeffrey Scott Glenn on Tuesday, Jul. 31, 2012, Filed Sep. 17, 2014.
Interference No. 105,981, Exhibit No. 1133, Curriculum vitae of Masad J. Damha, Ph.D., Filed Mar. 10, 2014.
Interference No. 105,981, Exhibit No. 1096, Lohmann et al. 1997, "Biochemical Properties of Hepatitis C Virus NS5B RNADependent RNA Polymerase and Identification of Amino Acid Sequence Motifs Essential for Enzymatic Activity," J. Virol. 71: 8416-28, Filed Mar. 10, 2014.
Interference No. 105,981, Exhibit No. 1079, Grakoui et al., 2001, "Bad Time for Bonzo? Experimental Models of Hepatitis C Virus Infection, Replication, and Pathogenesis," Hepatology 33: 489-95, Filed Mar. 10, 2014.
Interference No. 105,981, Exhibit No. 1006, Request for Certificate of Correction Under 37 C.F.R. § 1.322 with Form PTO/SB/44— Certificate of Correction, Filed Sep. 17, 2014.
Interference No. 105,981, Exhibit No. 1222, Carroll et al., 2003, "Inhibition of Hepatitis C Virus RNA Replication by 2'-Modified Nucleoside Analogs," J. Biol. Chem. 278: 11979-84, Filed Sep. 17, 2014.
Interference No. 105,981, Exhibit No. 1072, Mottola et al., Feb. 2002, "Hepatitis C Virus Nonstructural Proteins Are Localized in a Modified Endoplasmic Reticulum of Cells Expressing Viral Subgenomic Replicons," Virology 293: 31-43, Filed Mar. 10, 2014.
Interference No. 105,981, Exhibit No. 1230, Transcript of Deposition of Christoph Seeger, Ph.D. on Wednesday, Jul. 25, 2012, Filed Sep. 17, 2014.
Interference No. 105,981, Exhibit No. 1112, Furman et al., 2011, "Activity and the metabolic activation pathway of the potent and selective hepatitis C virus pronucleotide inhibitor PSI-353661," Antiviral Res. 91: 120-32, Filed Mar. 10, 2014.
Interference No. 105,981, Exhibit No. 1107, Carroll and LaFemina, "Nucleoside Analog Inhibitors of Hepatitis C Viral Replication," Antiviral Research: Strategies in Antiviral Drug Discovery 153-166 (Robert L. LaFemina, Ph.D., ed., 2009), Filed Mar. 10, 2014.
Interference No. 105,981, Exhibit No. 1065, Pietschmann et al., 2001, "Characterization of Cell Lines Carrying Self-Replicating Hepatitis C Virus RNAs," J. Virol. 75: 1252-64, Filed Mar. 10, 2014.
Interference No. 105,981, Exhibit No. 1064, Lohmann et al., 2001, "Mutations in Hepatitis C Virus RNAs Conferring Cell Culture Adaptation," J. Virol. 75: 1437-49, Filed Mar. 10, 2014.
Interference No. 105,981, Exhibit No. 1051, Yanagi et al., 1998, "Transcripts of a Chimeric cDNA Clone of Hepatitis C Virus Genotype 1b Are Infectious in Vivo," Virology 244: 161-72, Filed Mar. 10, 2014.
Interference No. 105,981, Exhibit No. 1014, Behrens et al., 1996, "Identification and properties of the RNA-dependent RNA polymerase of hepatitis C virus," Embo J. 15: 12-22, Filed Mar. 10, 2014.
Interference No. 105,981, Exhibit No. 1227, Transcript of Deposition of Christoph Seeger, Ph.D. on Wednesday, Jun. 25, 2014 [Copy of Clark Exhibit 2188], Filed Sep. 17, 2014.
Interference No. 105,981, Exhibit No. 1184-13, Substitute Specification (clean version), filed Sep. 17, 2008, from the file history of Sommadossi et al., in U.S. Appl. No. 12/131,868, filed Jun. 2, 2008, Filed Sep. 16, 2014.
Interference No. 105,981, Exhibit No. 1134, Damha et al., 2000, Nucleic Acids Res. 28(18): 3625-3635, Filed Mar. 10, 2014.
Interference No. 105,981, Exhibit No. 1089, Yi et al., Dec. 2002 (accepted for publication Jun. 21, 2002), "Subgenomic Hepatitis C Virus Replicons Inducing Expression of a Secreted Enzymatic Reporter Protein," Virology 304: 197-210, Filed Mar. 10, 2014.
Interference No. 105,981, Exhibit No. 1247, Clark Exhibit 2102, Interference 105,871, Substitute Declaration of Michael J. Otto, Ph.D., Filed Sep. 17, 2014.
Interference No. 105,981, Exhibit No. 1039, Ishii et al., 1999, "Expression of Hepatitis C Virus NS5B Protein: Characterization of Its RNA Polymerase Activity and RNA Binding," Hepatology 29: 1227-35, Filed Mar. 10, 2014.
Wader, Declaration re IN Application No. 6087/DELNP/2005 BDR Pre-Grant Opposition dated Feb. 17, 2015.
Wagner, et al., "Pronucleotides: Toward the In Vivo Delivery of Antiviral and Anticancer Nucleotides," Med. Res. Rev., 20(6):417-451 (2000).
Walker, et al., "HCV RNA-dependent RNA Polymerase as a Target for Antiviral Development," Current Opinion in Pharmacology, 2:535-540 (2002).
Walker, et al. "Hepatitis C Virus Therapies: Current Treatments, Targets and Future Perspectives," Antiviral Chemistry & Chemotherapy, 14:1-21 (2003).
Walton, et al., "Branched-Chain Sugar Nucleosides. V. Synthesis and Antiviral Properties of Several Branched-Chain Sugar Nucleosides," J. Med. Chem. 12:306-309 (1969).
Wang, Deposition Transcript dated Jul. 2, 2013, Exhibit 1647 in Interference No. 105,871.
Wang, Laboratory Notebook Excerpts, Exhibit 1271 in Interference No. 105,871.
Wang, Substitute Declaration dated Jun. 3, 2013, Exhibit 1432 in Interference No. 105,871.
Wang, Testimony dated Oct. 7, 2014, pp. 202-203, from *Idenix Pharmaceuticals, Inc.* v. *Gilead Sciences, Inc.*, UK High court of Justice, Chancery Division, Patents Court, Claim No. HP 14D 01069.
Wnuk, Declaration re IN Application No. 6087/DELNP/2005 India Cares, BDR, and Optimus Pre-Grant Oppostions dated Oct. 29, 2015.
Wnuk, Declaration re IN Patent No. 273003 Vector Oppostion dated Aug. 10, 2017.

(56) References Cited

OTHER PUBLICATIONS

Yang, Declaration re IN Application No. 6087/DELNP/2005 India Cares Pre-Grant Opposition dated Jun. 19, 2015.
Yang, et al., "Synthesis of 25-Fluorovitamin D3," Tetrahedron Lett., 27:2315-2316 (1977).
*Storer v. Clark*, U.S. Court of Appeals for the Federal Circuit, Appellant's Motion to Stay or, in the Alternative, Dismiss Without Prejudice to Reinstatement and Cross-Motion to Expedite the Appeal dated Aug. 4, 2015.
*Storer v. Clark*, U.S. Court of Appeals for the Federal Circuit, Appellee's Opposition to Appellant's Motion to Stay or Dismiss Without Prejudice to Reinstatement and Cross-Motion to Expedite the Appeal dated Aug. 4, 2015.
*Storer v. Clark*, U.S. Court of Appeals for the Federal Circuit, Order dated Aug. 7, 2015.
*Storer v. Clark*, U.S. Court of Appeals for the Federal Circuit, Corrected Brief for Appellants Ricard Storer, Gilles Gosselin, Jean-Pierre Sommadossi, and Paola LaColla dated Feb. 5, 2016.
*Storer v. Clark*, U.S. Court of Appeals for the Federal Circuit, Brief for the United States dated Feb. 19, 2016.
*Storer v. Clark*, U.S. Court of Appeals for the Federal Circuit, Appellee's Brief dated Feb. 22, 2016.
*Storer v. Clark*, U.S. Court of Appeals for the Federal Circuit, Citation of Supplemental Authority dated Apr. 8, 2016.
*Storer v. Clark*, U.S. Court of Appeals for the Federal Circuit, Reply Brief for Appellants Richard Storer, Gilles Gosselin, Jean-Pierre Sommadossi, and Paolo LaColla dated Apr. 11, 2016.
*Storer v. Clark*, U.S. Court of Appeals for the Federal Circuit, Corrected Appendix, vol. I of IV dated Apr. 22, 2016.
*Storer v. Clark*, U.S. Court of Appeals for the Federal Circuit, Corrected Appendix, vol. II of IV dated Apr. 22, 2016.
*Storer v. Clark*, U.S. Court of Appeals for the Federal Circuit, Corrected Appendix, vol. III of IV dated Apr. 22, 2016.
*Storer v. Clark*, U.S. Court of Appeals for the Federal Circuit, Corrected Appendix, vol. IV of IV dated Apr. 22, 2016.
*Storer v. Clark*, U.S. Court of Appeals for the Federal Circuit, Citation of Supplemental Authority dated Sep. 1, 2016.
*Storer v. Clark*, U.S. Court of Appeals for the Federal Circuit, Appellants' Petition for Panel Rehearing or Rehearing En Banc dated Aug. 7, 2017.
*Storer v. Clark*, U.S. Court of Appeals for the Federal Circuit, Intervenor's Opposition to Rehearing dated Sep. 22, 2017.
*Storer v. Clark*, U.S. Court of Appeals for the Federal Circuit, Response to Combined Petition for Rehearing and Rehearing En Banc dated Sep. 28, 2017.
*Storer v. Clark*, U.S. Court of Appeals for the Federal Circuit, Order on Petition for Panel Rehearing and Rehearing En Banc dated Nov. 3, 2017.
*Storer v. Clark*, U.S. Court of Appeals for the Federal Circuit, Mandate dated Nov. 13, 2017.
*Storer v. United States*, United States Waiver dated Apr. 2, 2018.
*Storer v. United States*, Clark Waiver dated Apr. 3, 2018.
Li, et al., "2'-C-Branched Ribonucleosides. 2. Synthesis of 2'-C-β-Trifluoromethyl Pyrimidine Ribonucleosides," Organic Letters 3(7):1025-1028 (2001).
IN Application No. 6087DELNP2005 Decision dated Jan. 13, 2015.
IN Application No. 6087DELNP2005 Decision dated May 9, 2016.
BR Application No. PI0410846-9 ABIA Opposition dated Sep. 14, 2015 (English).
BR Application No. PI0410846-9 Response to ABIA Opposition dated Dec. 9, 2015 (English).
BR Application No. PI0410846-9 Blanver Opposition (English).
IN Application No. 2079/DELNP/2011 Refusal Order dated Feb. 12, 2018.
EP Application Nos. 04775900.6, 11157832.4, 11157939.7, 11157954.6, and 13152340.9 Reply to Third Party observations dated Jan. 13, 2015.

Herdewijn, et al. "Synthesis of Nucleosides Fluorinated in the Sugar Moiety. The Application of Diethylaminosulfur Trifluoride to the Synthesis of Fluorinated Nucleosides," Nucleosides & Nucleotides, 8(1):65-96 (1989).
EP Application No. 13152340.9, Sep. 29, 2017 Summary of *Gilead Sciences, Inc.* v. *Idenix Pharmaceuticals, Inc.*, Federal court of Canada, Ottawa, Ontario, 2015 FC 1156, Docket T-1156-12, Public Judgment and Reasons dated Nov. 2, 2015.
BR Application No. PI0419345-8 Office Action Response dated Sep. 3, 2018.
BR Application No. PI0419345-8 Office Action Response dated Sep. 3, 2018 (English translation).
BR Application No. PI0410846-9 Blanver Farmaceutica e Farmoquimica SA Third Party Observations dated Aug. 2, 2018.
BR Application No. PI0410846-9 Blanver Farmaceutica e Farmoquimica SA Third Party Observations dated Aug. 2, 2018 (English translation).
BR Application No. PI0410846-9 Instituto de Tecnologia em Farmacos Third Party Observations dated Aug. 7, 2018.
BR Application No. PI0410846-9 Instituto de Tecnologia em Farmacos Third Party Observations dated Aug. 7, 2018 (English translation).
BR Application No. PI0312286-7 Office Action dated May 21, 2018.
BR Application No. PI0312286-7 Office Action dated May 21, 2018 (English translation).
Furman et al. (2011), "Chapter 21: Discovery and Development of PSI-6130/RG7128," in Antiviral Drugs: From Basic Discovery Through Clinical Trials (1st Ed., Kazmierski Ed.).
Hodge (2015), "Meeting Report: 28th International Conference on Antiviral Research in Rome, Italy," Antiviral Research 123:172-187.
Meijer (2003), "Development of a Novel Promoter System for Thioglycoside Activation and Its Application in the Synthesis of a GD3 Bis-Lactam," Lund University.
BR Application No. PI0410846-9, Opinion of Mr. Anand Grover dated Aug. 30, 2018.
EP Application No. 13152340.9 (EP Patent No. 2604620) Written Submission in Advance of Oral Proceedings by Medecins du Monde, Medici Senza Frontiere Onlus, and European Public Health Alliance dated Jul. 12, 2018, dated Jul. 18, 2018.
EP Application No. 13152340.9 (EP Patent No. 2604620) Written Submission in Advance of Oral Proceedings by Gillard dated Jul. 13, 2018, dated Jul. 18, 2018.
EP Application No. 13152340.9 (EP Patent No. 2604620) Submission by Gilead Pharmasset LLC dated Sep. 4, 2018.
EP Application No. 13152340.9 (EP Patent No. 2604620) decision maintaining patent dated Sep. 13, 2018.
BR Application No. PI0410846-9 Associacao Brasileira Interdisciplinar de AIDS Third Party Observations dated Sep. 3, 2018.
BR Application No. PI0410846-9 Associacao Brasileira Interdisciplinar de AIDS Third Party Observations dated Sep. 3, 2018 (English translation).
BR Application No. PI0410846-9 Blanver Farmaceutica e Farmoquimica SA Third Party Observations dated Sep. 3, 2018.
BR Application No. PI0410846-9 Blanver Farmaceutica e Farmoquimica SA Third Party Observations dated Sep. 3, 2018 (English translation).
BR Application No. PI0419345-8 Blanver Farmaceutica e Farmoquimica SA Third Party Observations dated Sep. 14, 2018.
BR Application No. PI0419345-8 Blanver Farmaceutica e Farmoquimica SA Third Party Observations dated Sep. 14, 2018 (English translation).
BR Application No. PI0410846-9 Notice of Allowance dated Sep. 13, 2018.
BR Application No. PI0410846-9 Notice of Allowance dated Sep. 13, 2018 (English translation).
BR Application No. PI0419345-8 Office Action dated Sep. 21, 2018.
BR Application No. PI0419345-8 Office Action dated Sep. 21, 2018 (English translation).
EP Application No. 13152340.9 (EP Patent No. 2604620) minutes of Sep. 13, 2018 oral proceedings mailed Oct. 2, 2018.

(56) References Cited

OTHER PUBLICATIONS

EP Application No. 13152340.9 (EP Patent No. 2604620) interlocutory decision in opposition proceedings mailed Oct. 2, 2018.
EP Application No. 13152340.9 (EP Patent No. 2604620) druckexemplar in opposition procedure dated Oct. 2, 2018.
GR Supplementary Protection Certificate Application No. 20160800060 Letter of Deficiencies dated Sep. 12, 2018.
GR Supplementary Protection Certificate Application No. 20160800060 Letter of Deficiencies dated Sep. 12, 2018 (English translation).
Interference No. 105,981, Exhibit No. 2003 (Substitute), Substitute Declaration of Christoph Seeger, Ph.D., Filed Mar. 31, 2014.
Interference No. 105,981, Exhibit No. 2130, Interference No. 105,871, Paper No. 924, Idenix Exhibit 1643 (entitled (by Idenix): "Deposition Transcript of Adel Moussa dated Jun. 13, 2013 (with errata sheet)"), Filed Sep. 18, 2014.
Interference No. 105,981, Exhibit No. 2137-6, Swarbrick, J. and Boylan, J.C., eds., Encyclopedia of Pharmaceutical Technology, vol. 13, Marcel Dekker, Inc. (1996), Filed Sep. 18, 2014.
Interference No. 105,981, Exhibit No. 2114, Interference No. 105,871, Paper No. 508, Idenix Exhibit 1241 (entitled (by Idenix): "Substitute Declaration of Alistair Stewart, signed May 30, 2013"), Filed May 23, 2014.
Interference No. 105,981, Exhibit No. 2110-23, Declaration of Prof. Dr. Chris Meier, signed Aug. 31, 2013 (with exhibits) (filed by Idenix in Oslo District Court case 12-155575TVI-OTIR/01), Filed Sep. 18, 2014.
Interference No. 105,981, Exhibit No. 1130, BIB Data Sheet, from the File History of Sommadossi et al., U.S. Appl. No. 10/608,907, filed Jun. 27, 2003, Filed Mar. 10, 2014.
Interference No. 105,981, Exhibit No. 1118, Lawitz et al., 2012, Abstract 7, J. Hepatol. 56: S4 [Substitute], Filed Mar. 10, 2014.
Interference No. 105,981, Exhibit No. 1181, Bibliographic Data dated Mar. 20, 2014 in Storer et al., U.S. Appl. No. 13/958,463, filed Aug. 2, 2013, Filed Sep. 16, 2014.
Interference No. 105,981, Exhibit No. 1179, Bibliographic Data dated Mar. 20, 2014 in Storer et al., U.S. Appl. No. 14/220,534, filed Mar. 20, 2014, Filed Sep. 17, 2014.
Interference No. 105,981, Exhibit No. 1196, The Structures drawn by Dr. Wnuk for (2'R)-2'-deoxy-2'-fluoro-2'-C-methyl uridine (beta-L) and (2' S)-2'-deoxy-2'-fluoro-2'-C-methyl uridine (beta-D), Filed Sep. 17, 2014.
Interference No. 105,981, Exhibit No. 1155, Pankiewicz et al., 1992, J. Org. Chem. 57(26): 7315-7321, Filed Mar. 10, 2014.
Interference No. 105,981, Exhibit No. 1148, Wachtmeister et al., 1999, Tetrahedron 55: 10761-10770 [Substitute], Filed Mar. 10, 2014.
Interference No. 105,981, Exhibit No. 1153, Olsen et al. 1991, Biochemistry 30(40): 9735-9741, Filed Mar. 10, 2014.
Interference No. 105,981, Exhibit No. 1145, Vorbrüggen and Ruh-Pohlenz, 2001, Handbook of Nucleoside Synthesis (John Wiley & Sons., Inc., New York), pp. 402-07, Filed Mar. 10, 2014.
Interference No. 105,981, Exhibit No. 1140, Matsuda et al., Chem. Pharm. Bull., 1987, 35(9): 3967-3970, Filed Mar. 10, 2014.
Interference No. 105,981, Exhibit No. 1101, Lohmann et al. 1999, "Selective Stimulation of Hepatitis C Virus and Pestivirus NS5B RNA Polymerase Activity by GTP," J. Biol. Chem. 274: 10807-15, Filed Mar. 10, 2014.
Interference No. 105,981, Exhibit No. 1094, Pawlotsky et al., 1998, "What Strategy Should Be Used for Diagnosis of Hepatitis C Virus Infection in Clinical Laboratories?" Hepatology 27: 1700-02, Filed Mar. 10, 2014.
Interference No. 105,981, Exhibit No. 1088, Office Action, dated Jan. 11, 2006, from the File History of Storer et al., U.S. Appl. No. 10/608,907, filed Jun. 27, 2003, Filed Mar. 10, 2014.
Interference No. 105,981, Exhibit No. 1250, Storer Objections to Evidence 1, served Mar. 17, 2014, Filed Sep. 17, 2014.
Interference No. 105,981, Exhibit No. 1207, Steffens et al., 1999 "The RNA-dependent RNA polymerases of different members of the family Flaviviridae exhibit similar properties in vitro," J. Gen.Virol. 80: 2583-90, Filed Sep. 17, 2014.

Interference No. 105,981, Exhibit No. 1203, Virol. Lai et al., 1999, "Mutational Analysis of Bovine Viral Diarrhea Virus RNADependent RNA Polymerase," J. Virol. 73: 10129-36, Filed Sep. 17, 2014.
Interference No. 105,981, Exhibit No. 1015, De Francesco et al., 1996, "RNA-Dependent RNA Polymerase of Hepatitis C Virus," Methods Enzymol. 275: 58-67 [Substitute], Filed Mar. 10, 2014.
Interference No. 105,981, Exhibit No. 1038, Lesburg et al., 2000, "Recent advances in the analysis of HCV NS5B RNAdependent RNA polymerase," Cum Opin. Investig. Drugs 1: 289-96, Filed Mar. 10, 2014.
Interference No. 105,981, Exhibit No. 1009, Amendment and Response, dated Jul. 24, 2008, from the File History of Storer et al., U.S. Appl. No. 10/608,907, filed Jun. 27, 2003, Filed Sep. 17, 2014.
Interference No. 105,981, Exhibit No. 1198, Pharmasset Chemistry Progress Report dated Jan. 31, 2003, Filed Sep. 17, 2014.
Interference No. 105,981, Exhibit No. 1016, Neddermann et al., 1997, "The Nonstructural Proteins of the Hepatitis C Virus: Structure and Functions," Biol. Chem. 378: 469-76, Filed Mar. 10, 2014.
Interference No. 105,981, Exhibit No. 1010, Amendment and Response, dated Jan. 20, 2009, from the File History of Storer et al., U.S. Appl. No. 10/608,907, filed Jun. 27, 2003, Filed Mar. 10, 2014.
Interference No. 105,981, Exhibit No. 1104, Amendment and Response, dated Jan. 20, 2009, from the File History of Storer et al., U.S. Appl. No. 10/608,907, filed Jun. 27, 2003, Filed Mar. 10, 2014.
Interference No. 105,981, Exhibit No. 1046, Schinazi et al., International Patent Application Publication No. WO 99/43691, published Sep. 2, 1999, Filed Mar. 10, 2014.
Interference No. 105,981, Exhibit No. 1105, Carroll et al., 2009, "Robust Antiviral Efficacy upon Administration of a Nucleoside Analog to Hepatitis C Virus-Infected Chimpanzees," Antimicrob. Agents Chemother. 53: 926-34, Filed Mar. 10, 2014.
Interference No. 105,981, Exhibit No. 1030, De Francesco & Migliaccio, 2005, "Challenges and successes in developing new therapies for hepatitis C," Nature 436: 953-60, Filed Mar. 10, 2014.
Interference No. 105,981, Exhibit No. 1210, Lai et al., 2000, "Generation and Characterization of a Hepatitis C Virus NS3 Protease-Dependent Bovine Viral Diarrhea Virus," J. Virol. 74: 6339-47, Filed Sep. 17, 2014.
Interference No. 105,981, Exhibit No. 1204, Koonin, 1991, "The phylogeny of RNA-dependent RNA polymerases of positivestrand RNA viruses,"J. Gen. Virol. 72: 2197-2206, Filed Sep. 17, 2014.
Interference No. 105,981, Exhibit No. 1059, Guo et al., 2001, "Effect of Alpha Interferon on the Hepatitis C Virus Replicon," J Virol. 75: 8516-23, Filed Mar. 10, 2014.
Interference No. 105,981, Exhibit No. 1237, Devos et al., U.S. Patent Application Publication No. WO 2003/0083307 A1, published May 1, 2003, Filed Sep. 17, 2014.
Interference No. 105,981, Exhibit No. 1220, Olsen et al., 2004, "A 7-Deaza-Adenosine Analog Is a Potent and Selective Inhibitor of Hepatitis C Virus Replication with Excellent Pharmacokinetic Properties," Antimicrob. Agents Chemother. 48: 3944-53, Filed Sep. 17, 2014.
Interference No. 105,981, Exhibit No. 1047, Beard et al., 1999, "An Infectious Molecular Clone of a Japanese Genotype 1b Hepatitis C Virus," Hepatology 30: 316-24, Filed Mar. 10, 2014.
Interference No. 105,981, Exhibit No. 1157, Meier et al., 1999, J. Med. Chem. 42(9): 1615-1624, Filed Mar. 10, 2014.
Interference No. 105,981, Exhibit No. 1152, Hayakawa et al., 1990, Chem. Pharm. Bull. 38(5): 1136-1139, Filed Mar. 10, 2014.
Interference No. 105,981, Exhibit No. 1110, Stuyver et al., 2006, "Inhibition of hepatitis C replicon RNA synthesis by β-D-2'-deoxy-2'-fluoro-2'-C-methylcytidine: a specific inhibitor of hepatitis C virus replication," Antiviral Chem. and Chemother. 17: 79-87, Filed Mar. 10, 2014.
Interference No. 105,981, Exhibit No. 1098, Oh et al., 1999, "A Recombinant Hepatitis C Virus RNA-Dependent RNA Polymerase Capable of Copying the Full-Length Viral RNA," J. Virol. 73: 7694-702, Filed Mar. 10, 2014.
Interference No. 105,981, Exhibit No. 1063, Frese et al., Mar. 2002 (accepted for publication Dec. 7, 2001), "Interferon-γ Inhibits Replication of Subgenomic and Genomic Hepatitis C Virus RNAs," Hepatology 35: 694-703, Filed Mar. 10, 2014.

(56) References Cited

OTHER PUBLICATIONS

Interference No. 105,981, Exhibit No. 1049, Hong et al., 1999, "Generation of Transmissible Hepatitis C Virions from a Molecular Clone in Chimpanzees," Virology 256: 36-44, Filed Mar. 10, 2014.
Interference No. 105,981, Exhibit No. 1008, Supplemental Amendment, dated Oct. 30, 2007, from the File History of Storer et al., U.S. Appl. No. 10/608,907, filed Jun. 27, 2003, Filed Sep. 17, 2014.
Interference No. 105,981, Exhibit No. 1217, Yanagida et al., 2004, "Inhibition of bovine viral diarrhea virus (BVDV) by mizoribine: synergistic effect of combination with interferon-α," Antiviral Res. 64: 195-201, Filed Sep. 17, 2014.
Interference No. 105,981, Exhibit No. 1069, Lanford and Bigger, Feb. 2002 (accepted for publication in Nov. 2001), "Advances in Model Systems for Hepatitis C Virus Research," Virology 293: 1-9, Filed Mar. 10, 2014.
Interference No. 105,981, Exhibit No. 1020, Tomei et al., 2000, "Biochemical characterization of a hepatitis C virus RNA dependent RNA polymerase mutant lacking the C-terminal hydrophobic sequence," J. Gen. Virol. 81: 759-67, Filed Mar. 10, 2014.
Interference No. 105,981, Exhibit No. 1013, Tomei, et al., 1993, "NS3 Is a Serine Protease Required for Processing of Hepatitis C Virus Polyprotein," J. Virol. 67: 4017-26, Filed Mar. 10, 2014.
Interference No. 105,981, Exhibit No. 1154, Pankiewicz et al., 1992, J. Org. Chem. 57(2): 553-559, Filed Mar. 10, 2014.
Interference No. 105,981, Exhibit No. 1149, Ikeda et al., 1998, Nucleic acids Res. 26(9): 2237-2244, Filed Mar. 10, 2014.
OM Patent Application No. 2005-112 Office Action.
OM Patent Application No. 2005-112 Office Action (English Translation).
EP Patent Application No. 04775900.6 Noting of Loss of Rights Pursuant to Rule 112(1) EPC dated Oct. 17, 2018.
AE Application No. 655/2005 First Examination Notice dated Oct. 17, 2018.
AE Application No. 655/2005 Search Report from Korean Intellectual Property Office accompanying First Examination Notice dated Oct. 17, 2018.
AE Application No. 655/2005 Examination Report from Korean Intellectual Property Office accompanying First Examination Notice dated Oct. 17, 2018.
English Translation of Abstract for CN1245808A (Espacenet).
English Translation of Description for CN1245808A (Clarivate Analytics).
OM Application No. 2005/00112 Appeal dated Jan. 15, 2019.
English Translation of OM Application No. 2005/00112 Appeal dated Jan. 15, 2019.
Counterarguments Against Appeal Decision for BR Patent Application No. PI 0419345-8 by Blanver Farmoquimica e Farmaceutica SA dated Feb. 1, 2019.
English Translation of Counterarguments Against Appeal Decision for BR Patent Application No. PI 0419345-8 by Blanver Farmoquimica e Farmaceutica SA dated Feb. 1, 2019.
Third Party Observations for BR Patent Application No. 12 2018 015050 5 by Blanver Farmoquimica e Farmaceutica SA dated Feb. 11, 2019.
English Translation of Third Party Observations for BR Patent Application No. 12 2018 015050 5 by Blanver Farmoquimica e Farmaceutica SA dated Feb. 11, 2019.

\* cited by examiner

MODIFIED FLUORINATED NUCLEOSIDE ANALOGUES

CROSS-REFERENCE TO RELATED PATENT APPLICATION

This application is a divisional application of Ser. No. 10/828,753, filed Apr. 21, 2004, which claims priority under 35 U.S.C. § 119 (e) to 60/474,368, filed May 30, 2003, the disclosure of which is hereby incorporated by reference in its entirety.

FIELD OF THE INVENTION

The present invention includes (2'R)-2'-deoxy-2'-fluoro-2'-C-methyl nucleosides having the natural β-D configuration and methods for the treatment of Flaviviridae infections, especially hepatitis C virus (HCV).

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest can harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring. Current treatments for HCV infection, which are restricted to immunotherapy with recombinant interferon-α alone or in combination with the nucleoside analog ribavirin, are of limited clinical benefit as resistance develops rapidly. Moreover, there is no established vaccine for HCV. Consequently, there is an urgent need for improved therapeutic agents that effectively combat chronic HCV infection.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. Therefore, NS5B polymerase is considered to be an essential component in the HCV replication complex (K. Ishi, et al., "Expression of Hepatitis C Virus NS5B Protein: Characterization of Its RNA Polymerase Activity and RNA Binding," *Heptology*, 29: 1227-1235 (1999); V. Lohmann, et al., "Biochemical and Kinetic Analysis of NS5B RNA-Dependent RNA Polymerase of the Hepatitis C Virus," *Virology*, 249: 108-118 (1998)). Inhibition of HCV NS5B polymerase prevents formation of the double-stranded HCV RNA and therefore constitutes an attractive approach to the development of HCV-specific antiviral therapies.

HCV belongs to a much larger family of viruses that share many common features.

Flaviviridae Viruses

The Flaviviridae family of viruses comprises at least three distinct genera: *pestiviruses*, which cause disease in cattle and pigs; *flaviruses*, which are the primary cause of diseases such as dengue fever and yellow fever; and *hepaciviruses*, whose sole member is HCV. The flavivirus genus includes more than 68 members separated into groups on the basis of serological relatedness (Calisher et al., *J. Gen. Virol*, 1993, 70, 37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the Dengue Hemorrhagic Fever viruses (DHF), yellow fever virus, shock syndrome and Japanese encephalitis virus (Halstead, S. B., *Rev. Infect. Dis.*, 1984, 6, 251-264; Halstead, S. B., *Science*, 239:476-481, 1988; Monath, T. P., *New Eng. J. Med*, 1988, 319, 64 1-643).

The *pestivirus* genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). *Pestivirus* infections of domesticated livestock (cattle, pigs and sheep) cause significant economic losses worldwide. BVDV causes mucosal disease in cattle and is of significant economic importance to the livestock industry (Meyers, G. and Thiel, H. J., Advances in Virus Research, 1996, 47, 53-118; Moennig V., et al, Adv. Vir. Res. 1992, 41, 53-98). Human *pestiviruses* have not been as extensively characterized as the animal pestiviruses. However, serological surveys indicate considerable *pestivirus* exposure in humans.

*Pestiviruses* and hepaciviruses are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are at least 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al. (1988) *Nature* 333:22; Bazan and Fletterick (1989) *Virology* 171: 637-639; Gorbalenya et al. (1989) *Nucleic Acid Res.* 17.3889-3897). Similarly, the NS5B proteins of pestiviruses and hepaciviruses have the motifs characteristic of RNA-directed RNA polymerases (Koonin, E. V. and Dolja, V. V. (1993) *Crir. Rev. Biochem. Molec. Biol.* 28:375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett (1991) *Virology* 184:341-350; Bartenschlager et al. (1993) *J. Virol.* 67:3835-3844; Eckart et al. (1993) *Biochem. Biophys. Res. Comm.* 192:399-406; Grakoui et al. (1993) *J. Virol.* 67:2832-2843; Grakoui et al. (1993) *Proc. Natl. Acad. Sci. USA* 90:10583-10587; Hijikata et al. (1993) *J. Virol.* 67:4665-4675; Tome et al. (1993) *J. Virol.* 67:4017-4026). The NS4A protein, in both cases, acts as a cofactor with the NS3 serine protease (Bartenschlager et al. (1994) *J. Virol.* 68:5045-5055; Failla et al. (1994) *J. Virol.* 68: 3753-3760; Xu et al. (1997) *J. Virol.* 71:53 12-5322). The NS3 protein of both viruses also functions as a helicase (Kim et al. (1995) *Biochem. Biophys. Res. Comm.* 215: 160-166; Jin and Peterson (1995) *Arch. Biochem. Biophys.*, 323:47-53; Warrener and Collett (1995) *J. Virol.* 69:1720-1726). Finally, the NS5B proteins of pestiviruses and hepaciviruses have the predicted RNA-directed RNA polymerases activity (Behrens et al. (1996) *EMBO.* 15:12-22; Lechmann et al. (1997) *J. Virol.* 71:8416-8428; Yuan et al. (1997) *Biochem. Biophys. Res. Comm.* 232:231-235; Hagedorn, PCT WO 97/12033; Zhong et al. (1998) *J. Virol.* 72.9365-9369).

Treatment of HCV Infection with Interferon

Interferons (IFNs) have been commercially available for the treatment of chronic hepatitis for nearly a decade. IFNs are glycoproteins produced by immune cells in response to viral infection. IFNs inhibit replication of a number of viruses, including HCV, and when used as the sole treatment for hepatitis C infection, IFN can in certain cases suppress serum HCV-RNA to undetectable levels. Additionally, IFN can normalize serum amino transferase levels. Unfortunately, the effect of IFN is temporary and a sustained response occurs in only 8%-9% of patients chronically infected with HCV (Gary L. Davis. Gastroenterology 18:S104-S114, 2000). Most patients, however, have difficulty tolerating interferon treatment, which causes severe flu-like symptoms, weight loss, and lack of energy and stamina.

A number of patents disclose Flaviviridae, including HCV, and treatments using interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Imakawa discloses the use of human interferon tau proteins for treating HCV. Other interferon-based treatments for HCV are disclosed in U.S. Pat. No. 5,676,942 to Testa et al., U.S. Pat. No. 5,372,808 to Blatt et al., and U.S. Pat. No. 5,849,696. A number of patents also disclose pegylated forms of interferon, such as U.S. Pat. Nos. 5,747,646, 5,792,834 and 5,834,594 to Hoffmann-La Roche; PCT Publication No. WO 99/32139 and WO 99/32140 to Enzon; WO 95/13090 and U.S. Pat. Nos. 5,738,846 and 5,711,944 to Schering; and U.S. Pat. No. 5,908,621 to Glue et al.

Interferon alpha-2a and interferon alpha-2b are currently approved as monotherapy for the treatment of HCV. ROFERON®-A (Roche) is the recombinant form of interferon alpha-2a. PEGASYS® (Roche) is the pegylated (i.e. polyethylene glycol modified) form of interferon alpha-2a. INTRON® A (Schering Corporation) is the recombinant form of Interferon alpha-2b, and PEG-INTRON® (Schering Corporation) is the pegylated form of interferon alpha-2b.

Other forms of interferon alpha, as well as interferon beta, gamma, tau and omega are currently in clinical development for the treatment of HCV. For example, INFERGEN (interferon alphacon-1) by InterMune, OMNIFERON (natural interferon) by Viragen, ALBUFERON by Human Genome Sciences, REBIF (interferon beta-1a) by Ares-Serono, Omega Interferon by BioMedicine, Oral Interferon Alpha by Amarillo Biosciences, and interferon gamma, interferon tau, and interferon gamma-1b by InterMune are in development.

Ribavirin

Ribavirin (1-β-D-ribofuranosyl-1-1,2,4-triazole-3-carboxamide) is a synthetic, non-interferon-inducing, broad spectrum antiviral nucleoside analog sold under the trade name, Virazole (The Merck Index, 11th edition, Editor: Budavari, S., Merck & Co., Inc., Rahway, N.J., p 1304, 1989). U.S. Pat. No. 3,798,209 and RE29,835 disclose and claim ribavirin. Ribavirin is structurally similar to guanosine, and has in vitro activity against several DNA and RNA viruses including Flaviviridae (Gary L. Davis. *Gastroenterology* 118: 5104-51 14, 2000).

Ribavirin reduces serum amino transferase levels to normal in 40% of patients, but it does not lower serum levels of HCV-RNA (Gary L. Davis, 2000). Thus, ribavirin alone is not effective in reducing viral RNA levels. Additionally, ribavirin has significant toxicity and is known to induce anemia. Ribavirin is not approved for monotherapy against HCV. It has been approved in combination with interferon alpha-2a or interferon alpha-2b for the treatment of HCV.

Ribavirin is a known inosine monophosphate dehydrogenase inhibitor that does not have specific anti-HCV activity in the HCV replicon system (Stuyver et al. *Journal of Virology*, 2003, 77, 10689-10694).

Combination of Interferon and Ribavirin

The current standard of care for chronic hepatitis C is combination therapy with an alpha interferon and ribavirin. The combination of interferon and ribavirin for the treatment of HCV infection has been reported to be effective in the treatment of interferon naïve patients (Battaglia, A. M. et al., *Ann. Pharmacother.* 34:487-494, 2000), as well as for treatment of patients when histological disease is present (Berenguer, M. et al. *Antivir. Ther.* 3(Suppl. 3):125-136, 1998). Studies have shown that more patients with hepatitis C respond to pegylated interferon-alpha/ribavirin combination therapy than to combination therapy with unpegylated interferon alpha. However, as with monotherapy, significant side effects develop during combination therapy, including hemolysis, flu-like symptoms, anemia, and fatigue. (Gary L. Davis, 2000). Combination therapy with PEG-INTRON® (peginterferon alpha-2b) and REBETOL® (Ribavirin, USP)

capsules are available from Schering Corporation. REBE-TOL® (Schering Corporation) has also been approved in combination with INTRON® A (Interferon alpha-2b, recombinant, Schering Corporation). Roche's PEGASYS® (pegylated interferon alpha-2a) and COPEGUS® (ribavirin), as well as Three River Pharmaceutical's Ribosphere® are also approved for the treatment of HCV.

PCT Publication Nos. WO 99/59621, WO 00/37110, WO 01/81359, WO 02/32414 and WO 03/02446 1 by Schering Corporation disclose the use of pegylated interferon alpha and ribavirin combination therapy for the treatment of HCV. PCT Publication Nos. WO 99/15 194, WO 99/64016, and WO 00/24355 by Hoffmann-La Roche Inc. also disclose the use of pegylated interferon alpha and ribavirin combination therapy for the treatment of HCV.

Additional Methods to Treat Flaviviridae Infections

The development of new antiviral agents for Flaviviridae infections, especially hepatitis C, is currently underway. Specific inhibitors of HCV-derived enzymes such as protease, helicase, and polymerase inhibitors are being developed. Drugs that inhibit other steps in HCV replication are also in development, for example, drugs that block production of HCV antigens from the RNA (IRES inhibitors), drugs that prevent the normal processing of HCV proteins (inhibitors of glycosylation), drugs that block entry of HCV into cells (by blocking its receptor) and nonspecific cytoprotective agents that block cell injury caused by the virus infection. Further, molecular approaches are also being developed to treat hepatitis C, for example, ribozymes, which are enzymes that break down specific viral RNA molecules, antisense oligonucleotides, which are small complementary segments of DNA that bind to viral RNA and inhibit viral replication, and RNA interference techniques are under investigation (Bymock et al. *Antiviral Chemistry & Chemotherapy*, 11:2; 79-95 (2000); De Francesco et al. in *Antiviral Research*, 58: 1-16 (2003); and Kronke et al., *J. Virol.*, 78:3436-3446 (2004).

Bovine viral diarrhea virus (BVDV) is a *pestivirus* belonging to the family Flaviviridae and has been used as a surrogate for in vitro testing of potential antiviral agents. While activity against BVDV may suggest activity against other flaviviruses, often a compound can be inactive against BVDV and active against another flavivirus. Sommadossi and La Colla have revealed ("Methods and compositions for treating flaviviruses and pestiviruses", PCT WO 01/92282) that ribonucleosides containing a methyl group at the 2' "up" position have activity against BVDV. However, it is unclear whether these compounds can inhibit other flaviviruses, including HCV in cell culture or at the HCV NS5B level. Interestingly while this publication discloses a large number of compounds that are 2'-methyl-2'-X-ribonucleosides, where X is a halogen, fluorine is not considered. Furthermore, a synthetic pathway leading to nucleosides halogenated at the 2' "down" position is not shown by these inventors.

Dengue virus (DENY) is the causative agent of Dengue hemorrhagic fever (DHF). According to the World Health Organization (WHO), two fifths of the world's population are now at risk for infection with this virus. An estimated 500,000 cases of DHF require hospitalization each year with a mortality rate of 5% in children.

West Nile virus (WNV), a flavivirus previously known to exist only in intertropical regions, has emerged in recent years in temperate areas of Europe and North America, presenting a threat to public health. The most serious manifestation of WNV infection is fatal encephalitis in humans. Outbreaks in New York City and sporadic occurrences in the Southern United States have been reported since 1999.

There is currently no preventive treatment of HCV, Dengue virus (DENY) or West Nile virus infection. Currently approved therapies, which exist only against HCV, are limited. Examples of antiviral agents that have been identified as active against the hepatitis C virus include:

1) Protease Inhibitors:

Substrate-based NS3 protease inhibitors (Attwood et al., PCT WO 98/22496, 1998; Attwood et al., *Antiviral Chemistry and Chemotherapy* 1999, 10, 259-273; Attwood et al., Preparation and use of amino acid derivatives as anti-viral agents, German Patent Pub. DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734) are being investigated.

Non-substrate-based NS3 protease inhibitors such as 2,4, 6-trihydroxy-3-nitro-benzamide derivatives (Sudo K. et al., *Biochemical and Biophysical Research Communications*, 1997, 238, 643-647; Sudo K. et al. *Antiviral Chemistry and Chemotherapy*, 1998, 9, 186), including RD3-4082 and RD3-4078, the former substituted on the amide with a 14 carbon chain and the latter processing a para-phenoxyphenyl group are also being investigated.

SCH 68631, a phenanthrenequinone, is an HCV protease inhibitor (Chu M. et al., Tetrahedron Letters 3 7:7229-7232, 1996). In another example by the same authors, SCH 351633, isolated from the fungus *Penicillium griseofulvum*, was identified as a protease inhibitor (Chu M. et al., *Bioorganic and Medicinal Chemistry Letters* 9:1949-1952). Nanomolar potency against the HCV NS3 protease enzyme has been achieved by the design of selective inhibitors based on the macromolecule eglin c. Eglin c, isolated from leech, is a potent inhibitor of several serine proteases such as *S. griseus* proteases A and B, α-chymotrypsin, chymase and subtilisin (Qasim M. A. et al., *Biochemistry* 36:1598-1607, 1997).

Several U.S. patents disclose protease inhibitors for the treatment of HCV. For example, U.S. Pat. No. 6,004,933 to Spruce et al. discloses a class of cysteine protease inhibitors for inhibiting HCV endopeptidase 2. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor. The use of restriction enzymes to treat HCV is disclosed in U.S. Pat. No. 5,538,865 to Reyes et al. Peptides as NS3 serine protease inhibitors of HCV are disclosed in WO 02/008251 to Corvas International, Inc. and WO 02/08187 and WO 02/008256 to Schering Corporation. HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 to Schering Corporation. Imidazoleidinones as NS3 serine protease inhibitors of HCV are disclosed in WO 02/08198 to Schering Corporation and WO 02/48157 to Bristol Myers Squibb. WO 98/17679 to Vertex Pharmaceuticals and WO 02/48116 to Bristol Myers Squibb also disclose HCV protease inhibitors.

2) Thiazolidine derivatives which show relevant inhibition in a reverse-phase HPLC assay with an NS3/4A fusion protein and NS5A/5B substrate (Sudo K. et al., *Antiviral Research*, 1996, 32, 9-18), especially compound RD-1-

6250, possessing a fused cinnamoyl moiety substituted with a long alkyl chain, RD4 6205 and RD4 6193;
3) Thiazolidines and benzanilides identified in Kakiuchi N. et al. *J. EBS Letters* 421, 217-220; Takeshita N. et al. *Analytical Biochemistry*, 1997, 247, 242-246;
4) A phenanthrenequinone possessing activity against protease in a SDS-PAGE and autoradiography assay isolated from the fermentation culture broth of *Streptomyces* sp., Sch 68631 (Chu M. et al., *Tetrahedron Letters*, 1996, 37, 7229-7232), and Sch 351633, isolated from the fungus *Penicillium griseofulvum*, which demonstrates activity in a scintillation proximity assay (Chu M. et al., *Bioorganic and Medicinal Chemistry Letters* 9, 1949-1952);
5) Helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);
6) Nucleotide polymerase inhibitors and gliotoxin (Ferrari R. et al. *Journal of Virology*, 1999, 73, 1649-1654), and the natural product cerulenin (Lohmann V. et al, *Virology*, 1998, 249, 108-118);
7) Antisense phosphorothioate oligodeoxynucleotides (S-ODN) complementary to sequence stretches in the 5' non-coding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 1999, 181, 251-257);
8) Inhibitors of IRES-dependent translation (Ikeda N. et al., Agent for the prevention and treatment of hepatitis C, Japanese Patent Pub. JP-8268890; Kai Y. et al. Prevention and treatment of viral diseases, Japanese Patent Pub. JP-10101591);
9) Ribozymes, such as nuclease-resistant ribozymes (Maccjak, D. J. et al., *Hepatology* 1999, 30, abstract 995) and those disclosed in U.S. Pat. No. 6,043,077 to Barber et al., and U.S. Pat. Nos. 5,869,253 and 5,610,054 to Draper et al.;
10) Nucleoside analogs have also been developed for the treatment of Flaviviridae infections.

Idenix Pharmaceuticals discloses the use of certain branched nucleosides in the treatment of flaviviruses (including HCV) and pestiviruses in International Publication Nos. WO 01/90121 and WO 01/92282. Specifically, a method for the treatment of hepatitis C virus infection (and flaviviruses and pestiviruses) in humans and other host animals is disclosed in the Idenix publications that includes administering an effective amount of a biologically active 1', 2', 3' or 4'-branched β-D or β-L nucleosides or a pharmaceutically acceptable salt or derivative thereof, administered either alone or in combination with another antiviral agent, optionally in a pharmaceutically acceptable carrier.

WO 2004/002422 to Idenix published Jan. 8, 2004 discloses a family of 2'-methyl nucleosides for the treatment of flavivirus infections. WO 2004/002999 to Idenix, published Jan. 8, 2004 discloses a series of 2' or 3' prodrugs of 1', 2', 3', or 4' branch nucleosides for the treatment of flavivirus infections including HCV infections.

Other patent applications disclosing the use of certain nucleoside analogs to treat hepatitis C virus infection include: PCT/CAOO/01316 (WO 01/32153; filed Nov. 3, 2000) and PCT/CAOI/00197 (WO 01/60315; filed Feb. 19, 2001) filed by BioChem Pharma, Inc. (now Shire Biochem, Inc.); PCT/US02/01531 (WO 02/057425; filed Jan. 18, 2002) and PCT/U502/03086 (WO 02/057287; filed Jan. 18, 2002) filed by Merck & Co., Inc., PCT/EPOT/09633 (WO 02/18404; published Aug. 21, 2001) filed by Roche, and PCT Publication Nos. WO 01/79246 (filed Apr. 13, 2001), WO 02/32920 (filed Oct. 18, 2001) and WO 02/48 165 by Pharmasset, Ltd.

WO 2004/007512 to Merck & Co. discloses a number of nucleoside compounds disclosed as inhibitors of RNA-dependent RNA viral polymerase. The nucleosides disclosed in this publication are primarily 2'-methyl-2'-hydroxy substituted nucleosides. WO 02/057287 to Merck et al. published Jul. 25, 2002, discloses a large genus of pyrimidine derivative nucleosides of the 2'-methyl-2'-hydroxy substitutions. WO 2004/009020 to Merck et al. discloses a series of thionucleoside derivatives as inhibitors of RNA dependent RNA viral polymerase. WO 03/105770 to Merck et al. discloses a series of carbocyclic nucleoside derivatives that are useful for the treatment of HCV infections.

PCT Publication No. WO 99/43691 to Emory University, entitled "2'-Fluoronucleosides" discloses the use of certain 2'-fluoronucleosides to treat HCV. U.S. Pat. No. 6,348,587 to Emory University entitled "2'-fluoronucleosides" discloses a family of 2'-fluoronucleosides useful for the treatment of hepatitis B, HCV, HIV and abnormal cellular proliferation. The 2' substitutent is disclosed to be in either the "up" or "down" position.

Eldrup et al. (Oral Session V, Hepatitis C Virus, Flaviviridae; 16$^{th}$ International Conference on Antiviral Research (Apr. 27, 2003, Savannah, Ga.)) described the structure activity relationship of 2'-modified nucleosides for inhibition of HCV.

Bhat et al. (Oral Session V, Hepatitis C Virus, Flaviviridae; 16$^{th}$ International Conference on Antiviral Research (Apr. 27, 2003, Savannah, Ga.); p A75) describe the synthesis and pharmacokinetic properties of nucleoside analogues as possible inhibitors of HCV RNA replication. The authors report that 2'-modified nucleosides demonstrate potent inhibitory activity in cell-based replicon assays.

Olsen et al. (Oral Session V, Hepatitis C Virus, Flaviviridae; 16$^{th}$ International Conference on Antiviral Research (Apr. 27, 2003, Savannah, Ga.) p A76) also described the effects of the 2'-modified nucleosides on HCV RNA replication.

11) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2,3-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961), and piperidines (U.S. Pat. No. 5,830,905 to Diana et al.).

12) Other compounds currently in preclinical or clinical development for treatment of hepatitis C virus infection include: Interleukin-10 by Schering-Plough, IP-SOl by Interneuron, Merimebodib (VX-497) by Vertex, AMANTADINE® (Symmetrel) by Endo Labs Solvay, HEPTA-ZYME® by RPI, IDN-6556 by Idun Pharma., XTL-002 by XTL., HCV/MFS9 by Chiron, CIVACIR® (hepatitis C Immune Globulin) by NABI, LEVOVIRIN® by ICN/Ribapharm, VIRAMIDINE® by ICN/Ribapharm, ZADAXIN® (thymosin alpha-1) by SciClone, thymosin plus pegylated interferon by Sci Clone, CEPLENE® (histamine dihydrochloride) by Maxim, VX 950/LY 570310 by Vertex/Eli Lilly, ISIS 14803 by Isis Pharmaceutical/Elan, IDN-6556 by Idun Pharmaceuticals, Inc., JTK 003 by AKROS Pharma, BILN-2061 by Boehringer Ingelheim, CellCept (mycophenolate mofetil) by Roche, T67, a β-tubulininhibitor, by Tularik, a therapeutic vaccine directed to E2 by Innogenetics, FK788 by Fujisawa Healthcare, Inc., 1 dB 1016 (Siliphos, oral silybin-phosphatdylcholine phytosome), RNA replication inhibitors (VP50406) by ViroPharma/Wyeth, therapeutic vaccine by Intercell, therapeutic vaccine by Epimmune/Genencor, IRES inhibitor by Anadys, ANA 245 and ANA 246 by Anadys, immunotherapy (Therapore) by Avant, protease inhibitor by Corvas/SChering, helicase inhibitor by Vertex, fusion inhibitor by Trimeris, T cell therapy by CellExSys, polymerase inhibitor by Biocryst, targeted RNA chemistry by PTC Therapeutics, Dication by Immtech, Int., protease inhibitor by Agouron, protease inhibitor by Chiron/Medivir, antisense therapy by AVI BioPharma, antisense therapy by Hybridon, hemopurifier by Aethlon Medical, therapeutic vaccine by Merix, protease inhibitor by Bristol-Myers Squibb/Axys, Chron-VacC, a therapeutic vaccine, by Tripep, UT 231 B by United Therapeutics, protease, helicase and polymerase inhibitors by Genelabs Technologies, IRES inhibitors by Immusol, R803 by Rigel Pharmaceuticals, INFERGEN® (interferon alphacon-1) by InterMune, OMNIFERON® (natural interferon) by Viragen, ALBUFERON® by Human Genome Sciences, REBIF® (interferon beta-1a) by Ares-Serono, Omega Interferon by BioMedicine, Oral Interferon Alpha by Amarillo Biosciences, interferon gamma, interferon tau, and Interferon gamma-1b by InterMune. Rigel Pharmaceuticals is developing a non-nucleoside HCV polymerase inhibitor, R803, that shows promise as being synergistic with IFN and ribavirin.

13) A summary of several investigational drugs, including several discussed above, that are currently in various phases of development for the treatment of HCV, are summarized below:

Nucleoside prodrugs have been previously described for the treatment of other forms of hepatitis. WO 00/09531 and WO 01/96353 to Idenix Pharmaceuticals, discloses 2'-deoxy-β-L-nucleosides and their 3'-prodrugs for the treatment of HBV. U.S. Pat. No. 4,957,924 to Beauchamp discloses various therapeutic esters of acyclovir.

In light of the fact that HCV infection has reached epidemic levels worldwide, and has tragic effects on the infected patient, there remains a strong need to provide new effective pharmaceutical agents to treat hepatitis C that have low toxicity to the host.

Further, given the rising threat of other flaviviridae infections, there remains a strong need to provide new effective pharmaceutical agents that have low toxicity to the host.

SUMMARY OF THE INVENTION

There is currently no preventive treatment of Hepatitis C virus (HCV), Dengue virus (DENV) or West Nile virus (WNV) infection, and currently approved therapies, which exist only against HCV, are limited. Design and development of pharmaceutical compounds is essential, especially those that are synergistic with other approved and investigational Flaviviridae, and in particular HCV, therapeutics for the evolution of treatment standards, including more effective combination therapies.

The present invention provides a (2'R)-2'-deoxy-2'-fluoro-2'-C-methyl nucleoside (β-D or β-L), or its pharmaceutically acceptable salt or prodrug thereof, and the use of such compounds for the treatment of a host infected with a virus belonging to the Flaviviridae family, including hepatitis C, West Nile Virus and yellow fever virus. In addition, the nucleosides of the present invention show actively against rhinovirus. Rhinoviruses (RVs) are small (30 nm), nonenveloped viruses that contain a single-strand ribonucleic acid (RNA) genome within an icosahedral (20-sided) capsid. RVs belong to the Picornaviridae family, which includes the genera *Enterovirus* (polioviruses, coxsackieviruses groups A and B, echoviruses, numbered enteroviruses) and Hepatovirus (hepatitis A virus). Approximately 101 serotypes are identified currently. Rhinoviruses

| Drug | Mechanism/Target | Company | U.S. Status |
|---|---|---|---|
| BILN-2061 | NS3 Serine-protease inhibitor | Boehringer Ingelheim | Phase II |
| ISIS 14803 | Antisense/Prevent Translation of RNA | ISIS/Elan | Phase II |
| Viramidine | Prodrug of Ribavirin | Ribapharm | Phase II |
| NM 283 | Inhibitor of HCV RNA Polymerase | Idenix | Phase II/III |
| VX-497 | IMPDH Inhibitor | Vertex | Phase I/II |
| JKT-003 | Inhibitor of HCV RNA Polymerase | Japan Tobacco/Akros | Phase I/II |
| Levovirin | L-Ribavirin analog | Ribapharm/Roche | Phase I/II |
| Isatoribine; ANA245 | Nucleoside analog Interact with TLR7 receptor | Anadys | Phase I |
| Albuferon | Immune modulator | Human Genome Sciences | Phase I |
| Peg-Infergen | Immune modulator | Intermune | Phase I |
| VX-950 | Inhibitor of HCV NS3-4A protease | Vertex | Preclinical |
| SCH 6 | Inhibitor of HCV NS3-4A protease | Schering Plough | Preclinical |
| R803 | Inhibitor of HCV RNA polymerase | Rigel | Phase I |
| HCV-086 | — | ViroPharma/Wyeth | Phase I |
| R1479 | Inhibitor of HCV RNA polymerase | Roche | Phase I | are most frequently associated with the common cold, nasopharyngitis, croup, pneumonia, otitis media and asthma exacerbations.

The inventor has made the unexpected discovery that the 2' substitutions on the β-D or β-L nucleosides of the present invention impart greater specificity for hepatitis C virus as well as exhibiting lower toxicity following administration to a host. The invention also includes a method for treating a Flaviviridae infection, including hepatitis C virus, West Nile Virus and yellow fever virus and rhinovirus infection, that includes the administration of an anti-virally effective amount of a β-D or β-L nucleoside disclosed herein, or its pharmaceutically acceptable salt or prodrug, optionally in a pharmaceutically acceptable carrier or diluent, optionally in combination or alternation with another effective antiviral agent.

The nucleosides of the present invention, possess the unique properties of having greater specificity for the hepatitis C virus and lower toxicity in culture or when administered into an animal. One potential, but non-limiting reason for this is the presence of the 2'-fluoro substitution on the ribose ring. For example, U.S. Pat. No. 6,348,587 to Schinazi et al., discloses a family of 2'-fluoro nucleoside compounds that are useful in the treatment of hepatitis C virus infection. In contrast, are 2'-methyl substitutions such as found in 2'-C-methylcytidine as shown in WO 2004/02999 to Idenix wherein the 2'-methyl substitution on the nucleoside ring at the 2' position is not specific to hepatitis C.

Thus, in one aspect, the antivirally effective nucleoside is a (2'R)-2'-deoxy-2'-fluoro-2'-C-methyl nucleoside (β-D or β-L) or its pharmaceutically acceptable salt or prodrug thereof of the general formula:

wherein
(a) Base is a naturally occurring or modified purine or pyrimidine base;
(b) X is O, S, $CH_2$, Se, NH, N-alkyl, CHW (R,S, or racemic), $C(W)_2$, wherein W is F, Cl, Br, or I;
(c) $R^1$ and $R^7$ are independently H, phosphate, including 5'-monophosphate, diphosphate, triphosphate, or a stabilized phosphate prodrug, H-phosphonate, including stabilized H-phosphonates, acyl, including optionally substituted phenyl and lower acyl, alkyl, including lower alkyl, O-substituted carboxyalkylamino or its peptide derivatives, sulfonate ester, including alkyl or arylalkyl sulfonyl, including methanesulfonyl and benzyl, wherein the phenyl group is optionally substituted, a lipid, including a phospholipid, an L or D-amino acid, a carbohydrate, a peptide, a cholesterol, or other pharmaceutically acceptable leaving group which when administered in vivo is capable of providing a compound wherein $R^1$ is H or phosphate; $R^2$ is OH or phosphate; $R^1$ and $R^2$ or $R^7$ can also be linked with cyclic phosphate group; and
(d) $R^2$ and $R^{2'}$ are independently H, $C_{1-4}$ alkyl, $C_{1-4}$ alkenyl, $C_{1-4}$ alkynyl, vinyl, $N_3$, CN, Cl, Br, F, I, $NO_2$, $C(O)O(C_{1-4}$ alkyl), $C(O)O(C_{1-4}$ alkyl), $C(O)O(C_{1-4}$ alkynyl), $C(O)O(C_{1-4}$ alkenyl), $O(C_{1-4}$ acyl), $O(C_{1-4}$ alkyl), $O(C_{1-4}$ alkenyl), $S(C_{1-4}$ acyl), $S(C_{1-4}$ alkyl), $S(C_{1-4}$ alkynyl), $S(C_{1-4}$ alkenyl), $SO(C_{1-4}$ acyl), $SO(C_{1-4}$ alkyl), $SO(C_{1-4}$ alkynyl), $SO(C_{1-4}$ alkenyl), $SO_2(C_{1-4}$ acyl), $SO_2(C_{1-4}$ alkyl), $SO_2(C_{1-4}$ alkynyl), $SO_2(C_{1-4}$ alkenyl), $O_3S(C_{1-4}$ acyl), $O_3S(C_{1-4}$ alkyl), $O_3S(C_{1-4}$ alkenyl), $NH_2$, $NH(C_{1-4}$ alkyl), $NH(C_{1-4}$ alkenyl), $NH(C_{1-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{1-4}$ alkynyl), $C(O)O(C_{1-4}$ alkenyl), $O(C_{1-4}$ acyl), $O(C_{1-4}$ alkyl), $O(C_{1-4}$ alkenyl), $S(C_{1-4}$ acyl), $S(C_{1-4}$ alkyl), $S(C_{1-4}$ alkynyl), $S(C_{1-4}$ alkenyl), $SO(C_{1-4}$ acyl), $SO(C_{1-4}$ alkyl), $SO(C_{1-4}$ alkynyl), $SO(C_{1-4}$ alkenyl), $SO_2(C_{1-4}$ acyl), $SO_2(C_{1-4}$ alkyl), $SO_2(C_{1-4}$ alkynyl), $SO_2(C_{1-4}$ alkenyl), $O_3S(C_{1-4}$ acyl), $O_3S(C_{1-4}$ alkyl), $O_3S(C_{1-4}$ alkenyl), $NH_2$, $NH(C_{1-4}$ alkyl), $NH(C_{1-4}$ alkenyl), $NH(C_{1-4}$ alkynyl), $NH(C_{1-4}$ acyl), $N(C_{1-4}$ alkyl)$_2$, $N(C_{1-4}$ acyl)$_2$, $R^2$ and $R^{2'}$ can be together to form a vinyl optionally substituted by one or two of $N_3$, CN, Cl, Br, F, I, $NO_2$; $OR^7$ and (e) $R^6$ is an optionally substituted alkyl (including lower alkyl), cyano (CN), $CH_3$, $OCH_3$, $OCH_2CH_3$, hydroxy methyl ($CH_2OH$), fluoromethyl ($CH_2F$), azido ($N_3$), CHCN, $CH_2N_3$, $CH_2NH_2$, $CH_2NHCH_3$, $CH_2N(CH_3)_2$, alkyne (optionally substituted), or fluoro.

In various aspects of the invention, the Base can be selected from wherein
(a) Y is N or CH.
(b) $R^3$, $R^4$ and $R^5$ are independently H, halogen (including F, Cl, Br, I), OH, OR', SH, SR', $NH_2$, NHR', NR'$_2$, lower alkyl of $C_1$-$C_6$, halogenated (F, Cl, Br, I) lower alkyl of $C_1$-$C_6$ such as $CF_3$ and $CH_2CH_2F$, lower alkenyl of $C_2$-$C_6$ such as CH=$CH_2$, halogenated (F, Cl, Br, I) lower alkenyl of $C_2$-$C_6$ such as CH=CHCl, CH=CHBr and CH=CHI, lower alkynyl of $C_2$-$C_6$ such as C≡CH, halogenated (F, Cl, Br, I) lower alkynyl of $C_2$-$C_6$, lower alkoxy of $C_1$-$C_6$ such as $CH_2OH$ and $CH_2CH_2OH$, halogenated (F, Cl, Br, I) lower alkoxy of $C_1$-$C_6$, $CO_2H$, $CO_2R'$, $CONH_2$, CONHR', CONR'$_2$, CH=$CHCO_2H$, CH=$CHCO_2R'$;

wherein R' is an optionally substituted alkyl of $C_1$-$C_{12}$ (particularly when the alkyl is an amino acid residue), cycloalkyl, optionally substituted alkynyl of $C_2$-$C_6$, optionally substituted lower alkenyl of $C_2$-$C_6$, or optionally substituted acyl.

In still another aspect, the (2'R)-2'-deoxy-2'-fluoro-2'-C-methyl nucleoside or its pharmaceutically acceptable salt or prodrug thereof can be of the formula:

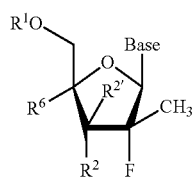

wherein (a) Base, Y, $R^1$, $R^2$, $R^{2'}$, $R^3$, $R^4$, $R^5$, $R^6$, $R^7$ and R' are as described above.

Various aspects of the present invention also include pharmaceutical compositions comprising any of the (2'R)-2'-deoxy-2'-fluoro-2'-C-methyl nucleoside (β-D or β-L) described herein or their pharmaceutically acceptable salts or prodrugs thereof and a pharmaceutically acceptable carrier.

The present invention also provides in various aspects, methods for the treatment or prophylaxis of hepatitis C virus infection, West Nile virus infection, a yellow fever viral infection or a rhinovirus infection comprising administering to a host an antivirally effective amount of a (2'R)-2'-deoxy-2'-fluoro-2'-C-methyl nucleoside disclosed herein. The invention also includes methods for treating or preventing Flaviviridae infection, including all members of the *Hepacivirus* genus (HCV), *Pestivirus* genus (BVDV, CSFV, BDV), or *Flavivirus* genus (Dengue virus, Japanese encephalitis virus group (including West Nile Virus), and Yellow Fever virus).

In various aspects, the (2'R)-2'-deoxy-2'-fluoro-2'-C-methyl β-D-nucleoside has an $EC_{50}$ (effective concentration to achieve 50% inhibition) when tested in an appropriate cell-based assay, of less than 15 micromolar, and more particularly, less than 10 or 5 micromolar. In other aspects, the nucleoside is enantiomerically enriched.

The present invention also provides methods for the treatment or prophylaxis of a hepatitis C virus infection, West Nile virus infection, a yellow fever viral infection or a rhinovirus infection in a host comprising administering an effective amount of a (2'R)-2'-deoxy-2'-fluoro-2'-C-methyl nucleosides (β-D or β-L) disclosed herein, or its pharmaceutically acceptable salt or prodrug thereof, in combination or alternation with one or more other effective antiviral agent(s), optionally in a pharmaceutically acceptable carrier or diluent thereof, as described herein. Nonlimiting examples of the types of antiviral agents or their prodrugs that can be used in combination with the compounds disclosed herein include, but are not limited to: interferon, including interferon alpha 2a, interferon alpha 2b, a pegylated interferon, interferon beta, interferon gamma, interferon tau and interferon omega; an interleukin, including interleukin 10 and interleukin 12; ribavirin; interferon in combination with ribavirin; a protease inhibitor including NS3 inhibitor; a helicase inhibitor; a polymerase inhibitor; gliotoxin; an IRES inhibitor; and antisense oligonucleotide; a thiazolidine derivative; a benzanilide, a ribozyme; another nucleoside, nucleoside prodrug or nucleoside derivative; a 1-amino-alkylcyclohexane; an antioxidant including vitamin E; squalene; amantadine; a bile acid; N-(phosphonoacetyl)-L-aspartic acid; a benzenedicarboxamide; polyadneylic acid; a benzimidazoles; thymosin; a beta tubulin inhibitor; a prophylactic vaccine; silybin-phosphatidlycholine phytosome; and mycophenolate.

The following non-limiting aspects illustrate some general methodology to obtain the nucleosides of the present invention. Specifically, the synthesis of the present nucleosides can be achieved by either of two general means:

1) alkylating the appropriately modified carbohydrate building block, subsequent fluorination, followed by coupling to form the nucleosides of the present invention (Scheme 1) or 2) glycosylation to form the nucleoside followed by alkylation and fluorination of the pre-formed nucleosides of the present invention (Scheme 2).

In addition, the L-enantiomers corresponding to the compounds of the invention can be prepared following the same general methods (Schemes 1 or 2), beginning with the corresponding L-carbohydrate building block or nucleoside L-enantiomer as the starting material.

Thus, the present invention includes at least the following general features:

(a) β-D and β-L nucleosides of the general formulas disclosed, or their pharmaceutically acceptable salts or prodrugs thereof, as described herein;

(b) processes for the preparation of the β-D and β-L nucleosides of the general formula disclosed, or their pharmaceutically acceptable salts or prodrugs thereof, as described herein;

(c) pharmaceutical compositions comprising a β-D or β-L nucleoside of the general formulas disclosed, or its pharmaceutically acceptable salt or prodrug thereof, in a pharmaceutically acceptable carrier or diluent thereof, as described herein, for the treatment or prophylaxis of a viral infection in a host;

(d) pharmaceutical compositions comprising a β-D or β-L nucleoside of the general formulas disclosed, or its pharmaceutically acceptable salt or prodrug thereof, in combination with one or more other effective antiviral agent(s), optionally in a pharmaceutically acceptable carrier or diluent thereof, as described herein, for the treatment or prophylaxis of a viral infection in a host;

(e) methods for the treatment or prophylaxis of a Flaviviridae infection, including hepatitis C virus, West Nile Virus and yellow fever virus and rhinovirus infection in a host comprising administering an effective amount of a β-D or β-L nucleoside of the general formulas disclosed, or its pharmaceutically acceptable salt or prodrug thereof, optionally in a pharmaceutically acceptable carrier or diluent thereof, as described herein;

(f) methods for the treatment or prophylaxis of a Flaviviridae infection, including hepatitis C virus, West Nile Virus and yellow fever virus and rhinovirus infection in a host comprising administering an effective amount of a β-D or β-L nucleoside of the general formulas disclosed, or its pharmaceutically acceptable salt or prodrug thereof, in combination or alternation with one or more other effective antiviral agent(s), optionally in a pharmaceutically acceptable carrier or diluent thereof, as described herein;

(g) use of a β-D or β-L nucleoside of the general formulas disclosed, or its pharmaceutically acceptable salt or prodrug thereof, optionally in a pharmaceutically acceptable carrier, as described herein, for the treatment or prophylaxis of a Flaviviridae infection, including hepatitis C virus, West Nile Virus and yellow fever virus and rhinovirus infection in a host;

(h) use of a β-D or β-L nucleoside of the general formulas disclosed, or its pharmaceutically acceptable salt or prodrug thereof, in combination or alternation with one or more other effective antiviral agent(s), optionally in a pharmaceutically acceptable carrier, as described herein, for the treatment or prophylaxis of a Flaviviridae infection, including hepatitis C virus, West Nile Virus and yellow fever virus and rhinovirus infection in a host;

(i) use of a β-D or β-L nucleoside of the general formulas disclosed, or its pharmaceutically acceptable salt or prodrug thereof, optionally in a pharmaceutically acceptable carrier, as described herein, in the manufacture of a medicament for the treatment or prophylaxis of a Flaviviridae infection, including hepatitis C virus, West Nile Virus and yellow fever virus and rhinovirus infection in a host;

(j) use of a β-D or β-L nucleoside of the general formulas disclosed, or its pharmaceutically acceptable salt or prodrug thereof, in combination or alternation with one or more other effective antiviral agent(s), optionally in a pharmaceutically acceptable carrier, as described herein, in the manufacture of a medicament for the treatment or prophylaxis of a Flaviviridae infection, including hepatitis C virus, West Nile Virus and yellow fever virus and rhinovirus infection in a host;

(k) use of a β-D or β-L nucleoside of the general formulas disclosed, or its pharmaceutically acceptable salt or prodrug thereof, optionally in a pharmaceutically acceptable carrier or diluent, as described herein, in a medical therapy, i.e. as antiviral for example for the treatment or prophylaxis of a Flaviviridae infection, including hepatitis C virus, West Nile Virus and yellow fever virus and rhinovirus infection;

(l) use of a β-D or β-L nucleoside of the general formulas disclosed, as described herein, or its pharmaceutically acceptable salt or prodrug thereof, i.e. as antiviral agent, in combination or alternation with one or more other effective therapeutic agent(s), i.e. another antiviral agent, optionally in a pharmaceutically acceptable carrier or diluent, as described herein, in a medical therapy, for example for the treatment or prophylaxis of a Flaviviridae infection, including hepatitis C virus, West Nile Virus and yellow fever virus and rhinovirus infection in a host.

DETAILED DESCRIPTION OF THE INVENTION

Figure 1A:
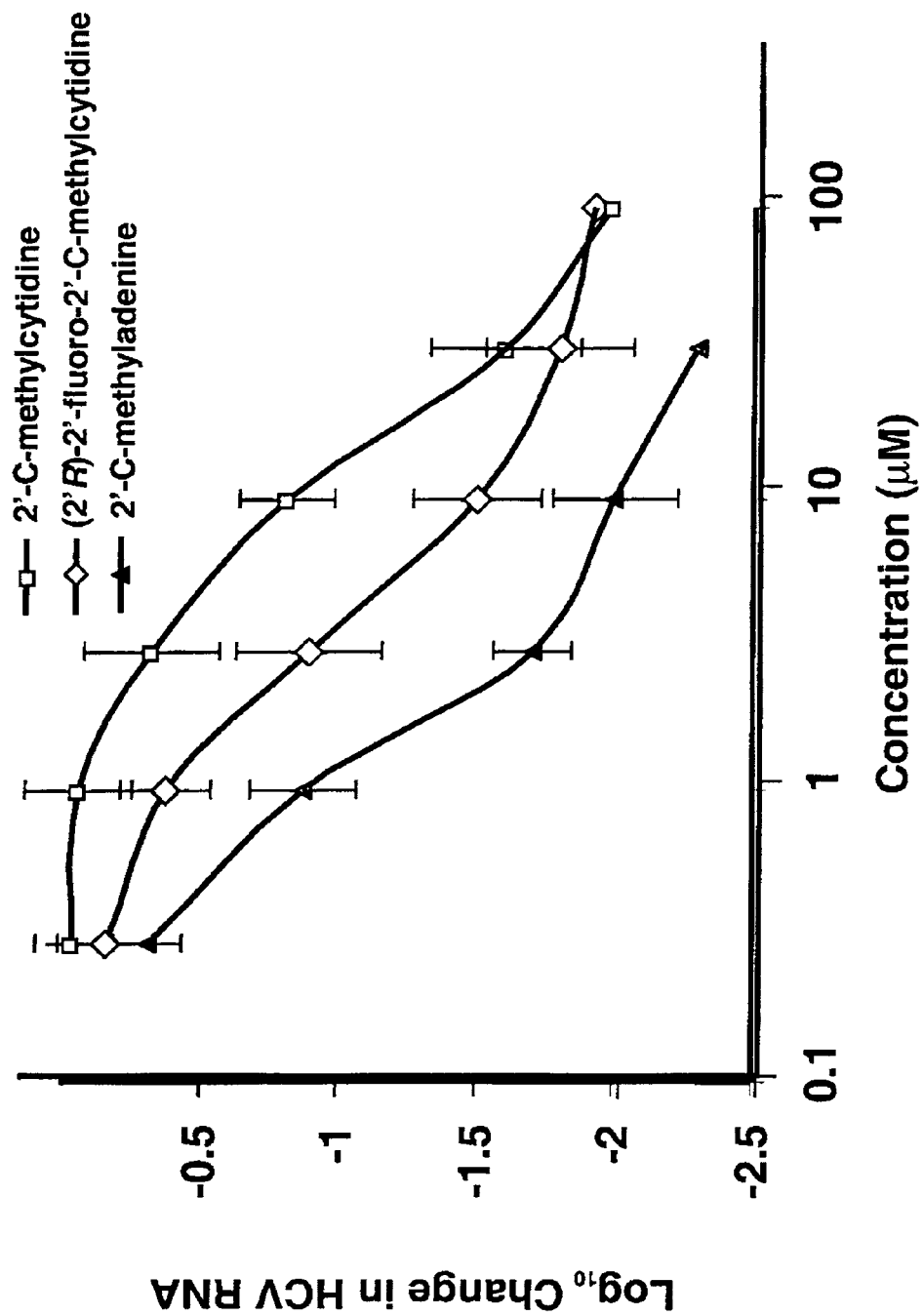
FIG. 1 is a graphical depiction of the dose-dependant reduction of the replicon HCV RNA based on the treatment with β-D-(2'R)-2'-deoxy-2'-fluoro-2'-C-methylcytidine. (A): The viral reduction was compared to the reduction of cellular RNA levels (ribosomal RNA) to obtain therapeutic index values. $EC_{90}$ which represents the effective concentration 90% at 96 hours following the dose dependant administration of (2'R)-2'-deoxy-2'-fluoro-2'-C-methylcytidine was determined to be 5 μM. (B): HCV RNA was significantly reduced in a dose-dependent manner for 7 days following treatment with 25 μM.

Various embodiments of the invention are now described in detail. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner in describing the compositions and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

The present invention provides (2'R)-2'-deoxy-2'-fluoro-2'-C-methyl nucleosides and their pharmaceutically acceptable salts and prodrugs for the treatment of hepatitis C virus infection, West Nile virus infection, a yellow fever viral infection or a rhinovirus infection in a host.

The disclosed compounds or their pharmaceutically acceptable derivatives or salts or pharmaceutically acceptable formulations containing these compounds are useful in the prevention and treatment of HCV infections. In addition, these compounds or formulations can be used prophylactically to prevent or retard the progression of clinical illness in individuals who are anti-HCV antigen positive or who have been exposed to HCV.

The compounds disclosed herein can be converted into a pharmaceutically acceptable ester by reaction with an appropriate esterifying agent, for example, an acid halide or anhydride. The compound or its pharmaceutically acceptable derivative can be converted into a pharmaceutically acceptable salt thereof in a conventional manner, for example, by treatment with an appropriate base. The ester or salt of the compound can be converted into the parent compound, for example, by hydrolysis.

Definitions

The term "independently" is used herein to indicate that the variable, which is independently applied, varies independently from application to application. Thus, in a compound such as $R^aXYR^a$, wherein $R^a$ is "independently carbon or nitrogen", both $R^a$ can be carbon, both $R^a$ can be nitrogen, or one $R^a$ can be carbon and the other $R^a$ nitrogen.

As used herein, the terms "enantiomerically pure" or "enantiomerically enriched" refers to a nucleoside composition that comprises at least approximately 95%, and preferably approximately 97%, 98%, 99% or 100% of a single enantiomer of that nucleoside.

As used herein, the term "substantially free of" or "substantially in the absence of" refers to a nucleoside composition that includes at least 85 or 90% by weight, preferably 95% to 98% by weight, and even more preferably 99% to 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term "alkyl," as used herein, unless otherwise specified, refers to a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Alkyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, or any other viable functional group that does not inhibit the pharmacological activity of this compound, either unprotected, or protected, as necessary, as known to those skilled in the art, for example, as taught in T. W. Greene and P. G. M. Wuts, "Protective Groups in Organic Synthesis," 3rd ed., John Wiley & Sons, 1999, hereby incorporated by reference.

The term "lower alkyl," as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The terms "alkylamino" or "arylamino" refer to an amino group that has one or two alkyl or aryl substituents, respectively.

The term "protected," as used herein and unless otherwise defined, refers to a group that is added to an oxygen, nitrogen, or phosphorus atom to prevent its further reaction or for other purposes. A wide variety of oxygen and nitrogen protecting groups are known to those skilled in the art of organic synthesis. Non-limiting examples include: C(O)-alkyl, C(O)Ph, C(O)aryl, $CH_3$, $CH_2$-alkyl, $CH_2$-alkenyl, $CH_2$Ph, $CH_2$-aryl, $CH_2$O-alkyl, $CH_2$O-aryl, $SO_2$-alkyl, $SO_2$-aryl, tert-butyldimethylsilyl, tert-butyldiphenylsilyl, and 1,3-(1,1,3,3-tetraisopropyldisiloxanylidene).

The term "aryl," as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen (F, Cl, Br, I), $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group.

The term "lower acyl" refers to an acyl group in which the non-carbonyl moiety is lower alkyl.

The term "purine" or "pyrimidine" base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-allylaminopurine, $N^6$-thioallyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrimidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-iodopyrimidine, $C^6$-Iodo-pyrimidine, $C^5$—Br-vinyl pyrimidine, $C^6$—Br-vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "acyl" or "O-linked ester" refers to a group of the formula C(O)R', wherein R' is an straight, branched, or cyclic alkyl (including lower alkyl), amino acid, aryl including phenyl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl groups in the esters optimally comprise a phenyl group. In particular, acyl groups include acetyl, trifluoroacetyl, methylacetyl, cyclopropylacetyl, cyclopropyl carboxy, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoroheptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl. When the term acyl is used, it is meant to be a specific and independent disclosure of acetyl, trifluoroacetyl, methylacetyl, cyclopropylacetyl, propionyl, butyryl, hexanoyl, heptanoyl, octanoyl, neo-heptanoyl, phenylacetyl, diphenylacetyl, α-trifluoromethylphenylacetyl, bromoacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, 2-thiopheneacetyl, tert-butylacetyl, trichloroacetyl, monochloro-acetyl, dichloroacetyl, methoxybenzoyl, 2-bromo-propionyl, decanoyl, n-pentadecanoyl, stearyl, 3-cyclopentyl-propionyl, 1-benzene-carboxyl, pivaloyl acetyl, 1-adamantane-carboxyl, cyclohexane-carboxyl, 2,6-pyridinedicarboxyl, cyclopropane-carboxyl, cyclobutane-carboxyl, 4-methylbenzoyl, crotonyl, 1-methyl-1H-indazole-3-carbonyl, 2-propenyl, isovaleryl, 4-phenylbenzoyl.

The term "amino acid" includes naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of α, β γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The term "host," as used herein, refers to a unicellular or multicellular organism in which the virus can replicate, including cell lines and animals, and preferably a human. Alternatively, the host can be carrying a part of the viral genome, whose replication or functions can be altered by the compounds of the present invention. The term host specifically refers to infected cells, cells transfected with all or part of the viral genome, and animals, in particular, primates and humans. In most animal applications of the present invention, the host is a human patient. Veterinary applications, in certain indications, however, are clearly anticipated by the present invention.

The term "pharmaceutically acceptable salt or prodrug" is used throughout the specification to describe any pharmaceutically acceptable form (such as an ester, phosphate ester, salt of an ester or a related group) of a compound which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

I. Active Compound, and Physiologically Acceptable Derivatives and Salts Thereof A (2'R)-2'-deoxy-2'-fluoro-2'-C-methyl nucleoside or its pharmaceutically acceptable salt or prodrug thereof is provided of the structure:

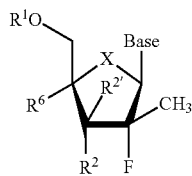

wherein Base refers to a naturally occurring or modified purine or pyrimidine base; X is O, S, $CH_2$, Se, NH, N-alkyl, CHW, $C(W)_2$, wherein W is F, Cl, Br, or I;

$R^1$ and $R^7$ are independently H, phosphate, including monophosphate, diphosphate, triphosphate, or a stabilized phosphate prodrug, H-phosphonate, including stabilized H-phosphonates, acyl, including optionally substituted phenyl and lower acyl, alkyl, including lower alkyl, O-substituted carboxyalkylamino or its peptide derivatives, sulfonate ester, including alkyl or arylalkyl sulfonyl, including methanesulfonyl and benzyl, wherein the phenyl group is optionally substituted, a lipid, including a phospholipid, an L or D-amino acid, a carbohydrate, a peptide, a cholesterol, or other pharmaceutically acceptable leaving group which when administered in vivo is capable of providing a compound wherein $R^1$ is H or phosphate; $R^2$ is OH or phosphate; $R^1$ and $R^2$ or $R^7$ can also be linked with cyclic phosphate group; and $R^2$ and $R^{2'}$ are independently H, $C_{1-4}$ alkyl, $C_{1-4}$ alkenyl, $C_{1-4}$ alkynyl, vinyl, $N_3$, CN, Cl, Br, F, I, $NO_2$, C(O)O ($C_{1-4}$ alkyl), C(O)O($C_{1-4}$ alkyl), C(O)O($C_{1-4}$ alkynyl), C(O)O($C_{1-4}$ alkenyl), O($C_{1-14}$ acyl), O($C_{1-14}$ alkyl), O($C_{1-4}$ alkenyl), S($C_{1-4}$ acyl), S($C_{1-4}$ alkyl), S($C_{1-4}$ alkynyl), S($C_{1-4}$ alkenyl), SO($C_{1-4}$ acyl), SO($C_{1-4}$ alkyl), SO($C_{1-4}$ alkynyl), SO($C_{1-4}$ alkenyl), $SO_2$($C_{1-4}$ acyl), $SO_2$($C_{1-4}$ alkyl), $SO_2$($C_{1-4}$ alkynyl), $SO_2$($C_{1-4}$ alkenyl), $O_3S$($C_{1-4}$ acyl), $O_3S$($C_{1-4}$ alkyl), $O_3S$($C_{1-4}$ alkenyl), $NH_2$, NH($C_{1-4}$ alkyl), NH($C_{1-4}$ alkenyl), NH($C_{1-4}$ alkynyl), NH($C_{1-4}$ acyl), N($C_{1-4}$ alkyl)$_2$, N($C_{1-18}$ acyl)$_2$, wherein alkyl, alkynyl, alkenyl and vinyl are optionally substituted by $N_3$, CN, one to three halogen (Cl, Br, F, I), $NO_2$, C(O)O($C_{1-4}$ alkyl), C(O)O($C_{1-4}$ alkyl), C(O)O($C_{1-4}$ alkynyl), C(O)O($C_{1-4}$ alkenyl), O($C_{1-14}$ acyl), O($C_{1-14}$ alkyl), O($C_{1-14}$ alkenyl), S($C_{1-4}$ acyl), S($C_{1-4}$ alkyl), S($C_{1-4}$ alkynyl), S($C_{1-4}$ alkenyl), SO($C_{1-4}$ acyl), SO($C_{1-4}$ alkyl), SO($C_{1-4}$ alkynyl), SO($C_{1-4}$ alkenyl), $SO_2$($C_{1-4}$ acyl), $SO_2$($C_{1-4}$ alkyl), $SO_2$($C_{1-4}$ alkynyl), $SO_2$($C_{1-4}$ alkenyl), $O_3S$($C_{1-4}$ acyl), $O_3S$($C_{1-4}$ alkyl), $O_3S$($C_{1-4}$ alkenyl), $NH_2$, NH($C_{1-4}$ alkyl), NH($C_{1-4}$ alkenyl), NH($C_{1-4}$ alkynyl), NH($C_{1-4}$ acyl), N($C_{1-4}$ alkyl)$_2$, N($C_{1-4}$ acyl)$_2$, $OR^7$, $R^2$ and $R^{2'}$ can be linked together to form a vinyl optionally substituted by one or two of $N_3$, CN, Cl, Br, F, I, $NO_2$; and $R^6$ is an optionally substituted alkyl (including lower alkyl), cyano (CN), $CH_3$, $OCH_3$, $OCH_2CH_3$, hydroxy methyl ($CH_2OH$), fluoromethyl ($CH_2F$), azido ($N_3$), CHCN, $CH_2N_3$, $CH_2NH_2$, $CH_2NHCH_3$, $CH_2N(CH_3)_2$, alkyne (optionally substituted), or fluoro.

In a second embodiment, a (2'R)-2'-deoxy-2'-fluoro-2'-C-methyl nucleoside or its pharmaceutically acceptable salt or prodrug thereof is provided of the structure:

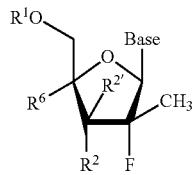

wherein Base, $R^1$, $R^2$, $R^{2'}$, $R^6$ and $R^7$ are as defined above.

A third embodiment provides a (2'R)-2'-deoxy-2'-fluoro-2'-C-methyl nucleoside or its pharmaceutically acceptable salt or prodrug thereof of the structure:

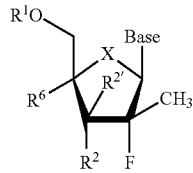

wherein X, $R^1$, $R^2$, $R^{2'}$, $R^6$ and $R^7$ are as defined above, and
Base is selected from

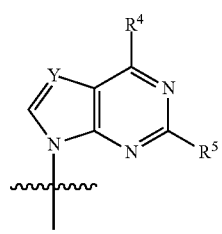
(a)

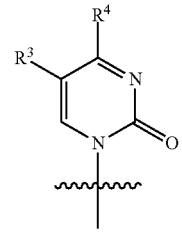
(b)

Y is N or CH;

$R^3$, $R^4$ and $R^5$ are independently H, halogen (including F, Cl, Br, I), OH, OR', SH, SR', $NH_2$, NHR', $NR'_2$, lower alkyl of $C_1$-$C_6$, halogenated (F, Cl, Br, I) lower alkyl of $C_1$-$C_6$ such as $CF_3$ and $CH_2CH_2F$, lower alkenyl of $C_2$-$C_6$ such as $CH=CH_2$, halogenated (F, Cl, Br, I) lower alkenyl of $C_2$-$C_6$ such as CH=CHCl, CH=CHBr and CH=CHI, lower alkynyl of $C_2$-$C_6$ such as C≡CH, halogenated (F, Cl, Br, I) lower alkynyl of $C_2$-$C_6$, lower alkoxy of $C_1$-$C_6$ such as $CH_2OH$ and $CH_2CH_2OH$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, CH=$CHCO_2R'$;

R' is an optionally substituted alkyl of $C_1$-$C_{12}$ (particularly when the alkyl is an amino acid residue), cycloalkyl, optionally substituted alkynyl of $C_2$-$C_6$, optionally substituted lower alkenyl of $C_2$-$C_6$, or optionally substituted acyl.

In a fourth embodiment, a (2'R)-2'-deoxy-2'-fluoro-2'-C-methyl nucleoside or its pharmaceutically acceptable salt or prodrug thereof is provided of the structure:

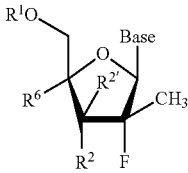

wherein Base is selected from

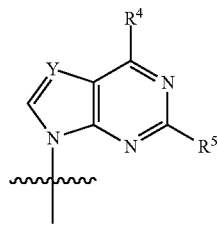
(a)

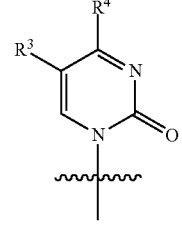
(b)

and, wherein $R^1$, $R^2$, $R^{2'}$, $R^3$, $R^4$, $R^5$, $R^6$ and Y are as defined above.

A fifth embodiment provides a (2'R)-2'-deoxy-2'-fluoro-2'-C-methyl nucleoside or its pharmaceutically acceptable salt or prodrug thereof of the structure:

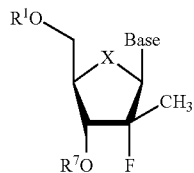

wherein Base refers to a naturally occurring or modified purine or pyrimidine base;

R⁷ is independently H, phosphate, including monophosphate, diphosphate, triphosphate, or a stabilized phosphate prodrug, H-phosphonate, including stabilized H-phosphonates, acyl, including optionally substituted phenyl and lower acyl, alkyl, including lower alkyl, O-substituted carboxyalkylamino or its peptide derivatives, sulfonate ester, including alkyl or arylalkyl sulfonyl, including methanesulfonyl and benzyl, wherein the phenyl group is optionally substituted, a lipid, including a phospholipid, an L or D-amino acid, a carbohydrate, a peptide, a cholesterol, or other pharmaceutically acceptable leaving group which when administered in vivo is capable of providing a compound wherein R¹ or R⁷ is independently H or phosphate; R¹ and R⁷ can also be linked with cyclic phosphate group; and wherein X and R¹ are as defined above.

In a sixth embodiment, a (2'R)-2'-deoxy-2'-fluoro-2'-C-methyl nucleoside or its pharmaceutically acceptable salt or prodrug thereof is provided of the structure:

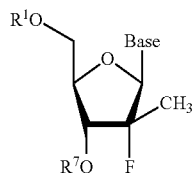

wherein Base refers to a naturally occurring or modified purine or pyrimidine base; and wherein R¹ and R⁷ are as defined above.

A seventh embodiment provides a (2'R)-2'-deoxy-2'-fluoro-2'-C-methyl nucleoside or its pharmaceutically acceptable salt or prodrug thereof of the structure:

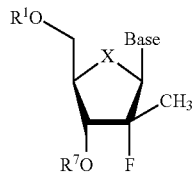

wherein Base is selected from

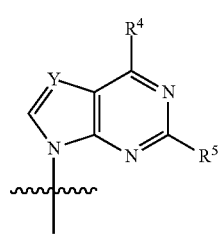

(a)

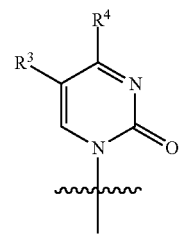

(b)

and wherein X, Y, R¹, R³, R⁴, R⁵, R⁷ and R' are as defined above.

In an eighth embodiment, a (2'R)-2'-deoxy-2'-fluoro-2'-C-methyl nucleoside or its pharmaceutically acceptable salt or prodrug thereof is provided of the structure:

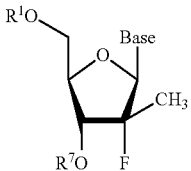

wherein Base is selected from (a)

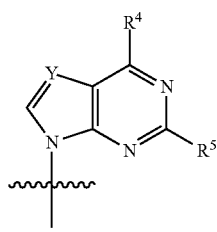

(b)

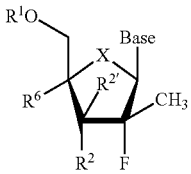

and, wherein Y, R¹, R³, R⁴, R⁵, R⁷ and R' are as defined above.

A ninth embodiment provides a (2'R)-2'-deoxy-2'-fluoro-2'-C-methyl nucleoside or its pharmaceutically acceptable salt or prodrug thereof of the structure:

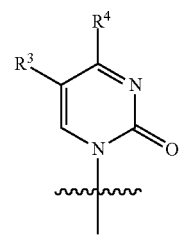

wherein Base is:

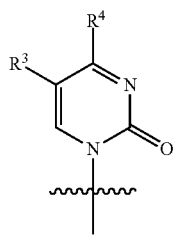

and wherein X is defined as above, $R^1$ is H, $R^2$ is OH, $R^{2'}$ is H, $R^3$ is H, $R^4$ is $NH_2$ or OH, and $R^6$ is H.

In a tenth embodiment, a (2'R)-2'-deoxy-2'-fluoro-2'-C-methyl nucleoside or its pharmaceutically acceptable salt or prodrug thereof is provided of the structure:

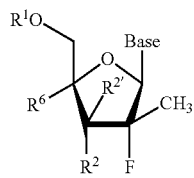

wherein Base is:

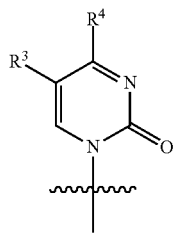

and wherein $R^1$ is H, $R^2$ is OH, $R^{2'}$ is H, $R^3$ is H, $R^4$ is $NH_2$ or OH, and $R^6$ is H.

An eleventh embodiment provides a (2'R)-2'-deoxy-2'-fluoro-2'-C-methyl nucleoside or its pharmaceutically acceptable salt or prodrug thereof of the structure:

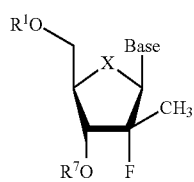

wherein Base is:

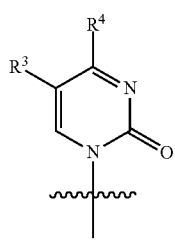

and wherein X is defined as above, $R^1$ is H, $R^3$ is H, $R^4$ is $NH_2$ or OH, $R^6$ is H, and $R^7$ is H.

In a twelfth embodiment, a (2'R)-2'-deoxy-2'-fluoro-2'-C-methyl nucleoside or its pharmaceutically acceptable salt or prodrug thereof is provided of the structure:

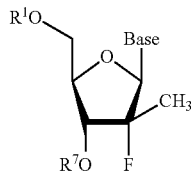

wherein Base is:

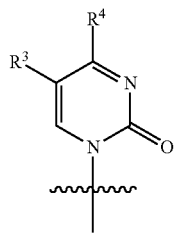

and wherein $R^1$ is H, $R^3$ is H, $R^4$ is $NH_2$ or OH, and $R^7$ is H.

A thirteenth embodiment provides a (2'R)-2'-deoxy-2'-fluoro-2'-C-methyl nucleoside or its pharmaceutically acceptable salt or prodrug thereof of the structure:

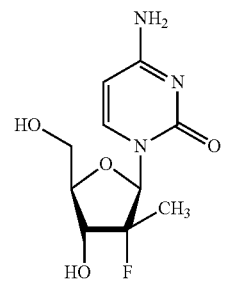

In a fourteenth embodiment, a (2'R)-2'-deoxy-2'-fluoro-2'-C-methyl nucleoside, its pharmaceutically acceptable salt or product thereof is provided by the structure:

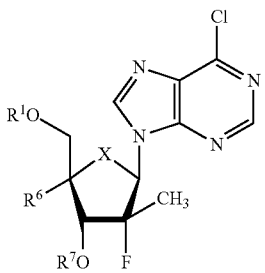

wherein X, $R^1$, $R^6$ and $R^7$ are as defined above.

In a fifteenth embodiment, a (2'R)-2'-deoxy-2'-fluoro-2'-C-methyl nucleoside, its pharmaceutically acceptable salt or product thereof is provided by the structure:

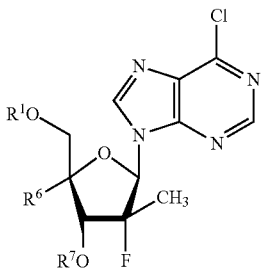

wherein $R^1$, $R^6$ and $R^7$ are as defined above.

In a sixteenth embodiment, a (2'R)-2'-deoxy-2'-fluoro-2'-C-methyl nucleoside nucleoside, its pharmaceutically acceptable salt or product thereof is provided by the structure:

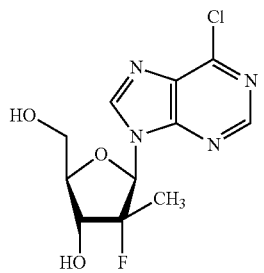

In a seventeenth embodiment, a (2'R)-2'-deoxy-2'-fluoro-2'-C-methyl nucleoside, its pharmaceutically acceptable salt or product thereof is provided by the structure:

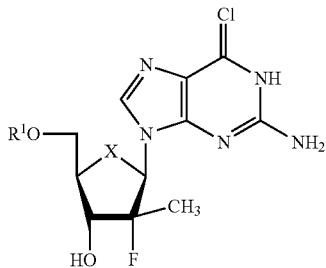

wherein X and $R^1$ are as defined above.

In an eighteenth embodiment, a (2'R)-2'-deoxy-2'-fluoro-2'-C-methyl nucleoside, its pharmaceutically acceptable salt or product thereof is provided by the structure:

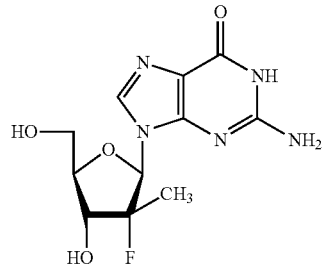

In a nineteenth embodiment, a (2'R)-2'-deoxy-2'-fluoro-2'-C-methyl nucleoside, its pharmaceutically acceptable salt or product thereof is provided by the structure:

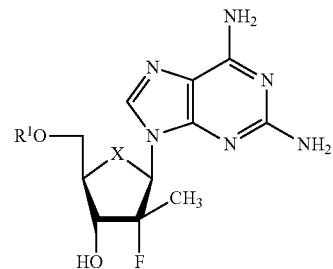

wherein X and $R^1$ are as defined above.

In a twentieth embodiment, a (2'R)-2'-deoxy-2'-fluoro-2'-C-methyl nucleoside, its pharmaceutically acceptable salt or product thereof is provided by the structure:

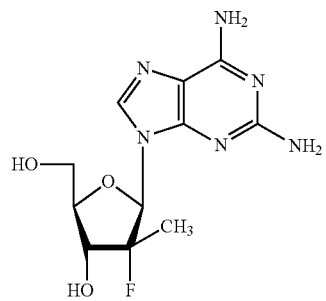

The present invention also contemplates 5'-triphosphate triphosphoric acid ester derivates of the 5'-hydroxyl group of a nucleoside compound of the present invention having the following general structural formula:

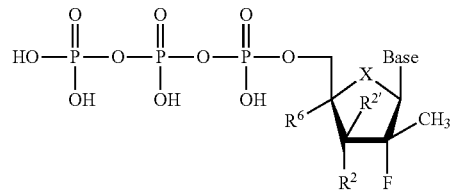

wherein Base, X, $R^2$, $R^{2'}$, and $R^6$ are as defined as above.

The compounds of the present invention are also intended to include pharmaceutically acceptable salts of the triphosphate ester as well as pharmaceutically acceptable salts of 5'-diphosphate and 5'-monophosphate ester derivatives of the following structural formulas, respectively.

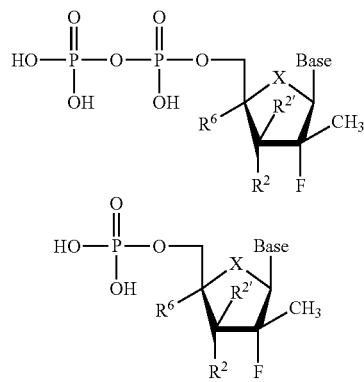

wherein Base, X, $R^2$, $R^2$ and $R^6$ are as defined above.

Further non-limiting examples of phosphoric acid derivatives are the nucleosides of the present invention are shown below:

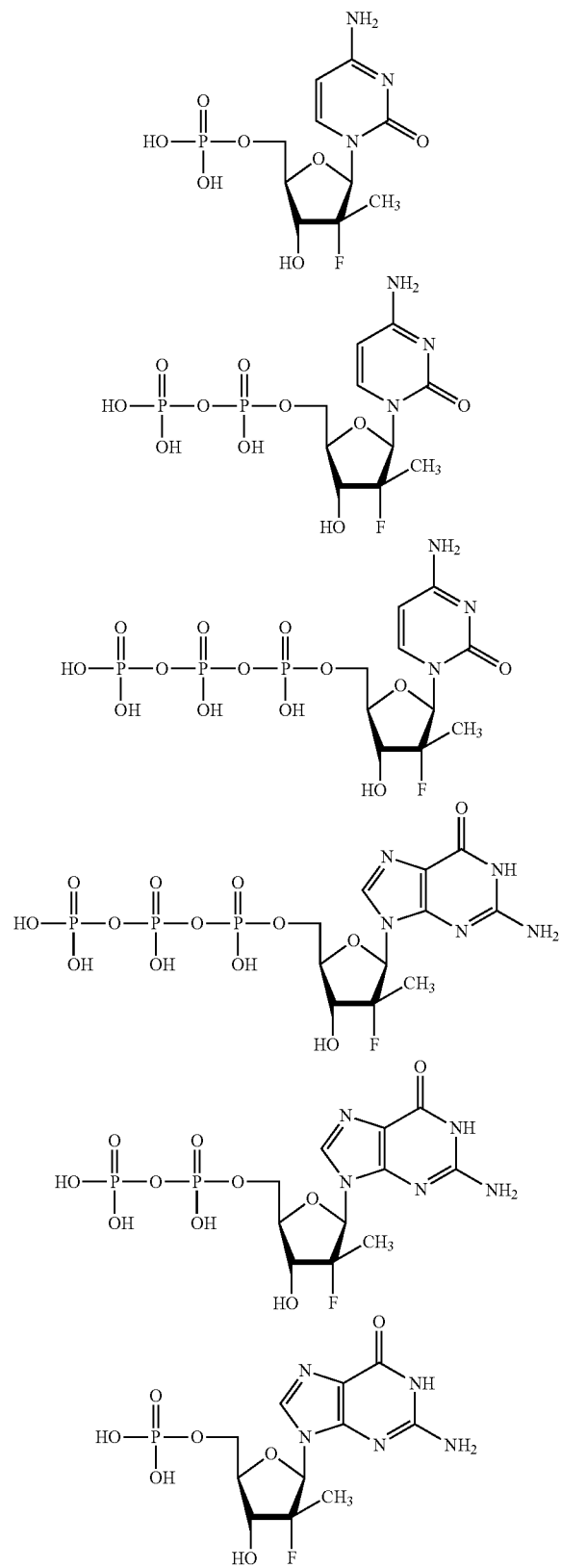

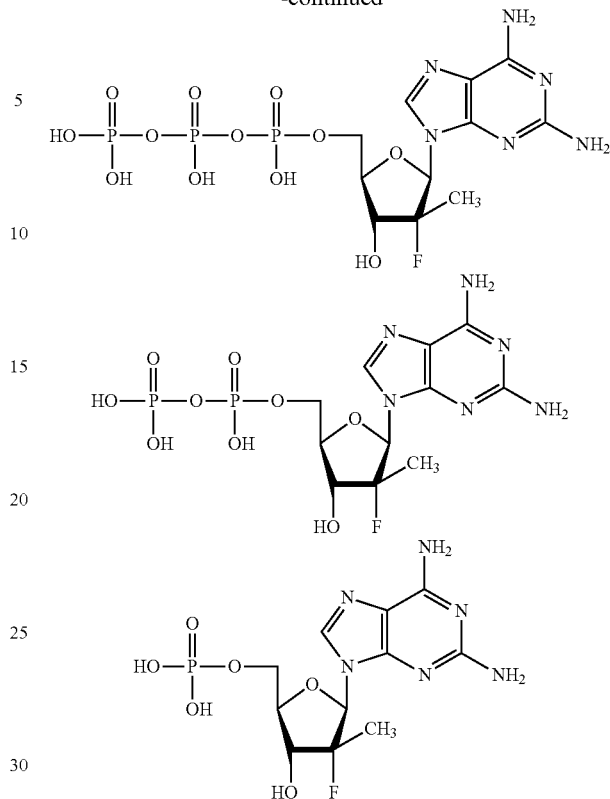

The present invention also contemplates that any phosphate nucleoside derivative can include a 5'-(S-acyl-2-thioethyl)phosphate or "SATE" mono or di-ester derivative of the 5'-monophosphates.

Alternative embodiments are also contemplated wherein the N-4 amino group on a phosphate nucleoside derivative can be replaced with H, F, Cl, Br or I.

Additional embodiments include 3' and/or 5' prodrugs as described in more detail herein.

In the various embodiments, the fluorinated derivatives are preferred. Fluorine is viewed as "isosteric" with hydrogen because of its size (Van der Waals radii for H is 1.20 Å and for F 1.35 Å). However, the atomic weight (18.998) and electronegativity of fluorine (4.0 [Pauling's scale], 4.000 [Sanderson's scale]) are more similar to oxygen (3.5 [Pauling]. 3.654 [Sanderson]) than hydrogen (2.1 [Pauling], 2.592 [Sanderson]) (March, J., "Advances in Organic Chemistry Reactions, Mechanisms, and Structure" Third edition, 1985, p. 14., Wiley Interscience, New York). Fluorine is known to be capable of forming a hydrogen bond, but unlike a hydroxyl group (which can act both as proton acceptor and proton donor) fluorine acts only as a proton acceptor. On the other hand, 2'-fluoro-ribonucleosides can be viewed as analogues of both ribonucleosides and deoxynucleosides. They may be better recognized by viral RNA polymerase at the triphosphate level than by the host RNA polymerase thus selectively inhibiting the viral enzyme.

II. Pharmaceutically Acceptable Salts and Prodrugs

In cases where compounds are sufficiently basic or acidic to form stable nontoxic acid or base salts, administration of the compound as a pharmaceutically acceptable salt may be appropriate. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1-17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses.* 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3'-deoxythymidine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. Nos. 5,149,794; 5,194,654; 5,223,263; 5,256,641; 5,411,947; 5,463,092; 5,543,389; 5,543,390; 5,543,391; and 5,554,728, all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

III. Pharmaceutical Compositions

Pharmaceutical compositions based upon a β-D or β-L compound disclosed herein or its pharmaceutically acceptable salt or prodrug can be prepared in a therapeutically effective amount for treating a Flaviviridae infection, including hepatitis C virus, West Nile Virus, yellow fever virus, and a rhinovirus infection, optionally in combination with a pharmaceutically acceptable additive, carrier or excipient. The therapeutically effective amount may vary with the infection or condition to be treated, its severity, the treatment regimen to be employed, the pharmacokinetics of the agent used, as well as the patient treated.

In one aspect according to the present invention, the compound according to the present invention is formulated preferably in a mixture with a pharmaceutically acceptable carrier. In general, it is preferable to administer the pharmaceutical composition in orally administrable form, but formulations may be administered via parenteral, intravenous, intramuscular, transdermal, buccal, subcutaneous, suppository or other route. Intravenous and intramuscular formulations are preferably administered in sterile saline. One of ordinary skill in the art may modify the formulation within the teachings of the specification to provide numerous formulations for a particular route of administration without rendering the compositions of the present invention unstable or compromising its therapeutic activity. In particular, a modification of a desired compound to render it more soluble in water or other vehicle, for example, may be easily accomplished by routine modification (salt formulation, esterification, etc.).

In certain pharmaceutical dosage forms, the prodrug form of the compound, especially including acylated (acetylated or other) and ether derivatives, phosphate esters and various salt forms of the present compounds, is preferred. One of ordinary skill in the art will recognize how to readily modify the present compound to a prodrug form to facilitate delivery of active compound to a targeted site within the host organism or patient. The artisan also will take advantage of favorable pharmacokinetic parameters of the prodrug form, where applicable, in delivering the desired compound to a targeted site within the host organism or patient to maximize the intended effect of the compound in the treatment of a Flaviviridae infection, including hepatitis C virus, West Nile Virus, yellow fever virus, and a rhinovirus infection.

The amount of compound included within therapeutically active formulations, according to the present invention, is an effective amount for treating the infection or condition, in preferred embodiments, a Flaviviridae infection, including hepatitis C virus, West Nile Virus, yellow fever virus, and a rhinovirus infection. In general, a therapeutically effective amount of the present compound in pharmaceutical dosage form usually ranges from about 50 mg to about 2,000 mg or more, depending upon the compound used, the condition or infection treated and the route of administration. For purposes of the present invention, a prophylactically or preventively effective amount of the compositions, according to the present invention, falls within the same concentration range as set forth above for therapeutically effective amount and is usually the same as a therapeutically effective amount.

Administration of the active compound may range from continuous (intravenous drip) to several oral administrations per day (for example, Q.I.D., B.I.D., etc.) and may include oral, topical, parenteral, intramuscular, intravenous, subcutaneous, transdermal (which may include a penetration enhancement agent), buccal and suppository administration, among other routes of administration. Enteric-coated oral tablets may also be used to enhance bioavailability and stability of the compounds from an oral route of administration. The most effective dosage form will depend upon the pharmacokinetics of the particular agent chosen, as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably mixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated for sustained release by standard techniques. The use of these dosage forms may significantly impact the bioavailability of the compounds in the patient.

For parenteral formulations, the carrier will usually comprise sterile water or aqueous sodium chloride solution, though other ingredients, including those that aid dispersion, also may be included. Where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present invention.

In particularly preferred embodiments according to the present invention, the compounds and compositions are used to treat, prevent or delay the onset of a Flaviviridae infection, including hepatitis C virus, West Nile Virus, yellow fever virus, and a rhinovirus infection. The present compounds are preferably administered orally, but may be administered parenterally, topically or in suppository form.

The compounds according to the present invention, because of their low toxicity to host cells in certain instances, may be advantageously employed prophylactically to prevent a Flaviviridae infection, including hepatitis C virus, West Nile Virus, yellow fever virus, and a rhinovirus infection or to prevent the occurrence of clinical symptoms associated with the viral infection or condition. Thus, the present invention also encompasses methods for the prophylactic treatment of viral infection, and in particular a Flaviviridae infection, including hepatitis C virus, West Nile Virus, yellow fever virus, and a rhinovirus infection. In this aspect, according to the present invention, the present compositions are used to prevent or delay the onset of a Flaviviridae infection, including hepatitis C virus, West Nile Virus, yellow fever virus, and a rhinovirus infection. This prophylactic method comprises administration to a patient in need of such treatment, or who is at risk for the development of the virus or condition, an amount of a compound according to the present invention effective for alleviating, preventing or delaying the onset of the viral infection or condition. In the prophylactic treatment according to the present invention, it is preferred that the antiviral compound utilized should be low in toxicity and preferably non-toxic to the patient. It is particularly preferred in this aspect of the present invention that the compound that is used should be maximally effective against the virus or condition and should exhibit a minimum of toxicity to the patient. In the case of a Flaviviridae infection, including hepatitis C virus, West Nile Virus, yellow fever virus, and a rhinovirus infection, compounds according to the present invention, which may be used to treat these disease states, may be administered within the same dosage range for therapeutic treatment (i.e., about 250 micrograms up to 1 gram or more from one to four times per day for an oral dosage form) as a prophylactic agent to prevent the proliferation of the viral infection, or alternatively, to prolong the onset of the viral infection, which manifests itself in clinical symptoms.

In addition, compounds according to the present invention can be administered in combination or alternation with one or more antiviral agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

IV. Stereoisomerism and Polymorphism

It is appreciated that nucleosides of the present invention have several chiral centers and may exist in and be isolated in optically active and racemic forms. Some compounds may exhibit polymorphism. It is to be understood that the present invention encompasses any racemic, optically active, diastereomeric, polymorphic, or stereoisomeric form, or mixtures thereof, of a compound of the invention, which possess the useful properties described herein. It being well known in the art how to prepare optically active forms (for example, by resolution of the racemic form by recrystallization techniques, by synthesis from optically-active starting materials, by chiral synthesis, or by chromatographic separation using a chiral stationary phase).

Carbons of the nucleoside are chiral, their nonhydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a nonnaturally occurring β-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the nonnaturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

Chiral chromatography, including simulated moving bed chromatography, is used in one embodiment. A wide variety of chiral stationary phases are commercially available.

Some of the compounds described herein contain olefinic double bonds and unless otherwise specified, are meant to include both E and Z geometric isomers.

In addition, some of the nucleosides described herein, may exist as tautomers, such as, keto-enol tautomers. The individual tautomers as well as mixtures thereof are intended to be encompassed within the compounds of the present invention as illustrated below.

A (2'R)-2'-deoxy-2'-fluoro-2'-C-methylcytidine:

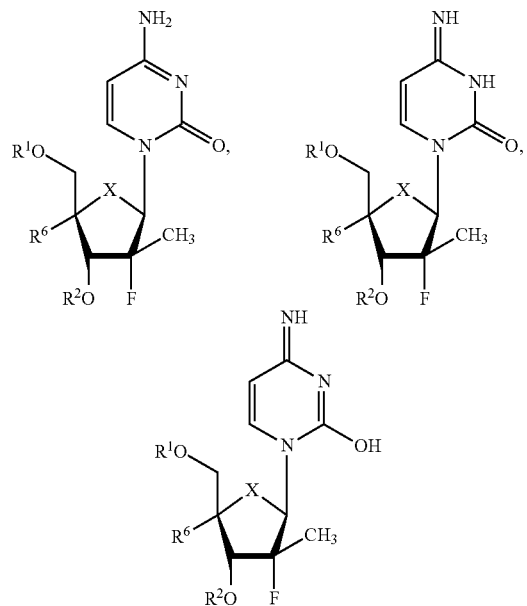

A (2'R)-2'-deoxy-2'-fluoro-2'-C-methylguanosine:

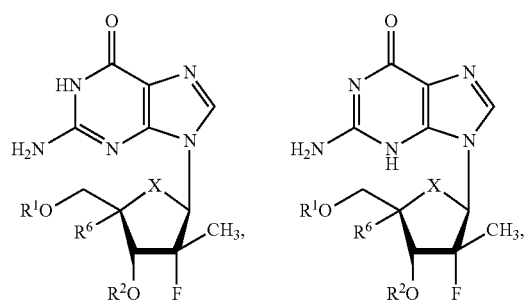

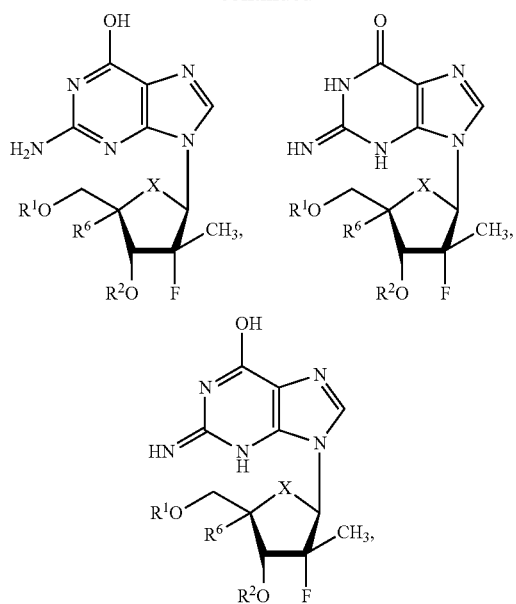

A (2'R)-2-amino-2'-deoxy-2'-fluoro-2'-C-methyladenosine:

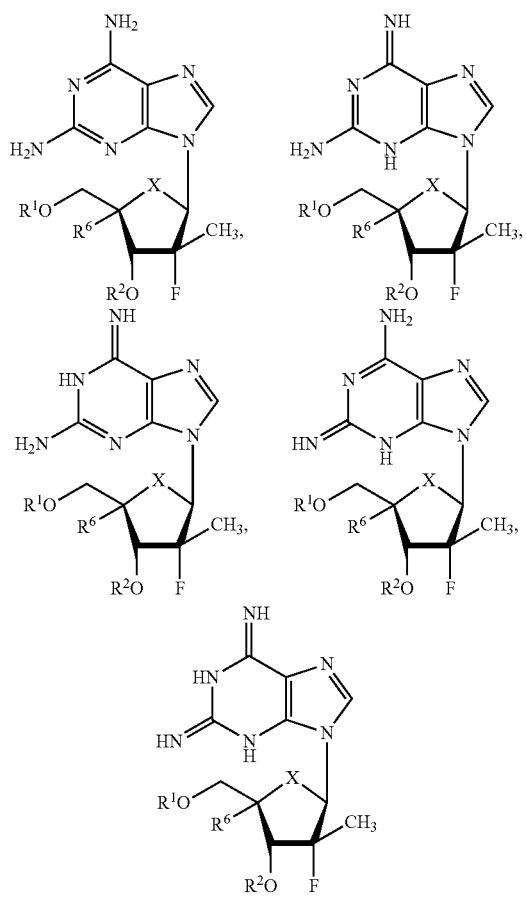

In each example above, the first drawn structure is the preferred form.

V. Prodrugs and Derivatives

The active compound can be administered as any salt or prodrug that upon administration to the recipient is capable of providing directly or indirectly the parent compound, or that exhibits activity itself. Nonlimiting examples are the pharmaceutically acceptable salts (alternatively referred to as "physiologically acceptable salts"), and a compound, which has been alkylated, acylated, or otherwise modified at the 5'-position, or on the purine or pyrimidine base (a type of "pharmaceutically acceptable prodrug"). Further, the modifications can affect the biological activity of the compound, in some cases increasing the activity over the parent compound. This can easily be assessed by preparing the salt or prodrug and testing its antiviral activity according to the methods described herein, or other methods known to those skilled in the art.

Pharmaceutically Acceptable Salts

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed by addition of acids, which form a physiological acceptable anion, for example, tosylate, methanesulfonate, acetate, citrate, malonate, tartrate, succinate, benzoate, ascorbate, α-ketoglutarate, α-glycerophosphate, formate, fumarate, propionate, glycolate, lactate, pyruvate, oxalate, maleate, and salicylate. Suitable inorganic salts may also be formed, including, sulfate, nitrate, bicarbonate, carbonate salts, hydrobromate and phosphoric acid. In a preferred embodiment, the salt is a mono- or di-hydrochloride salt.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made. In one embodiment, the salt is a hydrochloride, hydrobromide, or mesylate salt of the compound. In another embodiment, the pharmaceutically acceptable salt is a dihydrochloride, dihydrobromide, or dimesylate salt.

Nucleotide Prodrug Formulations

The nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono-, di- or triphosphate of the nucleoside reduces polarity and allows passage into cells. Examples of substituent groups that can replace one or more hydrogens on the phosphate moiety are ailcyl, aryl, steroids, carbohydrates, including sugars, 1,2-diacylglycerol and alcohols. Many are described in R. Jones and N. Bisehoferger, Antiviral Research, 1995, 27:1-17. Any of these can be used in combination with the disclosed nucleosides to achieve a desired effect.

In an alternative embodiment, the nucleoside is delivered as a phosphonate or a SATE derivative.

The active nucleoside can also be provided as a 2'-, 3'- and/or 5'-phosphoether lipid or a 2'-, 3'- and/or 5'-ether lipid. Non-limiting examples are described include the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." AIDS Res.

Hum. Retro Viruses. 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C A. Wallen, S. Piantadosi, and E. J. Modest. 1991. "Synthesis and evaluation of novel ether lipid nucleoside conjugates for anti-HIV activity." J. Med. Chem. 34:1408.1414; Hostetler, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymine diphosphate dimyristoylglycerol, a lipid prodrug of 3,-deoxythymine." Antlnzicrob. Agents Chemother. 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." J. Biol. Chem. 265:61127.

Nonlimiting examples of U.S. patents that disclose suitable lipophilic substituents that can be covalently incorporated into the nucleoside, preferably at the 2'-, 3'- and/or 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0350287, EP 93917054.4, and WO 91/19721.

Aryl esters, especially phenyl esters, are also provided. Nonlimiting examples are disclosed in DeLambert et al., J. Med. Chem. 37: 498 (1994). Phenyl esters containing a carboxylic ester ortho to the phosphate are also provided. Khaninei and Torrence, J. Med. Chem.; 39:41094115 (1996). In particular, benzyl esters, which generate the parent compound, in some cases using substituents at the ortho- or para-position to accelerate hydrolysis, are provided. Examples of this class of prodrugs are described by Mitchell et al., J. Chem. Soc. Perkin Trans. 12345 (1992); Brook, et al. WO 91/19721; and Glazier et al. WO 91/19721.

Cyclic and noncyclic phosphonate esters are also provided. Nonlimiting examples are disclosed in Hunston et al., J. Med. Chem. 27: 440-444 (1984) and Starrett et al. J. Med. Chem. 37: 1857-1864 (1994). Additionally, cyclic 3',5'-phosphate esters are provided. Nonlimiting examples are disclosed in Meier et al. *J. Med. Chem.* 22: 811-815 (1979). Cyclic 1',3'-propanyl phosphonate and phosphate esters, such as ones containing a fused aryl ring, i.e. the cyclosaligenyl ester, are also provided (Meier et al., *Bioorg. Med. Chem. Lett.* 7: 99-104 (1997)). Unsubstituted cyclic 1',3'-propanyl esters of the monophosphates are also provided (Farquhar et al., *J. Med. Chem.* 26: 1153 (1983); Farquhar et al., *J. Med. Chem.* 28: 1358 (1985)) were prepared. In addition, cyclic 1',3'-propanyl esters substituted with a pivaloyloxy methyloxy group at C-1' are provided (Freed et al., *Biochem. Pharmac.* 38: 3193 (1989); Biller et al., U.S. Pat. No. 5,157,027).

Cyclic phosphoramidates are known to cleave in vivo by an oxidative mechanism. Therefore, in one embodiment of the present invention, a variety of substituted 1',3' propanyl cyclic phosphoramidates are provided. Non-limiting examples are disclosed by Zon, *Progress in Med. Chem.* 19, 1205 (1982). Additionally, a number of 2'- and 3'-substituted proesters are provided. 2'-Substituents include methyl, dimethyl, bromo, trifluoromethyl, chloro, hydroxy, and methoxy; 3'-substituents including phenyl, methyl, trifluoromethyl, ethyl, propyl, i-propyl, and cyclohexyl. A variety of 1'-substituted analogs are also provided.

Cyclic esters of phosphorus-containing compounds are also provided. Non-limiting examples are described in the following:

di and tri esters of phosphoric acids as reported in Nifantyev et al., Phosphorus, Sulfur Silicon and Related Elements, 113: 1 (1996); Wijnberg et al., EP-180276 A1;

phosphorus (III) acid esters. Kryuchkov et al., Izy. Akad. Nauk SSSR, Ser. Khim. 6:1244 (1987). Some of the compounds were claimed to be useful for the asymmetric synthesis of L-Dopa precursors. Sylvain et al., DE3S12781 A1;

phosphoramidates. Shili et al., Bull. Inst. Chem. Acad. Sin, 41: 9 (1994); Edmundson et al., J. Chem. Res. Synop. 5:122 (1989); and phosphonates. Neidlein et al., Heterocycles 35: 1185 (1993).

$N^4$-acyl Prodrugs

The invention also provides $N^4$-acyl prodrugs. A non-limiting example of an $N^4$-acyl derivative of (2'R)-2'-F-2'-C-methylcytidine is shown below:

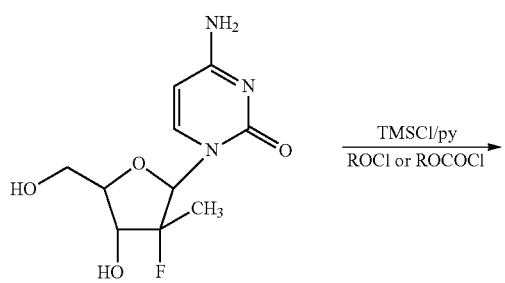

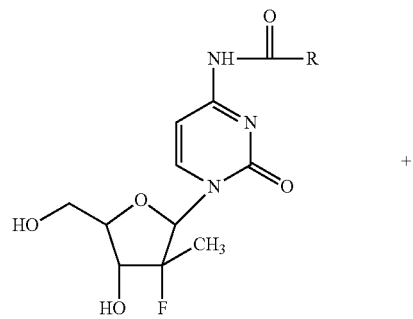

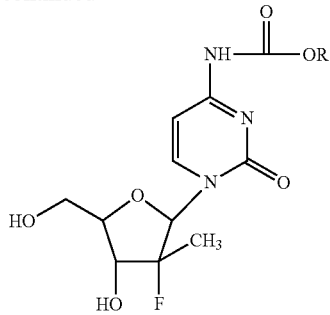

wherein R can be any acyl group as described herein.

The invention also contemplates other embodiments, wherein the prodrug of a (2'R)-2'-deoxy-2'-fluoro-2'-C-methyl nucleoside (β-D or β-L) includes biologically cleavable moieties at the 3' and/or 5' positions. Preferred moieties are natural of synthetic D or L amino acid esters, including D or L-valyl, though preferably L-amino acids esters, such as L-valyl, and alkyl esters including acetyl. Therefore, this invention specifically includes 3'-L or D-amino acid ester and 3',5'-L or D-diamino acid ester of (2'R)-2'-deoxy-2'-fluoro-2'-C-methyl nucleoside (β-D or β-L) nucleosides, preferably L-amino acid, with any desired purine or pyrimidine base, wherein the parent drug optionally has an $EC_{50}$ of less than 15 micromolar, and even more preferably less than 10 micromolar; 3'-(alkyl or aryl) ester or 3',5'-L-di(alkyl or aryl) ester of (2'R)-2'-deoxy-2'-fluoro-2'-C-methyl nucleoside (β-D or β-L) with any desired purine or pyrimidine base, wherein the parent drug optionally has an $EC_{50}$ of less than 10 or 15 micromolar; and prodrugs of 3',5'-diesters of (2'R)-2'-deoxy-2'-fluoro-2'-C-methyl nucleosides (β-D or β-L) wherein (i) the 3' ester is an amino acid ester and the 5'-ester is an alkyl or aryl ester; (ii) both esters are amino acid esters; (iii) both esters are independently alkyl or aryl esters; and (iv) the 3' ester is independently an alkyl or aryl ester and the 5'-ester is an amino acid ester, wherein the parent drug optionally has an $EC_{50}$ of less than 10 or 15 micromolar.

Non-limiting examples of prodrugs falling within the invention are:

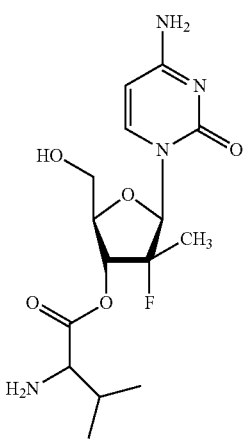

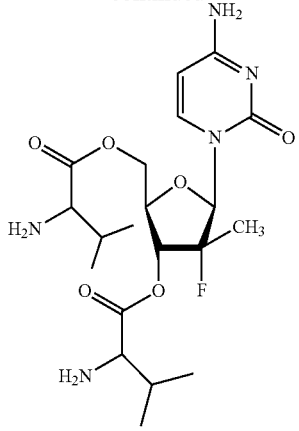

VI. Combination or Alternation Therapy

In another embodiment, for the treatment, inhibition, prevention and/or prophylaxis of any viral infection described herein, the active compound or its derivative or salt can be administered in combination or alternation with another antiviral agent. In general, in combination therapy, effective dosages of two or more agents are administered together, whereas during alternation therapy, an effective dosage of each agent is administered serially. The dosage will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

It has been recognized that drug-resistant variants of flaviviruses, pestiviruses or HCV can emerge after prolonged treatment with an antiviral agent. Drug resistance most typically occurs by mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

For example, one skilled in the art will recognize that any antiviral drug or therapy can be used in combination or alternation with any nucleoside of the present invention. Any of the viral treatments described in the Background of the Invention can be used in combination or alternation with the compounds described in this specification. Nonlimiting examples of the types of antiviral agents or their prodrugs that can be used in combination with the compounds disclosed herein include: interferon, including interferon alpha 2a, interferon alpha 2b, a pegylated interferon, interferon beta, interferon gamma, interferon tau and interferon omega; an interleukin, including interleukin 10 and interleukin 12; ribavirin; interferon alpha or pegylated interferon alpha in combination with ribavirin or levovirin; levovirin; a protease inhibitor including an NS3 inhibitor, a NS3-4A inhibitor; a helicase inhibitor; a polymerase inhibitor including HCV RNA polymerase and NS5B polymerase inhibitor; gliotoxin; an IRES inhibitor; and antisense oligonucleotide; a thiazolidine derivative; a benzanilide, a ribozyme; another nucleoside, nucleoside prodrug or nucleoside derivative; a 1-amino-alkylcyclohexane; an antioxidant including vitamin E; squalene; amantadine; a bile acid; N-(phosphonoacetyl)-L-aspartic acid; a benzenedicarboxamide; polyadenylic acid; a benzimidazoles; thymosin; a beta tubulin inhibitor; a prophylactic vaccine; an immune modulator, an IMPDH inhibitor; silybin-phosphatidylcholine phytosome; and mycophenolate.

Further nonlimiting examples of the types of drugs or their prodrugs described above include: acyclovir (ACV), ganciclovir (GCV or DHPG) and its prodrugs (e.g. valylganciclovir), E-5-(2-bromovinyl)-2'-deoxyuridine (BVDU), (E)-5-vinyl-1-β-D-arabonosyluracil (VaraU), (E)-5-(2-bromovinyl)-1-β-D-arabinosyluracil (BV-araU), 1-(2-deoxy-2-fluoro-β-D-arabinosyl)-5-iodocytosine (D-FIAC), 1-(2-deoxy-2-fluoro-β-L-arabinosyl)-5-methyluracil (L-FMAU, or clevudine), (S)-9-(3-hydroxy-2-phosphonylmethoxypropyl) adenine [(S)-HPMPA], (S)-9-(3-hydroxy-2-phosphonylmethoxypropyl)-2,6-diaminopurine [(S)-HPMPDAP], (S)-1-(3-hydroxy-2-phosphonyl-methoxypropyl)cytosine [(S)-HPMPC, or cidofivir], and (2S,4S)-1-[2-(hydroxymethyl)-1,3-dioxolan-4-yl]-5-iodouracil (L-5-IoddU), entecavir, lamivudine (3TC), LdT, LdC, tenofovir, and adefovir, the (−)-enantiomer of 2-hydroxymethyl-5-(5-fluorocytosin-1-yl)-1,3-oxathiolane ((−)-FTC); the (−)-enantiomer of 2-hydroxymethyl-5-(cytosin-1-yl)-1,3-oxathiolane (3TC); carbovir, acyclovir, famciclovir, penciclovir, AZT, DDI, DDC, L-(−)-FMAU, D4T, amdoxovir, Reverset, Racivir, abacavir, L-DDA phosphate prodrugs, and β-D-dioxolanyl-6-chloropurine (ACP), non-nucleoside RT inhibitors such as nevirapine, MKC-442, DMP-226 (sustiva), protease inhibitors such as indinavir, saquinavir, Kaletra, atazanavir; and anti-HIV compounds such as BILN-2061, ISIS 14803; viramidine, NM 283, VX-497, JKT-003, levovirin, isatoribine, albuferon, Peg-infergen, VX-950, R803, HCV-086, R1479 and DMP45.

Pharmaceutical Compositions

Hosts, including humans, infected with pestivirus, flavivirus, HCV infection, or any other condition described herein, or another organism replicating through a RNA-dependent RNA viral polymerase, or for treating any other disorder described herein, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for a Flaviviridae infection, including hepatitis C virus, West Nile Virus and yellow fever virus and rhinovirus infection will be in the range from about 50 to about 2000 mg one to four times per day. Lower doses may be useful, and thus ranges can include from 50-1,000 mg one to four times per day. The effective dosage range of the pharmaceutically acceptable salts and prodrugs can be calculated based on the weight of the parent nucleoside to be delivered. If the salt or prodrug exhibits activity in itself the effective dosage can be estimated as above using the weight of the salt or prodrug, or by other means known to those skilled in the art.

The compound is conveniently administered in unit any suitable dosage form, including but not limited to one containing 25 to 3000 mg, preferably 50 to 2000 mg of active ingredient per unit dosage form. An oral dosage of 50-1000 mg is usually convenient, including in one or multiple dosage forms of 50, 100, 200, 250, 300, 400, 500, 600, 700, 800, 900 or 1000 mgs. Also contemplated are doses of 0.1-50 mg, or 0.1-20 mg or 0.1-10.0 mg. Furthermore, lower doses may be utilized in the case of administration by a non-oral route, as, for example, by injection or inhalation.

Ideally the active ingredient should be administered to achieve peak plasma concentrations ($C_{max}$) of the active compound of from about 5.0 to 70 μM, preferably about 5.0 to 15 μM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

VII. Biological Methods

Antiviral Testing of Candidate Compounds with HCV Replicon System in Huh7 Cells.

Huh7 cells harboring the HCV replicon can be cultivated in DMEM media (high glucose, no pyruvate) containing 10% fetal bovine serum, 1× non-essential Amino Acids, Pen-Strep-Glu (100 units/liter, 100 microgram/liter, and 2.92 mg/liter, respectively) and 500 to 1000 microgram/milliliter G418. Antiviral screening assays can be done in the same media without G418 as follows: in order to keep cells in logarithmic growth phase, cells are seeded in a 96-well plate at low density, for example 1000 cells per well. The test compound is added immediately after seeding the cells and incubate for a period of 3 to 7 days at 37° C. in an incubator. Media is then removed, and the cells are prepared for total nucleic acid extraction (including replicon RNA and host RNA). Replicon RNA can then be amplified in a Q-RT-PCR protocol, and quantified accordingly. The observed differences in replicon HCV RNA levels compared to the untreated control is one way to express the antiviral potency of the test compound.

In another typical setting, a compound might reduce the viral RNA polymerase activity, but not the host RNA polymerase activity. Therefore, quantification of rRNA or beta-actin mRNA (or any other host RNA fragment) and comparison with RNA levels of the no-drug control is a relative measurement of the inhibitory effect of the test compound on cellular RNA polymerases.

Phosphorylation Assay of Nucleoside to Active Triphosphate

To determine the cellular metabolism of the compounds, Huh-7 cells are obtained from the American Type Culture Collection (Rockville, Md.), and are grown in 225 cm$^2$ tissue culture flasks in minimal essential medium supplemented with non-essential amino acids, 1% penicillin-streptomycin. The medium is renewed every three days, and the cells are sub cultured once a week. After detachment of the adherent monolayer with a 10 minute exposure to 30 mL of trypsin-EDTA and three consecutive washes with medium, confluent Huh-7 cells are seeded at a density of 2.5×10$^6$ cells per well in a 6-well plate and exposed to 10 μM of [$^3$H] labeled active compound (500 dpm/pmol) for the specified time periods. The cells are maintained at 37° C. under a 5% $CO_2$ atmosphere. At the selected time points, the cells are washed three times with ice-cold phosphate-buffered saline (PBS). Intracellular active compound and its respective metabolites are extracted by incubating the cell pellet overnight at −20° C. with 60% methanol followed by extraction with an additional 20 μL of cold methanol for one hour in an ice bath. The extracts are then combined, dried under gentle filtered air flow and stored at −20° C. until HPLC analysis.

Bioavailability Assay in Cynomolgus Monkeys

Within 1 week prior to the study initiation, the cynomolgus monkey is surgically implanted with a chronic venous catheter and subcutaneous venous access port (VAP) to facilitate blood collection and underwent a physical examination including hematology and serum chemistry evaluations and the body weight was recorded. Each monkey (six total) receives approximately 250 μCi of $^3$H-labeled compound combined with each dose of active compound at a dose level of 10 mg/kg at a dose concentration of 5 mg/mL, either via an intravenous bolus (3 monkeys, IV), or via oral gavage (3 monkeys, PO). Each dosing syringe is weighed before dosing to gravimetrically determine the quantity of formulation administered. Urine samples are collected via pan catch at the designated intervals (approximately 18-0 hours pre-dose, 0-4, 4-8 and 8-12 hours post-dosage) and processed. Blood samples are collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples are analyzed for the maximum concentration ($C_{max}$), time when the maximum concentration is achieved ($T_{max}$), area under the curve (AUC), half life of the dosage concentration ($T_{1/2}$), clearance (CL), steady state volume and distribution ($V_{ss}$) and bioavailability (F).

Bone Marrow Toxicity Assay

Human bone marrow cells are collected from normal healthy volunteers and the mononuclear population are separated by Ficoll-Hypaque gradient centrifugation as described previously by Sommadossi J-P, Carlisle R. "Toxicity of 3'-azido-3'-deoxythymidine and 9-(1,3~dihydroxy-2-propoxymethyl)guanine for normal human hematopoietic progenitor cells in vitro" Antimicrobial Agents and Chemotherapy 1987; 31:452-454; and Sommadossi J-P, Schinazi R F, Chu C K, Xie M-Y. "Comparison of cytotoxicity of the (−)- and (+)-enantiomer of 2',3'-dideoxy-3'-thiacytidine in normal human bone marrow progenitor cells" Biochemical Pharmacology 1992; 44:1921-1925. The culture assays for CFU-GM and BFU-E are performed using a bilayer soft agar or methylcellulose method. Drugs are diluted in tissue culture medium and filtered. After 14 to 18 days at 37° C. in a humidified atmosphere of 5% $CO_2$ in air, colonies of greater than 50 cells are counted using an inverted microscope. The results are presented as the percent inhibition of colony formation in the presence of drug compared to solvent control cultures.

Mitochondria Toxicity Assay

Fifty microliters of 2× drug dilutions were added per well in a 96 well plate. A "no drug" (media only) control was used to determine maximum amount of mitochondrial DNA produced and ribosomal DNA. 3TC @10 µM was used as a negative control, and ddC @10 µM was used as a toxic control. Ribosomal DNA levels were used to determine specific toxicity to mitochondria or generally cytotoxicity. HepG2 cells (5,000 cells/well at 50 µl) were added to the plate. The plate was incubated at 37° C. in a humidified 5% $CO_2$ atmosphere for 7 days. After incubation, the supernatant was removed and stored for lactic acid quantification, and total DNA was extracted from cells as described in the RNeasy 96 handbook (February 1999), pages 22-23. No DNA digestions were performed, therefore total RNA and DNA were extracted.

The extracted DNA was amplified and the change in mitochondrial DNA and ribosomal DNA for each sample was determined. The fold difference in mitochondrial DNA normalized for ribosomal DNA relative to control was calculated.

Lactic acid quantification was performed by the D-Lactic Acid/L-Lactic acid test kit (Boehringer Mannheim/R-Biopharm/Roche). The total amount of lactic acid produced for each sample was found as well as the fold change in lactic acid production (% of lactic acid/% of rDNA) as described in the manufacturers instructions.

Cytotoxicity Assay

50 µl of 2× drug dilutions were added per well in a 96 well plate. Final concentrations of drug ranged from 1 to 100 µM. A "no drug" (media only) control was used to determine the minimum absorbance values and a "cells+media only" control was used for maximum absorbance value. A solvent control was also used. Cells were then added (PBM: $5 \times 10^4$ cells/well; CEM: $2.5 \times 10^3$ cells/well; Vero, HepG2, Huh-7, and Clone A: $5 \times 10^3$ cells/well) and incubated at 37° C. in a humidified 5% $CO_2$ atmosphere for 3-5 days (PBM: 5 days; CEM: 3 days, all others: 4 days). After incubation, 20 µl of MTS dye was added from Cell Titer Aqueous One Solution Cell Proliferation Assay to each well and the plate was re-incubated for 2-4 hours. The absorbance (490 nm) was then read on an ELISA plate reader using the media only/no cell wells as blanks. Percent inhibition was found and used to calculate the $CC_{50}$.

In Vivo Toxicity in Mice

In vivo toxicity was also determined following injections into female Swiss mice of the various nucleosides disclosed in the present invention. Intraperitoneal injections were given on days 0, day 1, day 2, day 3, and day 5 of varying doses of the particular nucleoside. Separate animals were injected with vehicle as control groups. In these studies, each dosing group contained 5-10 mice. The average weight change in each of the mice was measured as a sign of toxicity of the compound.

(BVDV) Yield Reduction Assay

Madin-Darby Bovine Kidney (MDBK) cells were grown in Dulbecco's modified eagle medium supplemented with 10% horse serum and 100 µg/ml penicillin-streptomycin. Cells were seeded in a 96-well plate at $5 \times 10^3$ cells/well and incubated for 72h at 37° C. in a humidified 5% $CO_2$ atmosphere. Cells were infected with either cytopathic (NADL strain) or noncytopathic (SD-1 strain) BVDV at a virus dilution of 10-2 and incubated for 45 min. Cell monolayers were washed three times with medium. Fresh medium-containing test compounds in dose response concentrations or ribavirin, as a positive control, were added to cultures and medium containing no drug was added to the no-drug controls. After 72h incubation, supernatant was collected and viral RNA was extracted using the QIAmp Viral RNA Mini Kit (Qiagen, CA). Viral load was determined by Q-RT-PCR using primers specific for either NADL or SD-1 (1).

VIII. Synthetic Protocol

The following non-limiting embodiments illustrate some general methodologies to obtain the nucleosides of the present invention. Two representative general methods for the preparation of compounds of the present invention are outlined in Schemes 1 and 2 while more specific examples of these general methods are provided in Scheme 3 (Example 1), Scheme 4 (Example 2), Scheme 5 (Example 3), and Scheme 6 (Example 4). Scheme 1 represents a generalized process starting from a (2R) 2-deoxy-2-methyl-2-fluoro-carbohydrate and forms the nucleosides of the present invention by condensing with a nucleobase. Scheme 2 starts from a pre-formed, purine or pyrimidine nucleoside, optionally substituted at C-4' and constructs the C-2' (R) methyl, fluoro nucleosides of the present invention. While these schemes illustrate the syntheses of compounds of the present invention of general formulas (I) and (II) wherein there is a furanose ring in the β-D-ribo configuration, this is not intended to be a limitation on the scope of the process invention in any way, and they should not be so construed. Those skilled in the art of nucleoside and nucleotide synthesis will readily appreciate that known variations of the conditions and processes of the following preparative procedures and known manipulations of the nucleobase can be used to prepare these and other compounds of the present invention. Additionally, the L-enantiomers corresponding to the compounds of the invention can be prepared following the same methods, beginning with the corresponding L-carbohydrate building block or nucleoside L-enantiomer as the starting material.

1. Glycosylation of the Nucleobase with an Appropriately Modified Sugar

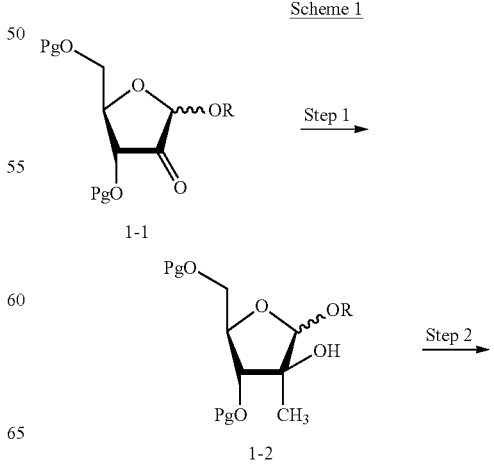

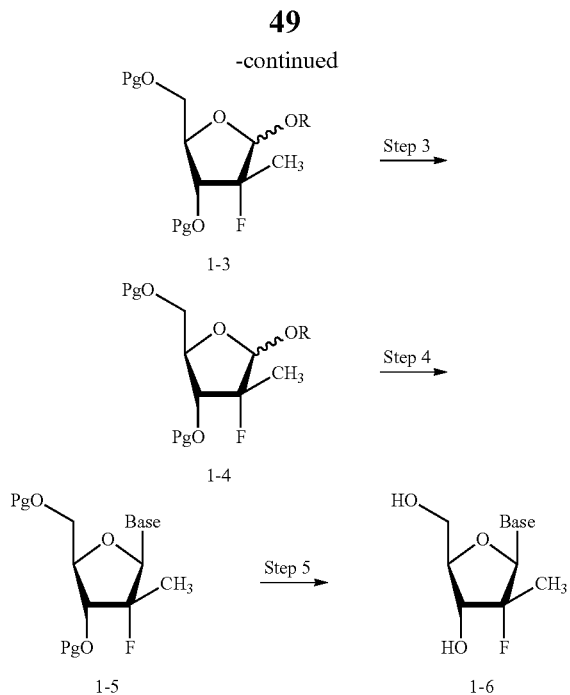

Pg = Protecting group
R = Lower alkyl, acyl, mesyl, benzoyl.
Base = as defined herein.

Step 1 in Scheme 1 introduces the 2-methyl group by using an appropriate alkylating agent such as methyllithium, trimethylaluminum, or methylmagnesium bromide in an anhydrous solvent such as tetrahydrofuran (THF), chloroform, or diethyl ether. Compounds I-1 through 1-4 can be purely α or β or they may exist as an anomeric mixture containing both α and β anomers in any ratio. However, the preferred anomeric configuration of structure 1-1 is β.

Step 2 introduces the fluorine atom at the 2-position of the alkyl furanoside. This can be achieved by treatment of the tertiary alcohol, 1-2, with a commercially available fluorinating reagent such as (diethylamino)sulfur trifluoride (DAST) or Deoxofluor in an anhydrous, aprotic solvent such as tetrahydrofuran, chloroform, dichloromethane, or toluene. Preferably the stereochemistry proceeds with inversion of configuration at C-2. That is, starting from a C-2 hydroxyl "up" (or arabinofuranoside) in structure 1-2, the C-2 fluorine is "down" in the intermediate ribofuranoside 1-3.

In step 3, the optional protecting groups (Pg) can be deprotected and reprotected to groups more suitable for the remaining manipulations (T. W. Greene and P. G. M. Wuts, "Protective Groups in Organic Synthesis," 3rd ed., John Wiley & Sons, 1999). For example, benzyl ethers (Bn) may be difficult to remove in the protected nucleoside, 1-5 and may be deprotected and replaced with a group more facile to remove from the nucleoside of structural type 1-5. Furthermore, the anomeric position (C-1) can also be optionally manipulated to a suitable group for the coupling reaction with the nucleobase (step 4). Several methods for anomeric manipulations are established to those skilled in the art of nucleoside synthesis. Some non-limiting examples by treatment of the alkyl furanoside (1-3, R=alkyl) with a mixture of acetic anhydride, acetic acid, and a catalytic amount of sulfuric acid (acetolysis) to provide structure 1-4 where R=Ac, with optional protecting groups. Also, the alkyl group in 1-3 may be converted to an acetate, benzoate, mesylate, tosylate, triflate, or tosylate, for example, by first hydrolyzing the 1-Oalkyl group to a 1-hydroxyl group by using a mineral acid consisting of but not limited to sulfuric acid, hydrochloric acid, and hydrobromic acid or an organic acid consisting of but not limited to trifluoroacetic acid, acetic acid, and formic acid (at ambient temperature or elevated temperature). The reducing sugar could then be converted to the desired carbohydrate by treatment with acetyl chloride, acetic anhydride, benzoyl chloride, benzoic anhydride, methanesulfonyl chloride, triflic anhydride, trifyl chloride, or tosyl chloride in the presence of a suitable base such as triethylamine, pyridine, or dimethylaminopyridine.

The nucleosidic linkage is constructed by treatment of intermediate 1-3 or 1-4 with the appropriate persilylated nucleobase in the presence of a lewis acid such as tin tetrachloride, titanium tetrachloride, trimethylsilyltriflate, or a mercury (II) reagent (HgO/HgBr$_2$) usually at an elevated temperature in an aprotic solvent such as toluene, acetonitrile, benzene, or a mixture of any or all of these solvents.

The optional protecting groups in the protected nucleosides or structural formula 1-5 can be cleaved following established deprotection methodologies (T. W. Greene and P. G. M. Wuts, "Protective Groups in Organic Synthesis," 3rd ed., John Wiley & Sons, 1999).

2. Modification of a Pre-Formed Nucleoside

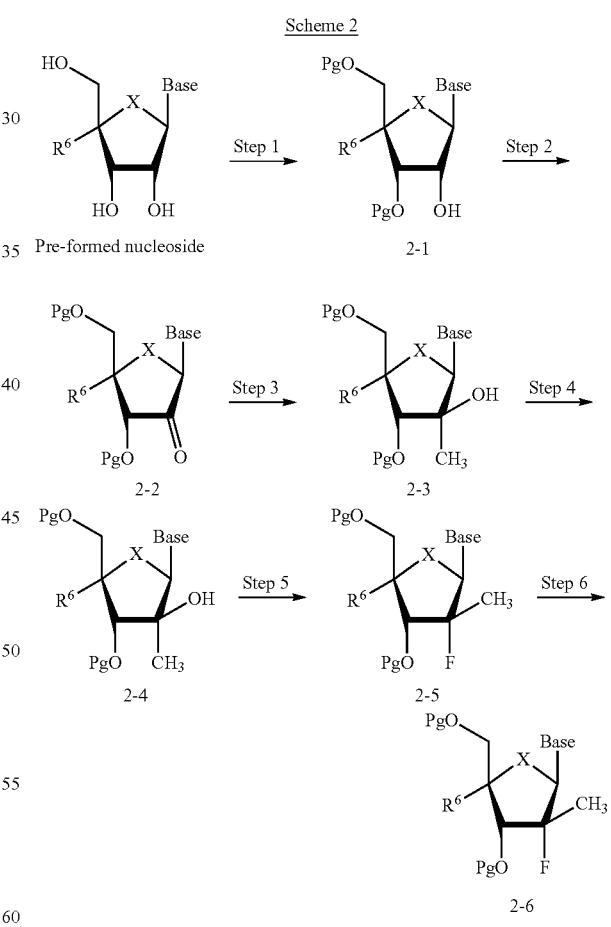

Pg = Protecting group
Base = as defined herein (optionally protected)
X = as defined herein
R$^6$ = as defined herein The starting material for this process is an appropriately substituted purine or pyrimidine nucleoside with a 2'-OH and 2'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by T. W. Greene and P. G. M. Wuts, "Protective Groups in Organic Synthesis," 3rd ed., John Wiley & Sons, 1999.

The purine or pyrimidine nucleoside can then be oxidized at the 2'-position with the appropriate oxidizing agent in a compatible solvent at a suitable temperature to yield the 2'-modified nucleoside. Possible oxidizing agents are a mixture of dimethylsulfoxide, trifluoroacetic anhydride or acetic anhydride (a Swern/Moffat oxidation), chromium trioxide or other chromate reagent, Dess-Martin periodinane, or by ruthenium tetroxide/sodium periodate.

The optionally protected nucleoside 2'-ketone is then alkylated using such alkylating agents methyllithium, trimethylaluminum, methylmagnesium bromide, or similar reagents in an anhydrous solvent such tetrahydrofuran (THF), chloroform, or diethyl ether usually at temperatures below 0° C. Compounds of the structural formula 2-3 are preferred to have the 2'(S) or 2'-methyl "down", 2'-OH "up" configuration.

The nucleoside of structure 2-3 can be deprotected and reprotected with a number of protecting groups such as an O-acyl (alkyl or aryl), O-sulfonyl, or an N-acyl (alkyl or aryl) for the base. This optional reprotection step need not be limited to protecting groups that function as chemical protecting groups. Other protecting groups such as long chain acyl groups of between 6 and 18 carbon units or amino acids can be introduced independently on the nucleobase or the sugar. The protecting groups can serve as prodrugs of the active substance.

Step 5 introduces the fluorine atom at the 2' position of the pre-formed nucleoside. This can be achieved by treatment of the tertiary alcohol, 2-4, with a commercially available fluorinating reagent such as (diethylamino)sulfur trifluoride (DAST) or Deoxofluor in an anhydrous, aprotic solvent such as tetrahydrofuran, chloroform, dichloromethane, or toluene. Preferably the stereochemistry proceeds with inversion of configuration at the 2' position. That is, starting from a C-2' hydroxyl "up" (or arabinonucleoside) in structure 2-4, the C-2' flourine is "down" in the intermediate nucleoside 2-5. The absolute configuration of a nucleoside of structure 2-4 is (2'S) while the absolute configuration of a nucleoside of structure 2-5 is (2'R).

Subsequently, the nucleosides of structural type 2-5 can be deprotected by methods well known to those skilled in the art, as taught by T. W. Greene and P. G. M. Wuts, "Protective Groups in Organic Synthesis," 3rd ed., John Wiley & Sons, 1999.

The following working examples provide a further understanding of the method of the present invention and further exemplify the general examples in Schemes 1 and 2 above. These examples are of illustrative purposes, and are not meant to limit the scope of the invention. Equivalent, similar or suitable solvents, reagents or reaction conditions may be substituted for those particular solvents, reagents or reaction conditions described without departing from the general scope of the method.

EXAMPLES

Example 1

Synthesis of (2'R)-2'-Deoxy-2'-Fluoro-2'-C-Methylcytidine Starting from a Carbohydrate

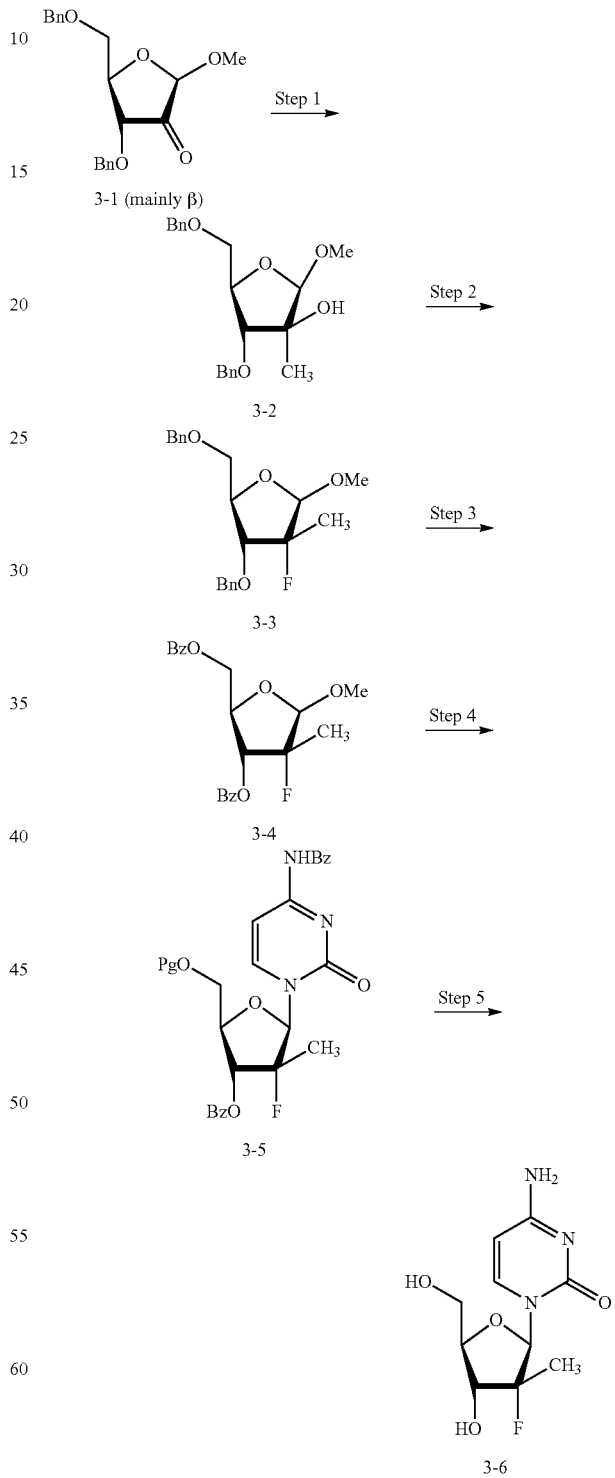

Bz = C(O)Ph
Bn = CH₂Ph

Step 1:

Compound 3-1 (7.7 g, 0.022 mmol) was dissolved in anhydrous diethyl ether and cooled to −78° C. To this solution was added MeLi (30 mL, 1.6 M in diethyl ether). After the reaction was complete, the mixture was treated with ammonium chloride (1 M, 65 mL) and the organic phase was separated, dried (Na$_2$SO$_4$), filtered, and concentrated to dryness. Silica gel chromatography followed by crystallization from diethyl ether-hexanes afforded pure compound 3-2 (6.31 g). $^1$H NMR (400 MHz, CDCl$_3$): δ 1.40 (s, 3H), 3.41 (s, 3H), 3.49 (dd, 1H, J=10.3, 6.89 Hz), 3.57 (dd, 1H, J=10.3, 3.88 Hz), 3.84 (d, 1H, J=7.3 Hz), 4.03 (m, 1H), 4.48 (s, 1H), 4.58 (m, 3H), 4.83 (d, 1H, J=11.6 Hz), 7.31-7.36 (m, 10H); $^{13}$C NMR (100 MHz, CDCl$_3$): δ 18.4, 55.4, 72.2, 73.4, 79.5, 80.2, 84.7, 107.4, 127.7, 127.8, 127.83, 128.5, 138.2, 138.3.

Step 2:

Compound 3-2 was dissolved in CH$_2$Cl$_2$ and was treated with DAST (4.0 mL, 30.3 mmol) at room temperature. The solution was stirred at room temp overnight. The so-obtained mixture was poured into sat NaHCO$_3$ (100 mL) and washed with sat NaHCO$_3$ (1×15 mL). The organic layer was further worked up in the usual manner. Silica gel chromatography (1:5 EtOAc-hexanes) gave crude compound 3-3 (0.671 g) that was sufficiently pure for the next step. $^1$H NMR (400 MHz, CDCl$_3$): δ 1.43 (d, 3H, J=22.8 Hz), 3.35 (s, 3H), 3.49 (dd, 1H, J=10.5, 5.4 Hz), 3.55 (dd, 1H, J=10.5, 4.1 Hz), 3.87 (dd, 1H, J=23.5, 7.5 Hz), 4.26 (m, 1H), 4.56 (d, 2H, J=6.9 Hz), 4.66 (d, 2H, J=8.2 Hz), 4.72 (d, 1H, J=10.8 Hz), 7.29-7.36 (m, 10H); $^{13}$C NMR (100 MHz, CDCl$_3$): δ 17.0 (d, J=24.4 Hz), 55.2, 77.1, 73.4, 73.8, 77.3, 80.3, 81.2 (d, J=16 Hz), 99.7 (d, J=178.9 Hz), 106.8 (d, J=32.0 Hz), 127.7, 127.8, 128.1, 128.3, 128.5, 128.6, 137.8, 138.3; $^{19}$F NMR (100 MHz, CDCl$_3$): δ −8.2 (m, 1F).

Step 3:

Compound 3-3 (0.39 g, 1.1 mmol) was dissolved in 1:2 EtOH-EtOAc and treated with Pd/C (~0.1 g) and cyclohexene (~1 mL). The mixture was heated to reflux overnight and then filtered through celite. The solvent was removed in vacuo and the residue was dissolved in pyridine (~5 mL). To this solution was added benzoyl chloride (0.22 mL, 1.83 mmol) and the mixture was stirred at room temp overnight. The pyridine was removed in vacuo and the residue was partitioned between CH$_2$Cl$_2$ and sat NaHCO$_3$ (10.0 mL). The organic phase was dried (Na$_2$SO$_4$), filtered, and the solution was concentrated to dryness. Column chromatography provided 0.350 g of pure compound 3-4. $^1$H NMR (400 MHz, CDCl$_3$): δ 1.53 (d, 3H, J=22.4 Hz), 3.39 (s, 3H), 4.46 (dd, 1H, J=11.6, 4.7 Hz), 4.58 (m, 1H), 4.65 (dd, 1H, J=11.6, 3.9 Hz), 4.87 (d, 1H, J=9.9 Hz), 5.64 (dd, 2H, J=24.1, 7.8 Hz), 7.29-7.36 (m, 10H); $^{19}$F NMR (100 MHz, CDCl$_3$): δ −7.5 (m, 1F).

Step 4:

A solution of bis(trimethylsilyl)-N-benzoylcytosine (0.28 g, 0.77 mmol) and compound 3-4 (0.20 g, 0.5 mmol) in 1,2 dichloroethane (2 mL) and toluene (2 mL) was treated with TMSOTf (0.15 mL, 0.77 mmol). After most of the starting material disappeared as judged by TLC, the solution was cooled to room temp, washed with water (1×5 mL), brine (1×5 mL), dried (Na$_2$SO$_4$), filtered, and concentrated to dryness. Flash chromatography followed by crystallization from CH$_2$Cl$_2$-hexanes afforded compound 3-5 (68 mg). mp 241° C.; $^1$H NMR (400 MHz, CDCl$_3$): δ 1.49 (d, 3H, J=22.4 Hz), 4.64 (dd, 1H, J=12.9, 3.4 Hz), 4.73 (app 1H, J=9.5 Hz), 4.89 (dd, 1H, J=12.7, 2.2 Hz), 5.56 (dd, 1H, J=20.7, 8.6 Hz), 6.52 (d, 1H, J=15.9 Hz), 7.38-7.67 (m, 10H), 7.89 (d, 2H, J=6.9 Hz), 8.07-8.11 (m, 5H), 8.67 (s, 1H); $^{19}$F NMR (100 MHz, CDCl$_3$): δ 2.85 (m, 1F).

Step 5:

Compound 3-5 (40 mg, 0.05 mmol) was dissolved in methanolic ammonia and stirred at room temp for 48 h. The solution was concentrated to dryness and chromatographed (SiO$_2$) eluting with 1:4 EtOH—CH$_2$Cl$_2$. The yield was about 12 mg of pure (2'R)-2'-deoxy-2'-fluoro-2'-C-methylcytidine, 3-6. $^1$H NMR (400 MHz, DMSO-d$_6$): δ 1.16 (d, 3H, J=22.0 Hz), 3.61 (dd, 1H, J=11.6, 5.2 Hz), 3.60-3.83 (m, 3H, J=10.5, 5.4 Hz), 5.24 (s, 1H, exchangeable with D$_2$O), 5.59 (s, 1H, exchangeable with D$_2$O), 5.71 (d, 1H, J=7.3 Hz), 6.08 (d, 1H, J=19.0 Hz), 7.24 (d, 1H, J=17.7 Hz, exchangeable with D$_2$O), 7.87 (d, 1H); $^{19}$F NMR (100 MHz, DMSO-d$_6$): δ 4.13 (m, 1F).

Example 2

Synthesis of (2'R)-2'-Deoxy-2'-Fluoro-2'-C-Methylcytidine Starting from Cytidine

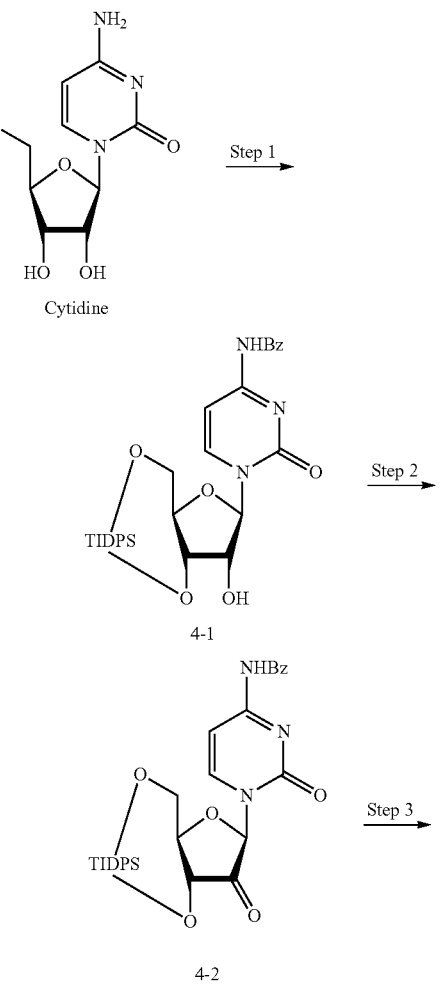

Scheme 4

Cytidine 4-1

4-2

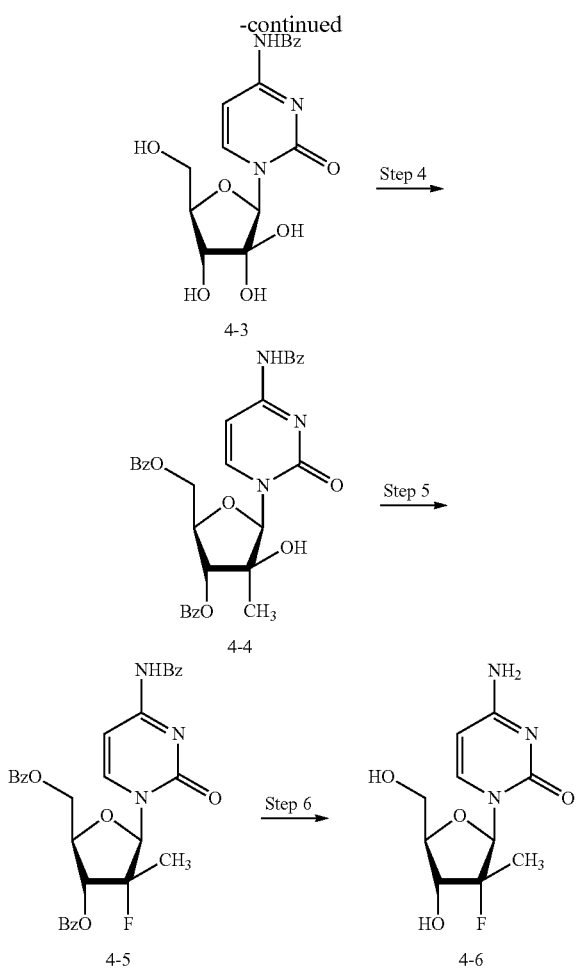

TIDPS=1,3-(1,1,3,3-Tetraisopropyldisiloxanylidene)

Step 1:

To a suspension of cytidine (100 g, 0.411 mol) in DMF (2.06 L) is added benzoic anhydride (102.4 g, 0.452 mol). The mixture was stirred at room temperature for 20 h. The DMF was removed in vacuo and the residue was triturated with diethyl ether. The resulting solid was collected by suction filtration and washed with diethyl ether (2×200 mL). Further drying in vacuo at room temperature gave the $N^4$ benzamide (140.6 g, 98.3%). A portion of this material (139.3 g, 0.401 mol) was dissolved in anhydrous pyridine (1.2 L) and was treated with 1,3-dichloro-1,1,3,3-tetraisopropyl-disiloxane (141.4 mL, 0.441 mol) at room temp. The solution was stirred at room temperature overnight. The mixture was concentrated to near dryness in vacuo and coevaporated with toluene (3×200 mL). The residue was treated with EtOAc (1.8 L) and washed with HCl (2×200 mL, 0.05 N), NaHCO$_3$ (5%, 2×400 mL). The organic layer was washed dried (Na$_2$SO$_4$), filtered, and evaporated to dryness. Compound 4-1 (256.5 g, >100%) was isolated as a white foam and used without further purification.

Step 2:

Compound 4-1 (236.5 g, 0.40 mol) was dissolved in dry THF (1.22 L). Anhydrous dmso (180.8 mL, 2.1 mol) was added and the resulting solution was cooled to between −20° C. and −15° C. Trifluoroacetic anhydride (90.6 mL, 0.64 mol) was added dropwise over 45 minutes and the solution was stirred between −20° C. and −15° C. for 2 hrs after which anhydrous triethylamine (223.5 mL, 1.6 mol) was added over 20 min. The crude reaction containing ketone 4-2 was dissolved in EtOAc (500 mL), and the resulting solution was washed with H$_2$O (3×400 mL), dried (Na$_2$SO$_4$) and the solvents were removed in vacuo to give a yellow solid that was purified on a silica gel column eluting with a stepwise gradient of Et$_2$O (0-60%) in hexanes followed by a stepwise gradient of EtOAc (50-100%) in hexanes. The crude ketone so-obtained (~192 g) was crystallized from petroleum ether to give ketone 4-2 (138.91 g, 57.5% from cytidine) as a white solid and 22 g of unreacted starting material, 4-1, as a yellow solid.

Step 3:

Compound 4-2 (48.57 g, 8.26 mmol) was dissolved in anhydrous toluene (~400 mL) and the solvent was removed in vacuo with exclusion of moisture. The residue was then further dried in vacuo (oil pump) for another 2 h. With strict exclusion of moisture, the residual foam was dissolved in anhydrous diethyl ether (1.03 L) under argon. The resulting solution was cooled to −78° C. under argon and MeLi (1.6 M, 258.0 mL, 0.413 mol) was added dropwise via additional funnel. After the addition was complete, the mixture was stirred for 2 h at −78° C. Aqueous 1 M NH$_4$Cl (500 mL) was added slowly. After warming to room temperature, the mixture was washed with H$_2$O (2×500 mL), dried (Na$_2$SO$_4$), and then concentrated to dryness to give a brown foam (~60 g, >100%).

The reaction was performed two more times using 37.62 g and 56.4 g of compound 4-2. The combined crude products (128.0 g, 0.212 mol) were dissolved in THF (1.28 L) and treated with concd HOAc (23 mL, 0.402 mol). To the solution was added TBAF (384.0 mL, 1 M in THF). The solution was stirred at room temp for 0.75 h and the mixture was treated with silica gel (750 g) and concentrated to dryness. The powder was placed on a silica gel column packed in CH$_2$Cl$_2$. Elution with 1:7 EtOH—CH$_2$Cl$_2$ afforded a dark waxy solid that was pre-adsorbed on silica gel (300 g) and chromatographed as before. Compound 4-3 (46.4 g, 53.0% from 4-2) was isolated as an off-white solid. $^1$H NMR (DMSO-d$_6$): δ 1.20 (s, 3H, CH$_3$), 3.62-3.69 (m, 2H,), 3.73-3.78 (m, 2H,), 5.19 (t, 1H, J=5.4 Hz, OH-5'), 5.25 (s, 1H, OH-2'), 5.52 (d, 1H, J=5.0 Hz, OH-3'), 5.99 (s, 1H, H-1'), 7.32 (d, 1H, J=5.8 Hz), 7.50 (Ψt, 2H, J=7.7 Hz), 7.62 (Ψt, 1H, J=7.3 Hz), 8.00 (d, 2H, J=7.3 Hz), 8.14 (d, 1H, J=6.9 Hz), 11.22 (s, 1H, NH). Anal. Calcd for C$_{17}$H$_{19}$N$_3$O$_6$.0.5H$_2$O: C, 55.13; H, 5.44; N, 11.35. Found: C, 55.21; H, 5.47; N, 11.33.

Step 4:

Compound 4-3 (46.0 g, 0.13 mol) was dissolved in anhydrous pyridine and concentrated to dryness in vacuo. The resulting syrup was dissolved in anhydrous pyridine under argon and cooled to 0° C. with stirring. The brown solution was treated with benzoyl chloride (30 mL, 0.250 mol) dropwise over 10 min. The ice bath was removed and stirring continued for 1.5 h whereby TLC showed no remaining starting material. The mixture was quenched by the addition of water (5 mL) and concentrated to dryness. The residue was dissolved in a minimal amount of CH$_2$Cl$_2$ and washed with satd NaHCO$_3$ (1×500 mL) and H$_2$O (1×500 mL). The organic phase was dried (Na$_2$SO$_4$) and filtered, concentrated to dryness and chromatographed on silica gel eluting with a stepwise gradient of EtOAc-hexanes (25-60%) to provide compound 4-4 as yellow foam (48.5 g, 67%). $^1$H NMR (CDCl$_3$): δ 1.64 (s, 3H, CH$_3$), 4.50 (m, 1H, H-4), 4.78-4.85 (m, 2H, H-5',5a'), 5.50 (d, 1H, J=3.4 Hz, H-3'), 6.42 (s, 1H, H-1'), 7.44-7.54 (m, 7H, Ar), 7.57-7.66 (m, 3H, Ar), 7.94 (d, 2H, J=7.8 Hz), 8.05-8.09 (m, 4H, Ar), 8.21 (d, 1H, J=7.3 Hz). Anal. Calcd for C$_{31}$H$_{27}$N$_3$O$_8$: C, 65.37; H, 4.78; N, 7.38. Found: C, 65.59; H, 4.79; N, 7.16.

Step 5:

Compound 4-4 (7.50 g, 0.013 mol) was dissolved in anhydrous toluene (150 mL) under argon and cooled to −20° C. DAST (2.5 mL, 18.9 mmol) was added slowly and the cooling bath was removed after the addition was complete. Stirring was continued for 1 h and the mixture was poured into satd NaHCO₃ (100 mL) and washed until gas evolution ceased. The organic phase was dried (Na₂SO₄), concentrated, and purified by silica gel chromatography eluting with 1:1 EtOAc-hexanes. Yield was 1.22 g (16.3%) of pure 4-5 as a white solid. mp 241° C. (CH₂Cl₂-hexanes); $^1$H NMR (CDCl₃): δ 1.49 (d, 3H, J=22.4 Hz, CH₃), 4.64 (dd, 1H, J=3.44, 12.9 Hz, H-5'), 4.73 (d, 1H, J=9.5 Hz, H-4'), 4.90 (dd, 1H, J=2.4, 12.7 Hz, H-5a'), 5.56 (dd, 1H, J=8.6, 20.7 Hz, H-3'), 6.52 (d, 1H, J=18.0 Hz, H-1'), 7.47-7.57 (m, 7H, Ar), 7.62-7.71 (m, 3H, Ar), 7.89 (d, 2H, J=6.9 Hz), 8.07-8.11 (m, 5H, Ar), 8.67 (bs, 1H, NH). $^{19}$F NMR (CDCl₃): δ 3.3 (m). Anal. Calcd for C₃₁H₂₆FN₃O₇·0.7H₂O: C, 63.74; H, 4.72; N, 7.20. Found: C, 63.71; H, 4.54; N, 7.20.

Step 6:

Compound 4-5 (6.30 g, 0.011 mol) was suspended in methanolic ammonia (ca 7 N, 150 mL) and stirred at room temperature overnight. The solvent was removed in vacuo, co-evaporated with methanol (1×20 mL), and pre-adsorbed onto silica gel. The white powder was placed onto a silica gel column (packed in CHCl₃) and the column was eluted with 9% EtOH in CHCl₃, then 17% EtOH and finally 25% EtOH in CHCl₃. Concentration of the fractions containing the product, filtration through a 0.4 μm disk, and lyophilization from water afforded compound 4-6, 2.18 g (76%). $^1$H NMR (DMSO-d₆): δ 1.17 (d, 3H, J=22.3 Hz, CH₃), 3.63 (dd, 1H, J=2.7, 13.7 Hz, H-5'), 3.70-3.84 (m, 3H, H-3', H-4', H-5a'), 5.24 (app s, 1H, OH-3'), 5.60 (d, 1H, J=5.4 Hz, H-5'), 5.74 (d, 1H, J=7.71 Hz, H-5), 6.07 (d, 1H, J=18.9 Hz, H-1'), 7.31 (s, 1H, NH₂), 7.42 (s, 1H, NH₂), 7.90 (d, 1H, J=7.3 Hz, H-6). $^{19}$F NMR (DMSO-d₆): δ 2.60 (m). Anal. Calcd for C₁₀H₁₄FN₃O₄·1.4H₂O: C, 44.22; H, 5.95; N, 14.77. Found: C, 42.24; H, 5.63; N, 14.54. Compound 4-6 (0.10 g, 0.386 mmol) was converted to the hydrochloride salt by dissolving in water (2 mL) and adjusting the pH to approximately 3.0 with 1 M HCl. The water was removed in vacuo and the residue was crystallized from aqueous EtOH to give 4-6 as the hydrochloride salt (71.0 mg). mp 243° C. (dec); $^1$H NMR (DMSO-d₆): δ 1.29 (d, 3H, J=22.6 Hz, CH₃), 3.65 (dd, 1H, J=2.3, 12.7 Hz, H-5'), 3.76-3.90 (m, 3H, H-3', H-4', H-5a'), 5.96 (d, 1H, J=17.3 Hz, H-1'), 6.15 (d, 1H, J=7.9 Hz, H-5), 8.33 (d, 1H, J=7.9 Hz, H-6), 8.69 (s, 1.5H, NH), 9.78 (s, 1.5H, NH). $^{19}$F NMR (DMSO-d₆): δ 1.69 (m). Anal. Calcd for C₁₀H₁₄FN₃O₄·HCl: C, 40.62; H, 5.11; N, 14.21. Found: C, 40.80; H, 5.09; N, 14.23.

Example 3

Synthesis of (2'R)-6-Chloro-2'-Deoxy-2'-Fluoro-2'-C-Methylpurine Starting from 6-Chloropurine Riboside Scheme 5

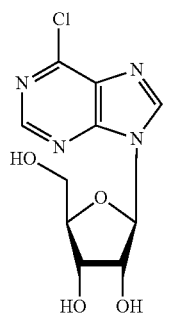

6-Chloropurine riboside

Step 1

-continued

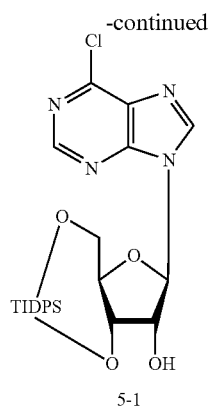

5-1

Step 2

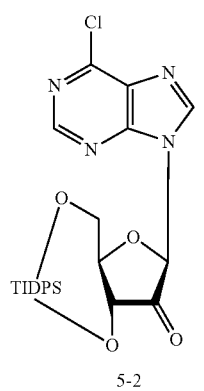

5-2

Step 3

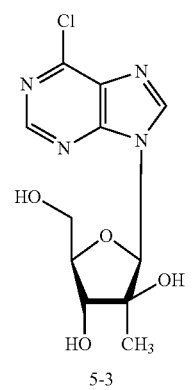

5-3

Step 4

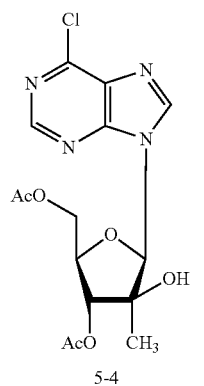

5-4

Step 5

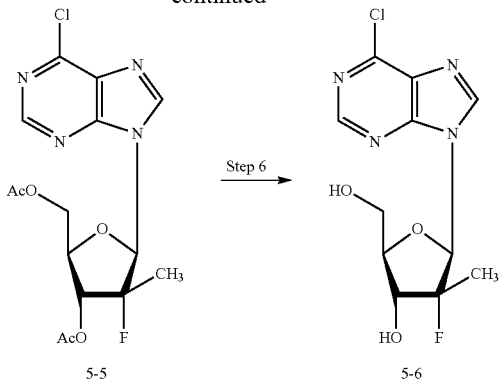

5-5

TIDPS = 1,3-(1,1,3,3-Tetraisopropyldisiloxanylidene)

Step 1:

The nucleoside, 6-chloropurine riboside, (3.18 g, 11.09 mmol) was dissolved in anhydrous pyridine (300 mL) and was treated dropwise with 1,3-dichloro-1,1,3,3-tetraisopropyl-disiloxane (4.08 mL, 12.75 mmol) at 0° C. under an argon atmosphere. The solution was brought to room temp and stirred overnight. The mixture was concentrated to near dryness in vacuo, dissolved in a minimal amount of chloroform, and washed with HCl (100 mL, 0.05 N) and NaHCO$_3$ (5%, 100 mL). The organic layer was dried (Na$_2$SO$_4$), filtered, and evaporated to dryness to afford compound 5-1 as an amber glass (6.10 g, >100%) that was used without further purification. $^1$H NMR (CDCl$_3$): δ 1.01-1.13 (m, 24H), 4.03-4.18 (m, 3H), 4.58 (d, 1H, J=5.2 Hz), 5.01 (m, 1H), 6.07 (s, 1H), 8.31 (s, 1H), 8.71 (s, 1H).

Step 2:

Compound 5-1 (7.13 g, 13.47 mmol) was dissolved in dry THF (35 mL). Anhydrous DMSO (5.11 mL, 72.06 mmol) was added and the resulting solution was cooled to between −20° C. and −15° C. Trifluoroacetic anhydride (3.06 mL, 21.69 mmol) was added dropwise over 45 minutes and the solution was stirred between −20° C. and −15° C. for 2 hrs after which anhydrous triethylamine (8.08 mL, 57.92 mmol) was added over 20 min. The crude reaction containing ketone 5-2 was dissolved in Et$_2$O (25 mL), and the resulting solution was washed with H$_2$O (2×50 mL), dried (Na$_2$SO$_4$) and the solvents were removed in vacuo to give a yellow solid that was purified on a silica gel column eluting with a stepwise stepwise gradient of 0-50% petroleum ether-diethyl ether afforded compound 5-2 as a mixture with the corresponding geminal diol. The glass was dissolved in CH$_2$Cl$_2$ and stirred over an excess of MgSO$_4$ for 36 h. The mixture, free from the geminal diol, was filtered, and evaporated to dryness to afford compound 5-2 as an amber glass (7.0 g, 97%). $^1$H NMR (CDCl$_3$): δ 1.01-1.13 (m, 24H), 4.09-4.22 (m, 3H), 5.55 (d, 1H, J=9.6 Hz), 5.80 (s, 1H), 8.19 (s, 1H), 8.61 (s, 1H).

Step 3:

A solution of compound 5-2 (7.0 g, 13.26 mmol) in anhydrous tetrahydrofuran (45 mL) was cooled to −78° C. with stirring under an argon atmosphere. To the solution was added methylmagnesium bromide (15.85 mL, 3.0 M in ethyl ether) dropwise over a 30 min period. After stirring for an additional 3 h at −78° C., the reaction was quenched by the careful addition of aqueous 1 M NH$_4$Cl (50.0 mL). After warming to room temperature, the mixture was washed with H$_2$O (2×500 mL), dried (Na$_2$SO$_4$), and concentrated to dryness to give a brown foam (3.8 g) that was dissolved in tetrahydrofuran (50 mL) and treated with a solution of TBAF (18.9 mL, 1 M solution in THF) and glacial acetic acid (0.85 mL) at room temp. The solution was stirred at room temp for 2 h, concentrated to dryness, and purified by silica gel chromatography to give compound 5-3 (2.0 g, 50%).

Step 4:

Compound 5-3 (0.491 g, 1.63 mmol) was dissolved in pyridine (3 mL) and treated with acetic anhydride (0.38 mL, 4.08 mmol) at room temp. The solution was stirred at room temp for 2 h after which time, the solution was concentrated to dryness and treated with diethyl ether (10 mL) and water (5 mL). The organic layer was further washed with water (2×10 mL), dried (Na$_2$SO$_4$), filtered, and evaporated to dryness to give compound 5-4 as a foam (0.450 g, 91.0%). $^1$H NMR (CDCl$_3$): δ 1.39 (s, 3H), 2.15 (s, 3H), 2.21 (s, 3H), 4.27 (m, 1H), 4.49 (dd, 1H, J=4.2, 11.9 Hz), 4.57 (dd, 1H, J=6.16, 11.9 Hz), 5.14 (d, 1H, J=3.1 Hz), 6.25 (s, 1H), 8.54 (s, 1H), 8.75 (s, 1H).

Step 5:

Compound 5-4 (0.100 g, 0.259 mmol) was dissolved in anhydrous toluene (3.0 mL) under argon and cooled to −20° C. DAST (0.2 mL, 1.55 mmol) was added slowly and the cooling bath was removed after the addition was complete. Stirring was continued for 1 h and the mixture was poured into satd NaHCO$_3$ (100 mL) and washed until gas evolution ceased. The organic phase was dried (Na$_2$SO$_4$), concentrated, and purified by silica gel chromatography eluting with 30% Et$_2$O-petroleum ether gave pure 5-5 (0.028 g, 27.9%). $^1$H NMR (CDCl$_3$): δ 1.24 (d, 3H, J=22.8 Hz), 2.20 (s, 3H), 2.22 (s, 3H), 4.41-4.55 (m, 3H), 4.47 (dd, 1H, J=9.2, 22.0 Hz), 6.37 (d, 1H, J=17.6 Hz), 8.45 (s, 1H), 8.82 (s, 1H).

Step 6:

Compound 5-5 (0.018 g, 0.047 mmol) was dissolved in methanol (5 mL) and treated with a solution of sodium methoxide (3.6 mg, 0.67 mmol) in methanol (5 mL). The solution was stirred at room temp for 1 h, neutralized with concd acetic acid and chromatographed on silica gel eluting with a stepwise gradient of Et$_2$O/methanol (0-5%) to afford compound 5-6 (0.010 g, 70.9%). $^1$H NMR (CDCl$_3$): δ 1.23 (d, 3H, J=22.4 Hz), 4.04 (dd, 1H, J=2.11, 12.5 Hz), 4.17 (dd, 1H, J=1.5, 9.2 Hz,), 4.25 (dd, 1H, J=1.9, 12.3 Hz), 4.61 (dd, 1H, J=9.2, 22.3 Hz), 6.37 (d, 1H, J=17.3 Hz), 8.70 (s, 1H), 8.78 (s, 1H).

Example 4

Synthesis of (2'R)-2'-Deoxy-2'-Fluoro-2'-C-Methyl-adenosine Starting from (2R)-6-Chloro-2'-Deoxy-2'-Fluoro-2'-C-Methylpurine

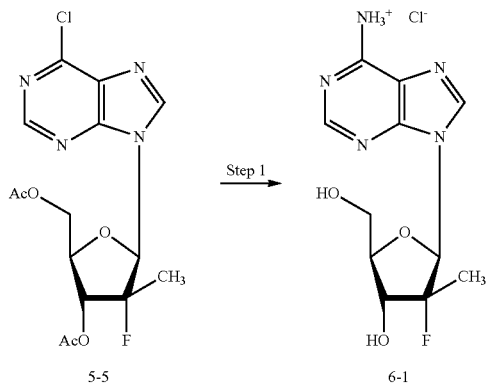

Step 1:

Compound 5-5 (0.100 g, 0.26 mmol) was heated in a pressure tube with methanolic ammonia (ca. 7 N, 25 mL) at 80° C. for 12 h. The crude reaction was pre-adsorbed onto silica gel and purified by column chromatography eluting with a stepwise gradient of Et$_2$O-MeOH (0-5%). The impure product was converted to the hydrochloride salt by dissolving the compound in a minimal amount of ethanol and treating the solution with 0.5 mL of a 0.6 M HCl solution. Concentration to near dryness gave compound 6-1 as off-white crystals (0.020 g, 24.2%). $^1$H NMR (CD$_3$OD): δ 1.19 (d, 3H, J=22.3 Hz), 3.88 (dd, 1H, J=2.7, 12.7 Hz), 4.06 (dd, 1H, J=2.1, 12.5 Hz,), 4.11 (app d, 1H, J=9.2 Hz), 4.35 (dd, 1H, J=9.4, 24.5 Hz), 6.35 (d, 1H, J=16.5 Hz), 8.43 (s, 1H), 8.85 (s, 1H).

Example 5

Antiviral Activity of (2R)-2'-Deoxy-2'-Fluoro-2'-C-Methylcytidine

HCV Replicon Assay

Figure 1B:
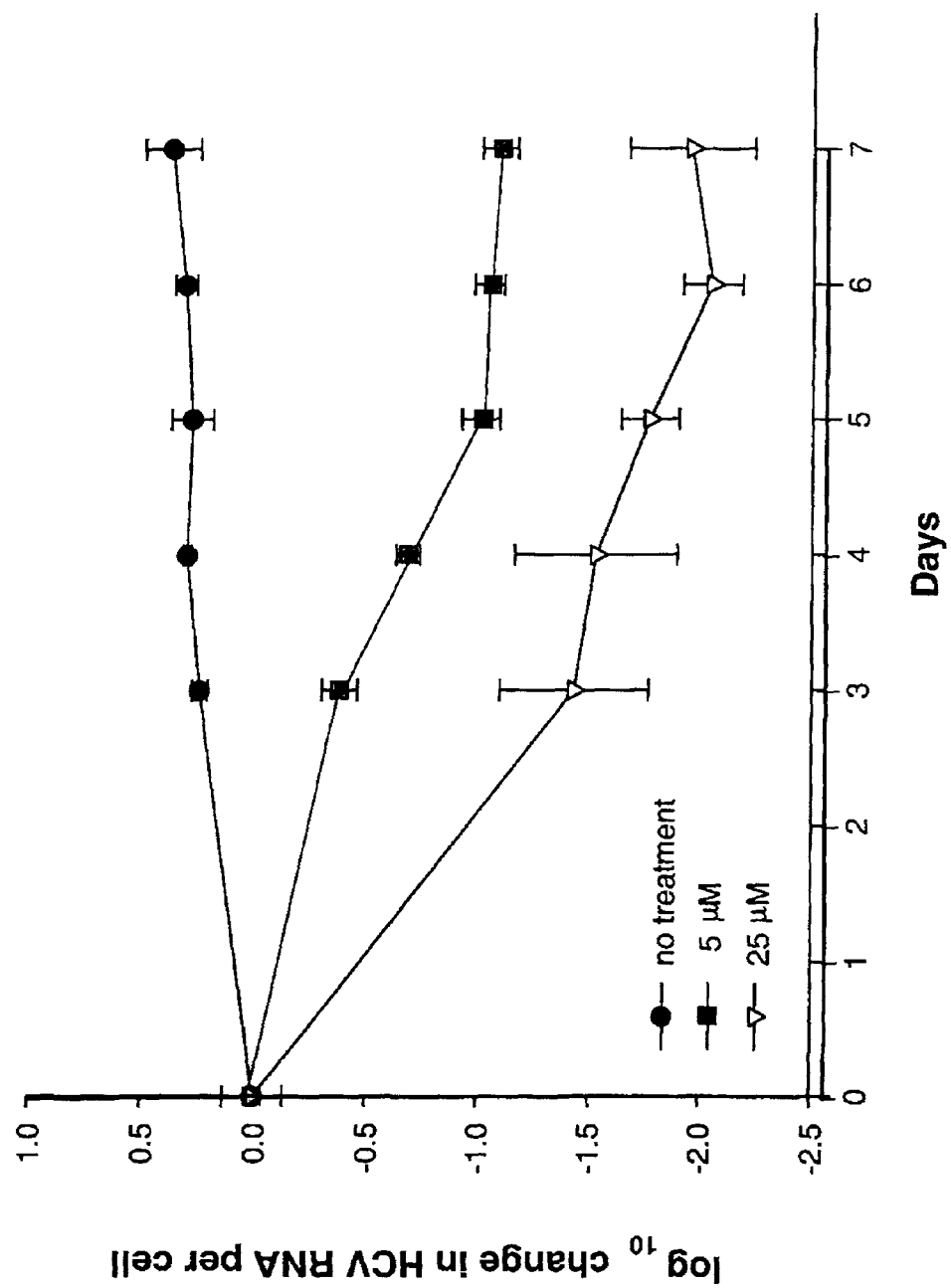

The anti-flavivirus activity of the compounds was determined as described by Stuyver, et al. ("Ribonucleoside analogue that blocks replication of bovine viral diarrhea and hepatitis C viruses in culture", Antimicrobial Agents and Chemotherapy 47:244-254 (2003)). The compound was dissolved in DMSO and added to the culture media at final concentrations ranging from 3 to 100 µM. A 4-days incubation resulted in dose-dependant reduction of the replicon HCV RNA (FIG. 1A). A 1-log reduction of replicon RNA (or EC$_{90}$ value) was reached at approximately 2.5 µM. Measurement of the reduction of rRNA gave an indication of the inhibitory effect on cellular polymerases. Subtraction of this cellular toxicity value from the antiviral values resulted in the therapeutic index line and EC$_{90}$ value. Based on these calculations, an average EC$_{90}$ value, corrected for cellular toxicity, of approximately 2.5 µM was obtained. FIG. 1A shows the dose-dependant reduction of the replicon HCV RNA based on the treatment with (2'R)-2'-deoxy-2'-fluoro-2'-C-methylcytidine. The viral reduction was compared to the reduction of cellular RNA levels (ribosomal RNA) to obtain therapeutic index values. EC$_{90}$ represents the effective concentration 90% at 96 hours following the dose dependant administration of (2'R)-2'-deoxy-2'-fluoro-2'-C-methylcytidine. FIG. 1B shows the prolonged reduction in replicon HCV RNA up to 7 days following treatment with 5 and 25 µM.

The activity of (2'R)-2'-deoxy-2'-fluoro-2'-C-methylcytidine in the replicon system is summarized in Table 1. The EC$_{90}$ values for (2'R)-2'-deoxy-2'-fluoro-2'-C-methylcytidine as well as 2'-C-methylcytidine and 2'-C-methyladenosine are shown for three separate replicon clones (HCV-WT (Wild Type), 9-13 and 21-5) as well as two other clones (S282T and rRNA). The EC$_{90}$ values for (2'R)-2'-deoxy-2'-fluoro-2'-C-methylcytidine were in the range of 1.6 to 4.6 µM for the replicon clones. In contrast the EC$_{90}$ values for 2'-C-methylcytidine were in the range of 6.6-37.4 µM. Interestingly, the EC$_{90}$ values for 2'-C-methyladenosine were comparable to those of (2'R)-2'-deoxy-2'-fluoro-2'-C-methylcytidine. The activity of (2'R)-2'-deoxy-2'-fluoro-2'-C-methylcytidine and 2'-C-methylcytidine in other replicons tested is shown in Table 2.

Polymerase Assay

Table 3 shows the potency of (2'R)-2'-deoxy-2'-fluoro-2'-C-methylcytidine-5'-triphosphate (TP) in the NS5B polymerase assay. The inhibitory concentration 50% was determined to be in the range of 1.7 to 7.7 µM.

Toxicity

A summary of the toxicity data for (2'R)-2'-deoxy-2'-fluoro-2'-C-methylcytidine using the mitochondrial toxicity assay is shown in Tables 6 and 7. Table 7 shows the lack of effects of (2'R)-2'-deoxy-2'-fluoro-2'-C-methylcytidine and 2'-C-methylcytidine on mitochondrial DNA synthesis and lack of effects on lactic acid increase in this assay. Results shows the relative lack of toxicity of (2'R)-2'-deoxy-2'-fluoro-2'-C-methylcytidine. Table 6 shows a cytotoxicity analysis in various cell lines (Clone A, Huh7, HepG2, MDBK, PBM, CEM, Vero, MRC-5). Cytotoxic concentration 50% (CC$_{50}$) was greater than 75-100 µM in all clones tested for (2'R)-2'-deoxy-2'-fluoro-2'-C-methylcytidine as well as 2'-C-methylcytidine. In contrast is the relative toxicity of 2'-C-methyladenosine.

The effects the nucleoside analogs tested on human bone marrow cells is depicted in Table 9. As shown, the IC$_{50}$ values for 2'-methyl-2'-fluorocytidine were significantly higher (98.2, BFU-E) and 93.9 (CFU-GM) as compared to 2'-methylcytadine or AZT. Results show that 2'-methyl-2'-fluorocytidine was significantly less toxic than compared to the other nucleoside compounds.

Animal Studies

Figure 2:
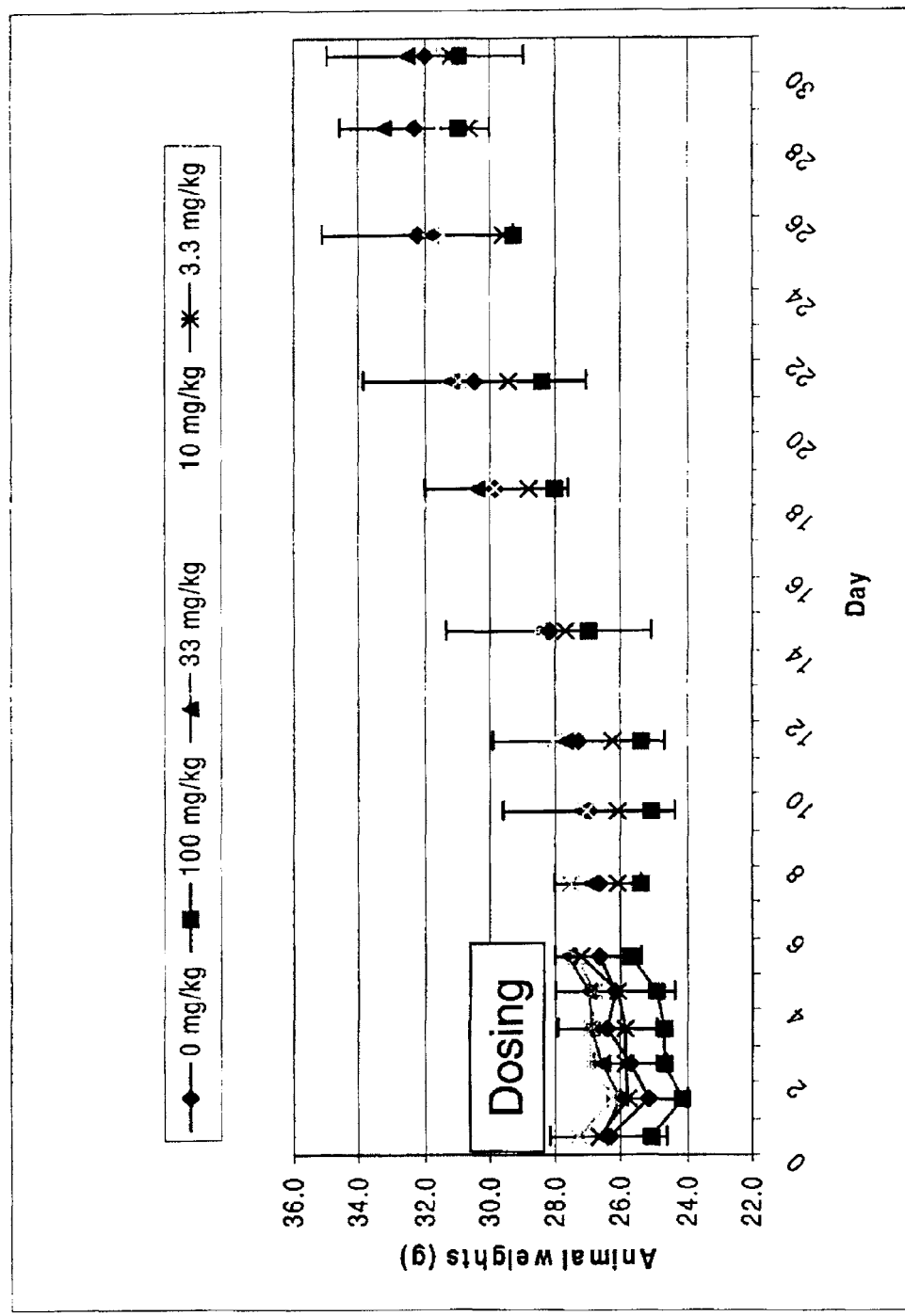
FIG. 2 depicts the average weight change (%) of female Swiss mice in the toxicity study of β-D-(2'R)-2'-deoxy-2'-fluoro-2'-C-methylcytidine at various doses. Intraperitoneal injections were given on days 0 to day 5 of the 0, 3.3, 10, 33, 100 mg/kg. Each dosing group contained 5 mice and no mice died during the 30-day study.

FIG. 2 depicts the average weight change (%) of female Swiss mice in vivo the toxicity analysis of (2'R)-2'-deoxy-2'-fluoro-2'-C-methylcytidine at various doses. Intraperitoneal injections were given on days 0 to day 5 of the 0, 3.3, 10, 33, 100 mg/kg. Each dosing group contained 5 mice and no mice died during the 30-day study. No significant toxicity was observed in the mice.

Figure 3:
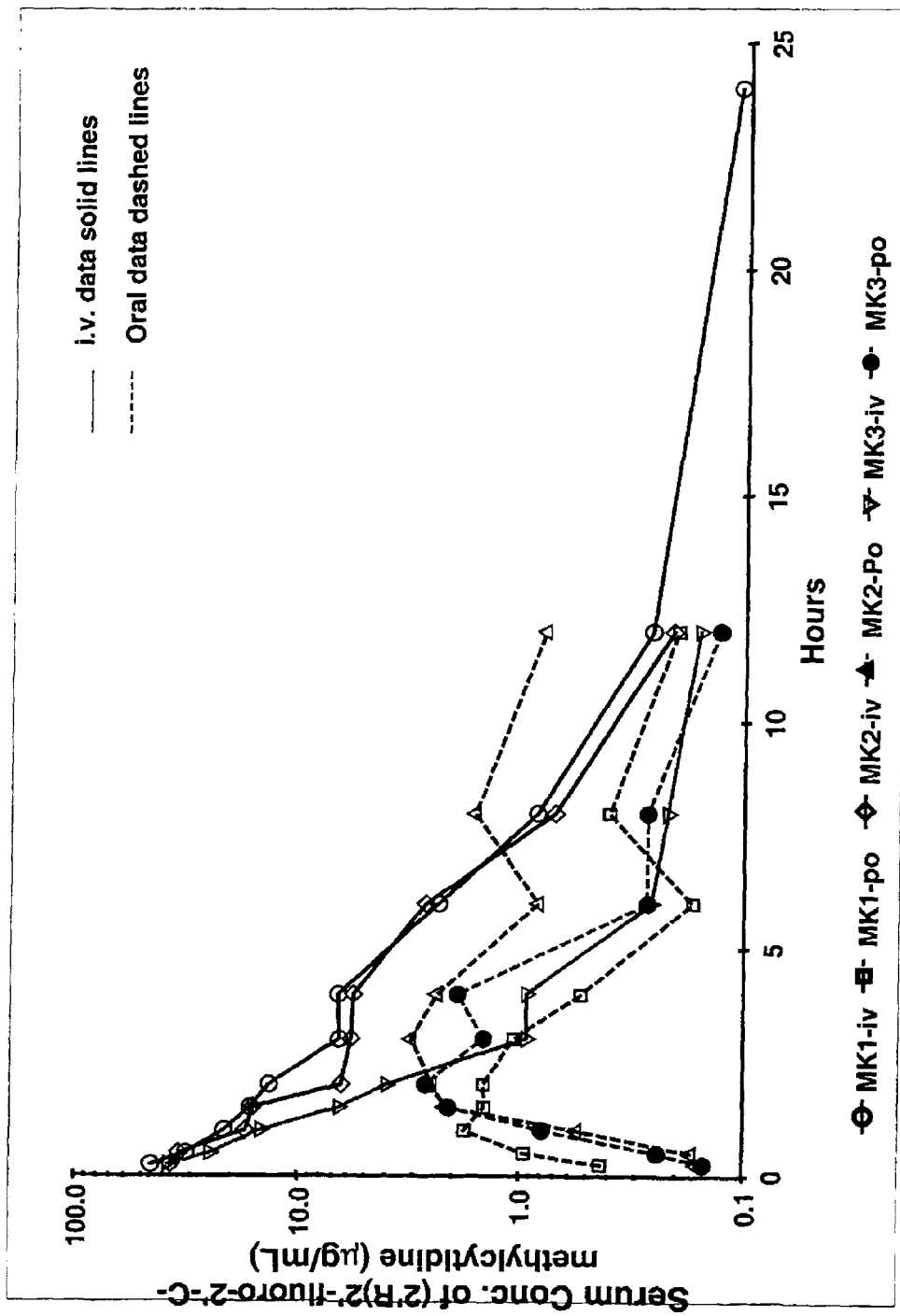
FIG. 3 depicts the pharmacokinetics of β-D-(2'R)-2'-deoxy-2'-fluoro-2'-C-methylcytidine in Rhesus monkeys given a single dose (33.3 mg/kg) oral or intravenous dose of β-D-(2'R)-2'-deoxy-2'-fluoro-2'-C-methylcytidine.

FIG. 3 and Table 6 summarize the pharmacokinetic parameters of (2'R)-2'-deoxy-2'-fluoro-2'-C-methylcytidine in Rhesus monkeys given a single dose (33.3 mg/kg) oral (Table 6, FIG. 3) or intravenous dose (FIG. 3) of (2'R)-2'-deoxy-2'-fluoro-2'-C-methylcytidine.

Other Antiviral Activity

Summary of the range of antiviral activity of (2'R)-2'-deoxy-2'-fluoro-2'-C-methylcytidine is shown in Table 4. Table shows that in addition to HCV virus (2'R)-2'-deoxy-2'-fluoro-2'-C-methylcytidine shows activity against Rhinovirus, West Nile virus, Yellow Fever virus, and Dengue virus.

Table 5 shows the lack of activity of (2'R)-2'-deoxy-2'-fluoro-2'-C-methylcytidine on HCV surrogate models BVDV as well as other viruses including HIV, HBV and Corona virus. In contrast, 2'-C-methylcytidine and 2'-C-methyladenosine show greater activity in the HCV surrogate model, BVDV. These results show the necessity for screening this series of compounds against the HCV replicon system versus surrogate HCV systems.

TABLE 1

Summary of the Anti-HCV Replicon Activity of (2'R)-2'-deoxy-2'-fluoro-2'-C-methylcytidine*

| Replicon | (2'R)-2'-deoxy-2'-fluoro-2'-C-methylcytidine | 2'-C-methylcytidine | 2'-C-methyladenosine |
| --- | --- | --- | --- |
| HCV-WT 1b | 4.6 ± 2.0 | 21.9 ± 4.3 | 2.1 ± 0.27 |
| S282T mut. 1b | 30.7 ± 11.7 | 37.4 ± 12.1 | >100 |
| 9-13 (subgenomic) | 4.6 ± 2.3 | 13.0 | 0.7 |
| 21-5 (full-length) | 1.6 ± 0.7 | 6.6 | 0.6 |

*Values represent EC$_{90}$ (µM)

TABLE 2

Activity of (2'R)-2'-deoxy-2'-fluoro-2'-C-methylcytidine and 2'-C-methylcytidine in other Replicons

| | (2'R)-2'-deoxy-2'-fluoro-2'-C-methylcytidine | | | 2'-C-methylcytidine | | |
|---|---|---|---|---|---|---|
| | | $IC_{90}$ ($\mu M$) | | | $IC_{90}$ ($\mu M$) | |
| Replicon | $EC_{90}$ ($\mu M$) | GAPDH | MTT | $EC_{90}$ ($\mu M$) | GAPDH | MTT |
| 1b (Ntat) | 3.8 | >100 | >100 | 27.2 | >100 | >100 |
| 1b (Btat) | 11.5 | >100 | >100 | 31.1 | >100 | >100 |
| 1a (pp1aSI-7) | 34.7 | >100 | >100 | 35.0 | >100 | >100 |

TABLE 3

HCV 1b NS5B Polymerase Assay ($IC_{50}$, $\mu M$)

| | (2'R)-2'-deoxy-2'-fluoro-2'-C-methylcytidine TP | 2'-C-methylcytidine TP | 2'-C-methyladenosine TP |
|---|---|---|---|
| Wild-Type NS5B | 1.7 ± 0.4[a]<br>7.7 ± 1.2[b] | 6.0 ± 0.5 | 20.6 ± 5.2 |
| S282T | 2.0[a]<br>8.3 ± 2.4[c] | 26.9 ± 5.5 | >100 |

[a]Values determined using batch 1;
[b]Value determined using batch 2 and 3; and
[c]Value determined using batch 2.

TABLE 4

Summary of Antiviral Activity of (2'R)-2'-deoxy-2'-fluoro-2'-C-methylcytidine

| Virus | Cell | $EC_{50}$, CPE ($\mu M$) | $EC_{50}$, NR[a] ($\mu M$) | $CC_{50}$, CPE ($\mu M$) | $CC_{50}$, NR[a] ($\mu M$) |
|---|---|---|---|---|---|
| West Nile | Vero | 32 | 12 | >100 | 32 |
| Dengue Type 2 | Vero | 32/55 | >100/>100 | >100 | >100 |
| Yellow Fever | Vero | 19/3.2 | 32/12 | >100 | >100 |
| Influenza A (H1N1) | MDCK | >100 | >100 | >100 | >100 |
| Influenza A (H3N2) | MDCK | >100 | >100 | >100 | >100 |
| Influenza B | MDCK | >100 | >100 | >100 | >100 |
| Rhinovirus Type 2 | KB | 25 | 20 | >100 | >100 |
| VEE | Vero | >100 | >100 | >100 | >100 |
| SARSCoV | Vero | >100 | >100 | >100 | >100 |

[a]NR = Neutral Red.

TABLE 5

Summary of Antiviral Activity of (2'R)-2'-deoxy-2'-fluoro-2'-C-methylcytidine

| Virus | (2'R)-2'-deoxy-2'-fluoro-2'-C-methylcytidine ($EC_{90}$, $\mu M$) | 2'-C-methylcytidine ($EC_{90}$, $\mu M$) | 2'-C-methyladenosine ($EC_{90}$, $\mu M$) |
|---|---|---|---|
| BVDVncp | >22 | 0.5 | 1.2 |
| BVDVcp | >100 | 2 | 1.5 |
| RSV | >100 | >100 | >100 |
| HIV[a] | >100 | ND | ND |
| HBV | >10 | >10 | ND |
| Coronavirus 229E | >100 | ND | ND |

ND = Not determined.

TABLE 6

Cytotoxicity Studies[a]

| Cell Line | (2'R)-2'-deoxy-2'-fluoro-2'-C-methylcytidine $CC_{50}$, $\mu M$ | 2'-C-methylcytidine $CC_{50}$, $\mu M$ | 2'-C-methyladenosine $CC_{50}$, $\mu M$ |
|---|---|---|---|
| CloneA | >100 | >100 | 37 |
| Huh7 | >100 | >100 | 30 |
| HepG2 | 75 | >100 | 58 |
| MDBK | >100 | >100 | |
| PBM | >100 | | |
| CEM | >100 | | |
| Vero | >100 | | |
| MRC-5 | >100 | | |

[a]Results determined using MTS assay.

TABLE 7

Mitochondrial Toxicity Study

| Compound | mtDNA Synthesis ($IC_{50}$, $\mu M$) | Lactic Acid Increase |
|---|---|---|
| (2'R)-2'-deoxy-2'-fluoro-2'-C-methylcytidine | >25 | No effect ≥ 33 $\mu M$ |
| 2'-C-methylcytidine | >25 | No effect ≥ 33 $\mu M$ |

TABLE 8

Preliminary PK Parameters in Rhesus Monkeys Following a Single Oral Dose of (2'R)-2'-deoxy-2'-fluoro-2'-C-methylcytidine at 33.3 mg/kg

| Parameter | Units | Mean ± SD |
|---|---|---|
| $C_{max}$ | $\mu M$ | 9.6 ± 2.7 |
| $T_{max}$ | hours | 2 ± 1 |
| $AUC_{0-last}$ | $\mu M \times h$ | 44.2 ± 22.2 |
| $T \frac{1}{2}$ | hours | 3.9 ± 0.1 |
| Bioavailability | F % | 21 ± 11 |

TABLE 9

Effect of Nucleoside Analogs on Human Bone Marrow Cells

| Compound (β-D-analog) | BFU-E $IC_{50}$ ($\mu M$) | CFU-GM $IC_{50}$ ($\mu M$) |
|---|---|---|
| 2'-fluoro-2'-C-methylcytidine | 98.2 | 93.9 |
| 2'-C-methylcytidine | 20.1 | 13.2 |
| AZT | 0.08 | 0.95 |

I claim:
1. A method for the treatment of hepatitis C infection, which comprises:

providing to a human subject in need thereof an antivirally effective amount of a (2'R)-2'-deoxy-2'-fluoro-2'-C-methyl nucleoside (β-D) or its pharmaceutically acceptable salt of the structure:
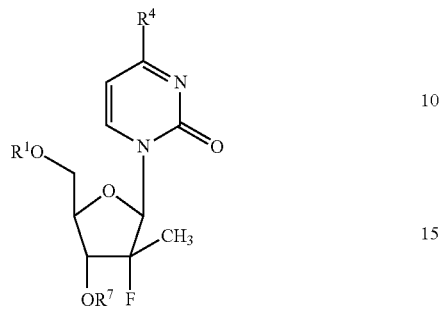
wherein $R^1$ and $R^7$ are independently H, a monophosphate, a diphosphate, or a triphosphate; and $R^4$ is $NH_2$ or OH.
* * * * *